(12) United States Patent
Devasthale et al.

(10) Patent No.: US 7,521,557 B2
(45) Date of Patent: Apr. 21, 2009

(54) PYRROLOPYRIDINE-BASED INHIBITORS OF DIPEPTIDYL PEPTIDASE IV AND METHODS

(75) Inventors: Pratik Devasthale, Plainsboro, NJ (US); Wei Wang, Princeton, NJ (US); Lawrence G. Hamann, North Grafton, MA (US); John M. Fevig, Doylestown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 2 days.

(21) Appl. No.: 11/430,657

(22) Filed: May 9, 2006

(65) Prior Publication Data

US 2006/0264457 A1 Nov. 23, 2006

Related U.S. Application Data

(60) Provisional application No. 60/682,968, filed on May 20, 2005.

(51) Int. Cl.
*C07D 471/02* (2006.01)
*A01N 43/42* (2006.01)
(52) U.S. Cl. ...................... 546/113; 514/300
(58) Field of Classification Search ............ 546/113
See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,647,576 A | 3/1987 | Hoefle et al. | |
| 4,681,893 A | 7/1987 | Roth | |
| 4,686,237 A | 8/1987 | Anderson | |
| 4,871,721 A | 10/1989 | Biller | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,346,701 A | 9/1994 | Heiber et al. | |
| 5,354,772 A | 10/1994 | Kathawala | |
| 5,385,929 A | 1/1995 | Bjorge et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |
| 5,594,016 A | 1/1997 | Ueno et al. | |
| 5,595,872 A | 1/1997 | Wetterau, II et al. | |
| 5,612,359 A | 3/1997 | Murugesan | |
| 5,614,492 A | 3/1997 | Habener | |
| 5,631,224 A | 5/1997 | Efendic et al. | |
| 5,686,104 A | 11/1997 | Mills et al. | |
| 5,691,322 A | 11/1997 | Robl | |
| 5,712,279 A | 1/1998 | Biller et al. | |
| 5,712,396 A | 1/1998 | Magnin et al. | |
| 5,739,135 A | 4/1998 | Biller et al. | |
| 5,753,675 A | 5/1998 | Wattanasin | |
| 5,760,246 A | 6/1998 | Biller et al. | |
| 5,770,615 A | 6/1998 | Cheng et al. | |
| 5,776,983 A | 7/1998 | Washburn et al. | |
| 5,827,875 A | 10/1998 | Dickson, Jr. et al. | |
| 5,885,983 A | 3/1999 | Biller et al. | |
| 5,962,440 A | 10/1999 | Sulsky | |
| 6,043,265 A | 3/2000 | Murugesan et al. | |
| 6,303,661 B1 * | 10/2001 | Demuth et al. | ................ 514/19 |
| 6,395,767 B2 | 5/2002 | Robl et al. | |
| 6,548,529 B1 | 4/2003 | Robl et al. | |
| 6,653,314 B2 | 11/2003 | Cheng et al. | |
| 6,995,183 B2 | 2/2006 | Hamann et al. | |

FOREIGN PATENT DOCUMENTS

| | | |
|---|---|---|
| EP | 0 221 025 | 5/1987 |
| EP | 0 142 146 | 8/1988 |
| EP | 1 323 710 A1 | 7/2003 |
| FR | 2 596 393 | 10/1987 |
| GB | 2 205 837 | 12/1988 |
| WO | WO 86/03488 | 6/1986 |
| WO | WO 86/07054 | 12/1986 |
| WO | WO 96/38144 | 12/1996 |

(Continued)

OTHER PUBLICATIONS

Elbannany, A. A. et al Heterocycles 1987, 26, 2323-2326.*

(Continued)

*Primary Examiner*—Rita J Desai
*Assistant Examiner*—John Mabry
(74) *Attorney, Agent, or Firm*—Burton Rodney

(57) ABSTRACT

Compounds are provided having the formula (I)

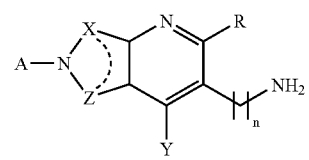

wherein R, X, Y, Z, A and n are as defined herein, which are inhibitors of dipeptidyl peptidase IV and thus are useful in treating diabetes and related diseases.

19 Claims, No Drawings

FOREIGN PATENT DOCUMENTS

| WO | WO 97/12613 | 4/1997 |
|---|---|---|
| WO | WO 97/12615 | 4/1997 |
| WO | WO 97/21993 | 6/1997 |
| WO | WO 98/42666 | 10/1998 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/39077 | 7/2000 |
| WO | WO 01/21602 | 3/2001 |
| WO | WO 01/68603 | 9/2001 |
| WO | WO 03/033671 | 4/2003 |
| WO | WO 2005/025504 | 3/2005 |

OTHER PUBLICATIONS

F.Z. Dorwald Side Reactions in Organic Synthesis: A Guide to Successful Synthesis Design 2005 Wiley-VCH Verlag GmbH & Co. KGaA, Wienheim.*

Ashworth, D.M. et al., "2-Cyanopyrrolidides as Potent, Stable Inhibitors of Dipeptidyl Peptidase IV", Bioorganic & Medicinal Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinal Chemistry Letters, vol. 6, No. 22, pp. 2745-2748 (1996).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Bundgaard, H., "Prodrugs as a means to improve the delivery of peptide drugs", Advanced Drug Delivery Reviews, vol. 8, pp. 1-38 (1992).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Eliel, E.L. et al., Basic Organic Stereochemistry, John Wiley & Sons, Inc., publ. pp. v-xi (table of contents) (2001).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Hara, S., "Ileal Na$^+$/bile acid cotransporter inhibitors", Drugs of the Future, vol. 24, No. 4, pp. 425-430 (1999).

Hughes, T.E. et al., "NVP-DPP728: (1-[[2-[(5-Cyanopyridin-2-yl)amino]ethyl]acetyl]-2-cyano-(S)-pyrrolidine), a Slow-Binding Inhibitor of Dipeptidyl Peptidase IV", Biochemistry, vol. 38, No. 36, pp. 11597-11603 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Kovtunenko, V.A. et al., "1-Imino-2R- and 1-imino-2R-3-phenylisoindolines", Ukrainskii Khimicheskii Zhurnal (Russian Edition), vol. 50, No. 11, pp. 1198-1203 (1984).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Nishio, T. et al., "Photoreactions of Isoindoline-1-thiones with Alkenes: Unusual Formation of Tricyclic Isoindolines", J. Org. Chem., vol. 57, No. 14, pp. 4000-4005 (1992).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Pirkle, W.H. et al., "Improved Chiral Derivatizing Agents for the Chromatographic Resolution of Racemic Primary Amines", J. Org. Chem., vol. 48, No. 15, pp. 2520-2527 (1983).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Stout, D.M., "Inhibitors of Acyl-CoA:Cholesterol O-Acyl Transferase (ACAT) as Hypocholestrolemic Agents. 6. The First Water-Soluble ACAT Inhibitor with Lipid-Regulating Activity. Inhibitors of Acyl-CoA:Cholesterol Actyltransferase (ACAT). 7. Development of a Series of Substituted N-Phenyl-N'-[(1-phenylcyclopentyl)-methyl]ureas with Enhanced Hypocholestrolemic Activity", Chemtracts-Organic Chemistry, vol. 8, pp. 359-362 (1995).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Widder, K.J. et al., eds., Section III: "Prodrugs", Methods in Enzymology, vol. 112, Academic Press, Inc., publ., pp. 309-396 (1985).

Wrobel, J. et al., "Conformationally Rigid Analogues of Aldose Reductase Inhibitor, Tolrestat. Novel Syntheses of Naphthalene-Fused γ-, δ-, and ε- Lactams", J. Org. Chem., vol. 55, No. 9, pp. 2694-2702 (1990).

Yamada, M. et al., "A Potent Dipeptide Inhibitor of Dipeptidiyl Peptidase IV", Bioorganic & Medicinal Chemistry Letters, vol. 8, pp. 1537-1540 (1998).

Kovtunenko, V.A. et al., "1-Imino-2R- and 1-Imino-2R-3-phenylisoindolines", Ukrainskii Khimicheskii Zhurnal (Russian Edition), vol. 50, No. 11, pp. 1198-1203 (1984) (English Translation).

A. Waldner, Helvetica Chimica Acta, vol. 71, 1988, pp. 493-497, "[4+2] Cycloaddition of alpha, beta-unsaturated hydrazones" Part 2 "Pyridine-2,3-dicarboximids via 1,4-dihydropyrimidines".

* cited by examiner

PYRROLOPYRIDINE-BASED INHIBITORS OF DIPEPTIDYL PEPTIDASE IV AND METHODS

This application claims a benefit of priority from U.S. Provisional Application No. 60/682,968 filed May 20, 2005, the entire disclosure of which is incorporated herein by reference.

FIELD OF THE INVENTION

The present invention relates to pyrrolopyridine-based inhibitors of dipeptidyl peptidase IV (DPP-4), and to a method for treating multiple diseases or disorders by employing such pyrrolopyrimidine-based inhibitors alone, or in combination with another type of therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1(7-36) is a 30 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo (t½≈1.5 min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1(7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

DESCRIPTION OF THE INVENTION

In accordance with the present invention, compounds of formula (I) are provided

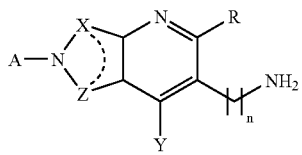

I wherein

⟩ represents one or two double bonds in the 5-membered ring, provided that the six-membered ring is an aromatic ring;

n is 1 or 2;

R is a functional group selected from the group consisting of hydrogen (H), halogen, $CF_3$, cyano (CN), amino, substituted amino, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein any such functional group may optionally be substituted with one to three substituents (where possible) selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

X and Z are the same or different and are independently selected from the group consisting of $CH_2$, CH, C=O, C=$CR_3R_4$, C=S, C=$NR_3$, and $CR_3R_4$, wherein $R_3$ and $R_4$ are alkyl or aryl;

A is a functional group selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl, cycloheteroalkylalkyl, O—$R_1$, cyano, amino, —C(O)—OH, —C(O)—$NR_1R_2$, —C(O)—$OR_1$, $S(O)_m$—$R_1$, —$S(O)_2NR_1R_2$, —$NR_1R_2$, —$NR_1$—C(O)$R_2$, —$NR_1$—$SO_2R_2$, wherein any such functional group may optionally be substituted with one to three substituents (where possible) selected from the group consisting of hydrogen, halo, alkyl, polyhaloalkyl, alkoxy, haloalkoxy, polyhaloalkoxy, carboxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, cycloheteroalkylaminocarbonyl, cycloheteroalkylcarbonyl, heteroarylaminocarbonyl, cycloheteroalkyl(alkyl)aminocarbonyl, cycloalkylsulfonyl(alkyl)amino, halosulfonyl(alkyl)amino, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, dialkylaminocarbonyl (where the alkyls are the same or different), alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

m is 0, 1 or 2;

$R_1$ and $R_2$ are the same or different and are (i) each independently a functional group selected from the group consisting of hydrogen (H), alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, arylalkyl, heteroaryl, heteroarylalkyl, cycloheteroalkyl and cycloheteroalkylalkyl, wherein either functional group may optionally be substituted with one to three substitutents (where possible) selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or (ii) $R_1$ and $R_2$ in $NR_1R_2$ may be taken together to form a 5- or 6-membered saturated or partially unsaturated ring system selected from the group consisting of heterocycloalkyl, heterobicycloalkyl, heteroaryl and bicycloheteroaryl, wherein such ring system may optionally be substituted with one to three substituents (where possible) selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; and Y is aryl or heteroaryl, wherein said aryl or heteroaryl group may optionally be substituted with one to five substituents (where possible) selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl.

The definition of formula I above includes all pharmaceutically acceptable salts, stereoisomers, and prodrug esters of formula I.

The compounds of formula I possess activity as inhibitors of DPP-4 in vivo and are useful in the treatment of diabetes and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, dyslipidemia, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Generally, the compounds of formula (I) will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

Specific embodiments of the invention include compounds of formula I having the structure:

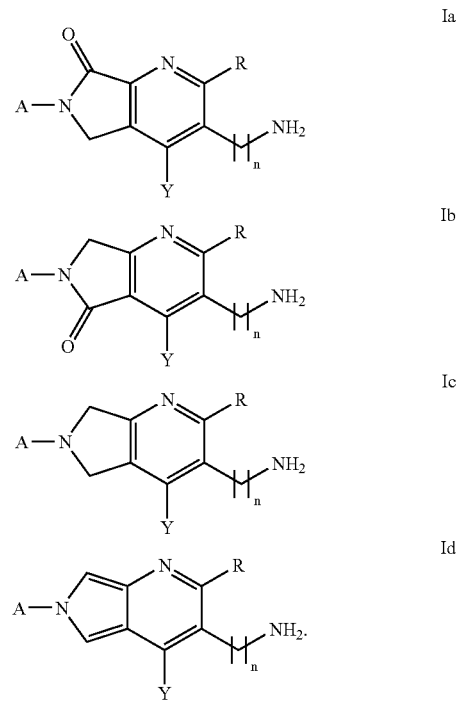

Further embodiments of the invention include compounds of formula I having the structure:

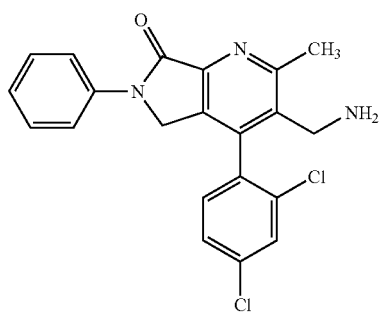

-continued
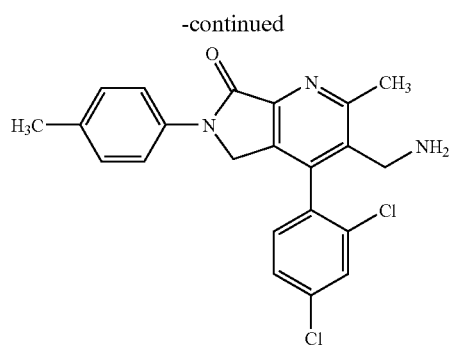
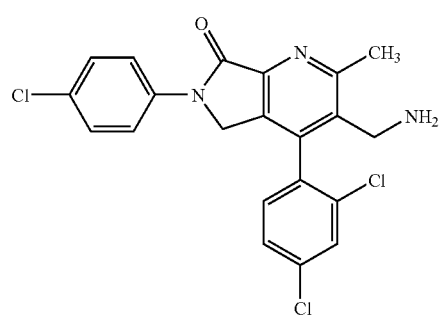
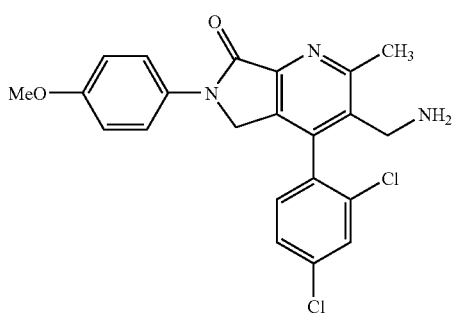
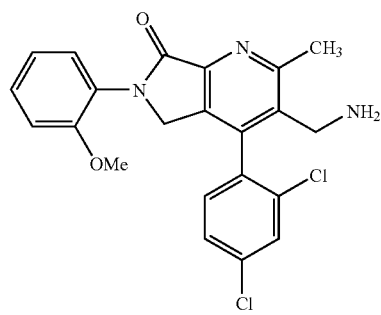
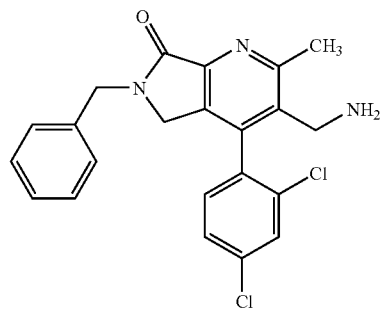
-continued
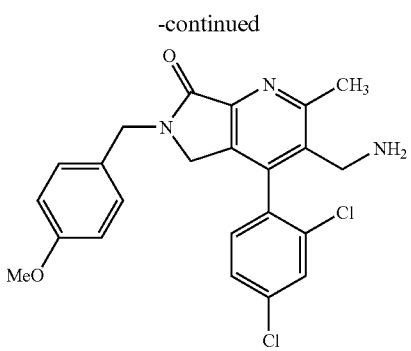
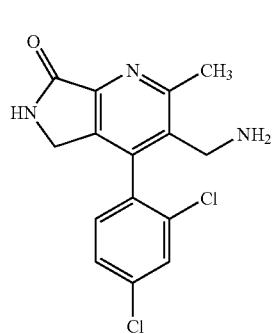
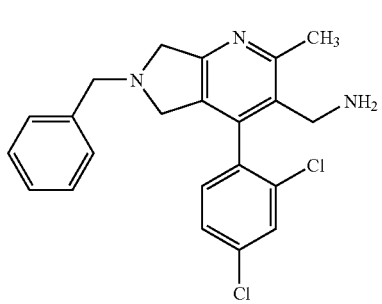
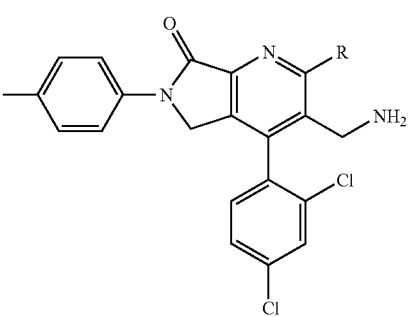
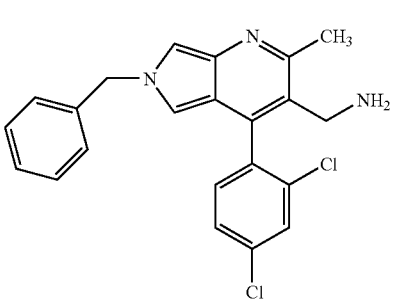

-continued
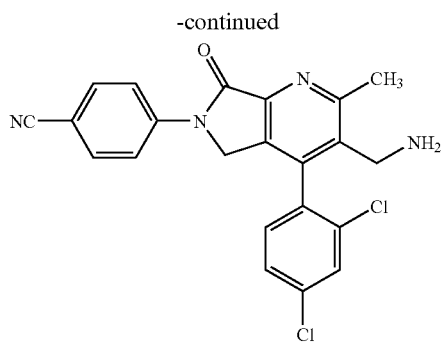
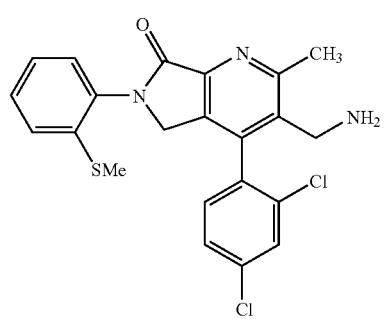
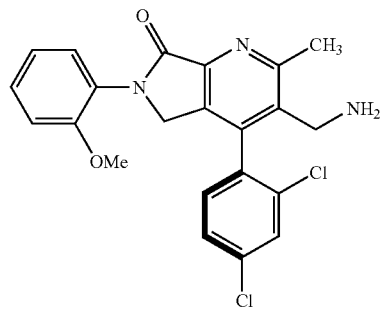
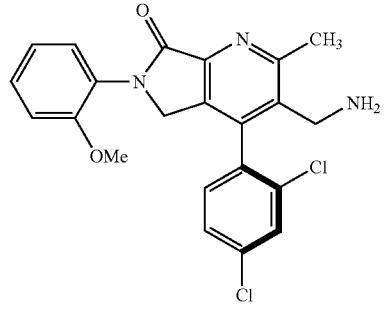
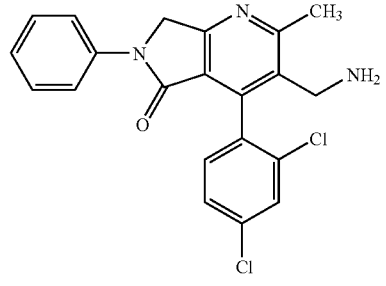
-continued
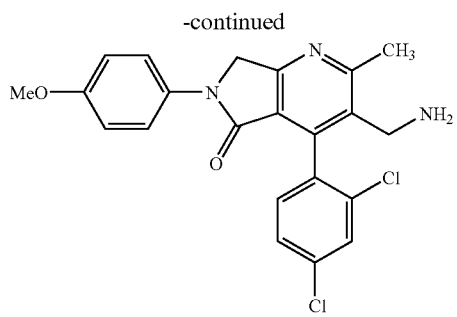
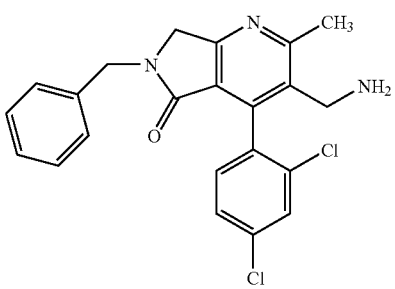
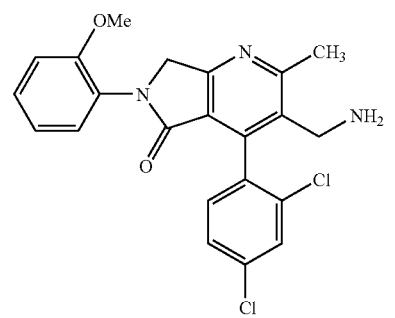
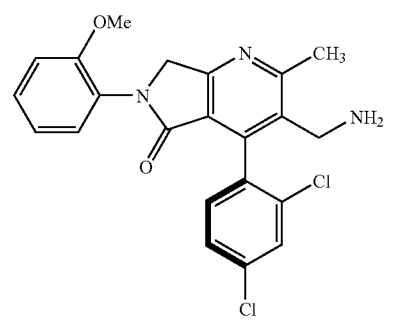
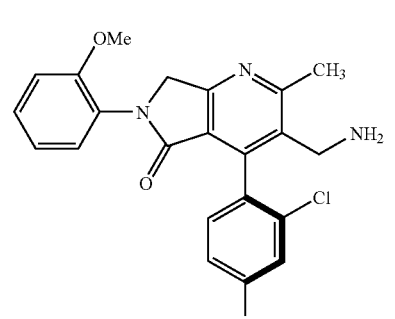

-continued
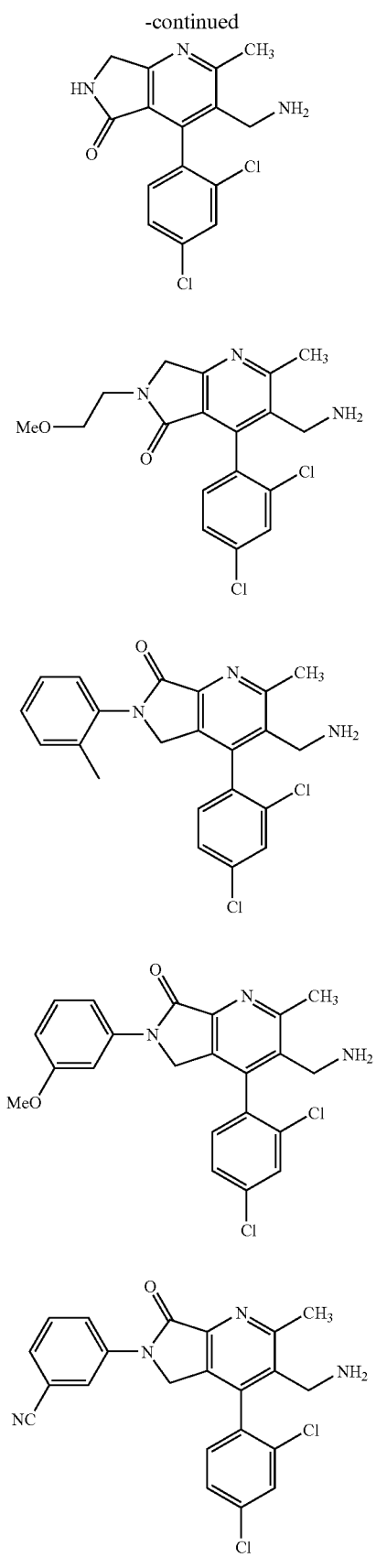
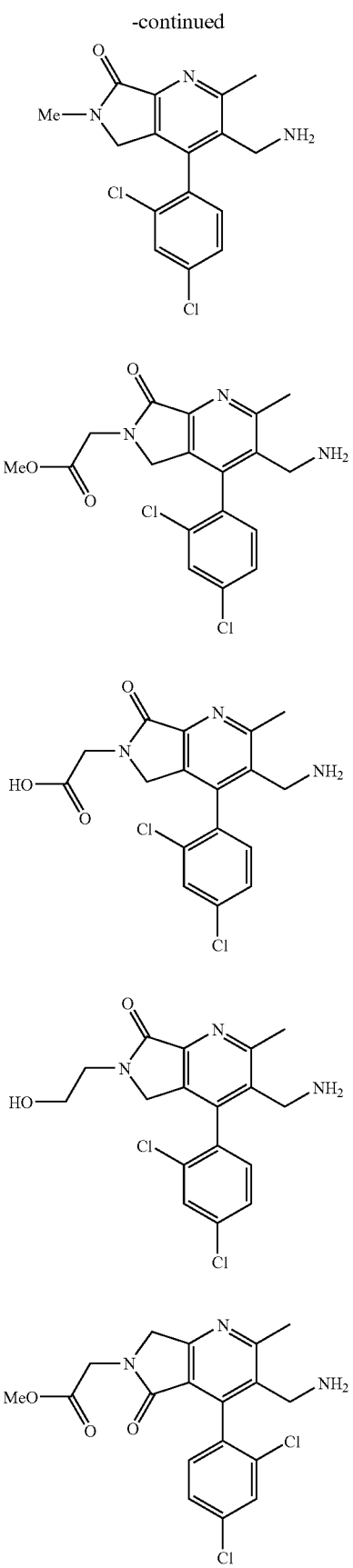

-continued
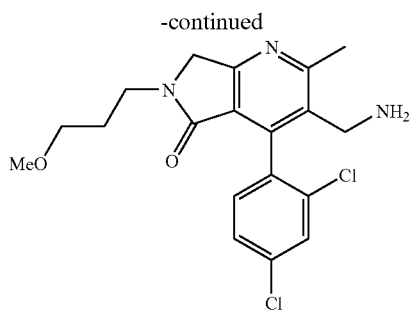
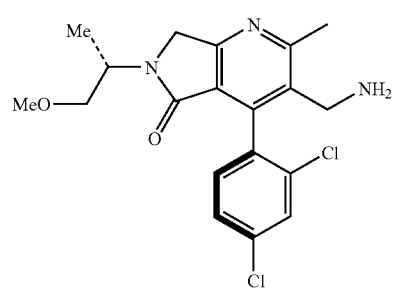
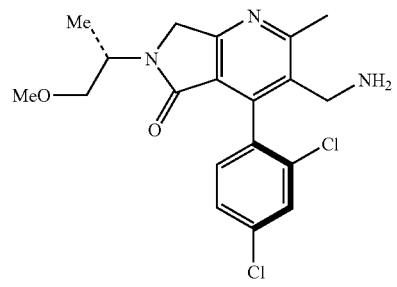
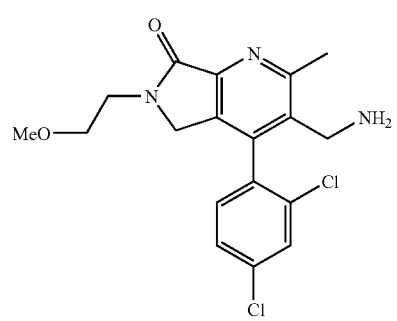
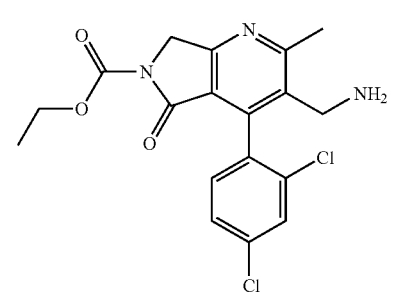
-continued
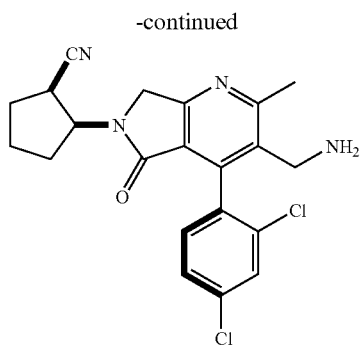
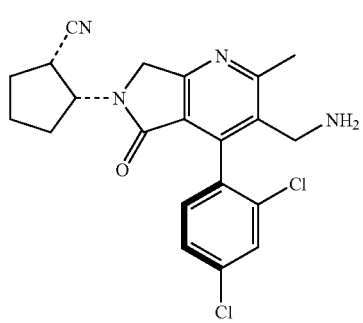
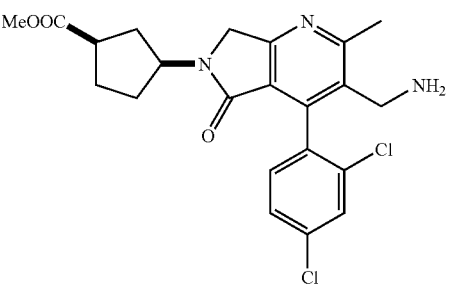
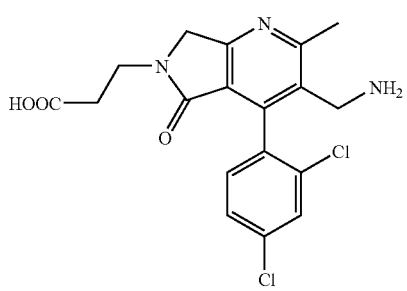
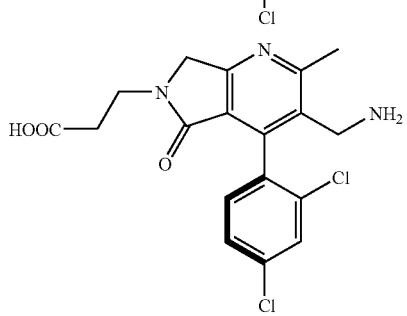

-continued
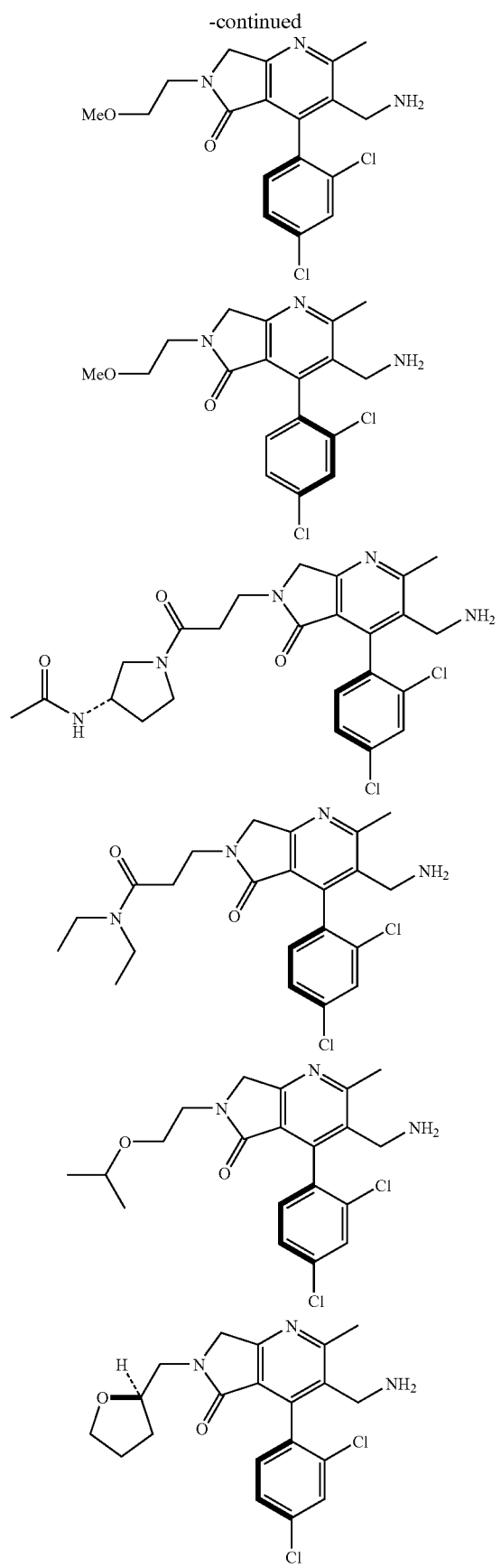
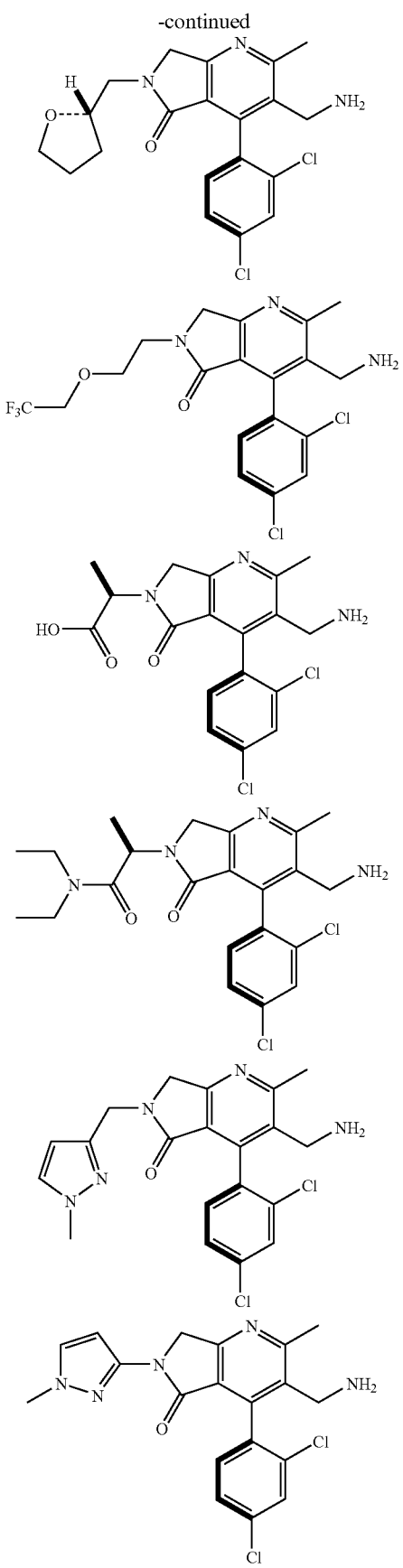

15
-continued
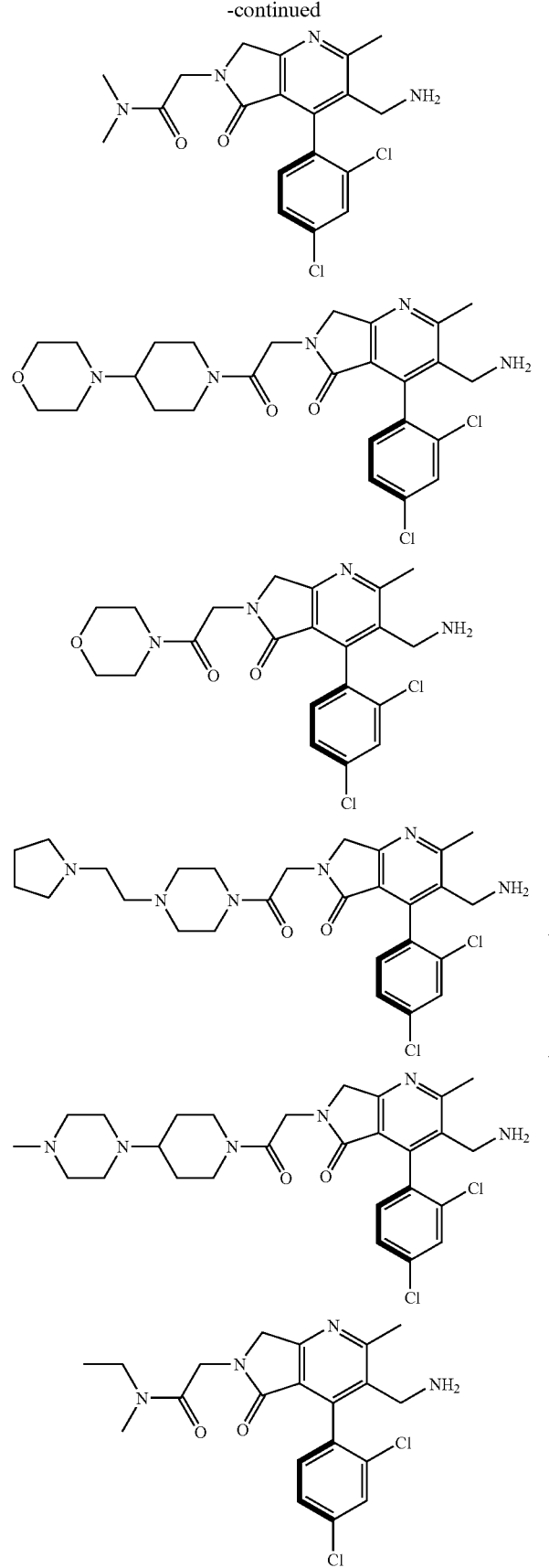
16
-continued
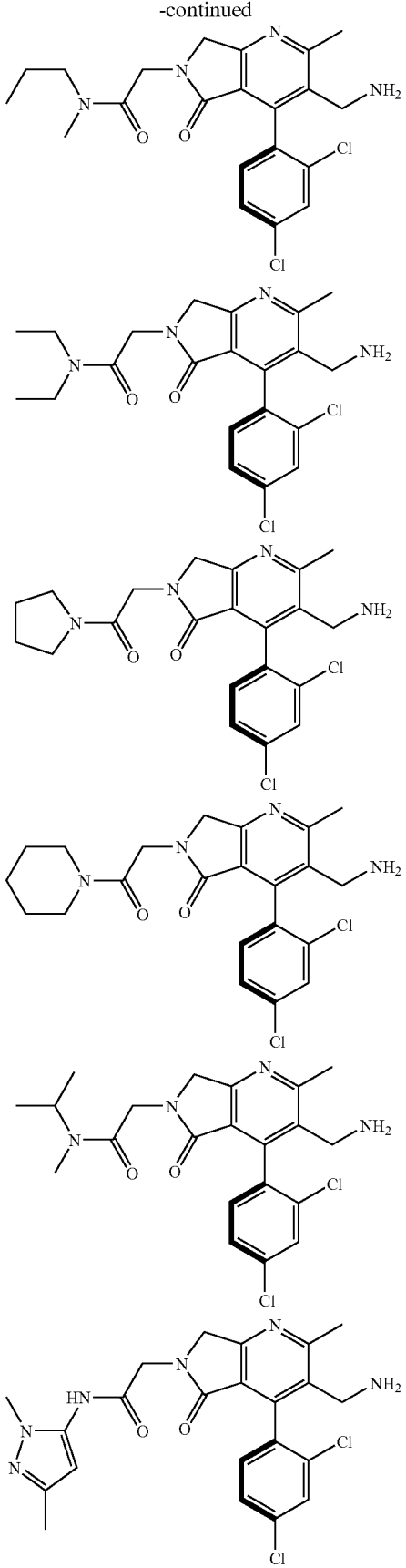

-continued
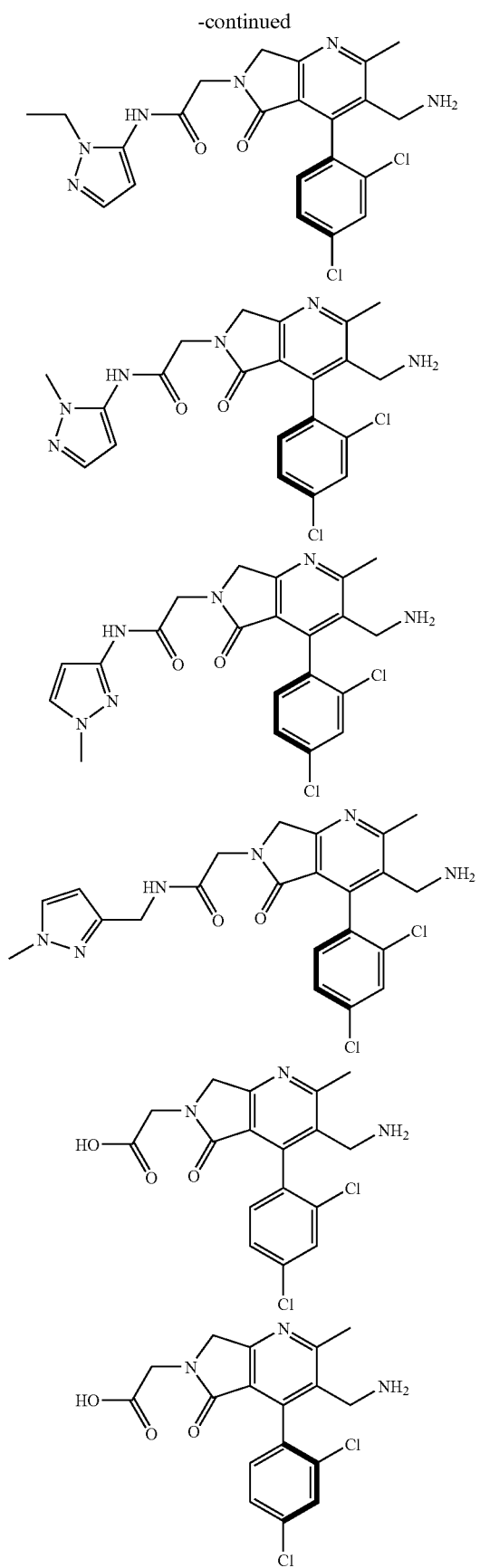
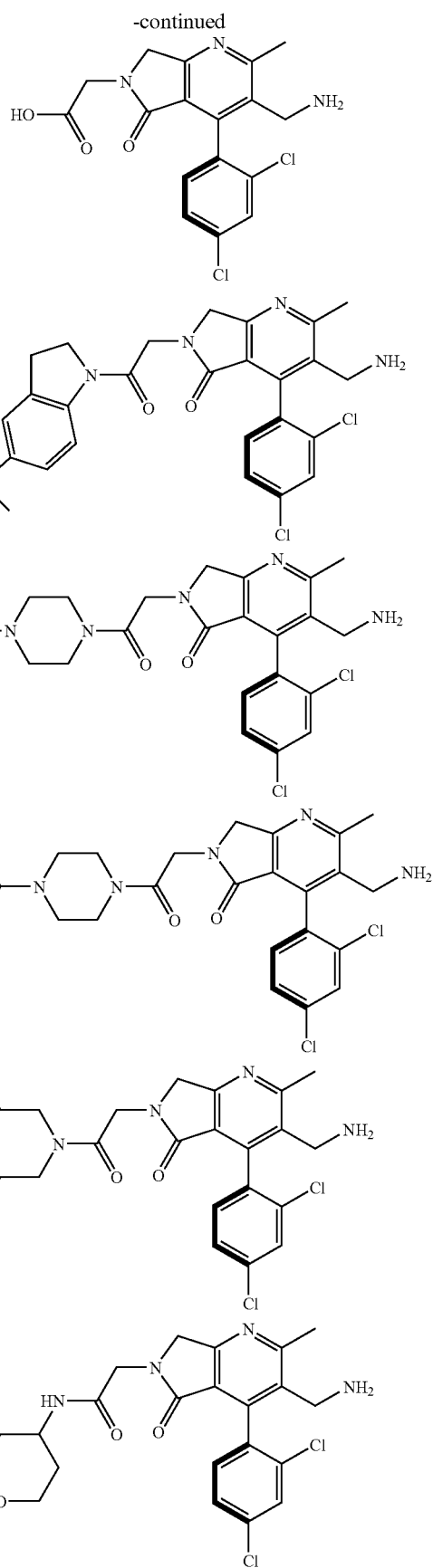

19
-continued
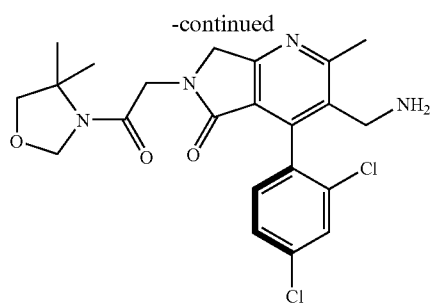
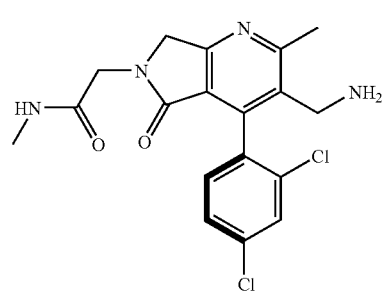
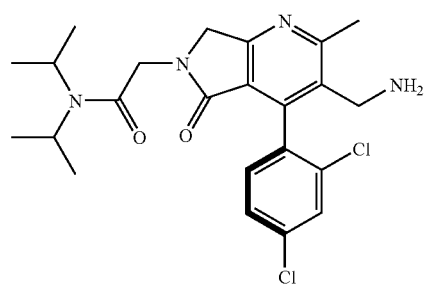
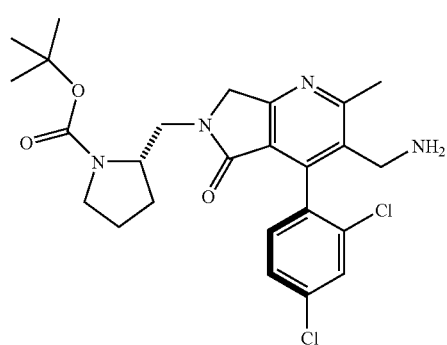
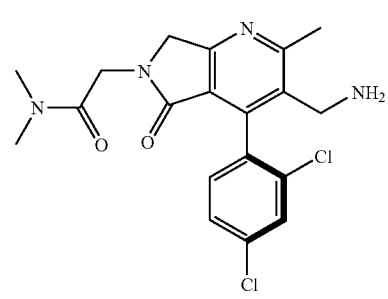
20
-continued
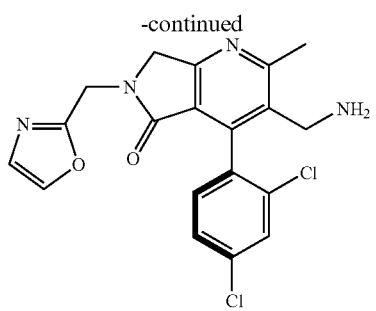
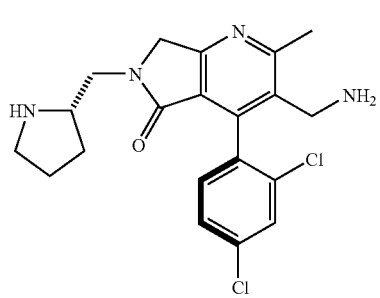
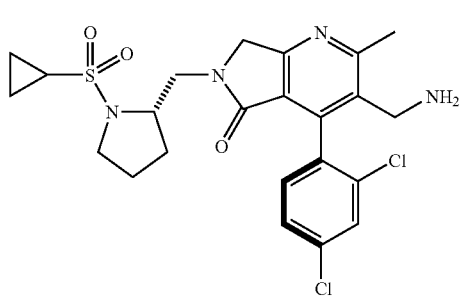
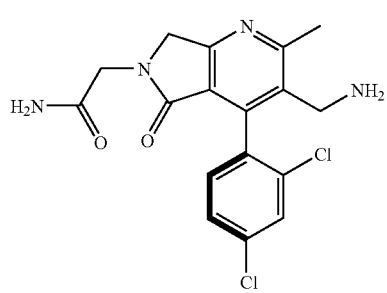
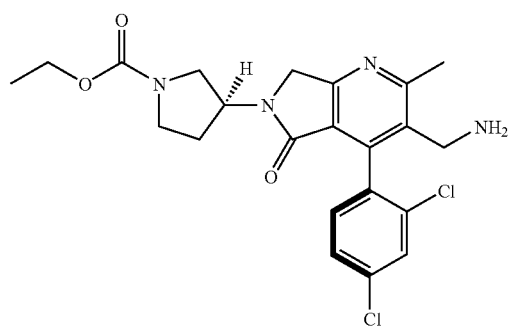

-continued
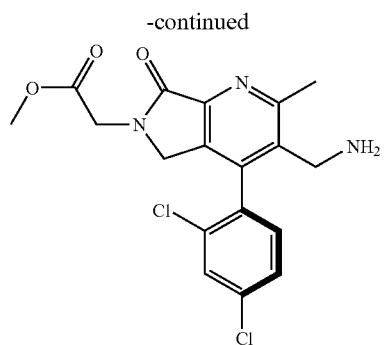
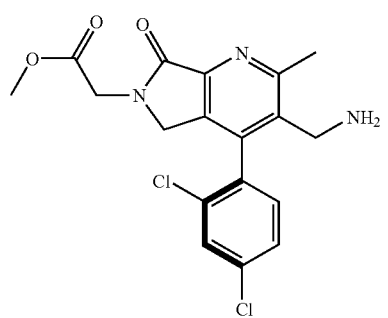
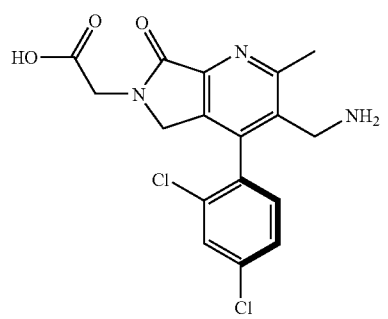
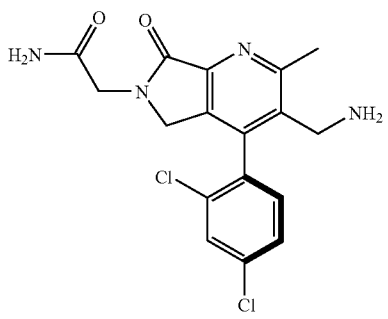
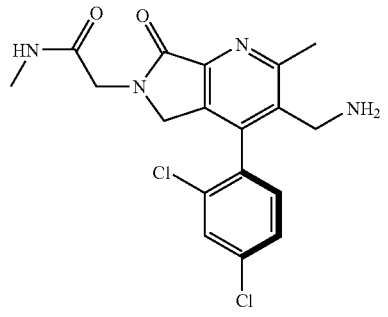
-continued
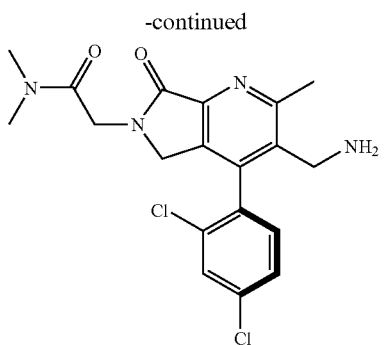
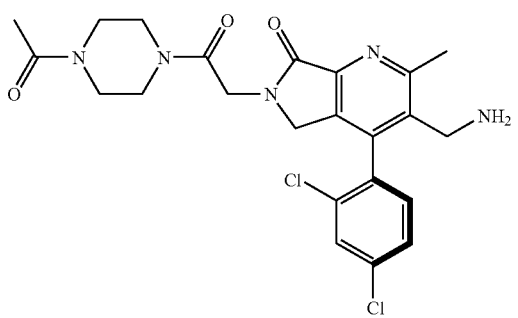
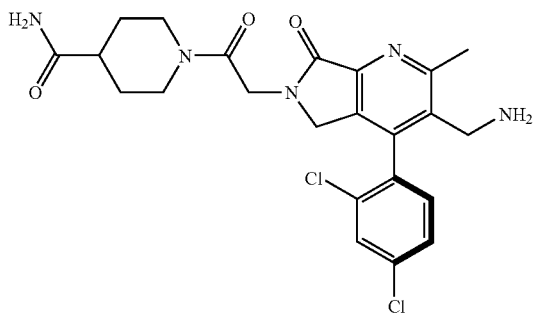
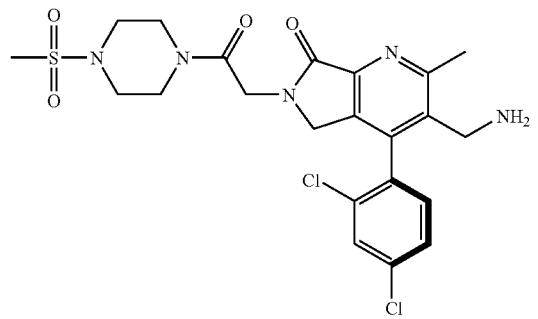
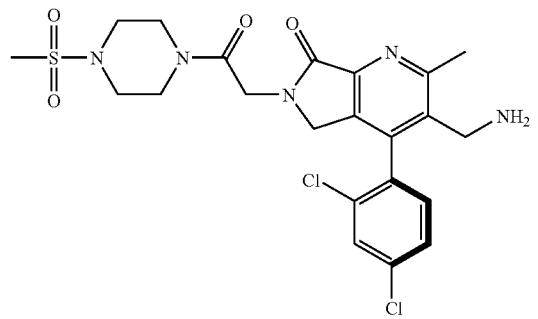

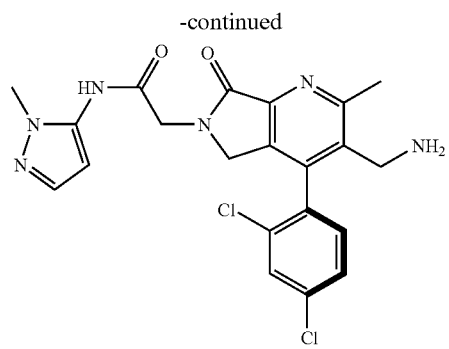
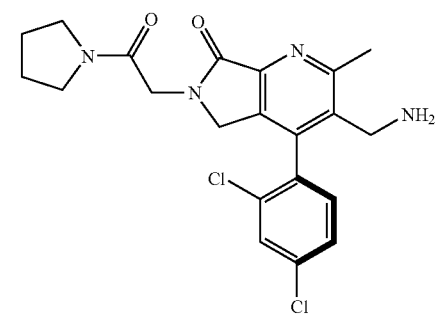
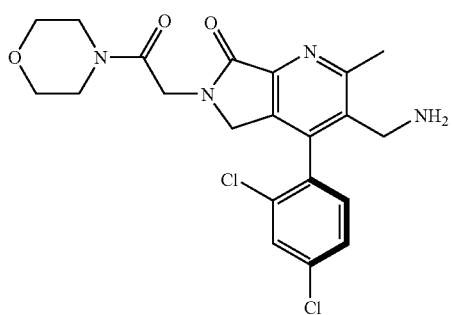
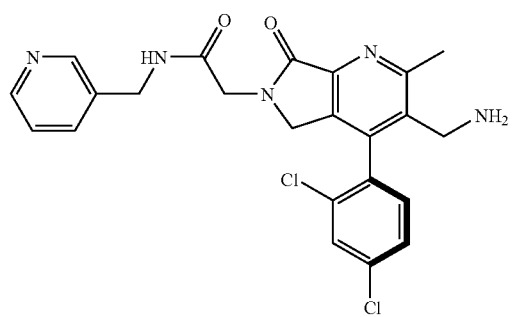
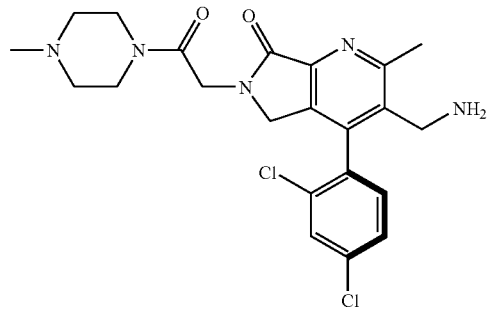
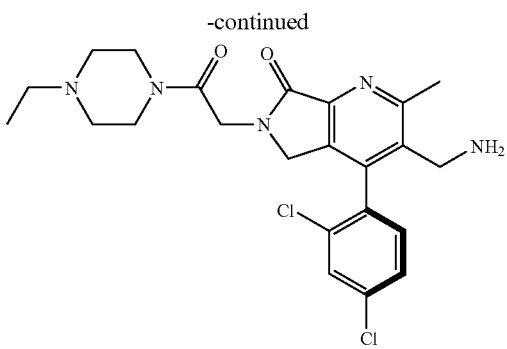
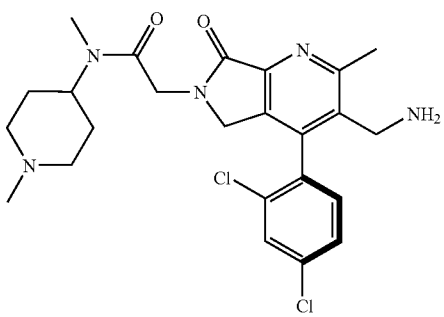
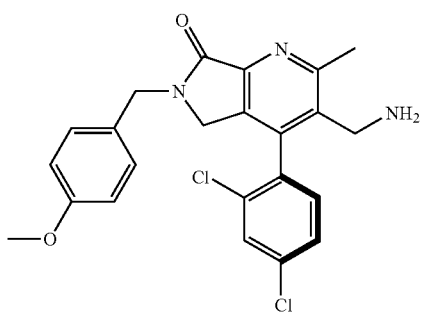
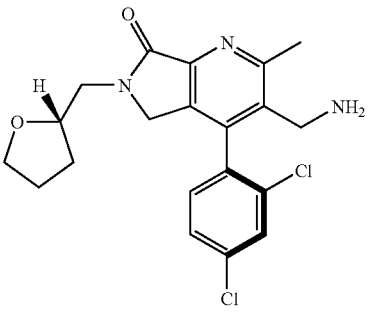
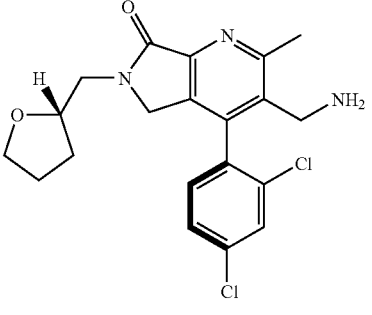

-continued
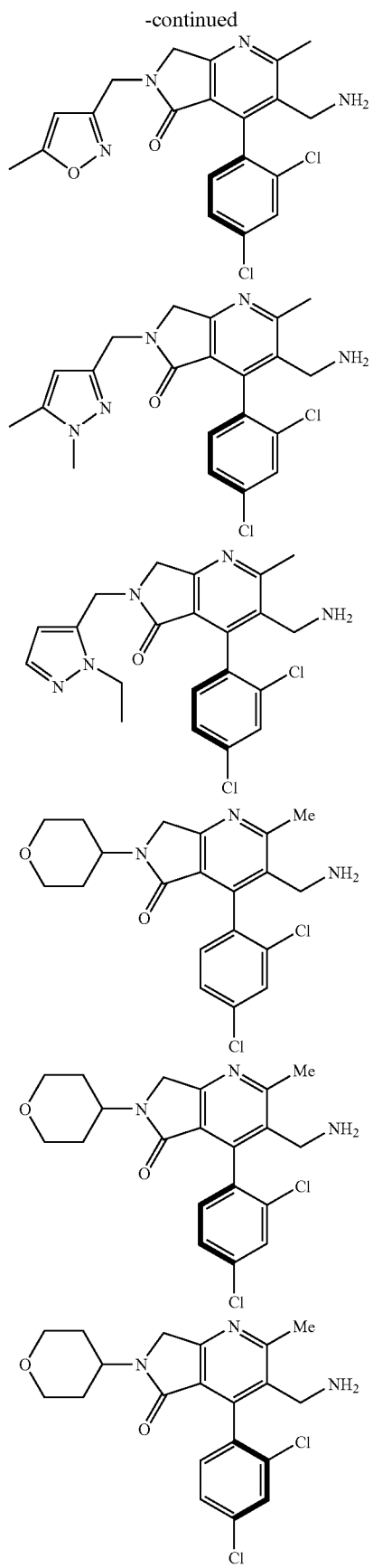
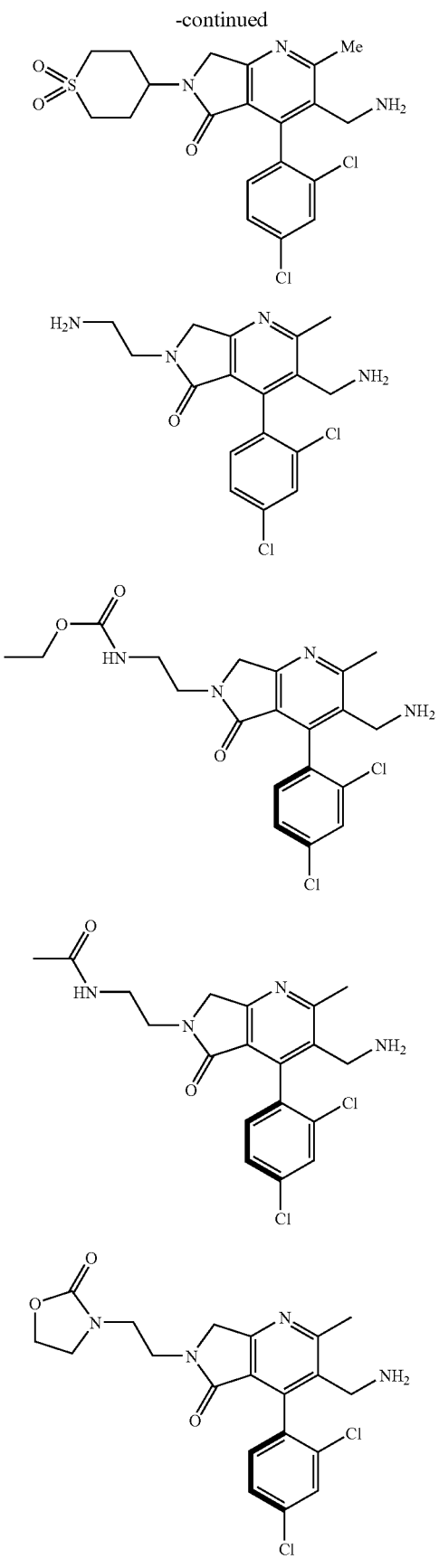

-continued
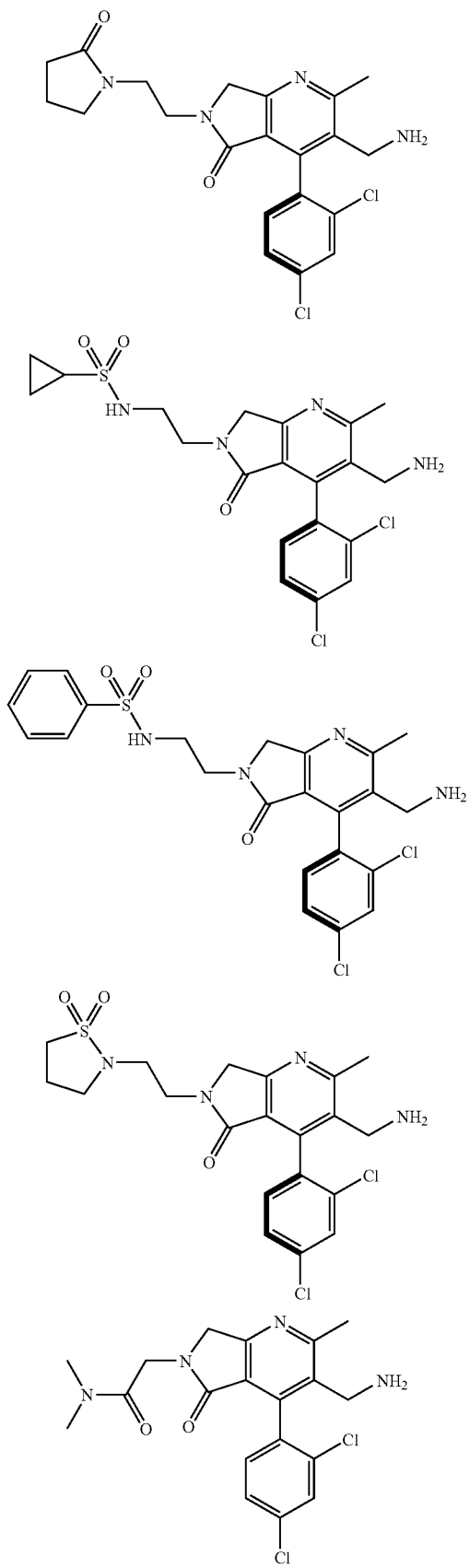
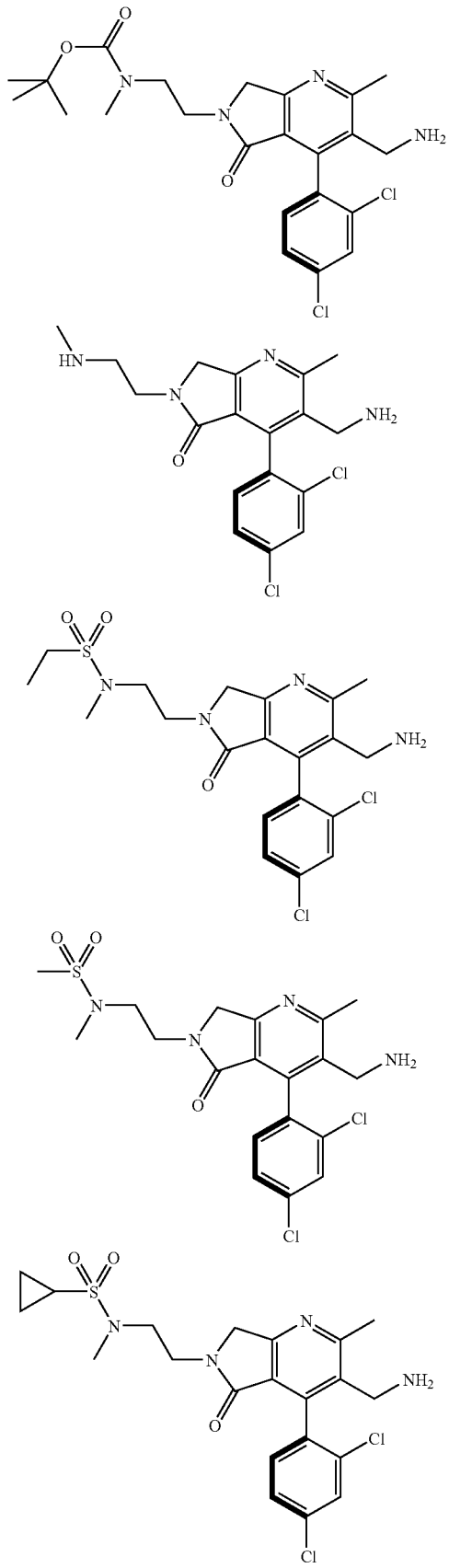

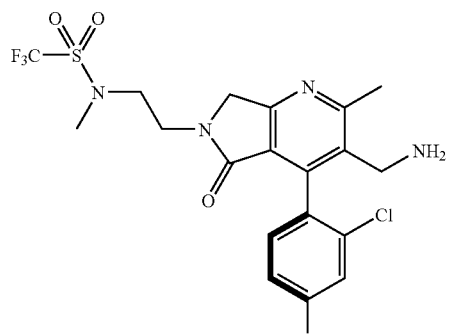
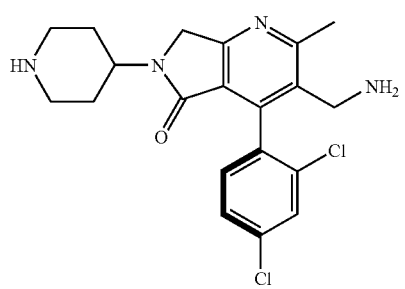
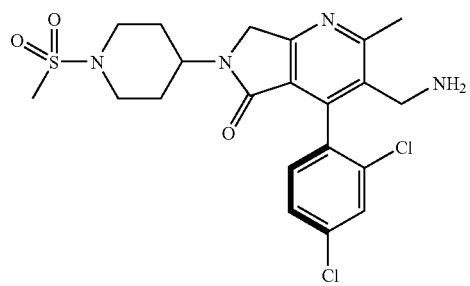
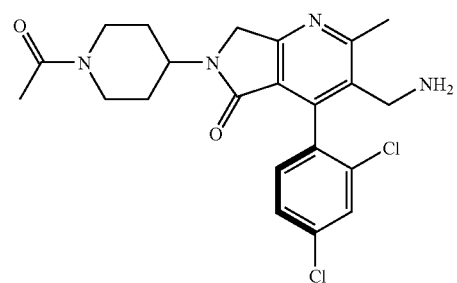
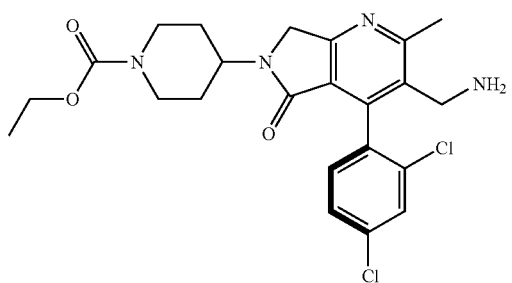
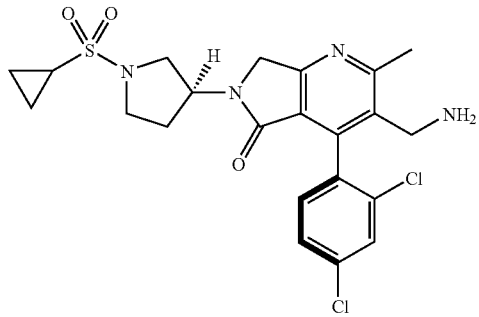
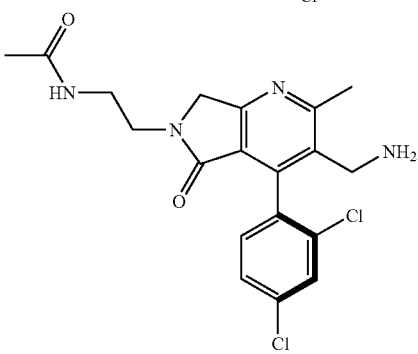
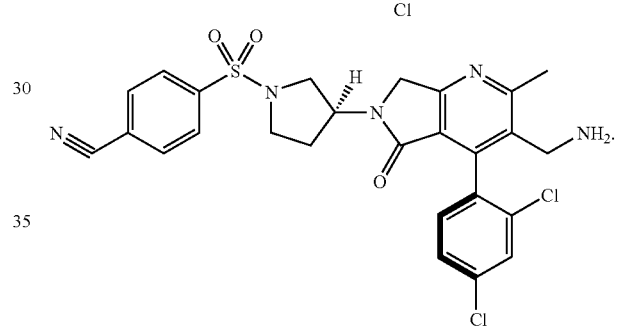
In addition, in accordance with the present invention, novel racemic or homochiral intermediates are provided having the structures:
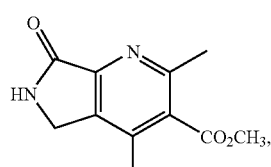
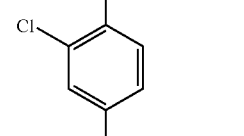
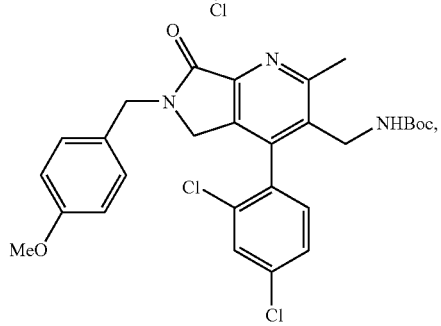

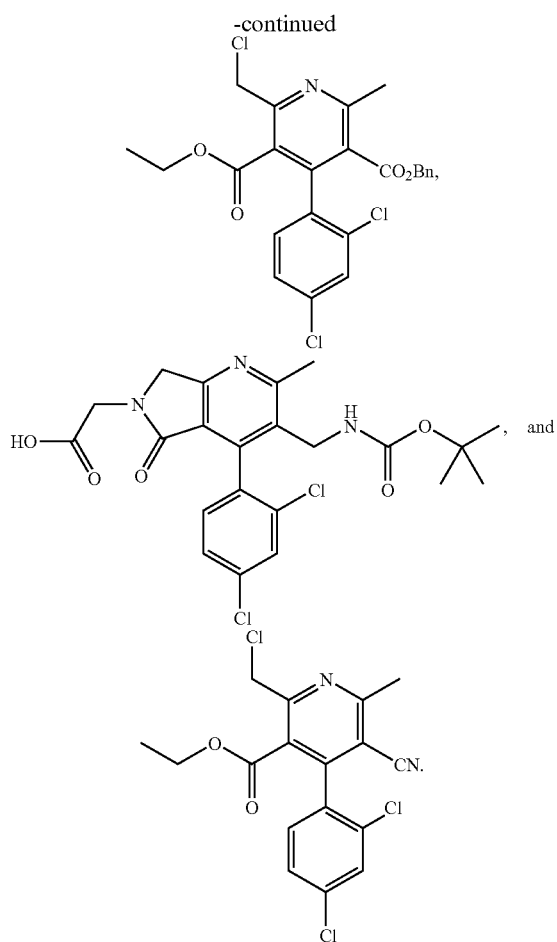

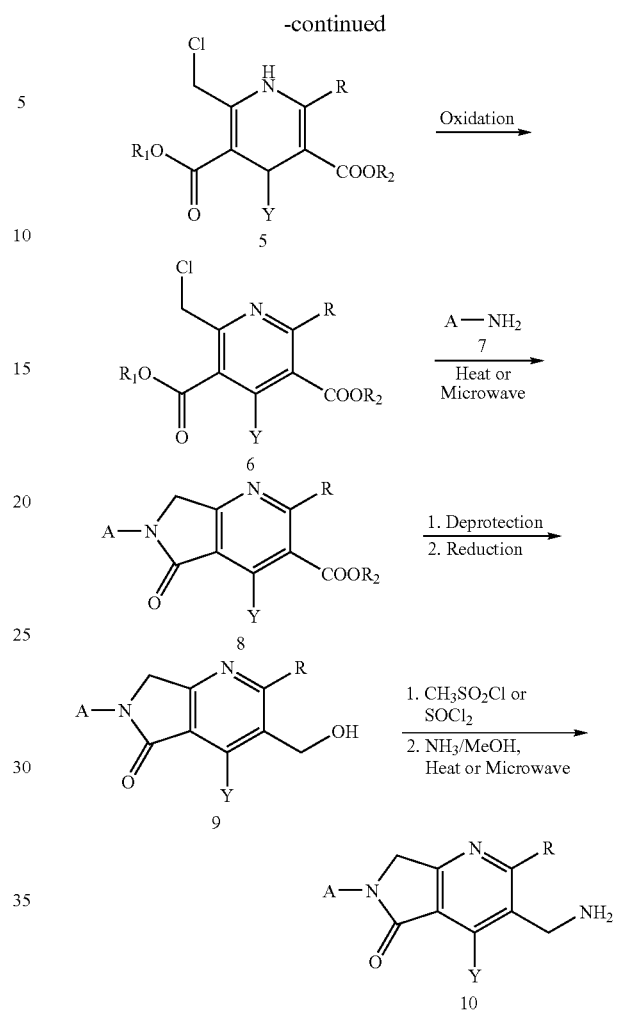

DETAILED DESCRIPTION OF THE INVENTION

The compounds of formula (I) of the invention can be prepared as shown below in the following reaction schemes and description thereof, as well by using as relevant published literature procedures that may be used by one skilled in the art. Exemplary reagents and procedures for these reactions appear hereinafter and in the working Examples.

SCHEME 1

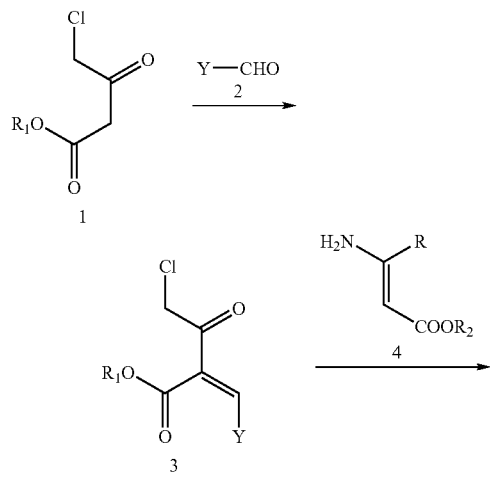

Scheme 1 provides a general route to prepare aminomethyl dihydropyrrolo[3,4-b]pyridin-5-ones of formula (10). A chloroketone of formula (1), obtained from commercial sources, can be reacted with aldehyde (2) to form the conjugated ester (3) which after reacting with enamine (4) can yield a dihydropyridine of formula (5). Enamines of formula (4) can be obtained from commercial sources or can be prepared by reaction of the corresponding acetoacetate with ammonia. Oxidation of dihydropyridine (5) to pyridine (6) can be performed with $MnO_2$, $HNO_3$, or other methods known in the art. Reaction of chloromethylpyridine (6) with aniline or amine A-$NH_2$ of the formula (7) (wherein A is as defined with respect to formula I) under conditions of thermal or microwave heating can afford dihydropyrrolo[3,4-b]pyridin-5-one (8). Transformation of ester (8) to primary alcohol (9) can be performed using any of the methods known in the art. For example, when $R_2$=Me, the ester (8) can be reduced with a suitable hydride reducing agent such as $LiBH_4$. When $R_2$=$PhCH_2$, ester (8) can be first hydrogenolyzed to an acid, converted to an activated ester such as a mixed anhydride and then reduced with a reducing agent such as $NaBH_4$. The resulting alcohol (9) can then be converted to a chloride or mesylate using reagents such as $CH_3SO_2Cl$ or $SOCl_2$. The desired primary amines (10) can then be obtained by reaction of the precursor chloride or mesylate with $NH_3$/MeOH under thermal or microwave heating conditions.

Scheme 2 describes a route to prepare dihydropyrrolo[3,4-b]pyridin-7-ones of formula (18).

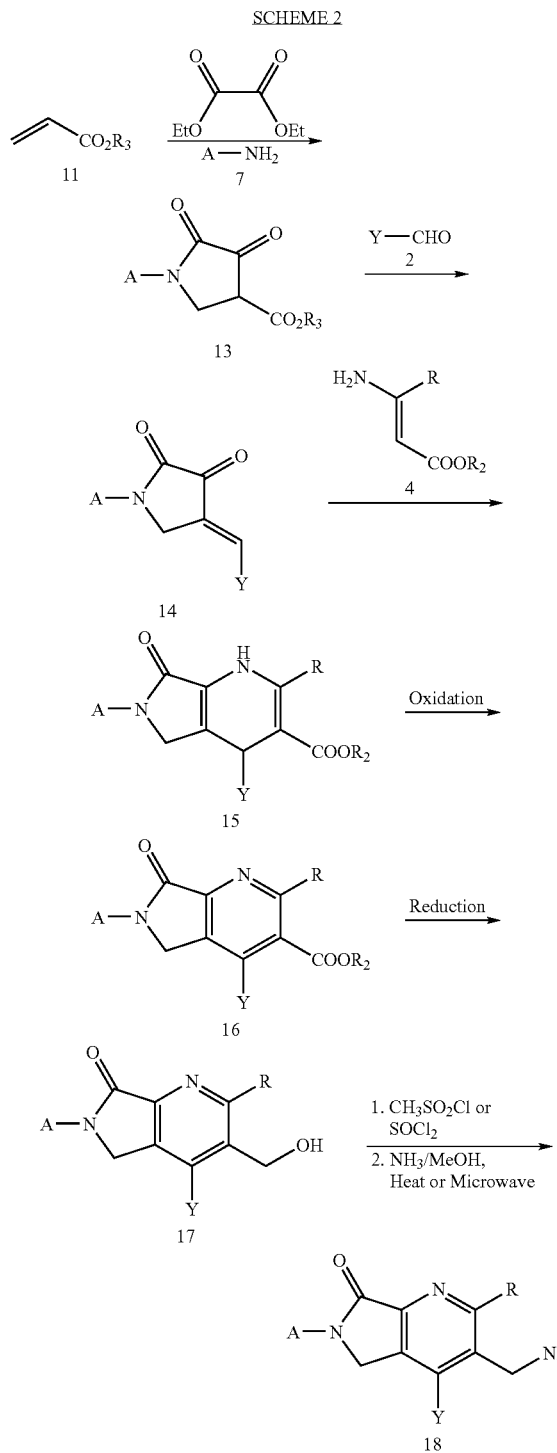

ine (4). Oxidation of dihydropyridine (15) to pyridine (16) can be performed with $MnO_2$, $HNO_3$, or other methods known in the art. Conversion of ester (16) to the primary amine (18) can be accomplished following the sequence similar to the one described in Scheme 1.

An alternative method of preparing dihydropyrrolo[3,4-b]pyridin-7-ones of formula (18) is described in Scheme 3.

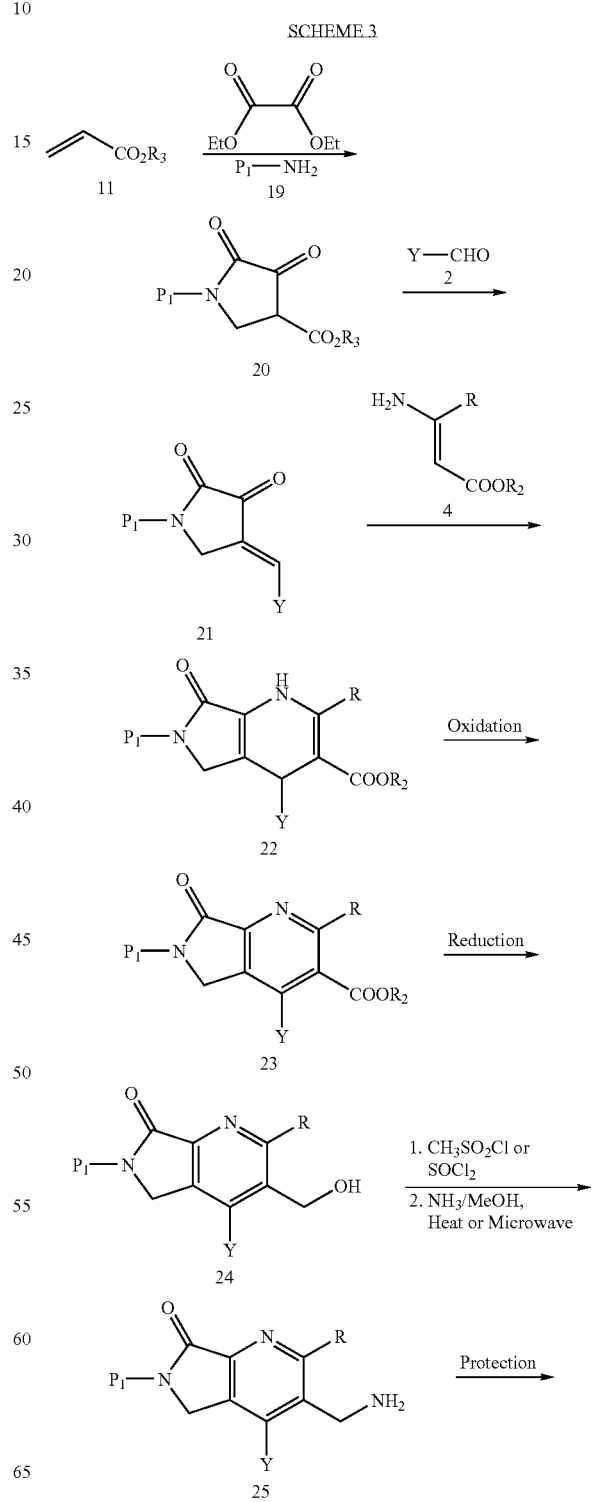

An acryloester of formula (11) can be condensed with an amine or aniline of formula (7) and dialkyloxalate of the type shown in formula (12) to afford dioxopyrrolidine carboxylate (13). Reacting (13) with aldehyde (2) in the presence of acid can yield conjugated ketone of formula (14). Dihydropyridine (15) can be obtained via condensation of (14) with enam- -continued

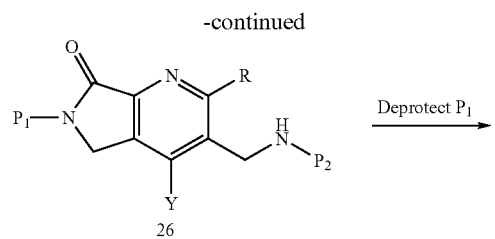

26

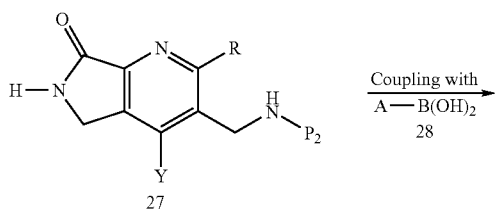

27

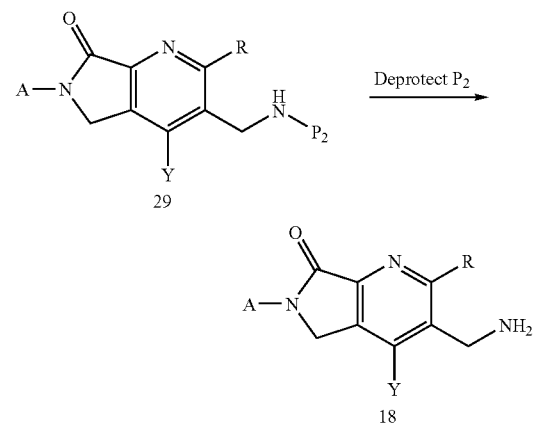

29

18

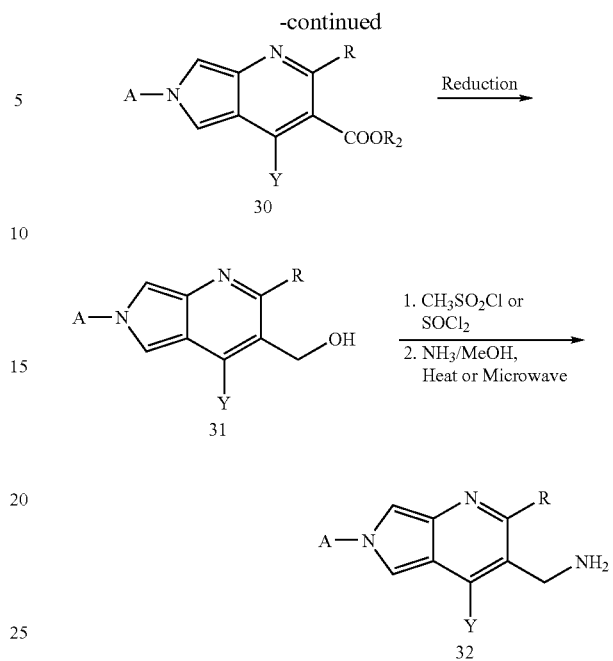

30

31

32

A general synthesis of 6,7-dihydro-5H-pyrrolo[3,4-b]pyridines (34) is shown in Scheme 5.

Primary amine (25) can be prepared from acryloester (11), dialkyloxalate (12) and amine $P_1$—$NH_2$ (19) following a sequence analogous to the one shown in Scheme 2. $P_1$ can be 4-methoxybenzyl, 4-methoxyphenyl, or any suitable protecting group that can be removed from lactam (26). Primary amine can be protected with a suitable protecting group ($P_2$) such as tert-butoxycarbonyl to yield differentially protected amino-lactam (26). Deprotection of $P_1$ group affords lactam (27). Lactam (27) can be coupled with boronic acid (28) to give lactam (29), which after deprotection of the $P_2$ group affords primary amine (18). Alternatively, other coupling methods known in the art can be used to convert lactam (27) to substituted lactam (29).

Scheme 4 provides a route to the preparation of pyrrolo[3,4-b]pyridines of formula (32). The lactam carbonyl on ester (16) can be selectively reduced to the pyrrolopyridine ester (30). An example of a suitable reducing agent would be DIBAL-H. Further reduction of pyrrolopyridine ester (30) can afford alcohol (31) which in turn can be functinalized as before to primary amine (32).

SCHEME 4

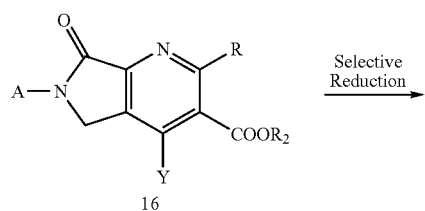

16

SCHEME 5

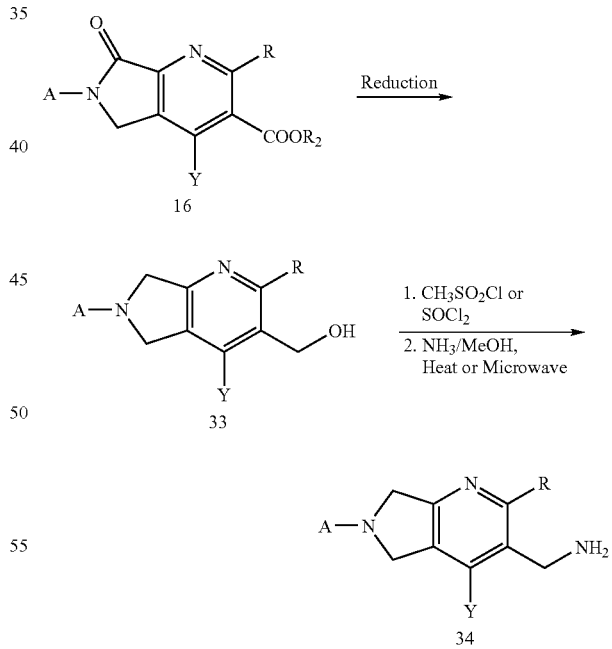

16

33

34

Lactam-ester (16) can be reduced to 6,7-dihydro-5H-pyrrolo[3,4-b]pyridine alcohol (33) with a reducing agent such as LAH. Further functionalization can be carried out as described before to yield primary amine (34).

Scheme 6 describes a route to 5,6-dihydropyrrolo[3,4-b]pyridin-7-ones of formula (35).

SCHEME 6

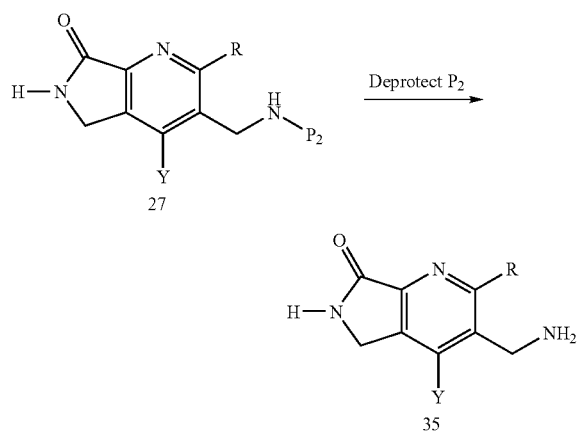

Deprotection of the $P_1$ group in lactam (27) can afford lactam-amine (35). When $P_1$=4-methoxyphenyl or 4-methoxybenzyl, the deprotection can be carried out in the presence of ceric ammonium nitrate.

SCHEME 7

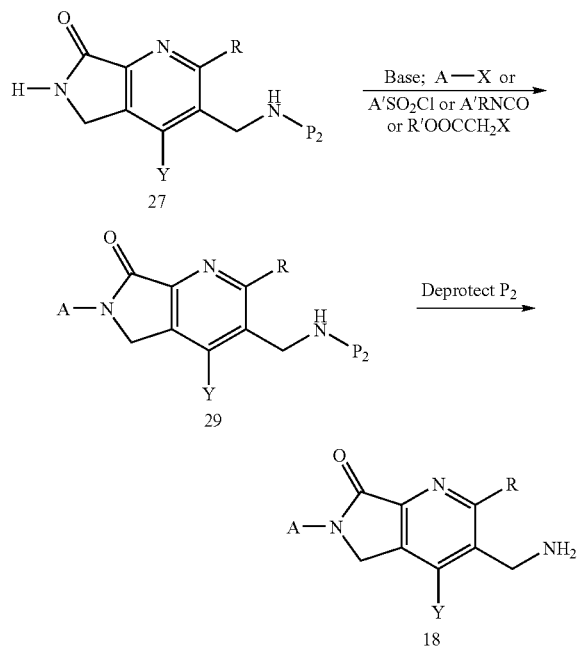

Deprotonation of lactam (27) with a base such as NaH followed by treatment with suitable electrophiles such as alkyl halides, aryl and alkyl sulfonyl chlorides, aryl and alkyl isocyanates and alkoxycarbonylmethyl halides can afford substituted lactams (29) which after deprotection can yield the corresponding primary amines (18). Alternatively, such a base-mediated functionalization can be done on ester (23) which can then be transformed into corresponding primary amines using a sequence analogous to the one shown in Scheme 3.

SCHEME 8

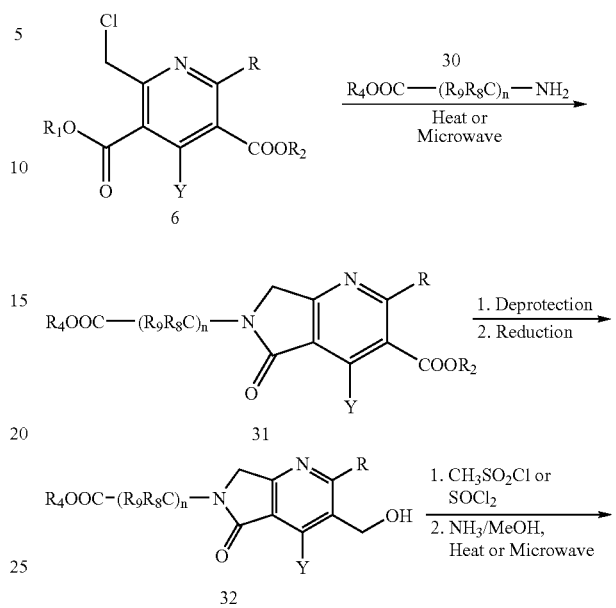

Scheme 8 provides a general route to prepare aminomethyl dihydropyrrolo[3,4-b]pyridin-5-ones of formula (35). Reaction of chloromethylpyridine (6) with a suitably protected aminoacid ester of the formula (30), where $R_8$ and $R_9$ can be $C_1$-$C_6$ alkyl, arylalkyl, heteroarylalkyl, cycloalkyl (3-6 membered), or F groups, under conditions of thermal or microwave heating can afford dihydropyrrolo[3,4-b]pyridin-5-one (31) and can further be processed as in Scheme 1 to obtain compound (33). Routine protection-deprotection methods can be employed to obtain N-protected acid (34) which can be coupled with primary or secondary amines in the presence of a suitable coupling reagent and then can N-deprotected to afford amide-amines (35). These amide-amines (35) can be obtained in pure enantiomeric form by separation of the final products (35) or any of the intermediates such as (6) or alcohol (32).

SCHEME 9

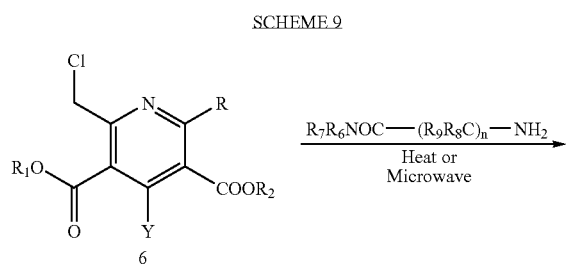

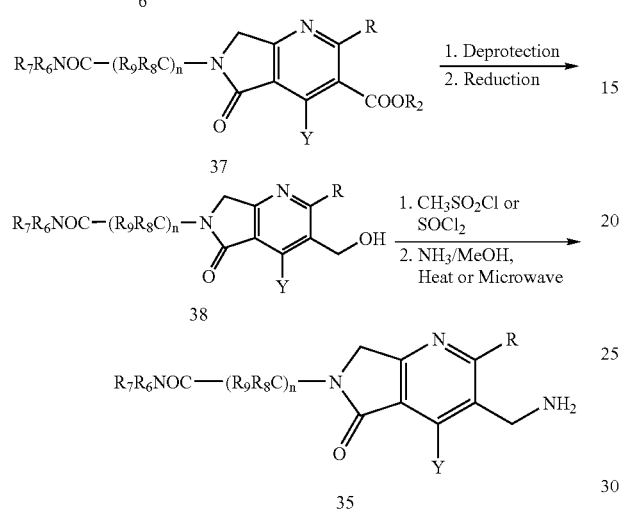

As shown in Scheme 9, amide-amines (35) can alternatively be made from amide-substituted alkylamines (36) following a sequence analogous to one shown in Scheme 8. These amide-amines (35) can be obtained in pure enantiomeric form by separation of the final products (35) or any of the intermediates such as (6) or alcohol (38).

The corresponding aminomethyl dihydropyrrolo[3,4-b] pyridin-7-ones (36)

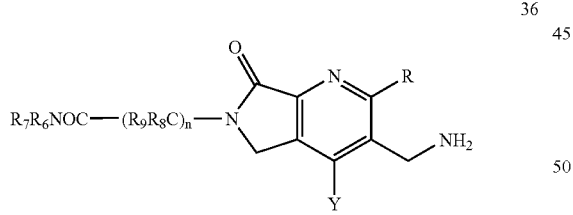

can be obtained by methods analogous to those described for aminomethyl dihydropyrrolo[3,4-b]pyridin-5-ones (35) in Schemes 8 and 9 starting for diester (37) or amide-ester (38).

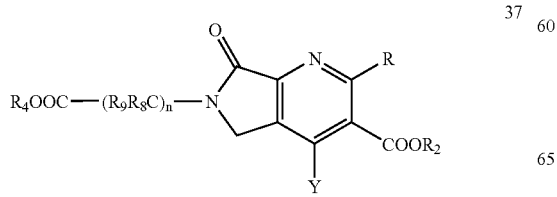

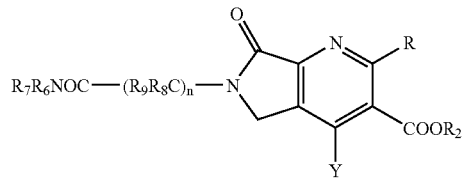

Diester (37) can be obtained using Scheme 7.starting from a suitably protected aminoacid ester.

SCHEME 10

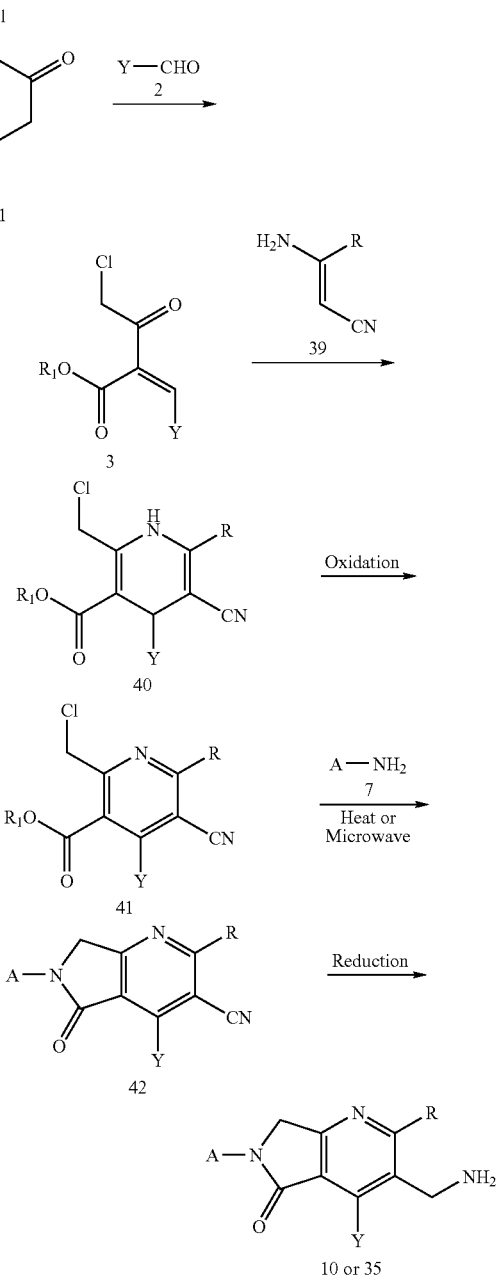

Amines such as (10) or (35) can alternatively be prepared using a sequence shown in Scheme 10. Intermediate (42) can be prepared in a manner similar to the one shown in Scheme 1 and then reduced to afford primary amines (10) or (35).

Additionally, compounds I with n=2 can be prepared via homologation of the corresponding carboxylic acids (for example 8 or 16 where $R_2$=H) using methods known in the art. Furthermore, the corresponding thiocarbonyl analogs (Compound I, X or Z is C=S) can be prepared from a suitable lactam intermediate (for example, 8 or 16 where $R_2$=alkyl, benzyl, or a suitable protecting group) using Lawesson's reagent (see for example, *J. Org. Chem.* 1992, 57(14), 4000-4005; *J. Org. Chem.* 1990, 55(9), 2694-2702). 5- or 7-Alkyl or arylmino-6,7-dihydro-5H-pyrrolo[3,4-b]pyridin-3-yl) methanamines (Compound I, X or Z is C=NR$_3$) can be prepared by condensation of the corresponding lactams (where X or Z is C=O) with alkyl or arylamines in the presence of POCl$_3$ (see for example, *Ukrainskii Khimicheskii Zhurnal* 1984, 50(11), 1198-1203).

All product amines that exist as atropisomers can be separated into individual enantiomers using methods known in the art. For example, resolution by crystallization of diastereomeric salts (tartaric acid or N-protected aminoacids; see for example, Eliel, Ernest L.; Wilen, Samuel H.; Doyle, Michael P. *Basic Organic Stereochemistry*, Wiley, 2001), chiral preparative HPLC, chiral supercritical fluid chromatography, use of enzymes, use of chiral derivatizing agents (see for example, *J. Org. Chem.* 1983, 48(15), 2520-2527), or preparation and chromatographic separation of diastereomeric derivatives. Alternatively, these methods can be applied to any of the intermediates in the synthesis of these product amines.

Definitions

The following definitions apply to the terms as used throughout this specification, unless otherwise limited in specific instances.

Unless otherwise indicated, the term "alkyl" or "alk" as used herein alone or as part of another group includes both branched and straight-chain saturated aliphatic hydrocarbon radicals/groups having the specified number of carbon atoms. In particular, "Alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. Unless otherwise constrained by the definition for the alkyl substituent, such alkyl groups can optionally be substituted with one or more substituents selected from a member of the group consisting of such as halo, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, arylsulfonyl, alkylsulfonyl, cycloalkylsulfonyl, nitro, cyano, thiol, haloalkyl, trihaloalkyl and/or alkylthio.

Unless otherwise indicated, the term "cycloalkyl", "carbocycle" or "carbocyclic" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes, for example cyclopropyl, cyclobutyl, cyclopentyl, cyclohexyl, cycloheptyl, cyclooctyl, cyclodecyl and cyclododecyl, cyclohexenyl,

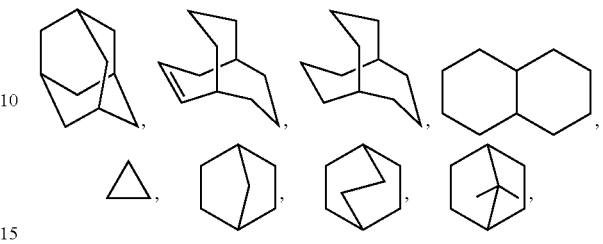

any of which groups may be optionally substituted with 1 or more substituents such as of the substituents for described herein for alkyl or aryl.

The term "Aryl" or "Ar" as used herein alone or as part of another group refers to an unsaturated aromatic carbocyclic group of from 5 to 20 carbon atoms having a single ring (e.g., phenyl) or multiple condensed (fused) rings (e.g., naphthyl or anthryl). Representative examples include, but are not limited to, aromatic radicals such as phenyl, naphthyl, tetrahydronaphthyl, indane and biphenyl. Unless otherwise constrained by the definition for the aryl substituent, such aryl groups can optionally be substituted with one or more substituents selected from a member of the group consisting of hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, any of the alkyl substituents described herein, or substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, cycloalkylsulfonyl, arylsulfinyl, arylsulfinylalkyl, arylsulfonylamino or arylsulfon-aminocarbonyl and/or any of the alkyl substituents set out herein.

Unless otherwise indicated, the term "cycloheteroalkyl", "heterocyclo", "heterocyclic group" or "heterocyclyl" as used herein alone or as part of another group refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "Heterocycle" or "Heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom, such as, but not limited to, the substituents described for alkyl or aryl herein, so long as the resulting compound is stable. For example:

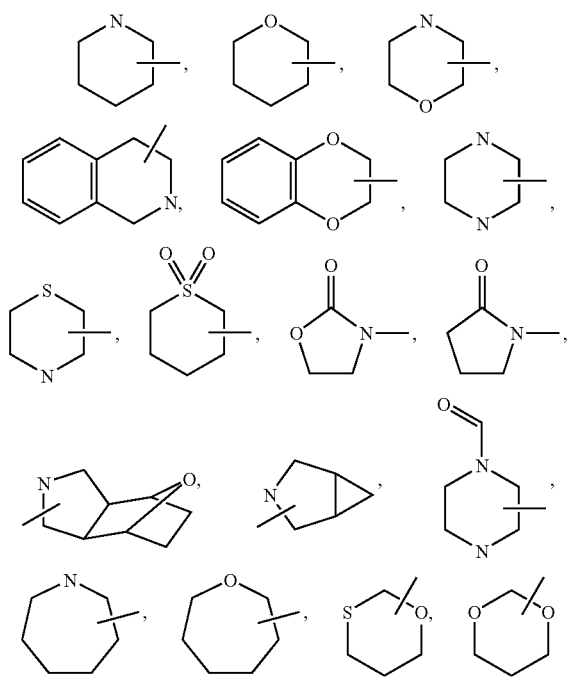

and the like.

"Heteroaryl" as used herein alone or as part of another group embraces unsaturated heterocyclic radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. Further, examples of heteroaryl groups include the following:

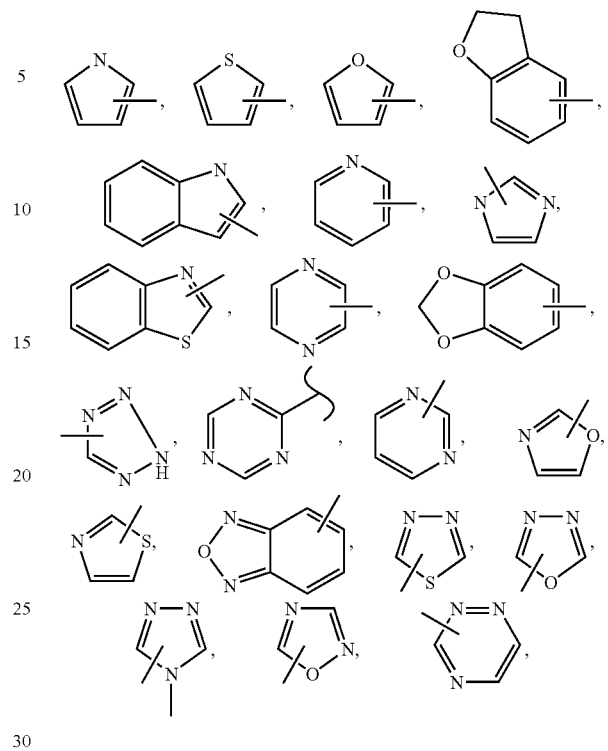

and the like. Unless otherwise constrained by the definition for the heteroaryl substituent, such heteroaryl groups can optionally be substituted with one or more substituents, such as those described for alkyl or aryl herein.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one or substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Optionally, said alkynyl group may be substituted with one or substituents, such as those substituents disclosed for alkyl.

The term "cycloalkenyl" as employed herein alone or as part of another group refers to partially unsaturated cyclic hydrocarbons containing 3 to 12 carbons, preferably 5 to 10 carbons and 1 or 2 double bonds. Exemplary cycloalkenyl groups include cyclobutenyl, cyclopentenyl, cyclohexenyl, cycloheptenyl, cyclooctenyl, cyclohexadienyl, and cycloheptadienyl. Optionally, said cycloalkenyl group may be substituted with one or substituents, such as those substituents disclosed for alkyl.

The term "bicycloalkyl" as employed herein alone or as part of another group includes saturated bicyclic ring groups such as, without limitation, [3.3.0]bicyclooctane, [4.3.0]bicyclononane, [4.4.0]bicyclodecane (decalin), [2.2.2]bicyclooctane, and so forth.

The term "polycycloalkyl" as employed herein alone or as part of another group includes two or more cycloalkyl ring systems, as defined herein, wherein at least one carbon atom is a part of at least two separately identifiable ring systems. The polycycloalkyl group may contain bridging between two carbon atoms, for example, bicyclo[1.1.0]butyl, bicyclo[3.2.1]octyl, bicyclo[5.2.0]nonyl, tricycl[2.2.1.0.sup.1]heptyl, norbornyl and pinanyl. The polycycloalkyl group may contain one or more fused ring systems, for example, decalinyl (radical from decalin) and perhydroanthracenyl. The polycycloalkyl group may contain a spiro union, in which a single atom is the only common member of two rings, for example, spiro[3.4]octyl, spiro[3.3]heptyl and spiro[4.5]decyl.

The term "halogen" or "halo" as used herein alone or as part of another group refers to chlorine, bromine, fluorine, and iodine as well as $CF_3$.

The term "alkoxy" or "alkyloxy" as used herein alone or as part of another group, refers to an alkyl group, as defined herein, appended to a parent molecular moiety through an alkyl group, as defined herein.

The term "haloalkoxy" as used herein alone or as part of another group refers to alkoxy radicals, as defined herein, further substituted with one or more halo atoms, such as fluoro, chloro or bromo, to provide haloalkoxy radicals. Examples include, without limitation, fluoromethoxy, chloromethoxy, trifluoromethoxy, trifluoromethoxy, fluoroethoxy and fluoropropoxy.

The term "acyl" as employed herein by itself or part of another group, as defined herein, refers to an organic radical linked to a carbonyl

group; examples of acyl groups include a substituent group attached to a carbonyl, such as alkanoyl, alkenoyl, aroyl, aralkanoyl, heteroaroyl, cycloalkanoyl, cycloheteroalkanoyl and the like.

The term "cycloalkylalkyl", "arylalkyl", "cycloheteroalkyl", "bicycloalkylalkyl" or "heteroarylalkyl" as used herein alone or as part of another group, refers to a cycloalkyl, an aryl, a cyclohetero, a bicycloalkyl or heteroaryl group, as defined herein, appended to a parent molecular moiety through an alkyl group, as defined herein. Representative examples of arylalkyl include, but are not limited to, benzyl, 2-phenylethyl, 3-phenylpropyl, and the like.

The term "cycloheteroalkylalkyl" as used herein alone or as part of another group refers to a cycloheteroalkyl group as defined herein. linked through a C atom or heteroatom to a $(CH_2)_r$ chain, where "r" can be 1 to 10.

The term "polyhaloalkyl" as used herein alone or as part of another group refers to an "alkyl" group as defined above, having 2 to 9, preferably from 2 to 5, halo substituents, such as $CF_3CH_2$, $CF_3$ or $CF_3CF_2CH_2$.

The term "polyhaloalkoxy" as used herein refers to an "alkoxy" or "alkyloxy" group as defined above having 2 to 9, preferably from 2 to 5, halo substituents, such as $CF_3CH_2O$—, $CF_3O$— or $CF_3CF_2CH_2O$—.

The term "thiol" or "thio" as used herein alone or as part of another group, refers to (—S) or (—S—).

The term "alkylthio" or "arylalkylthio" refers to an alkyl group or and arylalkyl group, as defined herein, linked to a parent molecular moiety through a thiol group.

The term "alkylthioalkyl" or "arylalkylthioalkyl" refers to an alkylthio group or and arylalkylthio group, as defined herein, linked to a parent molecular moiety through an alkyl group.

The term "hydroxy" as used herein alone or as part of another group, refers to a —OH group.

The term "hydroxyalkyl" as used herein alone or as part of another group, refers to a hydroxyl group, as defined herein, appended to a parent molecular moiety through a alkyl group, as defined herein.

The term "cyano" as used herein alone or as part of another group, refers to a —CN group.

The term "nitro" as used herein, refers to a —$NO_2$ group.

The term "sulfinyl", whether used alone or linked to other terms such as alkylsulfinyl, denotes respectively divalent radicals —S(O)—.

The term "alkylsulfinyl" as used herein alone or as part of another group, refers to an alkyl group, as defined herein, appended to a parent molecular moiety through a sulfinyl group, as defined herein.

The term "sulfonyl" as used herein alone or as part of another group, refers to an $SO_2$ group.

The term "alkylsulfonyl" or "aminosulfonyl", as used herein, refer to an alkyl or amino group, as defined herein, appended to a parent molecular moiety through a sulfonyl group, as defined herein.

The term "amino" as employed herein, refers to an —$NH_3$ group or an amine linkage: —$NR_a$—, wherein $R_a$ may be as described below in the definition for "substituted amino".

The term "substituted amino" as employed herein alone or as part of another group refers to amino substituted with one or two substituents. For example, $NR_aR_b$, wherein $R_a$ and $R_b$ may be the same or different and are, for example chosen from hydrogen, alkyl, cycloalkyl, alkenyl, cycloalkenyl, alkynyl, aryl, heteroaryl, heterocyclic, arylalkyl, heteroarylalkyl, cycloheteroalkyl, cycloheteroalkylalkyl, cycloalkylalkyl, haloalklyl, hydrooxyalkyl, alkoxyalkyl or thioalkyl. These substituents may optionally be further substituted with any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1piperazinyl, 4-arylalkyl-1piperazinyl, 4-diarylalkyl-1-piperazinyl, 1-pyrrolindinyl, 1-piperidinyl, or 1-azepinyl, optionally substituted with alkyl, alkoxy, alkylthio, halo, triflouromethyl or hydroxyl.

The term "dialkylamino" as employed herein alone, or as part of another group, refers to a substituted amino group having two alkyl substituents. For example, $NR_aR_b$, wherein $R_a$ and $R_b$ are each an alkyl group, as defined herein.

The term "carbonyl" as used herein, refers to a —C(O)— group.

The term "aminocarbonyl", "alkylcarbonyl", "alkoxycarbonyl", "arylcarbonyl", "alkynylaminocarbonyl", "alkylaminocarbonyl" and "alkenylaminocarbonyl" as used herein, refer to an amino group, alkyl group, alkoxy group, aryl group, alkynylamino group, alkylamino group or an alkenylamino group, as defined herein, appended to a parent molecular moiety through a carbonyl group, as defined herein.

The term "heteroarylamino", "arylamino", "alkylamino", "alkylcarbonylamino", "arylcarbonylamino", "alkylsulfonylamino", "alkylaminocarbonylamino" or "alkoxycarbonylamino" as used herein, refers to a heteroaryl, aryl, alkyl, alkylcarbonyl, arylcarbonyl, alkylsulfonyl, alkylaminocarbonyl or alkoxycarbonyl group as defined herein, appended to a parent molecular moiety through an amino group, as defined herein.

The term "sulfonamido" refers to —S(O)$_2$—NR$_a$R$_b$, wherein R$_a$ and R$_b$ are as defined above for "substituted amino".

The term "alkylcarbonyloxy" as used herein, refers to an "alkyl-CO—O—" group, wherein alkyl is as defined above.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a CH$_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (1) for example acetates, pivalates, methylcarbonates and benzoates, and include C$_{1-6}$alkylbenzyl, 4-methoxybenzyl, indanyl, phthalyl, methoxymethyl, C$_{1-6}$alkanoyloxy-C$_{1-6}$alkyl, e.g. acetoxymethyl, pivaloyloxymethyl or propionyloxymethyl, C$_{1-6}$alkoxycarbonyloxy-C$_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

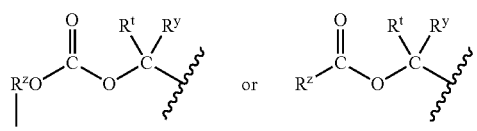

wherein R$^z$, R$^t$ and R$^y$ are H, alkyl, aryl or arylalkyl; however, R$^z$O cannot be HO.

Examples of such prodrug esters include

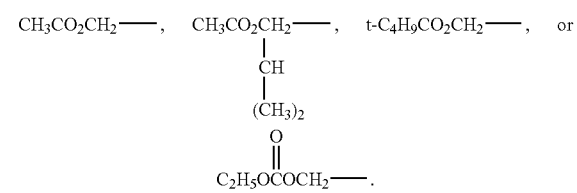

Other examples of suitable prodrug esters include

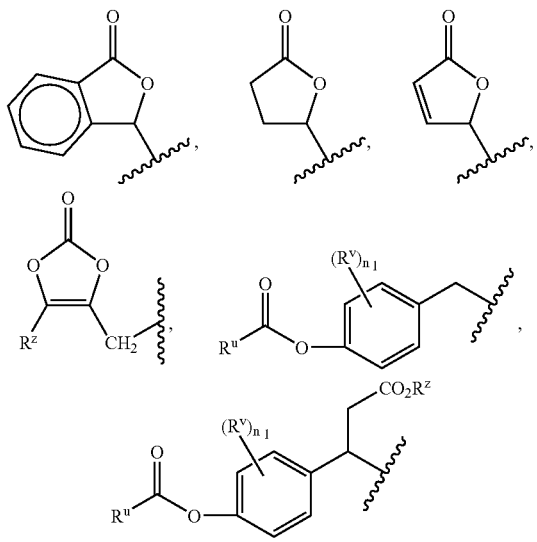

wherein R$^z$ can be H, alkyl (such as methyl or t-butyl), arylalkyl (such as benzyl) or aryl (such as phenyl); R$^v$ is H, alkyl, halogen or alkoxy, R$^u$ is alkyl, aryl, arylalkyl or alkoxyl, and n$_1$ is 0, 1 or 2.

For further examples of prodrug derivatives, see:
a) *Design of Prodrugs*, edited by H. Bundgaard, (Elsevier, 1985) and *Methods in Enzymology*, Vol. 112, pp. 309-396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, pp. 113-191 (1991);
c) H. Bundgaard, *Advanced Drug Delivery Reviews*, Vol. 8, pp. 1-38 (1992); and
d) *The Practice of Medicinal Chemistry*, Wermuth et al., Ch. 31 (Academic Press 1996).

All of the above references are incorporated herein by reference.

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

The conditions, diseases and maladies collectively referred to as "diabetic complications" include retinopathy, neuropathy and nephropathy, erectile dysfunction, delayed wound healing, and other known complications of diabetes.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

Utilities and Combinations

A. Utilities

The compounds of the present invention possess activity as inhibitors of the dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, dyslipidemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents, and appetite suppressants. Additional therapeutic agents suitable for combination with the compound of the present invention include agents for treating infertility, agents for treating polycystic ovary syndrome, agents for treating a growth disorder and/or frailty, an anti-arthritis agent, agents for preventing inhibiting allograft rejection in transplantation, agents for treating autoimmune disease, an anti-AIDS agent, agents for treating inflammatory bowel disease/syndrome, agents for treating anorexia nervosa and an anti-osteoporosis agent.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, PPARdelta agonists, PPARalpha/gamma/delta triple agonists, glycogen phosphorylase inhibitors, inhibitors of fatty acid binding protein (aP2), glucagon-like peptide-1 (GLP-1) or other agonists of the GLP-1 receptor, STLT2 inhibitors and other dipeptidyl peptidase IV (DPP4) inhibitors.

Other suitable thiazolidinediones include Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists, PPARdelta agonists, and PPAR alpha/gamma dual agonists include muraglitizar, peliglitazar, AR-HO39242 (Astra/Zeneca), GW-409544 (Glaxo-Wellcome), GW-501516 (Glaxo-Wellcome), LY-919818 (Lilly/Ligand), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable other DPP4 inhibitors include saxagliptin, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899,641, WO 01/868603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1), such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), PPAR agonists (as described above) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, $\alpha$-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitor for use in combination with the compound of the invention include SCH48461 (Schering-Plough), as well as those disclosed in Atherosclerosis 115, 45-63 (1995) and J. Med. Chem. 41, 973 (1998).

Examples of suitable ileal Na$^+$/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonsist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF), WO99/00353 (KaroBio) and WO00/039077 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physician's Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred.

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The compound of formula I will be employed in a weight ratio to the meglitinide, PPAR-gamma agonist, PPAR-alpha/gamma dual agonist, PPARdelta agonists, PPARalpha/gamma/delta triple agonist, aP2 inhibitor or other DPP4 inhibitor within the range from about 0.01:1 to about 100:1, preferably from about 0.2:1 to about 10:1.

The compound of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 mg to about 500 mg of a compound of formula I. The dose for adults is preferably between 1 and 2,000 mg per day, which can be administered in a single dose or in the form of individual doses from 1-4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitory activity of the compounds of the present invention may be determined by use of an in vitro assay system which measures the degree in inhibition of DPP-4-mediated cleavage of an appropriate substrate or pseudo-substrate. Inhibition constants (Ki values) for the DPP-4 inhibitors of the invention may be determined by the method described in the experimental section below.

Cloning, Expression and Purification of Human DPP-4

To generate human DPP-4, PCR (Red-tag polymerase, Sigma) was performed on Human cDNA from placenta (Clontech) using two primers, ACGCCGACGATGAAGACA and AGGTAAAGAGAAACATTGTT, based on the nucleotide sequence of the human clone (accession number M74777). PCR products were cloned into the pcDN4/His-Max TOPO vector (Invitrogene). For stable transfection of CHO-DG44 cells, DPP4 was rePCRed using primers GGTACCAGCGCAGAGGCTT and CTCGAGCTAAGGTAAAGAGAAACATTG to generate KpnI and XhoI sites.

The KpnI and XhoI sites were used to extract the N-terminal His tagged gene. The His tag, which could be cleaved and removed by Enterokinase, was included to allow purification using the TALON affinity column. The gene was then ligated into the KpnI and XhoI sites of the pD16 vector for stable transfection. Stable cell lines were generated by transfecting the expression vector into Chinese hamster ovary (CHO-DG44) cells using electroporation. The CHO-DG44 cell line was grown in PFCHO media supplemented with HT (glycine, hypoxanthine and thymidine, Invitrogene), glutamine and Recombulin (ICN). Then $1\times10^7$ cells/ml were collected, transfected with 60 μg of DNA using electroporation at 300V, and then transferred to a T75 flask. On the third day following transfection, the HT supplement was removed and selection was initiated with methotrexate (MTX, 10 nM, ICN). After a further 10 days the cells were plated into individual wells of 96 well plates. Every 10 days the concentration of MTX was increased two to three fold, up to a maximum of 400 nM. Final stable cell line selection was based on yield and activity of the expressed protein.

An attempt to purify recombinant DPP-4 using Talon resin was not efficient, resulting in small yields, with most of the DPP activity passing through the column. Therefore, protein was further purified using conventional anion exchange (Sepharose Q), gel filtration (S-200) and high resolution MonoQ columns. The final protein yielded a single band on SDS-PAGE gels. Amino acid sequence analysis indicated two populations of DPP-4 in the sample. One portion of the protein had 27 amino acids truncated from the N-terminus, while the other was lacking the N-terminal 37 amino acids. This suggests that during isolation the entire transmembrane domain (including His tag) is removed by proteases present in the CHO cells. Total protein concentration was measured using the Bradford dye method and the amount of the active DPP-4 was determined by titrating the enzyme with a previously characterized inhibitor (Ki=0.4 nM). No biphasic behavior was observed during inhibition or catalysis, suggesting that both protein populations are functionally identical.

DPP-4 Inhibition Assays

Inhibition of human DPP-4 activity was measured under steady-state conditions by following the absorbance increase at 405 nm upon the cleavage of the pseudosubstrate, Gly-Pro-pNA. Assays were performed in 96-well plates using a Thermomax plate reader. Typically reactions contained 100 μl of ATE buffer (100 mM Aces, 52 mM Tris, 52 mM ethanolamine, pH 7.4), 0.45 nM enzyme, either 120 or 1000 μM of substrate (S<Km and S>Km, Km=180 μM) and variable concentration of the inhibitor. To ensure steady-state conditions for slow-binding inhibitors, enzyme was preincubated with the compound for 40 minutes prior to substrate addition, to initiate the reaction. All serial inhibitor dilutions were in DMSO and final solvent concentration did not exceed 1%.

Inhibitor potency was evaluated by fitting inhibition data to the binding isotherm:

$$\frac{vi}{v} = \frac{\text{Range}}{1+\left(\frac{I}{IC_{50}}\right)^n} + \text{Background} \quad (1)$$

where vi is the initial reaction velocity at different concentrations of inhibitor I; v is the control velocity in the absence of inhibitor, range is the difference between the uninhibited velocity and background; background is the rate of spontaneous substrate hydrolysis in the absent of enzyme, n is the Hill coefficient.

Calculated $IC_{50}$s at each substrate concentration were converted to Ki assuming competitive inhibition according to:

$$Ki = \frac{IC_{50}}{\left(1+\frac{S}{Km}\right)} \quad (2)$$

All inhibitors were competitive as judged by a very good agreement of Ki values obtained from the assays at high and low substrate concentrations. In cases where $IC_{50}$ at the low substrate concentration was close to the enzyme concentration used in the assay, the data were fit to the Morrison equation[1], to account for the depletion of the free inhibitor:

$$\frac{vi}{v0} = 1 - \frac{(E+I+IC_{50})-\sqrt{(E+I+IC_{50})^2-4EI}}{2E} \quad (3)$$

where vi and v0 are the steady state velocities measured in the presence and absence of inhibitor, E enzyme concentration.

[1] Morrison, J F, Walsh, C T. Advances in Enzymology. 61 (1988), 201-206.

Each $IC_{50}$ was further refined to Ki, to account for the substrate concentration in the assay using equation (2).

Abbreviations

The following abbreviations are employed in the Examples and elsewhere herein:
Ph=phenyl
Bn=benzyl
i-Bu=iso-butyl
Me=methyl
Et=ethyl
Pr=propyl
Bu=butyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
DMSO=dimethylsulfoxide
EtOAc=ethyl acetate
Hex=hexanes
$CHCl_3$=chloroform
$CH_2Cl_2$=dichloromethane
THF=tetrahydrofuran
TFA=trifluoroacetic acid
Pd/C=palladium on carbon
$LiBH_4$=lithium borohydride
$NaBH_4$=sodium borohydride
MsCl=methanesulfonyl chloride
DIBAL-H=diisobutylaluminum hydride
TEA=triethylamine
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt=room temperature
sat or sat'd=saturated
aq.=aqueous
TLC=thin layer chromatography
$R_t$=retention time
mp=melting point
HPLC=high performance liquid chromatography
PrepHPLC=preparative HPLC
Solvent A (Prep HPLC): 90% $H_2O$/10% MeOH+0.1% TFA Solvent B (Prep HPLC): 90% MeOH/10% H₂O+0.1% TFA
LC/MS=high performance liquid chromatography/mass spectrometry
MS or Mass Spec=mass spectrometry
HRMS=high resolution mass spectrometry
NMR=nuclear magnetic resonance
equiv=equivalent(s)

EXAMPLES

The following examples are provided to describe the invention in further detail. These examples, which set forth the best mode presently contemplated for carrying out the invention, are intended to illustrate and not to limit the invention.

In general, preferred compounds of the present invention, such as the particular compounds disclosed in the following examples, have been identified to inhibit the catalytic activity of dipeptidyl peptidase IV at concentrations equivalent to, or more potently than, 10 μM, preferably 5 μM, more preferably 3 μM, thereby demonstrating that the compounds of the present invention possess utility as effective inhibitors of dipeptidyl peptidase IV. Potencies can be calculated and expressed as either inhibition constants (Ki values) or as IC$_{50}$ (inhibitory concentration 50%) values, and refer to activity measured employing the in vitro assay system described herein.

Example 1

3-(Aminomethyl)-4-(2,4-dichlorophenyl)-2-methyl-6-phenyl-6,7-dihydropyrrol[3,4-b]pyridine-5-one

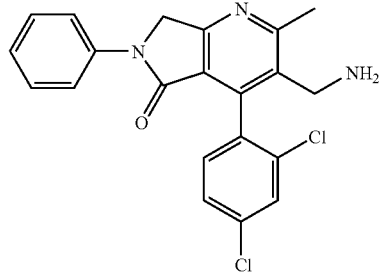

Example 1A

Ethyl 2-(chloromethyl)-4-(2,4-dichlorophenyl)-5-(2-methoxy-2-oxoethyl)-6-methyl-1,4-dihydropyridine-3-carboxylate

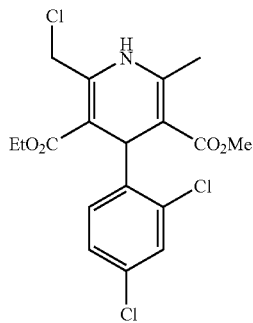

A mixture of 2,4-dichlorobenzaldehyde (2.3 g, 12.9 mmol), ethyl 4-chloro-3-oxobutanoate (2.2 g, 12.9 mmol), benzylamine (80.0 mg, 0.8 mmol), and acetic acid (55.0 mg, 0.9 mmol) in isopropyl alcohol (15 mL) was stirred at ambient temperature for 65 h. Methyl 3-aminocrotonate (1.6 g, 14.4 mmol) was added to the reaction mixture and stirring continued at ambient temperature for 24 h. The reaction was quenched with concentrated HCl (1 mL) and the mixture was stirred at ambient temperature for 2 h. The reaction mixture was then concentrated in vacuo, diluted with diethyl ether, filtered and evaporated. The residue was purified by flash chromatography (120 g column, 0 to 100% EtOAc/Hexanes) to yield Example 1A (4.2 g, 79% yield) as a yellow, sticky oil. ¹H NMR (400 MHz, CDCl₃) δ 1.22 (t, J=7.5 Hz, 3H), 2.36 (s, 3H), 3.63 (s, 3H), 4.11 (q, J=7.2 Hz, 2H), 4.86 and 4.97 (AB$_q$, J=14.0 Hz, 2H), 5.40 (s, 1H), 6.40 (broad s, 1H), 7.13 (dd, J=8.4, 2.2 Hz, 1H), 7.26-7.31 (m, 2H). [M+H]⁺=418.2.

Example 1B

3-Ethyl 5-methyl 2-(chloromethyl)-4-(2,4-dichlorophenyl)-6-methylpyridine-3,5-dicarboxylate

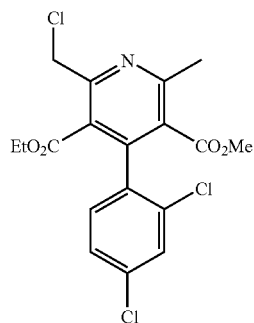

Example 1A (3.4 g, 8.1 mmol) was dissolved in acetic acid (15 mL) and 70% nitric acid/water (15 mL). The reaction mixture was stirred at ambient temperature for 72 h. The crude product (3.7 g) was purified by flash chromatography (120 g column, 0-100% EtOAc/Hexanes) to give Example 1B (1.9 g, 57% yield) as a pale yellow oil. ¹H NMR (400 MHz, CDCl₃) δ 1.02 (t, J=7.7 Hz, 3H), 2.66 (s, 3H), 3.60 (s, 3H), 4.10 (q, J=7.0 Hz, 2H), 4.80 and 4.93 (AB$_q$, J=11.0 Hz, 2H), 7.13 (d, J=7.0 Hz, 1H), 7.26-7.33 (m, 1H), 7.45 (s, 1H). [M+H]⁺=415.91.

Example 1C

Methyl 4-(2,4-dichlorophenyl)-2,7-dimethyl-5-oxo-6-phenyl-6,7-dihydro-5H-pyrrolo[3,4-b]pyridine-3-carboxylate

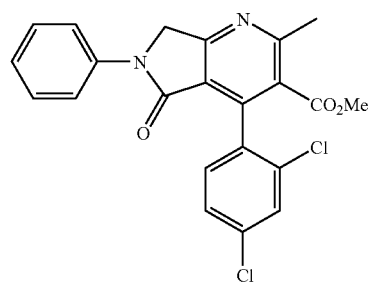

Method 1: A mixture of Example 1B (241 mg, 0.6 mmol) and aniline (60 mg, 0.6 mmol) in ethanol (10 mL) was refluxed for 72 h. The mixture was concentrated in vacuo. The residue was purified by flash chromatography (40 g column, 0 to 100% EtOAc/Hexanes) to give Example 1C (166 mg, 67% yield).

Method 2: A mixture of Example 1B (671 mg, 1.6 mmol) and aniline (168 mg, 1.8 mmol) in ethanol (5 mL) was heated to 175° C. for 45 min in the microwave. The reaction was purified by flash chromatography (120 g column, 0 to 100% EtOAC/Hexanes) to give Example 1C (485 mg, 71% yield) as a pale brown solid. $^1$H NMR (400 MHz, CDCl$_3$) δ 2.77 (s, 3H), 3.64 (s, 3H), 4.88 and 5.00 (AB$_q$, J=17.6 Hz, 2H), 7.13-7.20 (m, 2H), 7.33 (dd, J=8.4, 2.2 Hz, 1H), 7.36-7.44 (m, 2H), 7.53 (d, J=1.8 Hz, 1H), 7.79 (d, J=7.9 Hz, 2H). [M+H]$^+$=472.99.

Example 1D 4-(2,4-Dichlorophenyl)-3-(hydroxymethyl)-2,7-dimethyl-6-phenyl-6,7-dihydropyrrolo[3,4-b]pyridin-5-one

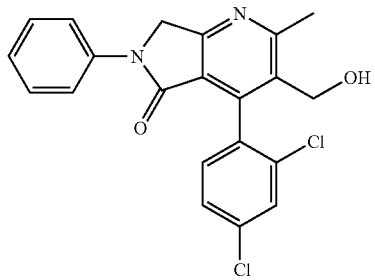

Procedure #1: To a solution of Example 1C (160 mg, 0.4 mmol) in THF (10 mL) was added 2M LiBH$_4$/THF (0.4 mL, 0.8 mmol). The mixture was allowed to stir at ambient temperature, and the reaction was followed by HPLC and LC/MS. Additional 2M LiBH$_4$/THF (0.8 mL, 1.6 mmol) was added, and the mixture was heated to 50° C. and stirred for 18 h. The reaction was quenched with saturated aqueous NaHCO$_3$, then diluted with EtOAc. The aqueous layer was extracted with EtOAc. The combined organic layers were washed with brine, dried (Na$_2$SO$_4$), and evaporated in vacuo. The residue was purified by flash chromatography (40 g column, 0 to 100% EtOAC/Hexanes) to give Example 1D (11.5 mg, 8% yield) as a pale yellow oil. $^1$H NMR (400 MHz, CDCl$_3$) δ 2.89 (s, 3H), 4.46 and 4.60 (AB$_q$, J=11.9 Hz, 2H), 4.85 and 4.90 (AB$_q$, J=17.2 Hz, 2H), 7.16 (t, J=7.5 Hz, 1H), 7.21 (d, J=7.9 Hz, 1H), 7.33-7.43 (m, 3H), 7.56 (d, J=1.8 Hz, 1H), 7.77 (d, J=7.9 Hz, 2H). [M+H]$^+$=399.20.

Procedure #2: A mixture of Example 1C (183 mg, 0.43 mmol), and lithium hydroxide (~200 mg) in THF/H$_2$O (4 mL) was allowed to stir at ambient temperature for 18 h. The reaction was then heated in the microwave for 1 h at 120° C. The reaction was quenched with 1N HCl and extracted into EtOAc. The combined organic layers were washed with brine, dried (Na$_2$SO$_4$), and evaporated to give the crude acid product (34 mg, 19% yield) as a pale yellow solid. $^1$H NMR (400 MHz, CDCl$_3$) δ 2.80 (s, 3H), 4.85 and 4.95 (AB$_q$, J=17.6 Hz, 2H), 7.15 (t, J=7.5 Hz, 1H), 7.20 (d, J=7.9 Hz, 1H), 7.30 (dd, J=8.9, 1.8 Hz, 1H), 7.37 (t, J=7.9 Hz, 2H), 7.49 (d, J=2.2 Hz, 1H), 7.76 (d, J=7.9 Hz, 2H). [M+H]$^+$=412.81.

To a solution of the acid (25 mg, 0.06 mmol) in THF was added ethyl chloroformate (24 μL, 0.25 mmol) followed by addition of triethylamine (50 μL, 0.36 mmol). Immediate precipitation was seen. The mixture was stirred at ambient temperature for 2 h, and was then filtered and washed with THF (1 mL×2). NaBH$_4$ (11 mg, 0.29 mmol) in H$_2$O (0.3 mL) was added dropwise to the filtrate. The mixture was allowed to stir at ambient temperature for 18 h and was diluted with EtOAc/H$_2$O. The organic layer was washed with brine, dried (Na$_2$SO$_4$), and evaporated to give crude Example 1D (11.5 mg) as a colorless oil.

Examples 1E and 1F 3-(Chloromethyl)-4-(2,4-dichlorophenyl)-2,7-dimethyl-6-phenyl-6,7-dihydropyrrolo[3,4-b]pyridin-5-one; and (4-(2,4-Dichlorophenyl)-2,7-dimethyl-5-oxo-6-phenyl-6,7-dihydro-5H-pyrrolo[3,4-b]pyridin-3-yl)methyl methanesulfonate

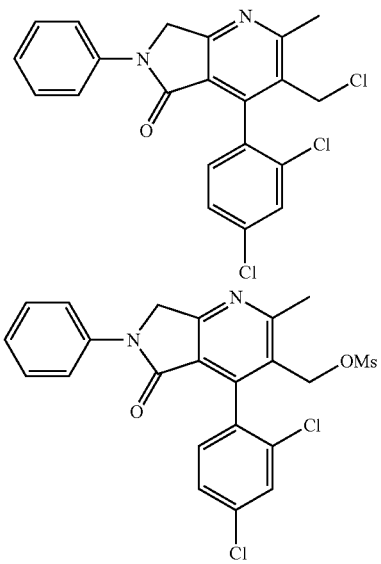

Procedure #1: To a solution of Example 1D (11.5 mg, 0.03 mmol) and triethylamine (15 mg, 0.15 mmol) in dichloromethane (2 mL) was added mesyl chloride (10 mg, 0.09 mmol). The mixture was allowed to stir at ambient temperature for 1 h. The solvent was evaporated, and the residue was purified by flash chromatography (4 g column, 0 to 100% EtOAC/Hexanes) to give a mixture of Examples 1E (5 mg, 42% yield) and 1F (4 mg, 29% yield).

Example 1E. $^1$H NMR (400 MHz, CDCl$_3$) δ 2.89 (s, 3H), 4.31 and 4.56 (AB$_q$, J=11.9 Hz, 2H), 4.87 and 4.93 (AB$_q$, J=17.6 Hz, 2H), 7.16 (t, J=7.5 Hz, 1H), 7.29 (d, J=8.4 Hz, 1H), 7.38 (t, J=7.9 Hz, 2H), 7.42 (dd, J=8.1, 2.0 Hz, 1H), 7.57 (d, J=2.2 Hz, 1H), 7.78 (d, J=7.9 Hz, 2H). [M+H]$^+$=417.18.

Example 1F. $^1$H NMR (400 MHz, CDCl$_3$) δ 2.89 (s, 3H), 2.90 (s, 3H), 4.89 and 4.95 (AB$_q$, J=17.6 Hz, 2H), 4.99 and 5.21 (AB$_q$, J=11.0 Hz, 2H), 7.18 (t, J=7.0 Hz, 1H), 7.23 (d, J=8.4 Hz, 1H), 7.34-7.45 (m, 3H), 7.58 (broad s, 1H), (d, J=8.8 Hz, 2H). [M+H]$^+$=477.24.

Procedure #2: To a solution of Example 1D (11.5 mg, 0.03 mmol) and triethylamine (30 μL, 0.22 mmol) in dichloromethane (2 mL) was added mesyl chloride (15 μL, 0.19 mmol). The mixture was allowed to stir at ambient temperature for 4 h. The solvent was evaporated, and the residue was purified by flash chromatography (4 g column, 0 to 100% EtOAC/Hexanes) to give a Example 1E (4 mg, 33%) as a colorless oil.

Example 1G 3-(Azidomethyl)-4-(2,4-dichlorophenyl)-2,7-dimethyl-6-phenyl-6,7-dihydropyrrolo[3,4-b]pyridin-5-one

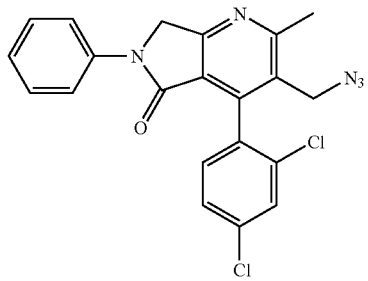

To separate flasks containing Examples 1E (5 mg, 0.01 mmol) and 1F (4 mg, 0.01 mmol) in DMF (5 mL each) was added sodium azide (5 mg, 0.08 mmol each). The mixtures were allowed to stir at ambient temperature for 18 h. The reactions were diluted with EtOAc and water. The organic layer was washed with brine, dried ($Na_2SO_4$), and evaporated in vacuo. The crude products were combined and purified by flash chromatography (4 g column, 0 to 100% EtOAC/Hexanes) to give Example 1G (5 mg, 58% yield) as a white solid. $^1$H NMR (400 MHz, $CDCl_3$) δ 2.85 (s, 3H), 4.24 and 4.31 ($AB_q$, J=13.6 Hz, 2H), 4.88 and 4.93 ($AB_q$, J=17.6 Hz, 2H), 7.17 (t, J=7.5 Hz, 1H), 7.21 (d, J=7.9 Hz, 1H), 7.38 (t, J=8.1 Hz, 2H), 7.42 (dd, J=8.4, 2.2 Hz, 1H), 7.58 (d, J=2.2 Hz, 1H), 7.78 (d, J=7.9 Hz, 2H). $[M+H]^+$=424.19.

Example 1

3-(Aminomethyl)-4-(2,4-dichlorophenyl)-2-methyl-6-phenyl-6,7-dihydropyrrolo[3,4-b]pyridin-5-one, TFA salt

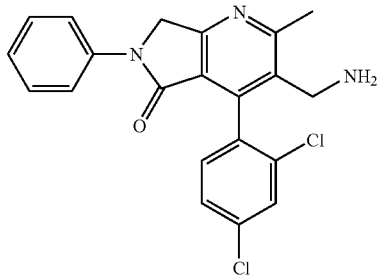

Procedure #1: To a mixture of the azide 1G (5 mg, 0.01 mmol) in $THF/H_2O$ (1.5 mL) was added polymer-bound triphenylphosphine (28 mg, 0.08 mmol). The mixture was allowed to stir at ambient temperature for 18 h and was then filtered and evaporated. The residue was purified by prep HPLC (YMC ODS 20×100 mm, 10 min gradient, 30 to 100% B/A, 20 ml/min) to give Example 1 (1.5 mg, 32% yield) as a colorless oil. $^1$H NMR (400 MHz, $CDCl_3+CD_3OD$ as cosolvent) δ 2.83 (s, 3H), 3.88 and 4.10 ($AB_q$, J=14.5 Hz, 2H), 4.85 and 4.90 ($AB_q$, J=18.5 Hz, 2H), 7.14 (t, J=7.0 Hz, 1H), 7.24-7.27 (m, 1H), 7.34 (t, J=7.9 Hz, 2H), 7.40 (dd, J=8.1, 2.0 Hz, 1H), 7.55 (d, J=1.8 Hz, 1H), 7.70 (d, J=8.8 Hz, 2H). HRMS: Calculated for $C_{21}H_{18}Cl_2N_3O$: 398.0827. Found: 398.0812. $[M+H]^+$=398.20.

Procedure #2: A mixture of Example 1E (4 mg, 0.0096 mmol) and 7M $NH_3$ in MeOH (4 mL) was heated in the microwave at 100° C. for 15 min. The solvent was evaporated, and the residue was taken up in EtOAc and saturated aqueous $NaHCO_3$. The organic layer was washed with brine, dried ($Na_2SO_4$), and evaporated. The residue was purified by Prep HPLC (YMC ODS 20×100 mm, 10 min gradient, 30 to 100% B/A) to give Example 1 (5.8 mg, quant.) as a TFA salt.

Example 2

3-(Aminomethyl)-4-(2,4-dichlorophenyl)-6-(4-methoxyphenyl)-2-methyl-6,7-dihydropyrrolo[3,4-b]pyridin-5-one

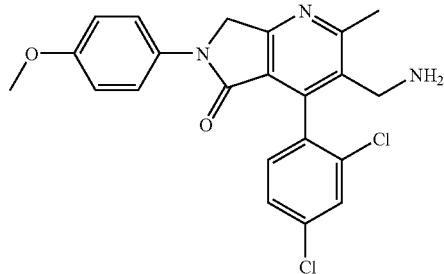

Example 2A (Z)-Benzyl 3-aminobut-2-enoate

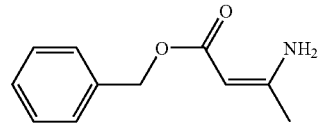

A mixture of benzyl acetoacetate 4.6 g, 24 mmol) and ammonium acetate (9.2 g, 119.5 mmol) in methanol (30 mL) was allowed to stir at ambient temperature for 72 h. The solvent was evaporated, and the residue was taken up in $CHCl_3/H_2O$. The combined organic layers were washed with brine, dried ($Na_2SO_4$), and evaporated to give Example 2A (4.3 g, 90% yield) as a golden oil. $^1$H NMR (400 MHz, $CDCl_3$) δ 1.91 (s, 3H), 4.60 (s, 1H), 5.12 (s, 2H), 7.24-7.40 (m, 5H).

Example 2B (Z)-Ethyl 2-(2,4-dichlorobenzylidene)-4-chloro-3-oxobutanoate

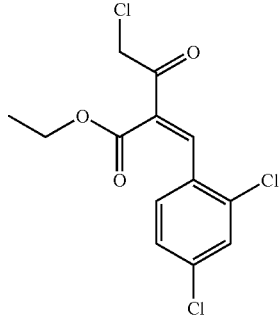

A solution 2,4-dichlorobenzaldehyde (4.6 g, 26.1 mmol), ethyl 4-chloro-3-oxobutanoate (4.5 g, 27.4 mmol), benzylamine (165 mg, 1.5 mmol), and acetic acid (118 mg, 2.0 mmol) in isopropyl alcohol (30 mL) stirred at ambient temperature for 96 h. The mixture was diluted with isopropyl alcohol to give a total volume of 50 mL and was saved as a stock solution (0.52 mmol/mL).

Example 2C

3-Benzyl 5-ethyl 6-(chloromethyl)-4-(2,4-dichlorophenyl)-2-methyl-1,4-dihydropyridine-3,5-dicarboxylate

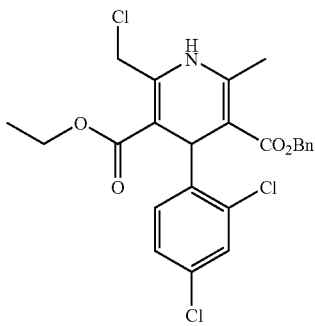

A mixture of stock solution 2B (25 mL, 13 mmol) and Example 2A (2.8 g, 14.5 mmol) in isopropyl alcohol (3 mL) was allowed to stir at ambient temperature for 18 h. The reaction was quenched with concentrated HCl (8 mL), and the mixture stirred at ambient temperature for 2 h. The reaction was concentrated in vacuo, diluted with diethyl ether, filtered and evaporated. The residue was purified by flash chromatography (120 g column, EtOAc/Hexanes) to give Example 2C (4.2 g, 65% yield) as a yellow, sticky oil. $^1$H NMR (400 MHz, CDCl$_3$) δ 1.19 (t, J=7.0 Hz, 3H), 2.35 (s, 3H), 4.05-4.15 (m, 2H), 4.82 and 4.97 (AB$_q$, J=14.1 Hz, 2H), 5.07 and 5.11 (AB$_q$, J=12.3 Hz, 2H), 5.41 (s, 1H), 6.37 (broad s, 1H), 7.07 (dd, J=8.4, 2.2 Hz, 1H), 7.16-7.32 (m, 5H), 7.35-7.38 (m, 2H).

Example 2D

3-Benzyl 5-ethyl 6-(chloromethyl)-4-(2,4-dichlorophenyl)-2-methylpyridine-3,5-dicarboxylate (a novel intermediate)

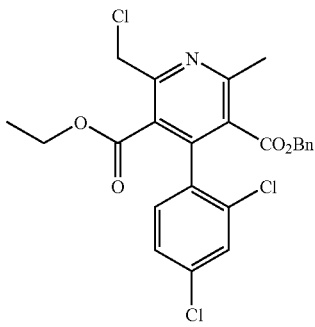

Example 2C (4.1 mg, 8.2 mmol) was dissolved in acetic acid (30 mL) and 70% nitric acid/water (25 mL). The reaction mixture was allowed to stir at ambient temperature for 18 h. The crude product (4.2 g) was purified by flash chromatography (120 g column, 0-100% EtOAc/Hex) to give Example 2D (2.7 g, 68% yield) as a pale yellow oil. $^1$H NMR (400 MHz, CDCl$_3$) δ 0.98 (t, J=7.3 Hz, 3H), 2.65 (s, 3H), 4.05 (q, J=7.0 Hz, 2H), 4.77 and 4.92 (AB$_q$, J=11.0 Hz, 2H), 5.04 (s, 2H), 7.01 (d, J=8.35 Hz, 1H), 7.07 (dd, J=8.4, 2.2 Hz, 1H), 7.10-7.14 (m, 2H), 7.21 (d, J=2.2 Hz, 1H), 7.28-7.28 (m, 3H). [M+H]$^+$=491.98.

Example 2E

Benzyl 4-(2,4-dichlorophenyl)-6-(4-methoxyphenyl)-2-methyl-5-oxo-6,7-dihydro-5H-pyrrolo[3,4-b]pyridine-3-carboxylate

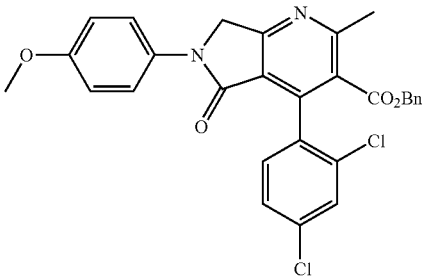

A mixture of Example 2D (199 mg, 0.4 mmol), and 4-methoxybenzenamine (61 mg, 0.5 mmol) in ethanol (3 mL) was heated on the microwave at 175° C. for 15 min. The solvent was evaporated, and the residue was purified by flash chromatography (12 g column, EtOAc/Hexanes) to give Example 2E (114.6 mg, 53% yield) as a golden oil. $^1$H NMR (400 MHz, CDCl$_3$) δ 2.76 (s, 3H), 3.79 (s, 3H), 4.81 and 4.90 (AB$_q$, J=17.6 Hz, 2H), 5.05 and 5.11 (AB$_q$, J=11.9 Hz, 2H), 6.89 (d, J=9.2 Hz, 2H), 7.03 (d, J=8.4 Hz, 1H), 7.08-7.16 (m, 3H), 7.28-7.38 (m, 4H), 7.66 (d, J=9.2 Hz, 2H). [M+H]$^+$= 533.06.

Example 2F 4-(2,4-Dichlorophenyl)-6-(4-methoxyphenyl)-2-methyl-5-oxo-6,7-dihydro-5H-pyrrolo[3,4-b]pyridine-3-carboxylic acid

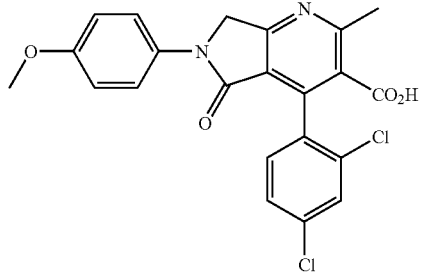

A mixture of Example 2E (114.6 mg, 0.2 mmol) and 10% Pd/C (44 mg) in ethyl acetate (15 mL) was stirred under a H$_2$(g) balloon at ambient temperature for 5 h. The reaction was filtered, evaporated and carried on to the next reaction without further purification.

Example 2G 4-2,4-Dichlorophenyl)-3-(hydroxymethyl)-6-(4-methoxyphenyl)-2-methyl-6,7-dihydropyrrolo[3,4-b]pyridin-5-one

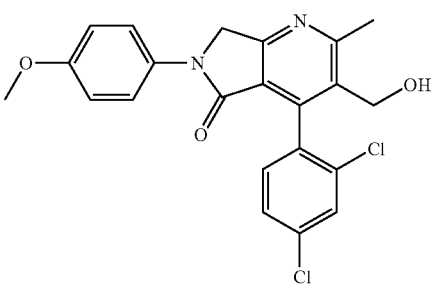

To a solution of the acid 2F (114 mg, 0.3 mmol) in THF (10 mL) was added ethyl chloroformate (50 μL, 0.5 mmol) followed by addition of triethylamine (150 μL, 1.1 mmol). The mixture was stirred at ambient temperature for 2 h and was filtered. NaBH₄ (50 mg, 1.3 mmol) was added to the filtrate, and the mixture stirred at ambient temperature for 18 h. The reaction was quenched with saturated aqueous NaHCO₃ and extracted into EtOAc. The combined organic layers were washed with brine, dried (Na₂SO₄), and evaporated. The residue was purified by flash chromatography (12 g column, EtOAc/Hexanes) to give Example 2G (10.5 mg, 10% yield) as a white solid. [M+H]⁺=429.10.

Example 2H 3-(Chloromethyl)-4-(2,4-dichlorophenyl)-6-(4-methoxyphenyl)-2-methyl-6,7-dihydropyrrolo[3,4-b]pyridin-5-one

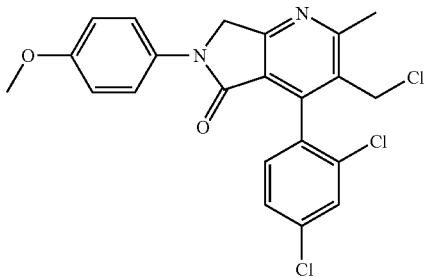

To a solution of alcohol 2G (10 mg, 0.02 mmol) in dichloromethane (4 mL) was added triethylamine (25 μL, 0.18 mmol) and mesyl chloride (20 μL, 0.26 mmol). The mixture was allowed to stir at ambient temperature for 18 h and was evaporated. The residue was purified by flash chromatography (4 g column, EtOAc/Hexanes) to give Example 2H (7 mg, 67% yield) as a colorless oil. ¹H NMR (400 MHz, CDCl₃) δ 2.89 (s, 3H), 3.80 (s, 3H), 4.31 and 4.56 (AB$_q$, J=11.9 Hz, 2H), 4.82 and 4.89 (AB$_q$, J=17.1 Hz, 2H), 6.87-6.94 (m, 2H), 7.29 (d, J=7.9 Hz, 1H), 7.41 (dd, J=7.9, 1.8 Hz, 1H), 7.56 (d, J=1.8 Hz, 1H), 7.63-7.70 (m, 2H). [M+H]⁺=446.90.

Example 2

3-(Aminomethyl)-4-(2,4-dichlorophenyl)-6-(4-methoxyphenyl)-2-methyl-6,7-dihydropyrrolo[3,4-b]pyridin-5-one, TFA salt

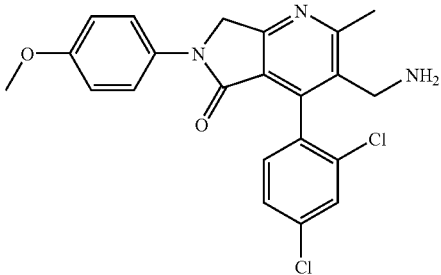

A mixture of chloride 2H (7 mg, 0.02 mmol) and 7M NH₃ in MeOH (4 mL) was heated in the microwave at 100° C. for 15 min. The solvent was removed in vacuo, and the residue was purified by prep HPLC (Phenomenex, 10 min gradient, 30 to 100% B) to give Example 2 (6.7 mg, 79% yield) as a TFA salt. ¹H NMR (400 MHz, CDCl₃) δ 2.86 (s, 3H), 3.80 (s, 3H), 3.97 and 4.20 (AB$_q$, J=14.5 Hz, 2H), 4.96 and 5.01 (AB$_q$, J=18.0 Hz, 2H), 6.94-7.00 (m, 2H), 7.36 (d, J=8.4 Hz, 1H), 7.54 (dd, J=8.4, 2.2 Hz, 1H), 7.59-7.65 (m, 2H), 7.72 (d, J=1.8 Hz, 1H). HRMS: Calculated for C₂₂H₂₀Cl₂N₃O₂: 428.0933. Found: 428.0943. [M+H]⁺=428.10.

Example 3

3-(Aminomethyl)-4-(2,4-dichlorophenyl)-6-(2-methoxyphenyl)-2-methyl-6,7-dihydropyrrolo[3,4-b]pyridin-5-one, TFA salt

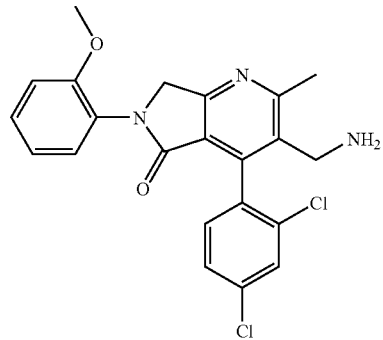

Example 3 was prepared using the same method described above for Example 2, with the exception that in step 2E 4-methoxybenzenamine was replaced with 2-methoxybenzenamine. ¹H NMR (400 MHz, CDCl₃) δ 2.87 (s, 3H), 3.83 (s, 3H), 3.99 and 4.22 (AB$_q$, J=14.5 Hz, 2H), 4.85-4.95 (m, 2H), 7.01 (broad t, J=7.5 Hz, 1H), 7.14 (broad d, J=8.4 Hz, 1H), 7.32 (dd, J=7.9, 1.8 Hz, 1H), 7.34-7.40 (m, 2H), 7.52 (dd, J=8.4, 2.2 Hz, 1H), 7.69 (d, J=2.2 Hz, 1H). HRMS: Calculated for C₂₂H₂₀Cl₂N₃O₂: 428.0933. Found: 428.0937. [M+H]⁺=428.12.

Example 3 was separated on a Chiralcel® OJ, 20μ, 5×50 cm column using an isocratic gradient of 15% EtOH-MeOH (50%) in heptane to afford individual enantiomers.

Example 3-1 (Enantiomer A; faster-moving): [α]$_D^{25}$+8.20; Purity by chiral analytical HPLC [Chiralcel® OJ 4.6×250 mm; 15% EtOH-MeOH (1:1; containing 0.1% DEA) in heptane (containing 0.1% DEA)]: >98%.

Example 3-2 (Enantiomer B; slower-moving): [α]$_D^{21}$-8.0°; Purity by chiral analytical HPLC [Chiralcel® OJ 4.6×250 mm; 15% EtOH-MeOH (1:1; containing 0.1% DEA) in heptane (containing 0.1% DEA)]: >98%.

Example 4

3-(Aminomethyl)-6-benzyl-4-(2,4-dichlorophenyl)-2-methyl-6,7-dihydropyrrolo[3,4-b]pyridin-5-one, TFA salt

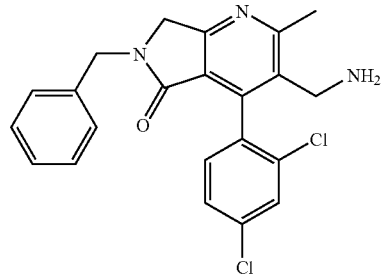

Example 4 was prepared using the same method described above for Example 2, with the exception that in step 2E 4-methoxybenzenamine was replaced with benzenemethylamine. ¹H NMR (400 MHz, CDCl₃) δ 2.81 (s, 3H), 3.96 and 4.19 (AB$_q$, J=14.5 Hz, 2H), 4.40 (s, 2H), 4.69 and 4.74 (AB$_q$, J=14.9 Hz, 2H), 7.25-7.40 (m, 6H), 7.54 (dd, J=7.9, 1.8 Hz, 1H), 7.71 (d, J=2.2 Hz, 1H). HRMS: Calculated for C₂₂H₂₀Cl₂N₃O: 412.0983. Found: 412.0995. [M+H]⁺=412.13.

Example 5

3-(Aminomethyl)-6-benzyl-4-(2,4-dichlorophenyl)-2-methyl-5,6-dihydropyrrolo[3,4-b]pyridin-7-one

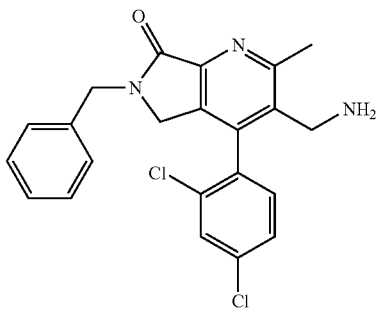

Example 5A

Ethyl 1-benzyl-4,5-dioxopyrrolidine-3-carboxylate

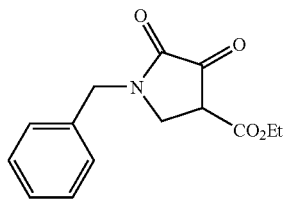

A mixture of benzylamine (3.63 g, 33.0 mmol), ethyl acrylate (3.6 mL, 33.0 mmol) in EtOH (10 mL) was stirred at room temperature for 16 h. Diethyl oxalate (4.5 mL, 33 mmol) and freshly-made sodium ethoxide solution in EtOH (generated from 0.9 g of sodium metal, 39.0 mmol, in 10 mL EtOH) were added. The mixture was heated at reflux for 1 h and it solidified. The volatiles were removed in vacuo. The crude product was diluted with $H_2O$ (50 mL) and the pH of the mixture was adjusted to 1 by adding conc. HCl. The mixture was subjected to filtration to afford Example 5A as a white solid (7.7 g, 88%). $^1$H NMR (400 MHz, $CD_3OD$) δ 1.26 (t, J=7.1 Hz, 3H), 3.89 (s, 3H), 4.22 (q, J=7.1 Hz, 2H), 4.65 (s, 2H), 7.20-7.40 (m, 5H). [M+Na]$^+$=284.23.

Example 5B (E)-4-(2,4-Dichlorobenzylidene)-1-benzylpyrrolidine-2,3-dione

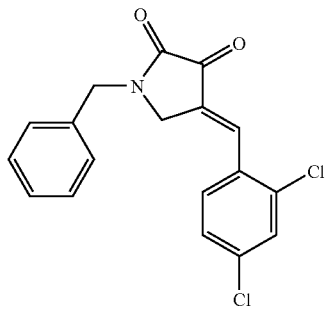

A mixture of Example 5A (1.3 g, 4.9 mmol), 2,4-dichlorobenzaldehyde (0.86 g, 4.9 mmol) in EtOH (20 mL)/20% aq. HCl (50 mL) was heated at reflux for 4 h. After cooling down to ambient temperature, the aqueous layer was decanted. The obtained chunky solid was collected and further recrystallized from EtOAc to afford Example 5B as a bright yellow solid (0.84 g, 48%). $^1$H NMR (400 MHz, $CDCl_3$) δ 4.31 (d, J=2.2 Hz, 2H), 4.79 (s, 2H), 7.20-7.42 (m, 7H), 7.51 (d, J=2.2 Hz, 1H), 8.01 (m, 1H). [M+H]$^+$=345.97.

Example 5C

Ethyl 6-benzyl-4-(2,4-dichlorophenyl)-2-methyl-7-oxo-4,5,6,7-tetrahydro-1H-pyrrolo[3,4-b]pyridine-3-carboxylate

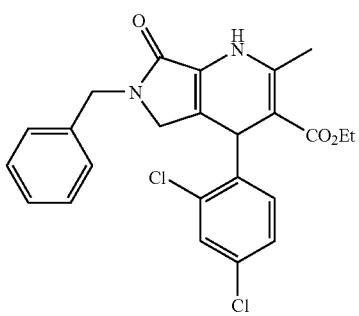

A stirred mixture of Example 5B (1.75 g, 50 mmol), ethyl β-aminocrotonate (0.685 g, 53 mmol) in acetic acid (4 mL) was heated to reflux for 1.5 h. The volatiles were removed under reduced pressure. The crude reaction product was washed with EtOAc (20 mL) and subjected to filtration to afford Example 5C as a white solid (1.62 g, 70%). $^1$H NMR (400 MHz, DMSO-$d_6$) δ 0.87 (t, J=7.5 Hz, 3H), 2.36 (s, 3H), 3.46 (d, J=18.9 Hz, 1H), 3.70-3.85 (m, 3H), 4.35 and 4.59 ($AB_q$, J 20=15.2 Hz, 2H), 5.30 (s, 1H), 7.10-7.32 (m, 6H), 7.37 (dd, J=8.3, 1.8 Hz, 1H), 7.49 (d, J=1.8 Hz, 1H), 9.31 (s, 1H). [M+H]$^+$=457.29

Example 5D

Ethyl 6-benzyl-4-(2,4-dichlorophenyl)-2-methyl-7-oxo-6,7-dihydro-5H-pyrrolo[3,4-b]pyridine-3-carboxylate

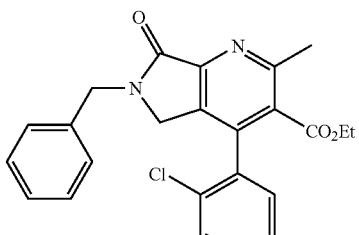

A stirred mixture of Example 5C (1.55 g, 34 mmol) in aq. 1N nitric acid (12.5 mL) was heated to reflux for 0.5 h and then cooled down to RT. The aqueous layer was decanted. The remaining solid residue was dissolved in EtOAc (50 mL). The organic layer was washed with $H_2O$ (10 mL), brine, dried ($MgSO_4$), filtered and concentrated under reduced pressure to afford Example 5D as a beige solid (1.5 g, 97%). $^1$H NMR (400 MHz, $CDCl_3$) δ 0.94 (t, J=7.5 Hz, 3H), 2.75 (s, 3H), 3.94 and 4.10 ($AB_q$, J=18.0 Hz, 2H), 4.02 (q, J=7.1 Hz, 2H), 4.61 and 4.89 ($AB_q$, J=15.0 Hz, 2H), 7.07 (d, J=8.3 Hz, 1H), 7.15-7.30 (m, 6H), 7.43 (d, J=1.8 Hz, 1H). [M+H]$^+$=455.29

Example 5E

6-Benzyl-4-(2,4-dichlorophenyl)-3-(hydroxymethyl)-2-methyl-5,6-dihydropyrrolo[3,4-b]pyridin-7-one

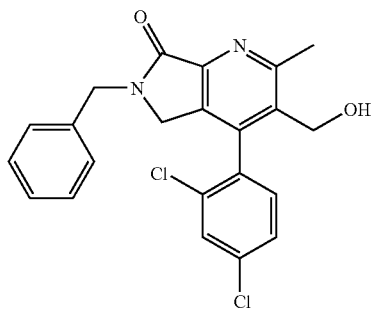

To a stirred solution of Example 5D (0.75 g, 1.64 mmol) in THF (15 mL) was added LiBH$_4$ (2M solution in THF, 1.23 mL, 2.46 mmol). After stirring for 16 h at room temperature, an additional portion of LiBH$_4$ (2M solution in THF, 1.00 mL, 2.0 mmol) was added. After stirring for another 48 h at room temperature, the reaction was quenched by addition of sat. NaHCO$_3$ solution (10 mL). The resulting mixture was diluted with EtOAc (125 mL), washed with H$_2$O and concentrated. The crude reaction product was purified by flash chromatography (silica gel, EtOAc/hexanes=1:1 to EtOAc/MeOH=95:5) to give Example 5E (0.23 g, 34%) as a solid. $^1$H NMR (400 MHz, CDCl$_3$) δ 2.87 (s, 3H), 3.87 and 3.95 (AB$_q$, J=17.6 Hz, 2H), 4.42 and 4.61 (AB$_q$, J=12.0 Hz, 2H), 4.67 and 4.90 (AB$_q$, J=14.5 Hz, 2H), 7.1-7.30 (m, 7H), 7.52 (d, J=2.2 Hz, 1H). [M+H]$^+$=413.27.

Example 5

3-(Aminomethyl)-6-benzyl-4-(2,4-dichlorophenyl)-2-methyl-5,6-dihydropyrrolo[3,4-b]pyridin-7-one, HCl salt

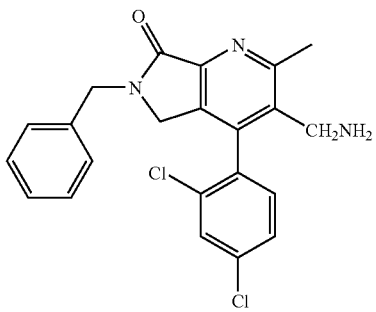

To a stirred solution of Example 5E (88 mg, 0.21 mmol) in CH$_2$Cl$_2$ (1 mL) was added MsCl (28 μL, 0.36 mmol) and Et$_3$N (60 μL, 0.43 mmol). The reaction mixture was kept at ambient temperature for 2.5 h and concentrated to give a crude product which was subjected to flash chromatography (silica gel, EtOAc/hexane=1:2 to 100% EtOAc) to give a chloride intermediate (74 mg, 80%). A mixture of chloride (72 mg, 0.17 mmol) and 7N ammonia in MeOH (7 mL) in sealed tube was irradiated in a microwave reactor at 50° C. for 15 min. After cooling down to ambient temperature, the volatiles were removed in vacuo. The crude product was purified by reverse-phase preparative HPLC to provide pure product. This product was redissolved in CH$_2$Cl$_2$ (3 mL) and 4N HCl in dioxane (30 μL) was added. The solvent was evaporated to dryness to give 3-(aminomethyl)-6-benzyl-4-(2,4-dichlorophenyl)-2-methyl-5,6-dihydropyrrolo[3,4-b]pyridin-7-one (Example 5), HCl salt (57 mg, 60% for 2 steps) as a white solid. $^1$H NMR (400 MHz, CD$_3$OD) δ 2.83 (s, 3H), 3.98 and 4.19 (AB$_q$, J=14.5 Hz, 2H), 4.03 and 4.12 (AB$_q$, J=18.5 Hz, 2H), 4.75 and 4.81 (AB$_q$, J=14.7 Hz, 2H), 7.24-7.34 (m, 5H), 7.37 (d, J=8.3 Hz, 1H), 7.54 (dd, J=8.3, 2.0 Hz, 1H), 7.74 (d, J=2.0 Hz, 1H). HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, R$_t$=3.27 min, 99% homogeneity index. LCMS: Calculated for C$_{22}$H$_{19}$Cl$_2$N$_3$O: 411.09. Found: 411.95 [M+H]$^+$. HRMS: Calculated for C$_{22}$H$_{20}$Cl$_2$N$_3$O: 412.0983. Found: 412.0998 [M+H]$^+$.

Example 6

6-(4-Methoxybenzyl)-3-(aminomethyl)-4-(2,4-dichlorophenyl)-2-methyl-5,6-dihydropyrrolo[3,4-b]pyridin-7-one, HCl salt

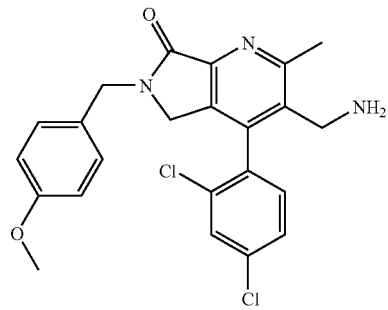

Example 6 was prepared using the same method described above for Example 5, with the exception that in step 5A benzylamine was replaced with 4-methoxybenzylnamine. $^1$H NMR (400 MHz, CD$_3$OD) δ 2.84 (s, 3H), 3.75 (s, 3H), 3.98 and 4.19 (AB$_q$, J=14.5 Hz, 2H), 3.99 and 4.09 (AB$_q$, J=18.0 Hz, 2H), 4.68 and 4.75 (AB$_q$, J=14.7 Hz, 2H), 6.87 (d, J=8.8 Hz, 2H), 7.21 (d, J=8.8 Hz, 2H), 7.37 (d, J=8.3 Hz, 1H), 7.56 (dd, J=8.3, 1.8 Hz, 1H), 7.76 (d, J=1.8 Hz, 1H). Phenomenex LUNA C-18 4.6×50 mm, 0 to 100% B over 4 minutes, 1 minute hold time, A=90% water, 10% methanol, 0.11% TFA, B=10% water, 90% methanol, 0.11% TFA, R$_t$=3.27 min, 99% homogeneity index. LCMS: Calculated for C$_{23}$H$_{21}$Cl$_2$N$_3$O$_2$: 441.10. Found: 442.17 [M+H]$^+$. HRMS: Calculated for C$_{23}$H$_{22}$Cl$_2$N$_3$O$_2$: 442.1089. Found: 442.1101 [M+H]$^+$.

Example 7

(6-Benzyl-4-(2,4-dichlorophenyl)-2-methyl-6H-pyrrolo[3,4-b]pyridin-3-yl)methanamine

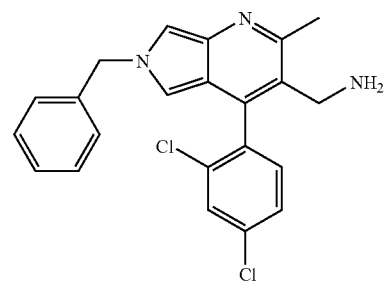

Example 7A

Ethyl 6-benzyl-4-(2,4-dichlorophenyl)-2-methyl-6H-pyrrolo[3,4-b]pyridine-3-carboxylate

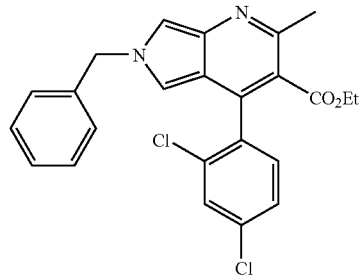

To a solution of Example 5D (0.102 g, 0.223 mmol) in THF (10 mL) was added DIBAL-H solution (1.5 mL, 1.5 M in toluene, 1.0 mmol). The mixture was stirred at RT for 1.5 h and quenched with sat. NaHCO$_3$ solution after which it was partitioned between water (5 mL) and EtOAc (150 mL). The organic phase was dried (MgSO$_4$) and concentrated in vacuo. The residue was chromatographed (SiO$_2$; EtOAc) to give the desired compound (55 mg; 63%) as a yellow foam. $^1$H NMR (400 MHz, CDCl$_3$) δ 0.91 (t, J=7.1 Hz, 3H), 2.62 (s, 3H), 4.01 (q, J=7.1 Hz, 2H), 5.23 (s, 2H), 6.64 (d, J=2.2 Hz, 1H), 7.01-7.30 (m, 8H), 7.44 (d, J=1.8 Hz, 1H). [M+H]$^+$=439.24.

Example 7B (6-Benzyl(2,4-dichlorophenyl)-2-methyl-6H-pyrrolo[3,4-b]pyridin-3-yl)methanol

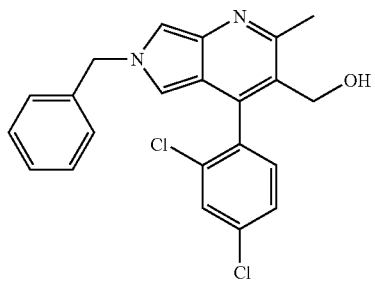

To a solution of Example 7A (55 mg, 0.125 mmol) in THF (15 mL) was added LAH solution (0.4 mL, 1 M in THF, 0.4 mmol). The mixture was stirred at RT for 1.5 h and quenched with sat. NaHCO$_3$ solution (1.5 mL) after which it was extracted with EtOAc (15 mL). The organic phase was dried (MgSO$_4$) and concentrated in vacuo. The residue was chromatographed (SiO$_2$; EtOAc) to give the desired compound (32 mg; 64%) as a yellow solid. $^1$H NMR (400 MHz, CDCl$_3$) δ 2.78 (s, 3H), 4.43 and 4.52 (AB$_q$, J=11.9 Hz, 2H), 5.28 (s, 2H), 6.55 (d, J=2.2 Hz, 1H), 7.06-7.38 (m, 2H), 7.20-7.38 (m, 6H), 7.53 (d, J=1.8 Hz, 1H). [M+H]$^+$=397.17.

Example 7

(6-Benzyl-4-(2,4-dichlorophenyl)-2-methyl-6H-pyrrolo[3,4-b]pyridin-3-yl)methanamine, HCl salt

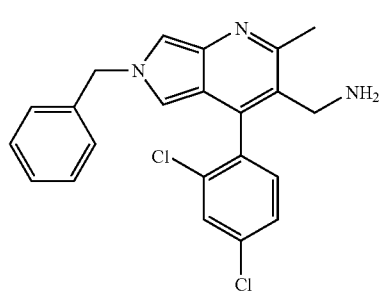

To a stirred solution of Example 7B (32 mg, 0.08 mmol) in CH$_2$Cl$_2$ (0.5 mL) was added MsCl (12 µL, 0.16 mmol) and Et$_3$N (32 µL, 0.213 mmol). The reaction was kept at ambient temperature for 0.5 h and concentrated to give crude product which was subjected to flash chromatography (silica gel, EtOAc/hexanes=1:1 to 100% EtOAc) to give a chloride intermediate (21 mg). A mixture of the obtained chloride (21 mg, 0.05 mmol) and 7N ammonia in MeOH (4 mL) in sealed tube was irradiated in a microwave reactor at 100° C. for 5 min. After cooling down to ambient temperature, the volatiles were removed in vacuo. The crude product was purified by reverse-phase preparative HPLC to provide pure product. This product was redissolved in CH$_2$Cl$_2$ (1 mL) and 4N HCl in dioxane (20 µL) was added. The solvent was evaporated to dryness to give (6-benzyl-4-(2,4-dichlorophenyl)-2-methyl-6H-pyrrolo[3,4-b]pyridin-3-yl)methanamine (Example 3), HCl salt (5.6 mg, 15% for 2 steps) as a yellow solid. $^1$H NMR (400 MHz, CD$_3$OD) δ 2.78 (s, 3H), 4.05 and 4.27(AB$_q$, J=13.9 Hz, 2H), 5.54 (s, 2H), 7.30-7.38 (m, 5H), 7.53 (d, J=8.3 Hz, 1H), 7.58 (d, J=2.2 Hz, 1H), 7.67 (dd, J=8.3, 2.2 Hz, 1H), 7.77 (d, J=2.2 Hz, 1H), 7.85 (d, J=2.2 Hz, 1H). HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, R$_t$=2.75 min, 99% homogeneity index. LCMS: Calculated for C$_{22}$H$_{19}$Cl$_2$N$_3$: 395.10. Found: 395.94 [M+H]$^+$. HRMS: Calculated for C$_{22}$H$_{20}$Cl$_2$N$_3$: 396.1034. Found: 396.1022 [M+H]$^+$.

Example 8

3-(Aminomethyl)-4-(2,4-dichlorophenyl)-2-methyl-6-phenyl-5,6-dihydropyrrolo[3,4-b]pyridin-7-one, HCl salt

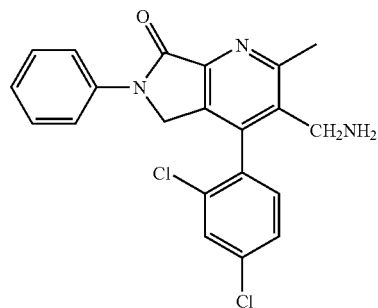

Example 8A

Ethyl 4-(2,4-dichlorophenyl)-2-methyl-7-oxo-6,7-dihydro-5H-pyrrolo[3,4-b]pyridine-3-carboxylate (a novel intermediate)

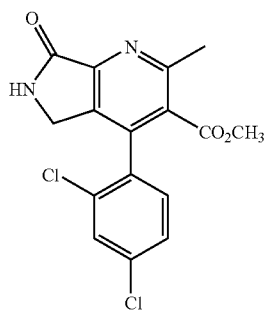

To a solution of Example 6D (100 mg, 0.21 mmol, prepared in a manner analogous to Example 5D)

Example 6D

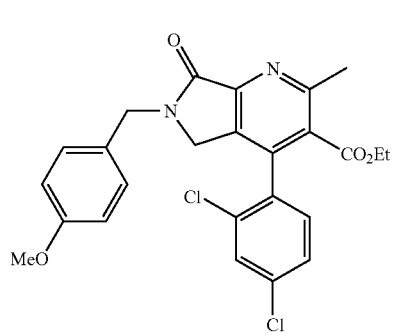

in $CH_3CN$ (3 mL) was added an aqueous solution of ammonium cerium nitrate (0.232 g, 0.42 mmol) in $H_2O$ (1.5 mL). The reaction mixture was stirred at 0° C. for 20 min, then diluted with EtOAc (30 mL). The organic phase was washed with sat. aqueous sodium sulfite solution (15 mL), dried ($MgSO_4$) and concentrated in vacuo to give the crude residue which was chromatographed ($SiO_2$; EtOAc to EtOAc/MeOH=95:5) to give Example 8A (28 mg, 38%) as a solid. $^1$H NMR (400 MHz, $CDCl_3$) δ 2.71 (s, 3H), 3.58 (s, 3H), 4.05 and 4.26 ($AB_q$, J=17.1 Hz, 2H), 7.09 (d, J=8.3 Hz, 1H), 7.25 (bs, 1H), 7.28 (d, J=2.2 Hz, 1H), 7.39 (dd, J=8.3, 2.2 Hz, 1H), $[M+H]^+$=351.06.

Example 8B

Methyl 4-(2,4-dichlorophenyl)-2-methyl-7-oxo-6-phenyl-6,7-dihydro-5H-pyrrolo[3,4-b]pyridine-3-carboxylate

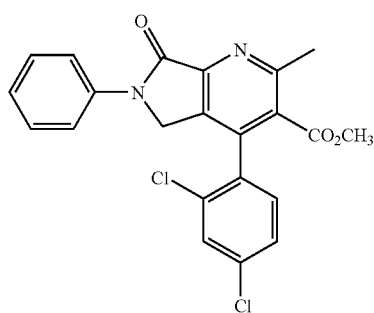

To a solution of the Example 8A (28 mg, 0.079 mmol) in dichloromethane (1.5 mL) was added phenylboronic acid (30 mg, 0.25 mmol), $Cu(OAc)_2$ (15.6 mg 0.08 mmol), $Et_3N$ (33.2 μL, 0.238 mmol), pyridine (25 μL, 0.31 mmol) and 4 Å molecular sieves (50 mg, pre-dried at 400° C. overnight). The vial was capped and air was allowed to pass into the reaction mixture, which was stirred at RT for 1.5 h. Volatiles were removed in vacuo and the residue was chromatographed ($SiO_2$; 1:1 hex:EtOAc to EtOAc) to give Example 8B (24 mg, 70%) as a solid. $^1$H NMR (400 MHz, $CDCl_3$) δ 2.74 (s, 3H), 3.60 (s, 3H), 4.45 and 4.64 ($AB_q$, J=17.0 Hz, 2H), 7.14 (d, J=8.3 Hz, 2H), 7.30-7.38 (m, 3H), 7.52 (d, J=2.2 Hz, 1H), 7.76 (dd, J=8.3, 2.2 Hz, 2H). $[M+H]^+$=427.08.

Example 8C 4-(2,4-Dichlorophenyl)-3-(hydroxymethyl)-2-methyl-6-phenyl-5,6-dihydropyrrolo[3,4-b]pyridin-7-one

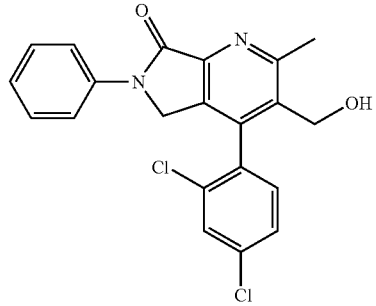

To a stirred solution of Example 8B (24 mg, 0.056 mmol) in THF (1.5 mL) was added $LiBH_4$ (0.03 mL, 2M solution in THF, 0.06 mmol) and MeOH (15 μL). After stirring 15 min at room temperature, the reaction was quenched by addition of sat. $NaHCO_3$ solution (1 mL). The reaction mixture was diluted with EtOAc (10 mL), washed with $H_2O$ and concentrated. The crude reaction product was purified by trituration from $Et_2O$ to Example 8C (17 mg, 77%) as white solid. $^1$H NMR (400 MHz, $CDCl_3$) δ 2.84 (s, 3H), 4.39 and 4.46 ($AB_q$, J=16.7 Hz, 2H), 4.40 (dd, J=11.8, 6.6 Hz, 1H), 4.57 (dd, J=11.8, 4.8 Hz, 1H), 7.11 (t, J=7.5 Hz, 1H), 7.24 (d, J=8.3 Hz, 1H), 7.32 (dd, J=8.3, 7.5 Hz, 2H), 7.38 (dd, J=8.3, 2.2 Hz, 1H), 7.55 (d, J=2.2 H, 1H), 7.74 (d, J=7.5 Hz, 2H), $[M+H]^+$=399.06.

Example 8

3-(Aminomethyl)-4-(2,4-dichlorophenyl)-2-methyl-6-phenyl-5,6-dihydropyrrolo[3,4-b]pyridin-7-one, HCl salt

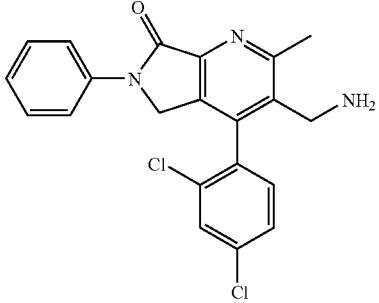

To a stirred solution of Example 8C (17 mg, 0.043 mmol) in $CH_2Cl_2$ (1 mL) was added MsCl (21 μL, 0.26 mmol) and $Et_3N$ (60 μL, 0.32 mmol). The reaction was kept at ambient temperature for 4 h and concentrated to give crude product which was diluted with EtOAc (10 mL) and washed with 0.1N aq HCl solution (2 mL). The organic phase was dried ($MgSO_4$) and concentrated in vacuo to give a chloride intermediate. A mixture of obtained chloride and 7N ammonia in MeOH (3 mL) in a sealed tube was irradiated in a microwave reactor at 100° C. for 15 min. After cooling down to ambient temperature, the volatiles were removed in vacuo. The crude product was purified by reverse-phase preparative HPLC to provide pure product. This product was redissolved in $CH_2Cl_2$ (2 mL) and 4N HCl in dioxane (10 μL) was added. The solvent was evaporated to dryness to give 3-(aminomethyl)-4-(2,4-dichlorophenyl)-2-methyl-6-phenyl-5,6-dihydropyrrolo[3,4-b]pyridin-7-one (Example 8), HCl salt (5.1 mg, 28% for 2 steps) as a white solid. $^1$H NMR (400 MHz, $CD_3OD$) δ 2.87 (s, 3H), 4.04 and 4.24 ($AB_q$, J=14.5 Hz, 2H), 4.63 and 4.78 ($AB_q$, J=17.0 Hz, 2H), 7.22 (t, J=7.5 Hz, 1H), 7.42 (dd, J=8.4, 7.5 Hz, 2H), 7.51 (d, J=8.4 Hz, 1H), 7.63 (dd, J=8.3, 2.2 Hz, 1H), 7.81-7.85 (m, 3H). HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, $R_f$=3.30 min, 99% homogeneity index. LCMS: Calculated for $C_{21}H_{17}Cl_2N_3O$: 397.08. Found: 398.06 [M+H]$^+$. HRMS: Calculated for $C_{21}H_{18}Cl_2N_3O$: 398.0827. Found: 398.0826 [M+H]$^+$.

Example 9

3-(Aminomethyl)-4-(2,4-dichlorophenyl)-6-(2-methoxyphenyl)-2-methyl-5,6-dihydropyrrolo[3,4-b]pyridin-7-one, HCl salt

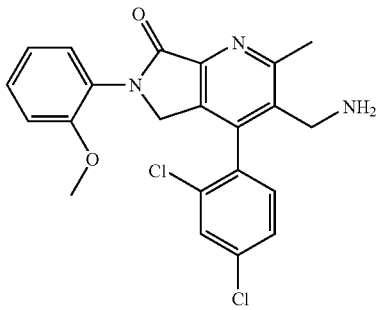

Example 9 was prepared using the same method described above for Example 8, with the exception that in step 8B phenylboronic acid was replaced with 2-methoxyphenylboronic acid. $^1$H NMR (400 MHz, CD$_3$OD) δ 2.89 (s, 3H), 3.80 (s, 3H), 4.04 and 4.26 (AB$_q$, J=14.5 Hz, 2H), 4.51 and 4.61 (AB$_q$, J=18.0 Hz, 2H), 7.00-7.17 (m, 2H), 7.35-7.43 (m, 2H), 7.50 (d, J=8.3 Hz, 1H), 7.59 (dd, J=8.3, 2.2 Hz, 1H), 7.79 (d, J=2.2 Hz, 1H). LCMS: Calculated for $C_{22}H_{19}Cl_2N_3O_2$: 427.09. Found: 427.94 [M+H]$^+$. HRMS: Calculated for $C_{22}H_{19}Cl_2N_3O_2$: 428.0933. Found: 428.0946 [M+H]$^+$.

Example 9 was separated on a Chiralcel® OJ, 20 µ, 5×50 cm column using an isocratic gradient of 15% EtOH-MeOH (50%) containing 0.1% diethylamine in heptane contaning 0.1% diethyl amine to afford individual enantiomers.

Example 9-1 (Enantiomer A; faster-moving): [α]$_D^{25}$−15.8° (c=0.2, MeOH); Purity by chiral analytical HPLC [Chiralcel® OJ 4.6×250 mm; 15% EtOH-MeOH (1:1; containing 0.1% DEA) in heptane (containing 0.1% DEA)]: 88% ee.

Example 9-2 (Enantiomer B; slower-moving): [α]$_D^{25}$+17.90 (c=0.2, MeOH); Purity by chiral analytical HPLC [Chiralcel® OJ 4.6×250 mm; 15% EtOH-MeOH (1:1; containing 0.1% DEA) in heptane (containing 0.1% DEA)]: 93% ee.

Example 10

(6-Benzyl-4-(2,4-dichlorophenyl)-2-methyl-6,7-dihydro-5H-pyrrolo[3,4-b]pyridin-3-yl)methanamine, HCl salt

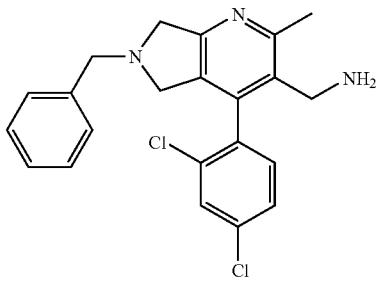

Example 10A (6-Benzyl-4-(2,4-dichlorophenyl)-2-methyl-6,7-dihydro-5H-pyrrolo[3,4-b]pyridin-3-yl)methanol

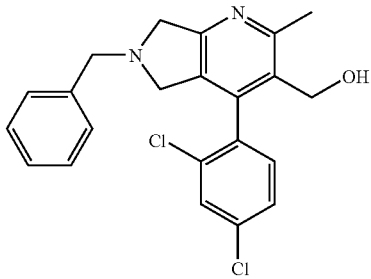

To a solution of Example 5D (0.360 g, 0.79 mmol) in THF (3.5 mL) was added LAH solution (5 mL, 1M in THF, 5 mmol) at 0° C. The mixture was allowed to warm to RT and stirred at RT for 1.5 h after which it was partitioned between water (5 mL) and EtOAc (150 mL). The organic phase was dried (MgSO$_4$) and concentrated in vacuo. The residue was chromatographed (SiO$_2$; continuous gradient from 100% hex to 100% EtOAc over 3 min, 100% EtOAc for 5 min) to give Example 10A (0.151 g; 48%) as a solid. $^1$H NMR (400 MHz, CDCl$_3$) δ 2.78 (s, 3H), 4.20-4.60 (m, 6H), 4.71 and 4.84 (AB$_q$, J=15.8 Hz, 2H), 7.19 (d, J=7.9 Hz, 1H), 7.47-7.53 (m, 6H), 7.78 (d, J=1.8 Hz, 1H). [M+H]$^+$=398.88.

Example 10

(6Benzyl-4-(2,4-dichlorophenyl)-2-methyl-6,7-dihydro-5H-pyrrolo[3,4-b]pyridin-3-yl)methanamine, HCl salt

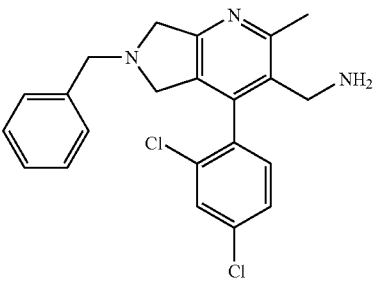

To a stirred solution of Example 10A (50 mg, 0.13 mmol) in CH$_2$Cl$_2$ (1.5 mL) was added MsCl (28 µL, 0.36 mmol) and Et$_3$N (53 µL, 0.39 mmol). The reaction was kept at ambient temperature for 2.5 h and concentrated to give a crude product which was subjected to flash chromatography (silica gel, 100% EtOAc to EtOAc/MeOH=95:5) to yield a chloride intermediate. A mixture of the obtained chloride and 7N ammonia in MeOH (3 mL) was irradiated in a sealed tube in a microwave reactor at 100° C. for 15 min. After cooling down to ambient temperature, the volatiles were removed in vacuo. The crude product was purified by reverse-phase preparative HPLC to provide pure product. This product was redissolved in CH$_2$Cl$_2$ (3 mL) and 4N HCl in dioxane (40 µL) was added. The solvent was evaporated to dryness to give (6-benzyl-4-(2,4-dichlorophenyl)-2-methyl-6,7-dihydro-5H-pyrrolo[3,4-b]pyridin-3-yl)methanamine (Example 10), HCl salt (21.1 mg, 35% for 2 steps) as a white solid. $^1$H NMR (400 MHz, CD$_3$OD) δ 2.75 (s, 3H), 3.89 and 4.15 (AB$_q$, J=14.5 Hz, 2H), 4.43 and 4.56 (AB$_q$, J=14.5 Hz, 2H), 4.63 (s, 2H), 4.75 (s, 2H), 7.43 (d, J=8.3 Hz, 1H), 7.47-7.53 (m, 3H), 7.54-7.58 (m, 2H), 7.69 (dd, J=8.3, 2.2 Hz, 1H), 7.78 (d, J=2.2 Hz, 1H). HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, $R_f$=2.10 min, 99% homogeneity index. LCMS: Calculated for $C_{22}H_{21}Cl_2N_3$: 397.11. Found: 398.09 [M+H]$^+$. HRMS: Calculated for $C_{22}H_{22}Cl_2N_3$: 398.1191. Found: 398.1175 [M+H]$^+$.

Example 11

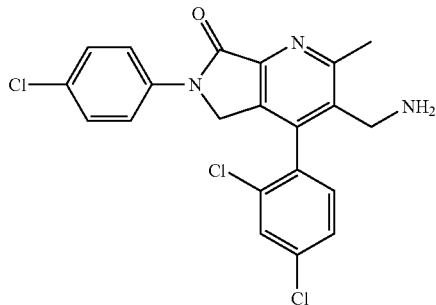

Example 11A tert-Butyl (6-(4-methoxybenzyl)-4-(2,4-dichlorophenyl)-2-methyl-7-oxo-6,7-dihydro-5H-pyrrolo[3,4-b]pyridin-3-yl)methylcarbamate (a novel intermediate)

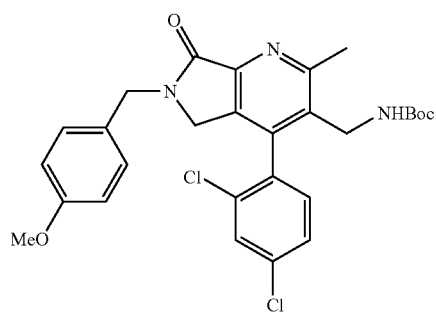

To a mixture of Example 6 (2.41 g, 5.47 mmol) in THF (50 mL) was added sat. aq. NaHCO$_3$ (15 mL), H$_2$O (5 mL), and Boc$_2$O (1.79 g, 8.20 mmol). The resulting mixture was stirred at RT overnight, diluted with EtOAc (100 mL) and stirred for a further 5 min. The organic layer was separated and evaporated in vacuo to yield a crude product which was recrystallized from EtOAc/Hexanes to give Example 11A as a white solid (2.33 g, 79%).

Example 11B tert-Butyl (4-(2,4-dichlorophenyl)-2-methyl-7-oxo-6,7-dihydro-5H-pyrrolo[3,4-b]pyridin-3-yl)methylcarbamate

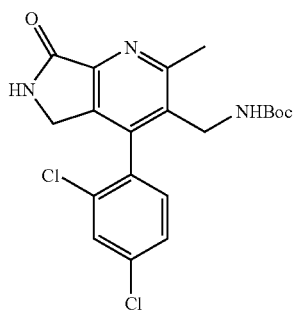

To a mixture of Example 11A (1.99 g, 3.68 mmol) in CH$_3$CN (80 mL) was added aq. ceric ammonium nitrate (5.76 g, 10.51 mmol). The resulting mixture was stirred at RT for 6 h and then allowed to stand in a refrigerator overnight. Solids were filtered and washed with H$_2$O (20 mL). The solids were further dispersed in EtOAc (80 mL), sonicated, and filtered to afford the desired product (Example 11B) as a beige solid. The filtrate was concentrated, treated with EtOAc (30 mL), and filtered to yield a second portion of Example 11B (total 1.44 g, 93%).

Example 11C tert-Butyl (6-(4-chlorophenyl)-4-(2,4-dichlorophenyl)-2-methyl-7-oxo-6,7-dihydro-5H-pyrrolo[3,4-b]pyridin-3-yl)methylcarbamate

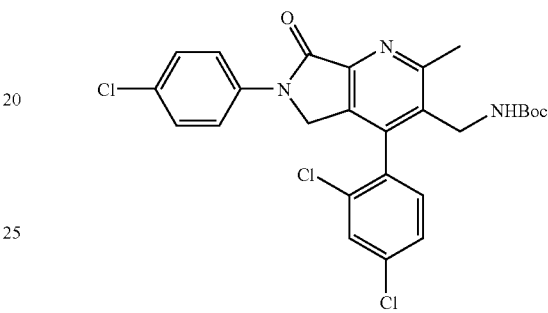

A mixture of Example 11B (29.8 mg, 0.071 mmol), 4-chlorophenylboronic acid (45 mg, 0.288 mmol), Cu(OAc)$_2$ (24 mg, 0.132 mmol), Et$_3$N (45 µL, 0.324 mmol), pyridine (60 µL, 0.743 mmol), and dichloroethane (1 mL) was heated at 75° C. for 1.5 h. Concentration in vacuo followed by flash chromatography (50% to 100% EtOAc/Hexanes) to yield a Example 11C which was further purified by recrystallization fom MeOH to give 23 mg (61%) of a solid.

Example 11

3-(Aminomethyl)-6-(4-chlorophenyl)-4-(2,4-dichlorophenyl)-2-methyl-5,6-dihydropyrrolo[3,4-b]pyridin-7-one, HCl salt

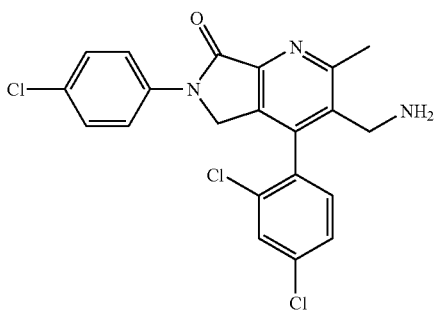

To a solution of Example 11C (20 mg, 0.038 mmol) in CH$_2$Cl$_2$ (1.2 mL) was added TFA (0.8 mL) and the resulting mixture stirred for 3 h. The reaction mixture was evaporated to dryness, redissolved in CH$_2$Cl$_2$ (1 mL) and 4N HCl/dioxane (40 µL) was added. The solvents were evaporated and the residue triturated with ether to yield Example 11 (10.0 mg, 57%). $^1$H NMR (400 MHz, CD$_3$OD) δ 2.78 (s, 3H), 3.96 and 4.17 (AB$_q$, J=14.5 Hz, 2H), 4.55 and 4.69 (AB$_q$, J=17.1 Hz, 2H), 7.30-7.35 (m, 2H), 7.40-7.45 (m, 1H), 7.55 (dd, J=8.3, 1.8 Hz, 1H), 7.74 (d, J=1.8 Hz, 1H), 7.76-7.81 (m, 2H). LCMS: Calculated for $C_{21}H_{16}Cl_3N_3O$: 431.04. Found: 431.98 [M+H]$^+$. HRMS: Calculated for $C_{21}H_{17}Cl_3N_3O$: 432.0437. Found: 432.0435 [M+H]$^+$.

Example 12

3-(Aminomethyl)-4-(2,4-dichlorophenyl)-2-methyl-5,6-dihydropyrrolo[3,4-b]pyridin-7-one, HCl salt

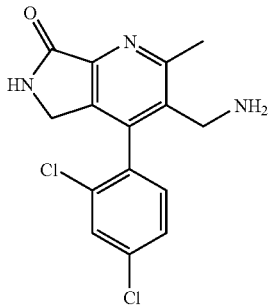

To a mixture of Example 11B (8.9 mg, 0.021 mmol) in $CH_2Cl_2$ (1 mL) was added TFA (0.5 mL) and the resulting mixture was stirred for 3 h at RT. The reaction mixture was evaporated in vacuo, the residue was redissolved in $CH_2Cl_2$ (1 mL) and 4N HCl/dioxane (40 μl) was added. The solvents were evaporated to dryness to yield Example 12 as a white solid (7.24 mg, 96%). $^1H$ NMR (400 MHz, $CD_3OD$) δ 2.76 (s, 3H), 3.92 and 4.14 ($AB_q$, J=14.0 Hz, 2H), 4.00 and 4.13 ($AB_q$, J=18.8 Hz, 2H), 7.38 (d, J=8.3 Hz, 1H), 7.51 (dd, J=8.3, 2.2 Hz, 1H), 7.70 (d, J=1.6 Hz, 1H). LCMS: Calculated for $C_{15}H_{13}Cl_2N_3O$: 321.04. Found: 322.02 $[M+H]^+$. HRMS: Calculated for $C_{15}H_{14}Cl_2N_3O$: 322.0514. Found: 322.0524 $[M+H]^+$.

Example 13

3-(Aminomethyl)-4-(2,4-dichlorophenyl)-2-methyl-6-p-tolyl-5,6-dihydropyrrolo[3,4-b]pyridin-7-one, HCl salt

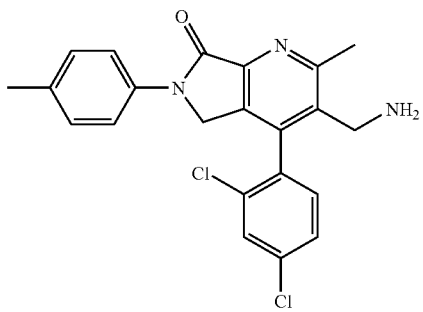

Example 13 was prepared using the same method described above for Example 11, with the exception that in step 11C 4-chlorophenylboronic acid was replaced with 4-methylphenylboronic acid. $^1H$ NMR (400 MHz, $CD_3OD$) δ 2.24 (s, 3H), 2.81 (s, 3H), 3.96 and 4.20 ($AB_q$, J=14.5 Hz, 2H), 4.53 and 4.68 ($AB_q$, J=17.6 Hz, 2H), 7.13-7.18 (m, 2H), 7.47-7.50 (m, 1H), 7.55 (dd, J=7.9, 1.8 Hz, 1H), 7.58-7.63 (m, 2H), 7.73 (d, J=1.8 Hz, 1H). LCMS: Calculated for $C_{22}H_{19}Cl_2N_3O$: 411.09. Found: 412.04 $[M+H]^+$. HRMS: Calculated for $C_{22}H_{20}Cl_2N_3O$: 412.0983. Found: 412.0993 $[M+H]^+$.

Example 14

3-(Aminomethyl)-4-(2,4-dichlorophenyl)-6-(4-methoxyphenyl)-2-methyl-5,6-dihydropyrrolo[3,4-b]pyridin-7-one, HCl salt

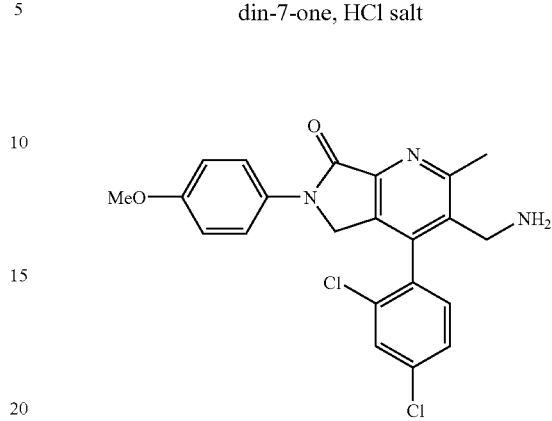

Example 14 was prepared using the same method described above for Example 11, with the exception that in step 11C 4-chlorophenylboronic acid was replaced with 4-methoxyphenylboronic acid. $^1H$ NMR (400 MHz, $CD_3OD$) δ 2.86 (s, 3H), 3.79 (s, 3H), 4.03 and 4.25 ($AB_q$, J=14.5 Hz, 2H), 4.58 and 4.74 ($AB_q$, J=17.6 Hz, 2H), 6.90-7.00 (m, 2H), 7.51 (d, J=8.3 Hz, 1H), 7.63 (dd, J=8.3, 2.2 Hz, 1H), 7.68-7.71 (m, 2H), 7.81 (d, J=2.2 Hz, 1H). LCMS: Calculated for $C_{21}H_6Cl_3N_3O$: 427.09. Found: 428.05 $[M+H]^+$. HRMS: Calculated for $C_{21}H_{17}Cl_3N_3O$: 428.0933. Found: 428.0941 $[M+H]^+$.

Example 15

3-(Aminomethyl)-4-(2,4-dichlorophenyl)-6-(4-fluorophenyl)-2-methyl-5,6-dihydropyrrolo[3,4-b]pyridin-7-one, HCl salt

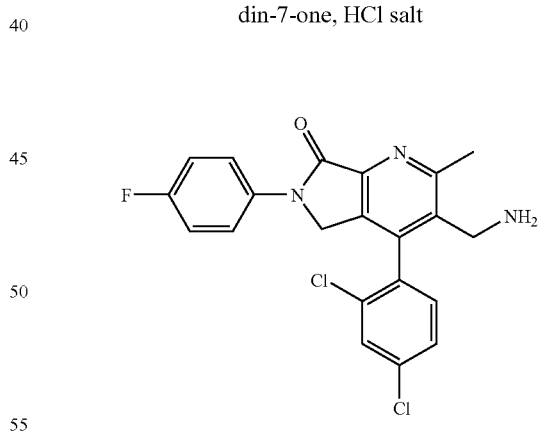

Example 15 was prepared using the same method described above for Example 11, with the exception that in step 11C 4-chlorophenylboronic acid was replaced with 4-fluorophenylboronic acid. $^1H$ NMR (400 MHz, $CD_3OD$) δ 2.89 (s, 3H), 4.05 and 4.27 ($AB_q$, J=14.3 Hz, 2H), 4.64 and 4.80 ($AB_q$, J=17.6 Hz, 2H), 7.12-7.18 (m, 2H), 7.54 (d, J=8.3 Hz, 1H), 7.63 (dd, J=8.3, 2.2 Hz, 1H), 7.82 (d, J=1.6 Hz, 1H), 7.83-7.87 (m, 2H). LCMS: Calculated for $C_{21}H_{16}Cl_2N_3OF$: 415.07. Found: 416.02 $[M+H]^+$. HRMS: Calculated for $C_{21}H_{17}Cl_2N_3OF$: 416.0733. Found: 416.0743 $[M+H]^+$.

Example 16

4-(3-(Aminomethyl)-4-(2,4-dichlorophenyl)-2-methyl-7-oxo-5H-pyrrolo[3,4-b]pyridin-6(7H)-yl)benzonitrile, HCl salt

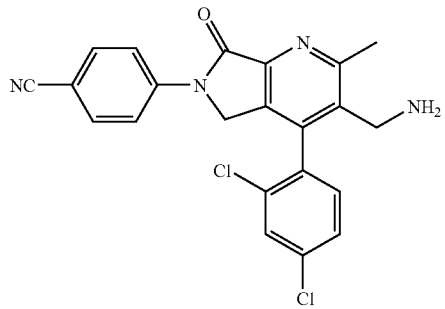

Example 16 was prepared using the same method described above for Example 11, with the exception that in step 11C 4-chlorophenylboronic acid was replaced with 4-cyanophenylboronic acid. $^1$H NMR (400 MHz, CD$_3$OD) δ 2.87 (s, 3H), 4.04 and 4.24 (AB$_q$, J=14.2 Hz, 2H), 4.69 and 4.82 (AB$_q$, J=17.1 Hz, 2H), 7.50 (d, J=8.3 Hz, 1H), 7.64 (dd, J=8.3, 2.2 Hz, 1H), 7.74-7.78 (m, 2H), 7.84 (d, J=2.2 Hz, 1H), 8.10-8.15 (m, 2H). LCMS: Calculated for C$_{22}$H$_{16}$Cl$_2$N$_4$O: 422.07. Found: 422.93 [M+H]$^+$. HRMS: Calculated for C$_{22}$H$_{17}$Cl$_2$N$_4$O: 423.0779. Found: 423.0790 [M+H]$^+$.

Example 17

3-(Aminomethyl)-4-(2,4-dichlorophenyl)-2-methyl-6-o-tolyl-5,6-dihydropyrrolo[3,4-b]pyridin-7-one, HCl salt

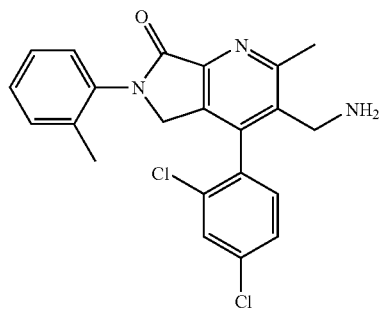

Example 17 was prepared using the same method described above for Example 8, with the exception that in step 8B phenylboronic acid was replaced with 2-methylphenylboronic acid. $^1$H NMR (400 MHz, CD$_3$OD) δ 2.20 (s, 3H), 2.88 (s, 3H), 4.04 and 4.25 (AB$_q$, J=14.2 Hz, 2H), 4.50 and 4.65 (AB$_q$, J=18.0 Hz, 2H), 7.25-7.40 (m, 4H), 7.51 (d, J=8.3 Hz, 1H), 7.60 (dd, J=8.3, 2.2 Hz, 1H), 7.79 (d, J=2.2 Hz, 1H), 8.10-8.15 (m, 2H). LCMS: Anal. Calculated for C$_{22}$H$_{19}$Cl$_2$N$_3$O: 411.09. Found: 412.04 [M+H]$^+$. HRMS: Calculated for C$_{22}$H$_{20}$Cl$_2$N$_3$O: 412.0983. Found: 412.0982 [M+H]$^+$.

Example 18

3-(Aminomethyl)-4-(2,4-dichlorophenyl)-2-methyl-6-(2-(methylthio)phenyl)-5,6-dihydropyrrolo[3,4-b]pyridin-7-one, HCl salt

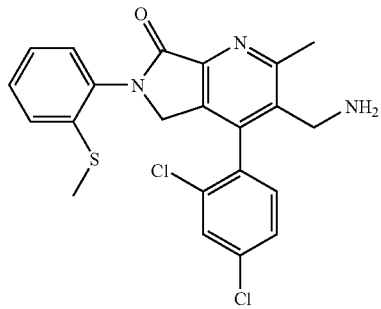

Example 18 was prepared using the same method described above for Example 8, with the exception that in step 8B phenylboronic acid was replaced with 2-methylthiophenylboronic acid. $^1$H NMR (400 MHz, CD$_3$OD) δ 2.43 (s, 3H), 2.88 (s, 3H), 4.03 and 4.25 (AB$_q$, J=14.5 Hz, 2H), 4.52 and 4.58 (AB$_q$, J=17.6 Hz, 2H), 7.24-7.35 (m, 2H), 7.42-7.46 (m, 2H), 7.48 (d, J=8.3 Hz, 1H), 7.60 (dd, J=8.3, 2.2 Hz, 1H), 7.79 (d, J=2.2 Hz, 1H). LCMS: Calculated for C$_{22}$H$_{19}$Cl$_2$N$_3$OS: 443.06. Found: 444.01 [M+H]$^+$. HRMS: Calculated for C$_{22}$H$_{19}$Cl$_2$N$_3$OS: 444.0704. Found: 444.0695 [M+H]$^+$.

Example 19

3-(Aminomethyl)-4-(2,4-dichlorophenyl)-6-(3-methoxyphenyl)-2-methyl-5,6-dihydropyrrolo[3,4-b]pyridin-7-one, HCl salt

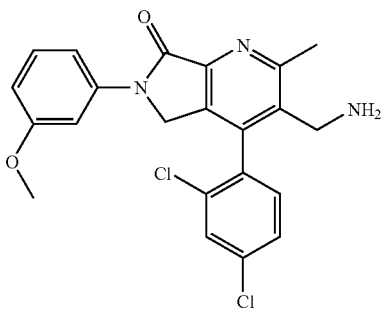

Example 19 was prepared using the same method described above for Example 11, with the exception that in step 11C 4-chlorophenylboronic acid was replaced with 3-methoxyphenylboronic acid. $^1$H NMR (400 MHz, CD$_3$OD) δ 2.86 (s, 3H), 3.80 (s, 3H), 4.03 and 4.24 (AB$_q$, J=14.5 Hz, 2H), 4.62 and 4.76 (AB$_q$, J=17.5 Hz, 2H), 6.80 (dt, J=7.0, 2.2 Hz, 1H), 7.26-7.35 (m, 2H), 7.50 (d, J=8.3 Hz, 1H), 7.56-7.60 (m, 1H), 7.63 (dd, J=8.3, 2.2 Hz, 1H), 7.82 (d, J=2.2 Hz, 1H). LCMS: Calculated for C$_{22}$H$_{19}$Cl$_2$N$_3$O$_2$: 427.09. Found: 428.04 [M+H]$^+$. HRMS: Calculated for C$_{22}$H$_{20}$Cl$_2$N$_3$O$_2$: 428.0933. Found: 428.0935 [M+H]$^+$.

Example 20

3-(Aminomethyl)-4-(2,4-dichlorophenyl)-2-methyl-6,7-dihydropyrrolo[3,4-b]pyridin-5-one, TFA salt

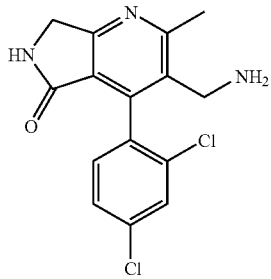

Example 20 was prepared using the same method described above for Example 2, with the exception that in step 2E 4-methoxybenzenamine was replaced with 7N $NH_3$ in MeOH. $^1$H NMR (400 MHz, $CDCl_3$) δ 2.84 (s, 3H), 3.95 and 4.19 ($AB_q$, J=14.9 Hz, 2H), 4.49 (s, 2H), 7.33 (d, J=8.4 Hz, 1H), 7.48-7.55 (m, 1H), 7.66-7.72 (m, 1H). HRMS: Calculated for $C_{15}H_{14}Cl_2N_3O$: 322.0514. Found: 322.0512. $[M+H]^+$=322.03.

Example 21

3-(Aminomethyl)-4-(2,4-dichlorophenyl)-6-(2-methoxyethyl)-2-methyl-6,7-dihydropyrrolo[3,4-b]pyridin-5-one, TFA salt

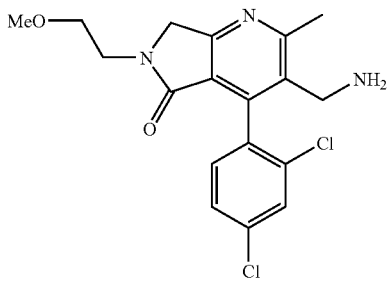

Example 21 was prepared using the same method described above for Example 2, with the exception that in step 2E, 4-methoxybenzenamine was replaced with 2-methoxyethylamine. $^1$H NMR (400 MHz, $CDCl_3$) δ 2.83 (s, 3H), 3.34 (s, 3H), 3.58-3.63 (m, 2H), 3.65-3.78 (m, 2H), 3.95 and 4.18 ($AB_q$, J=14.5 Hz, 2H), 4.62 (s, 2H), 7.33 (d, J=8.4 Hz, 1H), 7.52 (dd, J=8.1, 2.0 Hz, 1H), 7.70 (d, J=2.2 Hz, 1H). HRMS: Calculated for $C_{18}H_{20}Cl_2N_3O_2$: 380.0933. Found: 380.0941. $[M+H]^+$=379.91.

Example 22

3-(Aminomethyl)-4-(2,4-dichlorophenyl)-2,6-dimethyl-5,6-dihydropyrrolo[3,4-b]pyridin-7-one, HCl salt

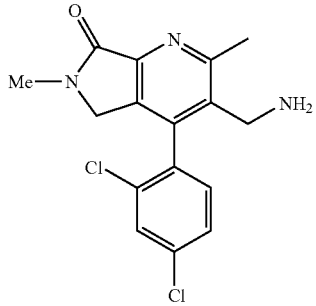

Example 22A

Methyl 4-(2,4-dichlorophenyl)-2,6-dimethyl-7-oxo-6,7-dihydro-5H-pyrrolo[3,4-b]pyridine-3-carboxylate

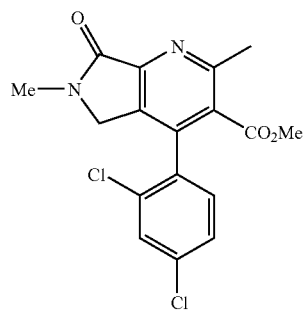

To a mixture of Example 8A (50 mg, 0.14 mmol) in DMF (0.8 mL) was added 95% NaH (6.2 mg, 0.26 mmol) and the resulting mixture stirred at r.t. for 15 min. The reaction mixture was allowed to stir for 5 h and then quenched with aq. NH4Cl. The mixture was extracted with EtOAc (×2) and the organic layer evaporated in vacuo to yield a crude product mixture which was purified by flash chromatography (50 to 100% EtOAc/Hexanes) to afford 37 mg (71%) of Example 22A as a colorless oil.

Example 22

3-Aminomethyl)-4-(2,4-dichlorophenyl)-2,6-dimethyl-5,6-dihydropyrrolo[3,4-b]pyridin-7-one, TFA salt

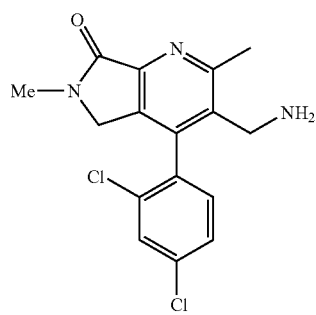

Example 22A was transformed to Example 22 using a sequence analogous to the one used for the conversion of Example 8B to Example 8. $^1$H NMR (400 MHz, $CDCl_3$) δ 2.80 (s, 3H), 3.14 (s, 3H), 3.98 and 4.16 ($AB_q$, J=14.4 Hz, 2H), 4.13 and 4.24 ($AB_q$, J=18.0 Hz, 2H), 7.41 (d, J=8.3 Hz, 1H), 7.56 (dd, J=8.3, 2.2 Hz, 1H), 7.75 (d, J=2.2 Hz, 1H). LCMS: Anal. Calcd. for $C_{16}H_{15}Cl_2N_3O$: 335.06. Found: 336.06 $[M+H]^+$. HRMS: Anal. Calcd. for $C_{16}H_{15}Cl_2N_3O$: 336.0670. Found: 336.0684 $[M+H]^+$.

Example 23

Methyl 2-(3-(aminomethyl)-4-(2,4-dichlorophenyl)-2-methyl-7-oxo-5H-pyrrolo[3,4-b]pyridin-6(7H)-yl)acetate, TFA salt

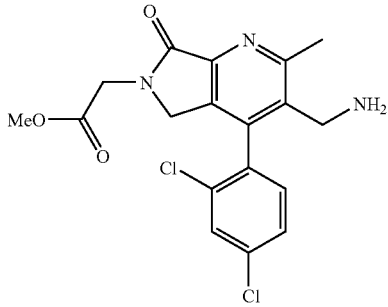

Example 23A

Methyl 2-(3-((tert-butoxycarbonyl)methyl)-4-(2,4-dichlorophenyl)-2-methyl-7-oxo-5H-pyrrolo[3,4-b]pyridin-6(7H)-yl)acetate

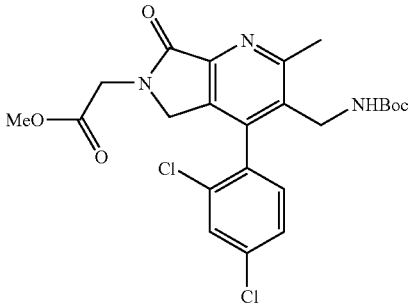

To a mixture of Example 11B (50 mg, 0.12 mmol) in DMF (1 mL) was added 95% NaH (2.8 mg, 0.11 mmol) and the mixture stirred at r.t. for 10 min and then sonicated for 30 sec. Methyl bomoacetate (0.025 mL, 0.26 mmol) was then added and th resulting mixture stirred overnight at r.t. Reaction mixture was quenched with 2 drops of 1N HCl and the mixuture evaporated in vacuo. The residue was taken up in EtOAc (10 mL) and washed with H$_2$O (2 mL). The organic layer was separated and evaporated in vacuo to give a crude product mixture which was purified by flash chromatography (100% EtOAc to 10% MeOH/EtOAc) to afford Example 23A (21 mg, 36%) a a colorless oil. $^1$H NMR (400 MHz, CDCl$_3$) δ 2.84 (s, 3H), 3.73 (s, 3H), 4.02 and 4.25 (AB$_q$, J=14.5 Hz, 2H), 4.25 and 4.34 (AB$_q$, J=17.6 Hz, 2H), 4.39 and 4.45 (AB$_q$, J=18.0 Hz, 2H), 7.45 (d, J=8.3 Hz, 1H), 7.57 (dd, J=8.3, 2.2 Hz, 1H), 7.79 (d, J=2.2 Hz, 1H). LCMS: Anal. Calcd. for C$_{18}$H$_{17}$Cl$_2$N$_3$O$_3$: 393.06. Found: 394.06 [M+H]$^+$.

Example 23

Methyl 2-(3-(aminomethyl)-4-(2,4-dichlorophenyl)-2-methyl-7-oxo-5H-pyrrolo[3,4-b]pyridin-6(7H)-yl)acetate, TFA salt

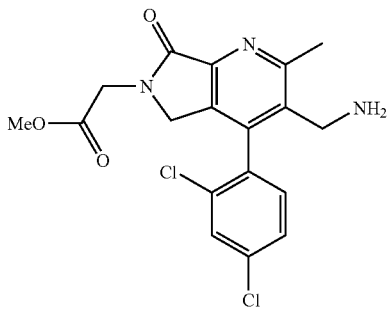

To a solution of Example 23A (21 mg, 0.042 mmol) in CH$_2$Cl$_2$ (0.7 mL) was added TFA (0.3 mL) and the resulting mixture stirred for 2 h. Solvents were removed and the residue purified by prep HPLC (Phenomenex, 10 min gradient, 30 to 100% B) to give Example 23. TFA salt (16.8 mg, 71%) as a white powder. $^1$H NMR (400 MHz, CDCl$_3$) δ. HRMS: Calculated for C$_{18}$H$_{18}$Cl$_2$N$_3$O$_3$: 394.0725. Found: 394.0728 [M+H]$^+$; [M+H]$^+$=394.06.

Example 24

3-(3-(Aminomethyl)-4-(2,4-dichlorophenyl)-2-methyl-7-oxo-5H-pyrrolo[3,4-b]pyridin-6(7H)-yl)benzonitrile, HCl salt

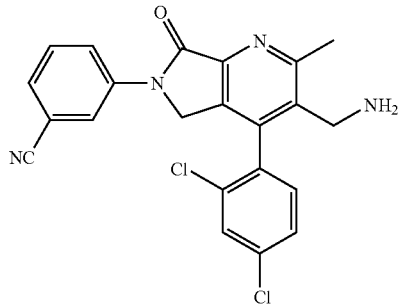

Example 14 was prepared using the same method described above for Example 11, with the exception that in step 11C 4-chlorophenylboronic acid was replaced with 3-cyanophenylboronic acid. $^1$H NMR (400 MHz, CD$_3$OD) δ 2.88 (s, 3H), 4.04 and 4.26 (AB$_q$, J=14.5 Hz, 2H), 4.70 and 4.84 (AB$_q$, J=17.1 Hz, 2H), 7.53 (d, J=8.3 Hz, 1H), 7.54-7.62 (m, 2H), 7.64 (dd, J=8.3, 2.2 Hz, 1H), 7.82 (d, J=2.2 Hz, 1H), 8.12 (dt, J=8.8, 1.8 Hz, 1H), 8.38-8.42 (m, 1H). LCMS: Anal. Calculated for C$_{22}$H$_{16}$Cl$_2$N$_4$O: 422.07. Found: 423.04 [M+H]$^+$. HRMS: Anal. Calculated for C$_{22}$H$_{17}$Cl$_2$N$_4$O: TBD. Found: TBD [M+H]$^+$.

Example 25

2-(3-(Aminomethyl)-4-(2,4-dichlorophenyl)-2-methyl-7-oxo-5H-pyrrolo[3,4-b]pyridin-6(7H)-yl)acetic acid, TFA salt

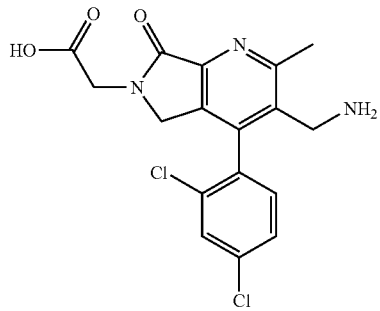

To a solution of Example 23A (50 mg, 0.10 mmol) in THF (1 mL) was added aqueous LiOH solution (14 mg in 0.8 mL H$_2$O, 0.33 mmol) and the resulting mixture stirred for 2 h. The mixture was acidified to pH=4 with 1N aqueous HCl. Organic volatiles were removed in vacuo and the aqueous phase was extracted with EtOAc (5 ml). The organic extracts was concentrated in vacuo to give the a carboxylic acid.

To a mixture of this carboxylic acid in CH$_2$Cl$_2$ (1 mL) was added TFA (0.35 mL) and the resulting mixture stirred for 2 h. Solvents were removed and the residue was purified by prep HPLC (Phenomenex, 10 min gradient, 15 to 100% B) to give Example 25. TFA salt (9.1 mg, 18%) as a white powder. $^1$H NMR (400 MHz, CD$_3$OD) δ 2.84 (s, 3H), 4.00 and 4.22 (AB$_q$, J=14.5 Hz, 2H), 4.26 and 4.34 (AB$_q$, J=18.0 Hz, 2H), 4.36 and 4.42 (AB$_q$, J=18.1 Hz, 2H), 7.44 (d, J=8.3 Hz, 1H), 7.60 (dd, J=8.3, 2.2 Hz, 1H), 7.80 (d, J=2.2 Hz, 1H). LCMS: Anal. Calculated for C$_{17}$H$_{15}$Cl$_2$N$_3$O$_3$: 379.05. Found: 380.00 [M+H]$^+$. HRMS: Anal. Calculated for C$_{17}$H$_{16}$Cl$_2$N$_3$O$_3$: TBD. Found: TBD [M+H]$^+$.

Example 26

3-(Aminomethyl)-4-(2,4-dichlorophenyl)-6-(2-hydroxyethyl)-2-methyl-5,6-dihydropyrrolo[3,4-b]pyridin-7-one, TFA salt

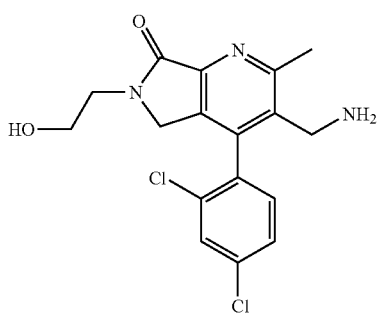

To a solution of Example 22A (172 mg, 0.15 mmol) in THF (3.5 mL) was added 2M LiBH$_4$/THF (0.2 mL, 0.4 mmol). The mixture was allowed to stir at ambient temperature for 2 h then quenched with saturated aqueous NaHCO$_3$ solution (0.5 mL). The reaction mixture was extracted with EtOAc (8 mL). The organic extracts were concentrated in vacuo. The residue was chromatographed (SiO$_2$; EtOAc) to give the desire alcohol product Part A (96 mg, 42%) as a colorless foam.

To a mixture of this alcohol product (35 mg, 0.075 mmol) in CH$_2$Cl$_2$ (1 mL) was added TFA (0.5 mL) and the resulting mixture stirred for 2 h. Solvents were removed and the residue was purified by prep HPLC (Phenomenex, 10 min gradient, 20 to 100% B) to give Example 26. TFA salt (9.0 mg, 25%) as a white powder. $^1$H NMR (400 MHz, CD$_3$OD) δ 2.83 (s, 3H), 3.69-3.73 (m, 2H), 3.74-3.79 (m, 2H), 4.01 and 4.23 (AB$_q$, J=14.8 Hz, 2H), 4.28 and 4.37 (AB$_q$, J=18.1 Hz, 2H), 7.45 (d, J=8.3 Hz, 1H), 7.59 (dd, J=8.3, 2.2 Hz, 1H), 7.80 (d, J=2.2 Hz, 1H). LCMS: Anal. Calculated. for C$_{17}$H$_{17}$Cl$_2$N$_3$O$_2$: 365.07. Found: 366.05 [M+H]$^+$. HRMS: Anal. Calculated. for C$_{17}$H$_{18}$Cl$_2$N$_3$O$_2$: TBD. Found: TBD [M+H]$^+$.

Example 27

3-(Aminomethyl)-4-(2,4-dichlorophenyl)-6-(2-methoxyethyl)-2-methyl-5,6-dihydropyrrolo[3,4-b]pyridin-7-one, TFA salt

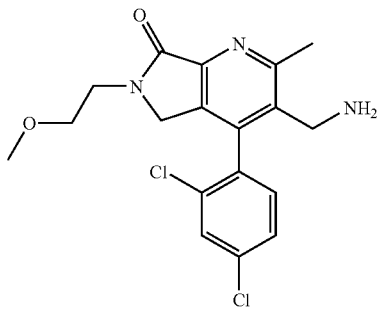

A mixture of Example 26 part A compound (420 mg, 0.875 mmol), Ag$_2$O (0.75 g, 3.25 mmol), iodomethane (0.55 mL, 8.74 mmol) in CH$_3$CN (10 ml) was stirred at ambient temperature for 5 days. The solid residue was removed via filtration. The filtrate was concentrated and chromatographed (SiO$_2$; EtOAc) to give the desire methyl ether product (103 mg, 24%) as colorless foam.

To a mixture of this methyl ether product (103 mg, 0.21 mmol) in CH$_2$Cl$_2$ (1.4 mL) was added TFA (0.6 mL) and the resulting mixture stirred for 2 h. Solvents were removed and the residue purified by prep HPLC (Phenomenex, 10 min gradient, 20 to 100% B) to give Example 27. TFA salt (17.3 mg, 16%) as a white powder. $^1$H NMR (400 MHz, CD$_3$OD) δ 2.83 (s, 3H), 3.30 (s, 3H), 3.61 (t, J=5.3 Hz, 2H), 3.78 (t, J=5.3 Hz, 2H), 4.02 and 4.25 (AB$_q$, J=14.5 Hz, 2H), 4.24 and 4.34 (AB$_q$, J=18.3 Hz, 2H), 7.46 (d, J=8.3 Hz, 1H), 7.58 (dd, J=8.3, 2.2 Hz, 1H), 7.77 (d, J=2.2 Hz, 1H). LCMS: Anal. Calculated. for C$_{18}$H$_{19}$Cl$_2$N$_3$O$_2$: 379.09. Found: 380.11 [M+H]$^+$. HRMS: Anal. Calculated. for C$_{18}$H$_{20}$Cl$_2$N$_3$O$_2$: 380.0933. Found: 380.0938 [M+H]$^+$.

Example 28

Methyl 2-(3-(aminomethyl)-4-(2,4-dichlorophenyl)-2-methyl-5-oxo-5H-pyrrolo[3,4-b]pyridin-6(7H)-yl)acetate, TFA salt

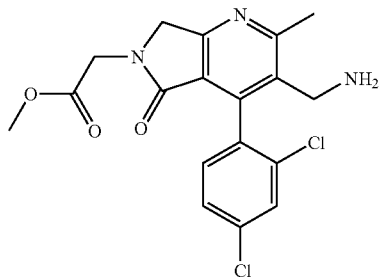

Example 28A

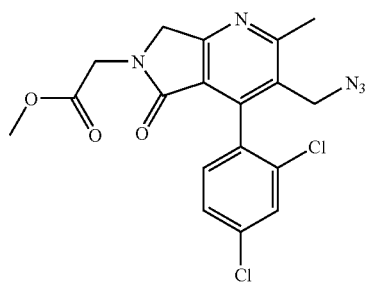

Example 28A was prepared using the same method described above for Example 1G with the exception that 3-(chloromethyl)-4-(2,4-dichlorophenyl)-2,7-dimethyl-6-phenyl-6,7-dihydropyrrolo[3,4-b]pyridin-5-one was replaced with methyl 2-(3-(chloromethyl)-4-(2,4-dichlorophenyl)-2-methyl-5-oxo-5H-pyrrolo[3,4-b]pyridin-6(7H)-yl)acetate. $^1$H NMR (400 MHz, CDCl$_3$): δ 2.82 (s, 3H), 3.74 (s, 3H), 4.25 and 4.42 (AB$_q$, J=17.6 Hz, 2H), 4.24 and 4.31 (AB$_q$, J=13.6 Hz, 2H), 4.56 and 4.61 (AB$_q$, J=17.6 Hz, 2H), 7.19 (d, J=8.4 Hz, 1H), 7.40 (dd, J=8.4, 2.2 Hz, 1H), 7.55 (d, J=2.2 Hz, 1H). LCMS: 420.03 [M+H]$^+$.

Example 28

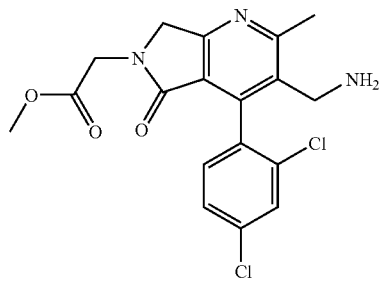

Example 28A (15 mg, 0.036 mmol), Ph₃P (23 mg, 2.5 mmol), THF (1 mL), and H₂O (0.5 mL) were stirred at RT for 4 h. The reaction mixture was filtered, washed with MeOH, evaporated and the residue purified by preparative HPLC (Phenomenex LUNA 5μ C18(2) 21.2×100 mm; 8 min gradient; 20 to 100% B; 20 mL/min) to afford Example 28 TFA salt (1.94 mg, 10%) as a colorless oil. $^1$H NMR (400 MHz, CD₃OD) δ 2.85 (s, 3H), 3.75 (s, 3H), 3.97 and 4.20 (AB$_q$, J=14.4 Hz, 2H), 4.33 and 4.41 (AB$_q$, J=17.9 Hz, 2H), 4.62 (s, 2H), 7.33 (d, J=8.3 Hz, 1H), 7.52 (dd, J=8.3, 2.0 Hz, 1H), 7.69 (d, J=2.0 Hz, 1H). LCMS: 394.01 [M+H]⁺. HRMS: Calculated. for C₁₈H₁₈Cl₂N₃O₃: 394.0725. Found: 394.0727 [M+H]⁺.

Example 29

3-(Aminomethyl)-4-(2,4-dichlorophenyl)-6-(3-methoxypropyl)-2-methyl-6,7-dihydropyrrolo[3,4-b]pyridin-5-one, TFA salt

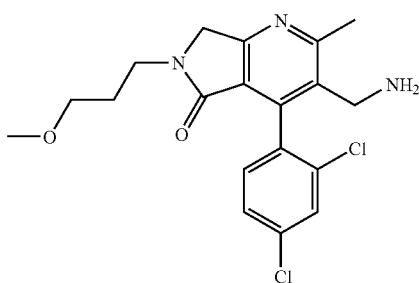

Example 29 was prepared using the same method described above for Example 2 with the exception that in step 2E, 4-methoxybenzeneamine was replaced by 3-methoxypropylamine. $^1$H NMR (400 MHz, CD₃OD) δ 1.85-1.95 (m, 2H), 2.83 (s, 3H), 3.27 (s, 3H), 3.41 (t, J=5.9 Hz, 2H), 3.63 (t, J=7.0 Hz, 2H), 3.94 and 4.13 (AB$_q$, J=14.4 Hz, 2H), 4.53 and 4.58 (AB$_q$, J=18.5 Hz, 2H), 7.33 (d, J=7.9 Hz, 1H), 7.52 (dd, J=8.4, 2.2 Hz, 1H), 7.69 (d, J=2.2 Hz, 1H). LCMS: 394.10 [M+H]⁺. HRMS: Anal. Calculated for C₁₉H₂₂Cl₂N₃O₂: 394.1089. Found: 394.1099 [M+H]⁺.

Example 30

3-(Aminomethyl)-4-((S)-2,4-dichlorophenyl)-6-((S)-1-methoxypropan-2-yl)-2-methyl-6,7-dihydropyrrolo[3,4-b]pyridin-5-one, TFA salt [Isomer A]

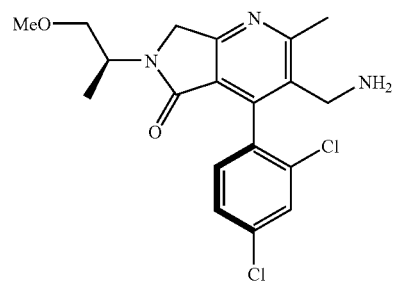

Example 30 was prepared using the same method described above for Example 2, with the exception that in step 2E, 4-methoxybenzenamine was replaced with (S)-1-methoxypropan-2-amine. Diastereomeric mixture was separated by preparative HPLC (Phenomenex, 10 min gradient, 10 to 100% B) to give Example 30. TFA salt and Example 31. TFA salt as white powders. Stereochemical assignment tentative.

Example 30. $^1$H NMR (400 MHz, CD₃OD) δ 1.26 (d, J=7.0 Hz, 3H), 2.83 (s, 3H), 3.32 (s, 3H), 3.49 (dd, J=10.1, 4.4 Hz, 1H), 3.59 (dd, J=12.1 Hz, 7.9 Hz, 1H), 3.95 and 4.18 (AB$_q$, J=14.5 Hz, 2H), 4.52-4.54 (m, 1H), 4.50 and 4.55 (AB$_q$, J=18.9 Hz, 2H), 7.32 (d, J=8.4 Hz, 1H), 7.52 (dd, J=8.4, 1.8 Hz, 1H), 7.70 (d, J=2.2 Hz, 1H). LCMS: 394.10 [M+H]⁺. HRMS: Calculated for C₁₉H₂₂Cl₂N₃O₂: 394.1089. Found: 394.1104 [M+H]⁺.

Example 31

3-(Aminomethyl)-4-((R)-2,4-dichlorophenyl)-6-((S)-1-methoxypropan-2-yl)-2-methyl-6,7-dihydropyrrolo[3,4-b]pyridin-5-one, TFA salt [Isomer B]

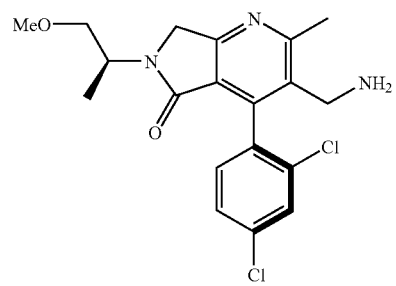

$^1$H NMR (400 MHz, CD₃OD) δ 1.27 (d, J=7.0 Hz, 3H), 2.83 (s, 3H), 3.31 (s, 3H), 3.49 (dd, J=10.1, 4.4 Hz, 1H), 3.59 (dd, J=10.1 Hz, 7.9 Hz, 1H), 3.94 and 4.18 (AB$_q$, J=14.5 Hz, 2H), 4.46-4.55 (m, 1H), 4.48 and 4.57 (AB$_q$, J=18.5 Hz, 2H), 7.33 (d, J=8.4 Hz, 1H), 7.52 (dd, J=8.4, 2.2 Hz, 1H), 7.70 (d, J=2.2 Hz, 1H). LCMS: 394.10 [M+H]⁺. HRMS: Calculated for C₁₉H₂₂Cl₂N₃O₂: 394.1089. Found: 394.1073 [M+H]⁺.

Example 32

Ethyl 3-(aminomethyl)-4-(2,4-dichlorophenyl)-2-methyl-5-oxo-5H-pyrrolo[3,4-b]pyridine-6(7H)-carboxylate, TFA salt

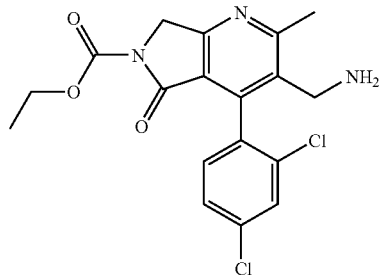

Example 32A tert-Butyl (4-(2,4-dichlorophenyl)-2-methyl-5-oxo-6,7-dihydro-5H-pyrrolo[3,4-b]pyridin-3-yl)methylcarbamate

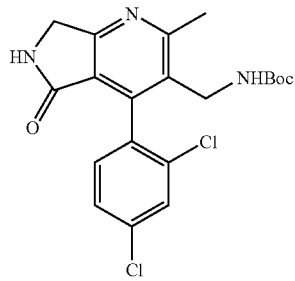

A mixture of Example 20 (47 mg, 0.096 mmol), 1M Boc$_2$O/THF (0.18 mL, 0.18 mmol), NaHCO$_3$ (160 mg, 1.9 mmol) and THF (5 mL) was stirred at RT overnight, taken up in EtOAc and H$_2$O and transferred to a separatory funnel. The aqueous layer was extracted with EtOAc (×2), washed with brine, dried (Na$_2$SO$_4$), filtered and evaporated to yield the crude product 32A which was used as such for the next step without purification. [M+H]$^+$=422.15.

Example 32B

Ethyl 3-((tert-butoxycarbonylamino)methyl)-4-(2,4-dichlorophenyl)-2-methyl-5-oxo-5H-pyrrolo[3,4-b]pyridine-6(7H)-carboxylate

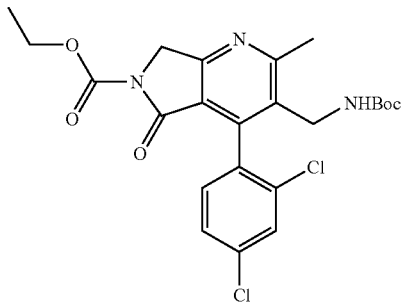

To a solution of the above crude product, Example 32A in CH$_2$Cl$_2$ (5 mL) was added Et$_3$N (0.1 mL, 0.72 mmol) followed by EtOCOCl (0.04 mL, 0.42 mmol) and the mixture was stirred at RT overnight. LC indicated ~10% conversion. DMAP (10 mg) followed by additional EtOCOCl (0.1 mL, 1.05 mmol) was added and mixture allowed to stir at RT overnight. Evaporation and flash chromatography (40 g silica, 0% to 100% EtOAc/Hexanes) yielded 18.5 mg of Example 32B as a colorless oil (39% for 2 steps). [M+H]$^+$=494.22.

Example 32

Ethyl 3-(aminomethyl)-4-(2,4-dichlorophenyl)-2-methyl-5-oxo-5H-pyrrolo[3,4-b]pyridine-6(7H)-carboxylate, TFA salt

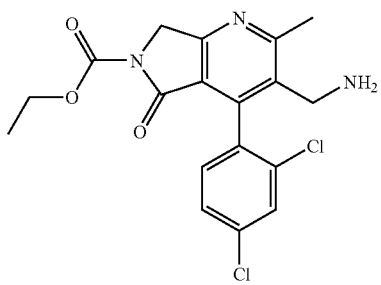

To a solution of Example 32B (18 mg, 0.046 mmol) in CH$_2$Cl$_2$ (1 mL) was added TFA (1 mL) dropwise and the mixture stirred at RT for 1 h. Mixture was evaporated and purified by PrepHPLC (Phenomenex LUNA 5μ C18(2) 21.2×100 mm; 8 min gradient; 0% to 100% B; 20 mL/min) to yield 16.8 mg (91%) of a white powder. $^1$H NMR (400 MHz, CD$_3$OD) δ 1.35 (t, J=7.3 Hz, 3H), 2.86 (s, 3H), 3.97 and 4.19 (AB$_q$, J=14.5 Hz, 1H), 4.33 (q, J=7.0 Hz, 2H), 4.84-4.95 (m, 2H), 7.32 (d, J=7.9 Hz, 1H), 7.54 (dd, J=8.4, 2.2 Hz, 1H), 7.72 (d, J=2.2 Hz, 1H). HRMS: Calculated for C$_{18}$H$_{18}$Cl$_2$N$_3$O$_3$: 394.0725. Found: 394.0726 [M+H]$^+$.

Example 33

(1R,2S)-2-((S)-3-(Aminomethyl)-4-(2,4-dichlorophenyl)-2-methyl-5-oxo-5H-pyrrolo[3,4-b]pyridin-6-(7H)-yl)cyclopentanecarbonitrile, TFA salt and (1R,2S)-2-((R)-3-(Aminomethyl)-4-(2,4-dichlorophenyl)-2-methyl-5-oxo-5H-pyrrolo[3,4-b]pyridin-6-(7H)-yl)cyclopentanecarbonitrile, TFA salt

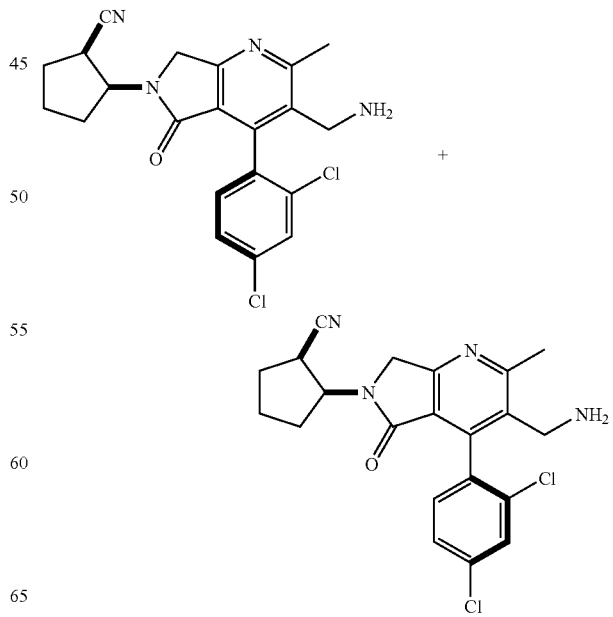

Example 33A (1R,2S)-2-((S)-4-(2,4-Dichlorophenyl)-3-(hydroxymethyl)-2-methyl-5-oxo-5H-pyrrolo[3,4-b]pyridin-6(7H)-yl)cyclopentanecarboxamide and (1R,2S)-2-((R)-4-(2,4-dichlorophenyl)-3-(hydroxymethyl)-2-methyl-5-oxo-5H-pyrrolo[3,4-b]pyridin-6(7H)-yl)cyclopentanecarboxamide

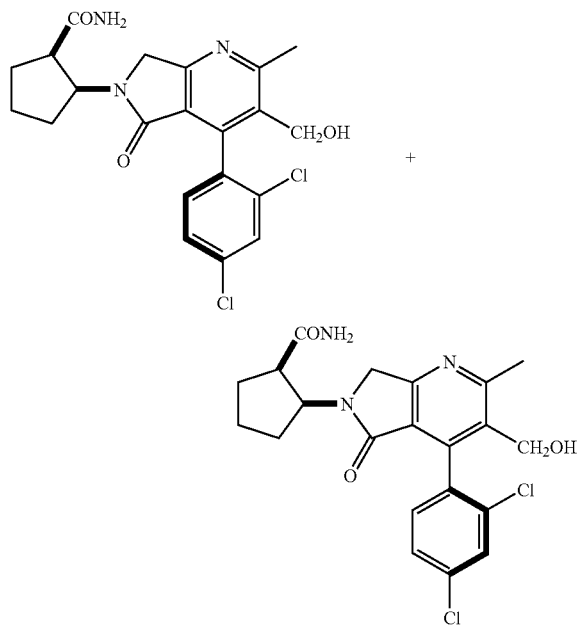

Example 33A, as a diastereomeric mixture, was prepared from Example 2D (racemic) and (±)-cis-2-aminocyclopentanecarboxamide following a sequence similar to Example 2G. [M+Na]$^+$=456.2.

Example 33B (1R,2S)-2-((R)-3-(Chloromethyl)-4-(2,4-dichlorophenyl)-2-methyl-5-oxo-5H-pyrrolo[3,4-b]pyridin-6(7H)-yl)cyclopentanecarbonitrile and (1R,2S)-2-((S)-3-(Chloromethyl)-4-(2,4-dichlorophenyl)-2-methyl-5-oxo-5H-pyrrolo[3,4-b]pyridin-6(7H)-yl)cyclopentanecarbonitrile

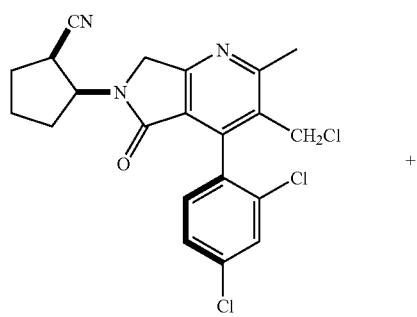

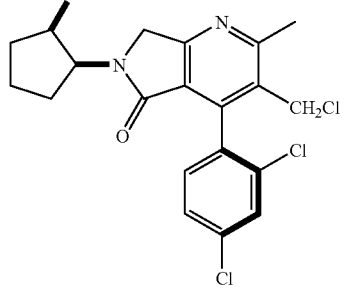

A mixture of crude Example 33A (0.22 mmol) was subjected to chlorination as in Example 2H to afford a diastereomeric mixture of chlorides (Example 33B) where the primary amide also dehydrated to the nitrile. Diastereomer 1: [M+H]$^+$=434.12. Diastereomer 2: [M+H]$^+$=434.13

Example 33

(1R,2S)-2-((S)-3-(Aminomethyl)-4-(2,4-dichlorophenyl)-2-methyl-5-oxo-5H-pyrrolo[3,4-b]pyridin-6(7H)-yl)cyclopentanecarbonitrile, TFA salt and (1R,2S)-2-((R)-3-(Aminomethyl)-4-(2,4-dichlorophenyl)-2-methyl-5-oxo-5H-pyrrolo[3,4-b]pyridin-6(7H)-yl)cyclopentanecarbonitrile, TFA salt

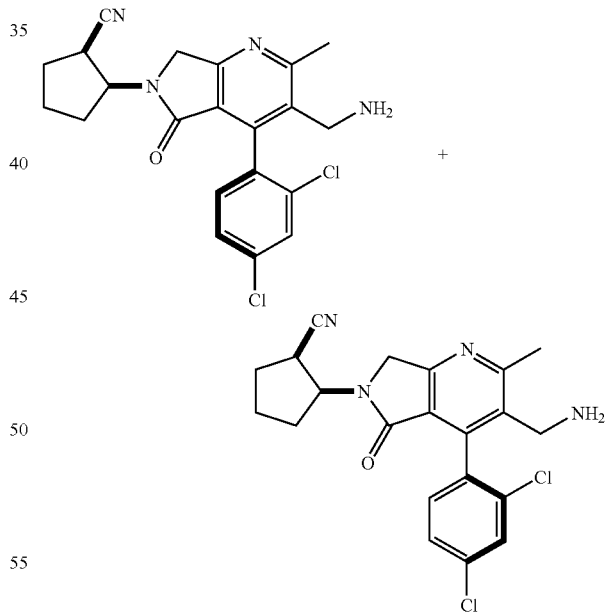

Ammonolysis as in Example 33B yielded a diastereomeric mixture of amines (Example 33). $^1$H NMR (400 MHz, CD$_3$OD) δ 1.66-1.84 (m, 1H), 1.97-2.27 (m, 5H), 2.85 (s, 3H), 3.35-3.47 (m, J=6.6 Hz, 1H), 3.94 and 4.21 (AB$_q$, J=14.5 Hz, 1H), 4.64-4.78 (m, 4H), 7.36 (d, J=8.4 Hz, 1H), 7.54 (dd, J=8.4, 1.8 Hz, 1H), 7.71 (d, J=2.2 Hz, 1H). HRMS: Calculated for C$_{21}$H$_{21}$Cl$_2$N$_4$O: 415.1092. Found: 415.1085 [M+H]$^+$.

Example 34

(1S,2R)-2-((S)-3-Aminomethyl)-4-(2,4-dichlorophenyl)-2-methyl-5-oxo-5H-pyrrolo[3,4-b]pyridin-6(7H)-yl)cyclopentanecarbonitrile, TFA salt and (1S,2R)-2-((R)-3-(Aminomethyl)-4-(2,4-dichlorophenyl)-2-methyl-5-oxo-5H-pyrrolo[3,4-b]pyridin-6(7H)-yl)cyclopentanecarbonitrile, TFA salt

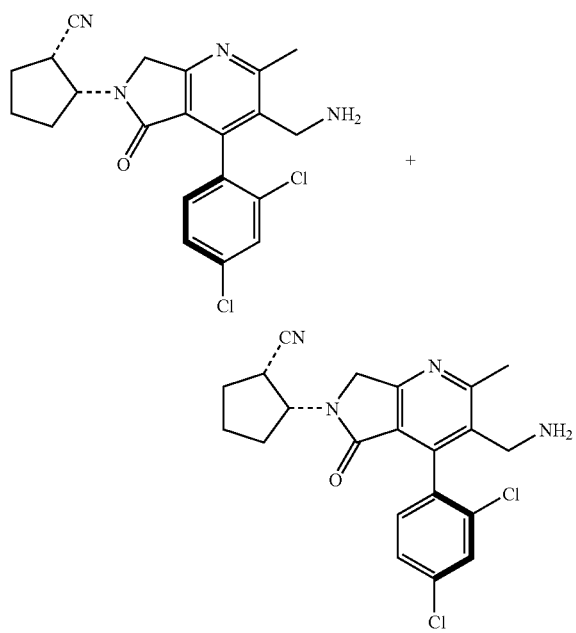

Example 34 was prepared as in Example 33 above except that diastereomer 2 from Example 33B was used. $^1$H NMR (400 MHz, CD$_3$OD) δ 1.66-1.80 (m, 1H), 1.99-2.26 (m, 5H), 2.84 (s, 3H), 3.38-3.49 (m, J=6.6 Hz, 1H), 3.98 and 4.17 (d, J=14.5 Hz, 1H), 4.68 (d, J=18.0 Hz, 1H), 4.75 (d, J=18.0 Hz, 1H), 7.32 (d, J=8.4 Hz, 1H), 7.52 (dd, J=8.4, 2.2 Hz, 1H), 7.71 (d, J=1.8 Hz, 1H). HRMS: Calculated for C$_{21}$H$_{21}$Cl$_2$N$_4$O: 415.1092. Found: 415.1084 [M+H]$^+$.

Example 35

(1R,3S)-Methyl 3-((S)-3-(aminomethyl)-4-(2,4-dichlorophenyl)-2-methyl-5-oxo-5H-pyrrolo[3,4-b]pyridin-6(7H)-yl)cyclopentanecarboxylate, TFA salt and (1R,3S)-Methyl 3-((R)-3-(aminomethyl)-4-(2,4-dichlorophenyl)-2-methyl-5-oxo-5H-pyrrolo[3,4-b]pyridin-6(7H)-yl)cyclopentanecarboxylate, TFA salt

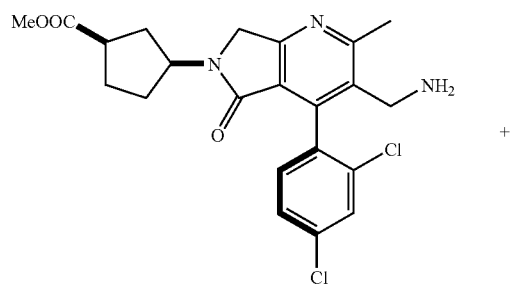

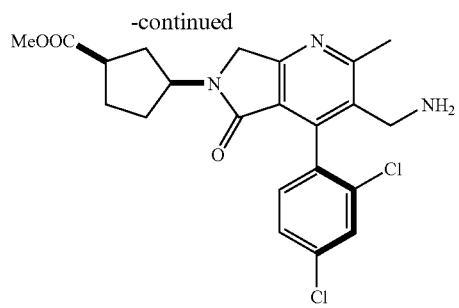

Example 35, as a mixture of diastereomers, was prepared from (1R,3S)-methyl 3-aminocyclopentanecarboxylate and racemic Example 2D using a sequence similar to the one used for Example 2. $^1$H NMR (400 MHz, CD$_3$OD, racemate) δ 1.75-2.10 (m, 5H), 2.14-2.32 (m, 1H), 2.83 (s, 3H), 2.89-3.02 (m, 1H), 3.67/3.69 (s, 3H), 3.94 and 4.18 (AB$_q$, J=14.5 Hz, 2H), 4.49-4.67 (m, 2H), 7.31 (d, J=8.4 Hz, 1H), 7.52 (dd, J=8.4, 1.8 Hz, 1H), 7.69 (d, J=2.2 Hz, 1H). HRMS: Calculated for C$_{22}$H$_{24}$Cl$_2$N$_3$O$_3$: 448.1195. Found: 448.1203 [M+H]$^+$.

Example 36

3-(3-(Aminomethyl)-4-(2,4-dichlorophenyl)-2-methyl-5-oxo-5H-pyrrolo[3,4-b]pyridin-6(7H)-yl)propanoic acid, TFA salt

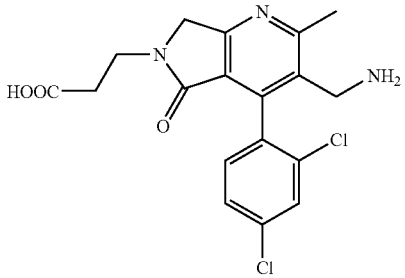

Example 36A

Benzyl 6-(3-tert-butoxy-3-oxopropyl)-4-(2,4-dichlorophenyl)-2-methyl-5-oxo-6,7-dihydro-5H-pyrrolo[3,4-b]pyridine-3-carboxylate

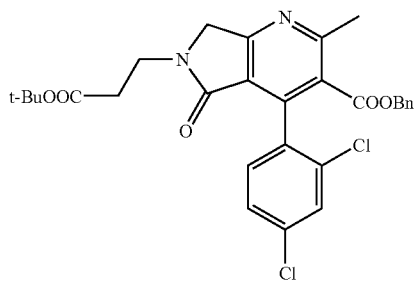

A mixture of racemic Example 2D (308 mg, 0.625 mmol), 3-aminopropionic acid t-butyl ester hydrochloride (143 mg, 0.79 mmol), Et$_3$N (0.25 mL, 1.8 mmol), and DMA (5 mL) was heated in a microwave reactor at 100° C. for 30 min. The reaction mixture was diluted with EtOAc (30 mL), washed with H$_2$O (30 mL×2), brine (30 mL), dried (Na$_2$SO$_4$), filtered and evaporated to yield a residue which was purified by flash chromatography (40 g silica, 0% to 100% EtOAc/Hexanes) to afford Example 36A (226 mg, 65%) as a colorless oil.

Example 36B tert-Butyl 3-(3-aminomethyl)-4-(2,4-dichlorophenyl)-2-methyl-5-oxo-5H-pyrrolo[3,4-b]pyridin-6(7H)-yl)propanoate

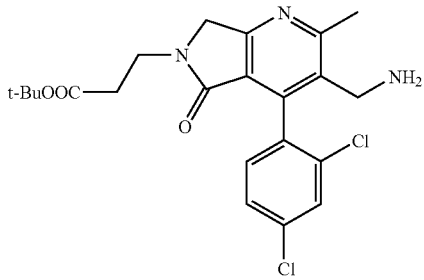

Example 36B was obtained from Example 36A as a crude free base following a sequence similar to one described for Example 2.

Example 36

3-(3-(Aminomethyl)-4-(2,4-dichlorophenyl)-2-methyl-5-oxo-5H-pyrrolo[3,4-b]pyridin-6(7H)-yl)propanoic acid, TFA salt

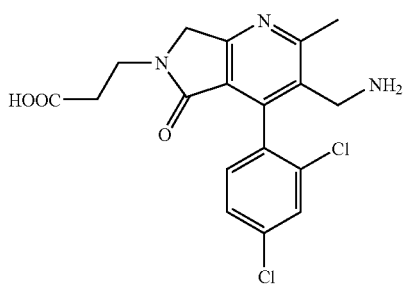

To a solution of crude Example 36B (0.17 mmol) in CH$_2$Cl$_2$ (5 mL) was added TFA (1 mL) dropwise at RT and the mixture stirred at RT for 2 h. Mixture was evaporated and purified by Preparative HPLC (Phenomenex LUNA 5µ C18 (2) 21.2×100 mm; 8 min gradient; 0% to 100% B; 20 mL/min) to yield 60.5 mg (70% for last 2 steps) of a white powder. $^1$H NMR (400 MHz, CD$_3$OD, racemate) δ 2.67 (t, J=6.8 Hz, 2H), 2.83 (s, 3H), 3.73-3.85 (m, 2H), 3.94 and 4.18 (AB$_q$, J=14.5 Hz, 2H), 4.62 (s, 2H), 7.32 (d, J=8.4 Hz, 1H), 7.52 (dd, J=8.1, 2.0 Hz, 1H), 7.70 (d, J=1.8 Hz, 1H). HRMS: Calculated for C$_{18}$H$_{18}$Cl$_2$N$_3$O$_3$: 394.0725. Found: 394.0735 [M+H]$^+$.

Example 37

(S)-3-(3-(Aminomethyl)-4-(2,4-dichlorophenyl)-2-methyl-5-oxo-5H-pyrrolo[3,4-b]pyridin-6(7H)-yl)propanoic acid, TFA salt

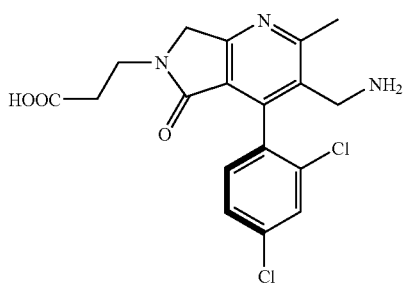

Example 37A (S)-3-Benzyl 5-ethyl 6-(chloromethyl)-4-(2,4-dichlorophenyl)-2-methylpyridine-3,5-dicarboxylate (a novel intermediate)

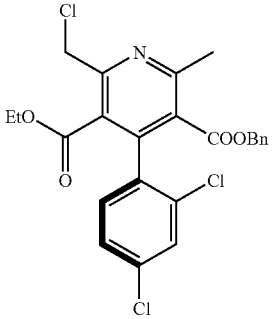

Example 2D was separated into individual atropisomers using Supercritical Fluid Chromatography (SFC). Conditions: Whelk 0-1 SS, 500×20 mm, 10 micron; 35° C.; 5% IPA with 0.1% DEA in SFC-CO$_2$; 100 bar; 60 mL/min; 220 nm. Faster-moving isomer: Example 37A. [α]$_D^{25}$+54.45° (c 10.21 mg/mL, CHCl$_3$)

Example 37B (R)-3-Benzyl 5-ethyl 6-(chloromethyl)-4-(2,4-dichlorophenyl)-2-methylpyridine-3,5-dicarboxylate (a novel intermediate)

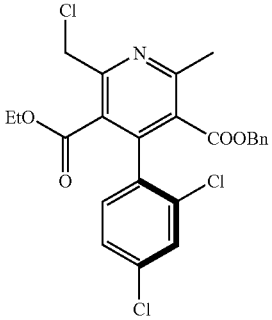

Slower-moving isomer from above SFC separation. [α]$_D^{25}$−52.87° (c 10.21 mg/mL, CHCl$_3$).

Example 37

(S)-3-(3-(Aminomethyl)-4-(2,4-dichlorophenyl)-2-methyl-5-oxo-5H-pyrrolo[3,4-b]pyridin-6(7H)-yl)propanoic acid, TFA salt

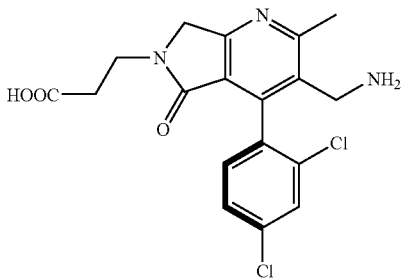

Example 37 was prepared using the sequence described for Example 36 except that Example 37A was used instead of racemic Example 2D.

Example 38

(S)-3-(Aminomethyl)-4-(2,4-dichlorophenyl)-6-(2-methoxyethyl)-2-methyl-6,7-dihydro-5H-pyrrolo[3,4-b]pyridin-5-one, TFA salt

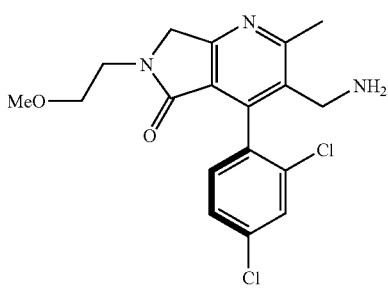

Example 38 was prepared using the sequence described for Example 21 except that Example 37A was used instead of racemic Example 2D. Chiral HPLC (Chiralpak AS 4.6×250 mm, 5% EtOH-MeOH (1:1) in heptane containing 0.1% DEA): Rt=14.3 min, >97% ee. $^1$H NMR (400 MHz, CD$_3$OD) δ 2.83 (s, 3H), 3.34 (s, 3H), 3.60 (t, J=5.3 Hz, 2H), 3.65-3.80 (m, 2H), 3.95 and 4.18 (AB$_q$, J=14.5 Hz, 2H), 4.62 (s, 2H), 7.33 (d, J=8.4 Hz, 1H), 7.52 (dd, J=8.1, 2.0 Hz, 1H), 7.69 (d, J=2.2 Hz, 1H). HRMS: Calculated for C$_{18}$H$_{20}$Cl$_2$N$_3$O$_2$: 380.0933. Found: 380.0929 [M+H]$^+$.

Example 39

(R)-3-(Aminomethyl)-4-(2,4-dichlorophenyl)-6-(2-methoxyethyl)-2-methyl-6,7-dihydro-5H-pyrrolo[3,4-b]pyridin-5-one, TFA salt

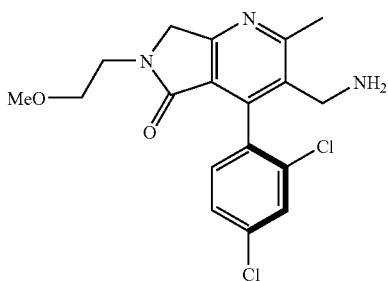

Example 39 was prepared using the sequence described for Example 21 except that Example 37B was used instead of racemic Example 2D. Chiral HPLC (Chiralpak AS 4.6×250 mm, 5% EtOH-MeOH (1:1) in heptane containing 0.1% DEA): Rt=16.2 min, >97% ee. $^1$H NMR (400 MHz, CD$_3$OD) δ 2.83 (s, 3H), 3.34 (s, 3H), 3.60 (t, J=5.1 Hz, 2H), 3.65-3.80 (m, 2H), 3.95 and 4.19 (AB$_q$, J=14.5 Hz, 2H), 4.62 (s, 2H), 7.33 (d, J=8.4 Hz, 1H), 7.52 (dd, J=8.4, 2.2 Hz, 1H), 7.69 (d, J=1.8 Hz, 1H). HRMS: Calculated for C$_{18}$H$_{20}$Cl$_2$N$_3$O$_2$: 380.0933. Found: 380.0931 [M+H]$^+$.

Example 40

N—((S)-1-(3-((S)-3-(Aminomethyl)-4-(2,4-dichlorophenyl)-2-methyl-5-oxo-5H-pyrrolo[3,4-b]pyridine-6(7H)-yl)propanoyl)pyrrolidin-3-yl)acetamide, TFA salt

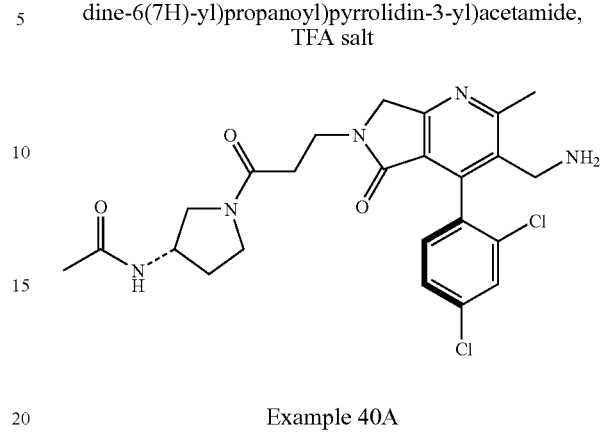

Example 40A (S)-3-(3-((tert-Butoxycarbonylamino)methyl)-4-(2,4-dichlorophenyl)-2-methyl-5-oxo-5H-pyrrolo[3,4-b]pyridin-6(7H)-yl)propanoic acid

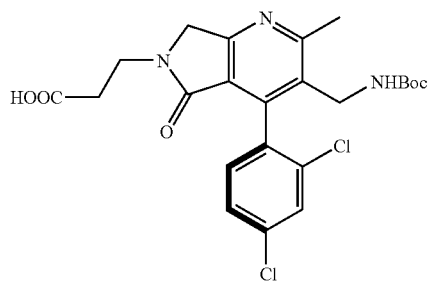

To a mixture of Example 37, TFA salt (82 mg, 0.16 mmol), sat. aq. NaHCO$_3$ (1 mL) and THF (5 mL) was added Boc$_2$O (50 mg, 0.23 mmol) and the resulting mixture stirred at RT overnight, diluted with EtOAc (25 mL) and 1N HCl (25 mL) and transferred to a separatory funnel. Aqueous layer was extracted with EtOAc (25 mL×2), organic layer was washed with brine, dried (Na$_2$SO$_4$), filtered and evaporated to yield 93 mg of crude Example 40A. [M+H]$^+$=494.27.

Example 40B tert-Butyl ((S)-6-(3-((S)-3-acetamidopyrrolidin-1-yl)-3-oxopropyl)-4-(2,4-dichlorophenyl)-2-methyl-5-oxo-6,7-dihydro-5H-pyrrolo[3,4-b]pyridin-3-yl)methylcarbamate

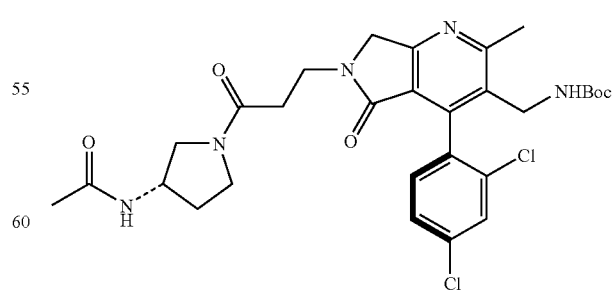

To a solution of crude Example 40A (~0.05 mmol) in THF (3 mL) was added PyBOP (54 mg, 0.104 mmol) followed by (3S)-(−)-acetamidopyrrolidine and DIEA (0.05 mL, 0.287 mmol) and the resuting mixture was stirred at RT overnight.

Mixture was diluted with EtOAc, washed with 1N HCl, brine, dried (Na$_2$SO$_4$), filtered, and evaporated to yield a residue which was purified by preparative HPLC (Phenomenex LUNA 5µ C18(2) 21.2×100 mm; 8 min gradient; 40% to 100% B; 20 mL/min) to yield 32 mg (~100% for last 2 steps) of a colorless oil.

Example 40

N—((S)-1-(3-((S)-3-Aminomethyl)-4-(2,4-dichlorophenyl)-2-methyl-5-oxo-5H-pyrrolo[3,4-b]pyridine-6(7H)-yl)propanoyl)pyrrolidin-3-yl)acetamide, TFA salt

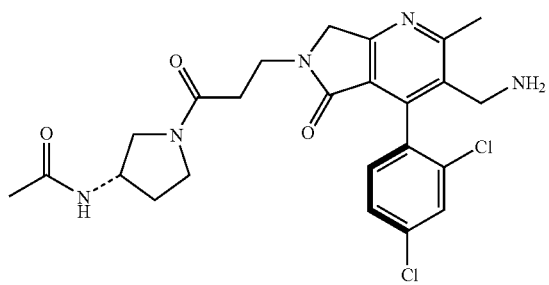

To a solution of Example 40B (32 mg, 0.053 mmol) in CH$_2$Cl$_2$ (3 mL) was added TFA (1 mL) dropwise and the mixture stirred ar RT overnight. Evaporation followed by purification by preparative HPLC (Phenomenex LUNA 5µ C18(2) 21.2×100 mm; 8 min gradient; 0% to 100% B; 20 mL/min) to yield 19.1 mg (58%) of a white powder. $^1$H NMR (400 MHz, CD$_3$OD) Rotamers, δ 1.85 and 1.87 (both s, 3H), 1.90-2.23 (m, 1H), 2.63-2.75 (m, 2H), 3.34-3.46 (m, 1H), 3.51-3.62 (m, 1H), 3.65-3.82 (m, 1H), 3.85-3.98 (m, 2H), 4.17 and 4.18 (part of AB$_q$, J=14.5 Hz, 1H), 4.25-4.36 (m, 1H), 4.56-4.72 (m, 1H), 7.319/7.322 (d, J=8.40 Hz, 1H), 7.50-7.54 (m, 1H), 7.69-7.71 (m, 1H). HRMS: Calculated for C$_{24}$H$_{28}$Cl$_2$N$_5$O$_3$: 504.1569. Found: 504.1551 [M+H]$^+$.

Example 41

(S)-3-(3-(Aminomethyl)-4-(2,4-dichlorophenyl)-2-methyl-5-oxo-5H-pyrrolo[3,4-b]pyridin-6(7H)-yl)-N,N-diethylpropanamide, TFA salt

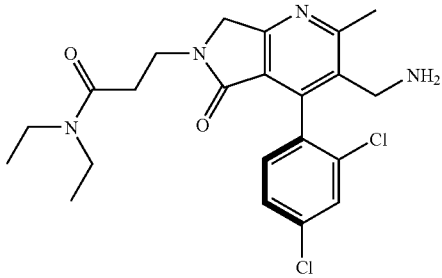

Example 41 was prepared from Example 40A and Et$_2$NH using a sequence similar to one described for Example 40. $^1$H NMR (400 MHz, CD$_3$OD) δ1.06 (t, J=7.0 Hz, 3H), 1.14 (t, J=7.0 Hz, 3H), 2.54-2.80 (m, 2H), 2.83 (s, 3H), 3.32-3.38 (m, 4H), 3.82 (t, J=6.8 Hz, 2H), 3.94 and 4.18 (AB$_q$, J=14.5 Hz, 2H), 4.60 and 4.65 (AB$_q$, J=18.9 Hz, 2H), 7.32 (d, J=8.40 Hz, 1H), 7.51 (dd, J=8.1, 2.0 Hz, 1H), 7.69 (d, J=1.8 Hz, 1H). HRMS: Calculated for C$_{22}$H$_{27}$Cl$_2$N$_4$O$_2$: 449.1511. Found: 449.1506 [M+H]$^+$.

Example 42

(S)-3-(Aminomethyl)-4-(2,4-dichlorophenyl)-6-(2-isopropoxyethyl)-2-methyl-6,7-dihydro-5H-pyrrolo[3,4-b]pyridin-5-one, TFA salt

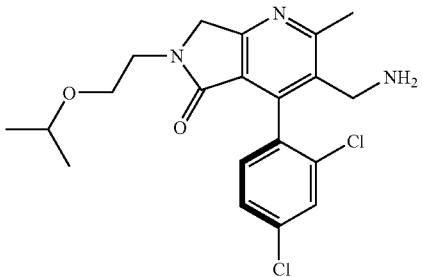

Example 42 was prepared from Example 36A and 2-isopropoxyethylamine using a sequence similar to one described for Example 38. $^1$H NMR (400 MHz, CD$_3$OD) 1.11 (d, J=6.2 Hz, 6H), 2.84 (s, 3H), 3.54-3.74 (m, 5H), 3.95 and 4.19 (AB$_q$, J=14.5 Hz, 2H), 4.63 and 4.68 (AB$_q$, J=18.9 Hz, 2H), 7.33 (d, J=7.90 Hz, 1H), 7.52 (dd, J=8.4, 2.2 Hz, 1H), 7.69 (d, J=2.2 Hz, 1H). HRMS: Calculated for C$_{20}$H$_{24}$Cl$_2$N$_3$O$_2$: 408.1246. Found: 408.1237 [M+H]$^+$.

Example 43

(S)-3-(Aminomethyl)-4-(2,4-dichlorophenyl)-2-methyl-6-(((R)-tetrahydrofuran-2-yl)methyl)-6,7-dihydro-5H-pyrrolo[3,4-b]pyridin-5-one, TFA salt

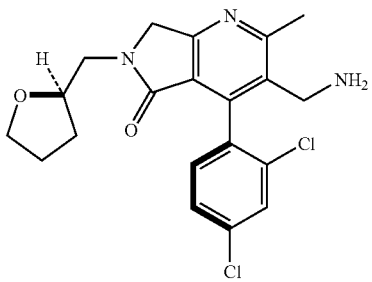

Example 43 was prepared from Example 36A and (R)-(tetrahydrofuran-2-yl)methanamine using a sequence similar to one described for Example 38. $^1$H NMR (400 MHz, CD$_3$OD) δ1.53-1.65 (m, 1H), 1.83-1.94 (m, 2H), 1.95-2.06 (m, 1H), 2.83 (s, 3H), 3.52 (dd, J=14.1 hz, 7.9 Hz, 1H), 3.66-3.76 (m, 2H), 3.82-3.90 (m, 1H), 3.95 and 4.18 (AB$_q$, J=14.5 Hz, 2H), 4.06-4.15 (m, 1H), 4.60 and 4.71 (AB$_q$, J=18.9 Hz, 2H), 7.33 (d, J=7.91 Hz, 1H), 7.52 (dd, J=8.1, 2.0 Hz, 1H), 7.69 (d, J=1.8 Hz, 1H). HRMS: Calculated for C$_{20}$H$_{22}$Cl$_2$N$_3$O$_2$: 406.1089. Found: 406.1085 [M+H]$^+$. [α]$_D^{25}$ −15.08° (c 1.9 mg/mL, EtOH).

Example 44

(S)-3-(Aminomethyl)-4-(2,4-dichlorophenyl)-2-methyl-6-(((S)-tetrahydrofuran-2-yl)methyl)-6,7-dihydro-5H-pyrrolo[3,4-b]pyridin-5-one, TFA salt

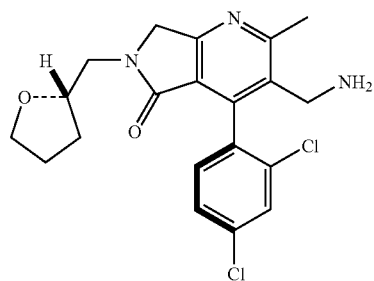

Example 44 was prepared from Example 36A and (S)-(tetrahydrofuran-2-yl)methanamine using a sequence similar to one described for Example 38. $^1$H NMR (400 MHz, CD$_3$OD) δ 1.53-1.65 (m, 1H), 1.83-1.94 (m, 2H), 1.95-2.06 (m, 1H), 2.83 (s, 3H), 3.49 (dd, J=14.5 Hz, 7.7 Hz, 1H), 3.66-3.76 (m, 2H), 3.82-3.90 (m, 1H), 3.95 and 4.19 (AB$_q$, J=14.5 Hz, 2H), 4.06-4.15 (m, 1H), 4.63 and 4.71 (AB$_q$, J=18.9 Hz, 2H), 7.34 (d, J=7.91 Hz, 1H), 7.51 (dd, J=8.4, 1.8 Hz, 1H), 7.68 (d, J=2.2 Hz, 1H). HRMS: Calculated for C$_{20}$H$_{22}$Cl$_2$N$_3$O$_2$: 406.1089. Found: 406.1092 [M+H]$^+$. [α]$_D^{25}$+10.270 (c 2.2 mg/mL, EtOH).

Example 45

(S)-3-(Aminomethyl)-4-(2,4-dichlorophenyl)-2-methyl-6-(2-(2,2,2-trifluoroethoxy)ethyl)-6,7-dihydro-5H-pyrrolo[3,4-b]pyridin-5-one, TFA salt

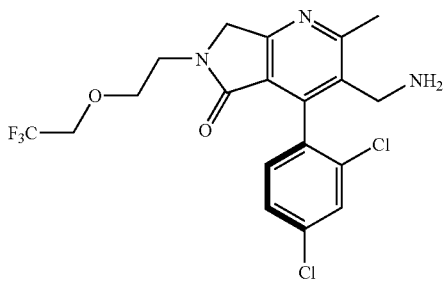

Example 45 was prepared from Example 36A and 2-(2,2,2-trifluoroethoxy)ethanamine using a sequence similar to one described for Example 38.

$^1$H NMR (400 MHz, CD$_3$OD) δ 2.84 (s, 3H), 3.73-3.78 (m, 2H), 3.84 (t, J=3.84 hz, 2H), 3.84 (t, J=5.1 Hz, 2H), 3.91-4.00 (m, 2H), 4.19 (part of AB$_q$, J=14.5 Hz, 1H), 4.64 (s, 2H), 7.34 (d, J=8.4 Hz, 1H), 7.51 (dd, J=8.4, 2.2 Hz, 1H), 7.68 (d, J=1.8 Hz, 1H). HRMS: Calculated for C$_{19}$H$_{19}$Cl$_2$F$_3$N$_3$O$_2$: 448.0806. Found: 448.0798 [M+H]$^+$.

Example 46

(R)-2-((S)-3-(Aminomethyl)-4-(2,4-dichlorophenyl)-2-methyl-5-oxo-5H-pyrrolo[3,4-b]pyridin-6(7H)-yl) propanoic acid, TFA salt

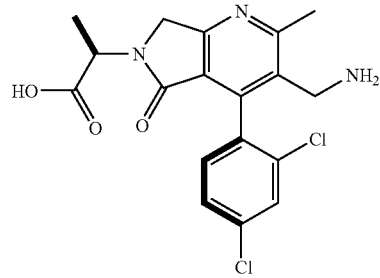

Example 46 was prepared from Example 36A and (R)-tert-butyl 2-aminopropanoate using a sequence similar to one described for Example 38 followed by TFA-mediated cleavage of the t-butyl ester as described in Example 40. $^1$H NMR (400 MHz, CD$_3$OD) possible rotamers; data for major rotamer: δ 1.60 (d, J=7.5 Hz, 3H), 2.85 (s, 3H), 3.95 and 4.21 (AB$_q$, J=14.5 Hz, 2H), 4.56-4.68 (m, 2H), 4.90 (q, J=7.5 Hz, 1H), 7.35 (d, J=8.4 Hz, 1H), 7.51 (dd, J=8.4, 2.2 Hz, 1H), 7.68 (d, J=2.2 Hz, 1H). [M+H]$^+$=394.23.

Example 47

(R)-2-((S)-3-(Aminomethyl)-4-(2,4-dichlorophenyl)-2-methyl-5-oxo-5H-pyrrolo[3,4-b]pyridin-6(7H)-yl)-N,N-diethylpropanamide, TFA salt

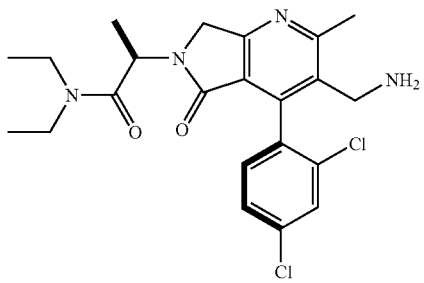

Example 47 was prepared from Example 46 and Et$_2$NH using a 3-step sequence similar to one described for Example 40. $^1$H NMR (400 MHz, CD$_3$OD) possible rotamers; data for major rotamer: δ 1.09 (t, J=7.3 Hz, 3H), 1.20 (t, J=7.0 Hz, 3H), 1.52 (d, J=7.0 Hz, 3H), 2.84 (s, 3H), 3.18-3.28 (m, 4H), 3.93 and 4.20 (AB$_q$, J=14.5 Hz, 2H), 4.67 and 4.80 (AB$_q$, J=18.0 Hz, 2H), 5.24 (q, J=7.0 Hz, 1H), 7.33 (d, J=8.4 Hz, 1H), 7.52 (dd, J=8.4, 2.2 Hz, 1H), 7.69 (d, J=2.2 Hz, 1H). HRMS: Calculated for C$_{22}$H$_{27}$Cl$_2$N$_4$O$_2$: 449.1511. Found: 449.1524 [M+H]$^+$.

Example 48

(S)-3-(Aminomethyl)-4-(2,4-dichlorophenyl)-2-methyl-6-((1-methyl-1H-pyrazol-3-yl)methyl)-6,7-dihydro-5H-pyrrolo[3,4-b]pyridin-5-one, TFA salt

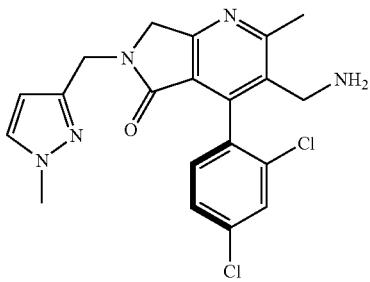

Example 48 was prepared from Example 36A and (1-methyl-1H-pyrazol-3-yl)methanamine using a sequence similar to one described for Example 38. $^1$H NMR (400 MHz, CD$_3$OD) δ 2.82 (s, 3H), 3.34 (s, 2H), 3.85 (s, 3H), 3.95 and 4.19 (AB$_q$, J=14.1 Hz, 2H), 4.66 and 4.72 (AB$_q$, J=15.2 Hz, 2H), 6.18 (d, J=2.2 Hz, 1H), 7.35 (d, J=8.4 Hz, 1H), 7.48-7.57 (m, 1H), 7.70 (d, J=2.2 Hz, 1H). HRMS: Calculated for C$_{20}$H$_{20}$Cl$_2$N$_5$O$_2$: 416.1045. Found: 416.1046 [M+H]$^+$.

Example 49

(S)-3-(Aminomethyl)-4-(2,4-dichlorophenyl)-2-methyl-6-(1-methyl-1H-pyrazol-3-yl)-6,7-dihydro-5H-pyrrolo[3,4-b]pyridin-5-one, TFA salt

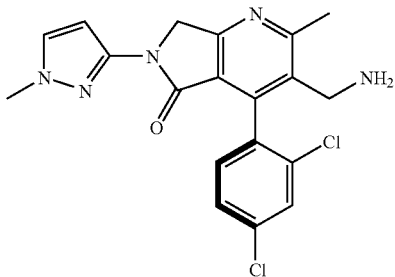

Example 49 was prepared from Example 36A and 1-methyl-1H-pyrazol-3-amine using a sequence similar to one described for Example 38. $^1$H NMR (400 MHz, CD$_3$OD) δ 2.86 (s, 3H), 3.86 (s, 3H), 3.97 and 4.20 (AB$_q$, J=14.5 Hz, 2H), 4.98 (br s, 2H), 6.65 (d, J=2.2 Hz, 1H), 7.36 (d, J=8.4 Hz, 1H), 7.52 (d, J=2.6 Hz, 1H), 7.55 (dd, J=8.4, 2.2 Hz, 1H), 7.73 (d, J=1.8 Hz, 1H). HRMS: Calculated for C$_{19}$H$_{18}$Cl$_2$N$_5$O: 402.0888. Found: 402.0891 [M+H]$^+$.

Example 50

(S)-2-(3-(Aminomethyl)-4-(2,4-dichlorophenyl)-2-methyl-5-oxo-5H-pyrrolo[3,4-b]pyridin-6(7H)-yl)-N,N-dimethylacetamide, TFA salt

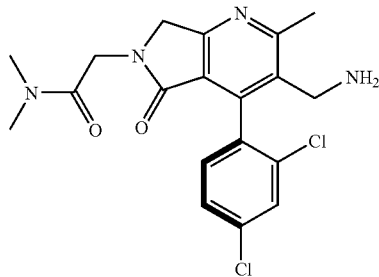

Procedure A:

Example 50A

Benzyl 6-(2-tert-butoxy-2-oxoethyl)-4-(2,4-dichlorophenyl)-2-methyl-5-oxo-6,7-dihydro-5H-pyrrolo[3,4-b]pyridine-3-carboxylate

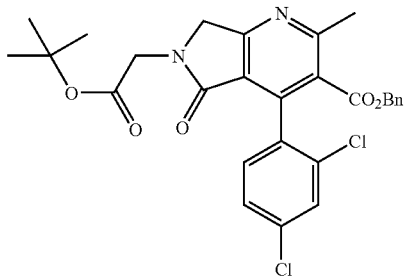

A mixture of 3-benzyl 5-ethyl 6-(chloromethyl)-4-(2,4-dichlorophenyl)-2-methylpyridine-3,5-dicarboxylate (10.59 g, 21.43 mmol), glycine tert-butyl ester hydrochloride (8.26 g, 49.29 mmol) and triethylamine (8.94 mL, 64.29 mmol) in N,N-dimethylacetamide (200 mL) was heated to 100° C. for 2 h and then cooled to ambient temperature. The resulting mixture was partitioned between EtOAc and H$_2$O and the aqueous layer was extracted further with EtOAc (2×). The combined organic extracts were washed with H$_2$O and brine, dried (Na$_2$SO$_4$) and evaporated under reduced pressure. The residue was purified by flash chromatography (330 g column, 0 to 100% EtOAc/Hexanes) to give Example 50A (9.34 g, 77.2% yield) as a light yellow solid. $^1$H NMR (500 MHz, CDCl$_3$). δ 1.44 (s, 9H), 2.74 (s, 3H), 4.13 and 4.29 (AB$_q$, J=17.6 Hz, 2H), 4.56 (s, 2H), 5.05 and 5.07 (AB$_q$, J=11.8, 2H), 7.00 (d, J=8.3 Hz, 1H), 7.06-7.16 (m, 2H), 7.21-7.40 (m, 5H). [M+H]$^+$=541.2.

Example 50B 6-(2-tert-Butoxy-2-oxoethyl)-4-(2,4-dichlorophenyl)-2-methyl-5-oxo-6,7-dihydro-5H-pyrrolo[3,4-b]pyridine-3-carboxylic acid

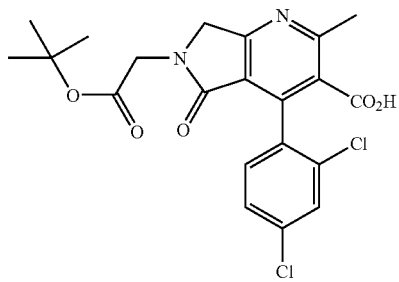

A mixture of Example 50A (9.33 g, 17.23 mmol) and 10% palladium on carbon (1.36 g) in EtOAc (150 mL) was stirred in the presence of hydrogen (balloon) at ambient temperature for 2 h. The reaction mixture was filtered through a pad of Celite and washed with MeOH and CH$_2$Cl$_2$. The filtrate was evaporated under reduced pressure to give crude Example 50B (8.13 g, 100% yield) as a dark yellow solid. $^1$H NMR (400 MHz, CD$_3$OD) δ 1.45 (s, 9H), 2.75 (s, 3H), 4.23 and 4.28 (AB$_q$, J=18.0 Hz, 2H), 4.63 and 4.58 (AB$_q$, J=18.0 Hz, 2H), 7.27 (d, J=8.4 Hz, 1H), 7.39 (dd, J=8.1, 2.0 Hz, 1H), 7.55 (d, J=2.2 Hz, 1H). [M+H]$^+$=451.2

Example 50C tert-Butyl 2-(4-(2,4-dichlorophenyl)-3-(hydroxymethyl)-2-methyl-5-oxo-5H-pyrrolo[3,4-b]pyridin-6(7H)-yl)acetate

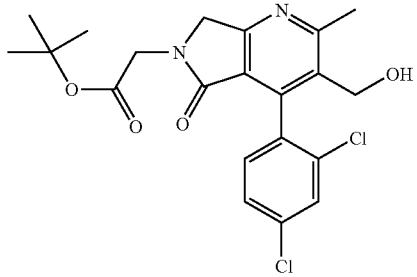

To a stirred mixture of Example 50B (1.18 g, 2.5 mmol) and triphenylphosphine resin (5.07 g, 7.5 mmol) in $CH_2Cl_2$ (80 mL)) at ambient temperature was added trichloroacetonitrile (0.75 mL, 7.5 mmol) dropwise. The mixture was stirred at ambient temperature for 2.5 h and additional triphenylphosphine resin (0.33 g, 0.5 mmol) and trichloroacetonitrile (50 μL, 0.5 mmol) were added. After 30 min, the mixture was filtered and the filtrate was concentrated in vacuo to give tert-butyl 2-(3-(chlorocarbonyl)-4-(2,4-dichlorophenyl)-2-methyl-5-oxo-5H-pyrrolo[3,4-b]pyridin-6(7H)-yl)acetate (1.12 g) as a light yellow solid, which was used directly in subsequent reaction.

To a solution of the above acid chloride (0.93 g, 1.98 mmol) in THF (30 mL) at 0° C. was added lithium tri-tert-butoxyaluminohydride dropwise during a period of 5 min. The mixture was stirred at 0° C. for 20 min, quenched with $H_2O$ (1.3 mL) and concentrated in vacuo. Purification of the residue by flash chromatography (40 g column, 0 to 100% EtOAc/Hexanes) afforded Example 50C (690.4 mg, 80% for 2 steps) as an off-white solid. $^1H$ NMR (500 MHz, $CD_3OD$) δ 1.45 (s, 9H), 2.84 (s, 3H), 4.20 and 4.26 ($AB_q$, J=17.6, 2H), 4.32 and 4.58 ($AB_q$, J=12.1 Hz, 2H), 4.56 (s, 2H), 7.32 (d, J=8.3 Hz, 1H), 7.44 (d, J=8.3 Hz, 1H), 7.59 (s, 1H). $[M+H]^+$=437.2.

Isomer A and Isomer B of Example 50C (R)-tert-Butyl 2-(4-(2,4-dichlorophenyl)-3-(hydroxymethyl)-2-methyl-5-oxo-5H-pyrrolo[3,4-b]pyridin-6(7H)-yl)acetate and (S)-tert-butyl 2-(4-(2,4-dichlorophenyl)-3-(hydroxymethyl)-2-methyl-5-oxo-5H-pyrrolo[3,4-b]pyridin-6(7H)-yl)acetate

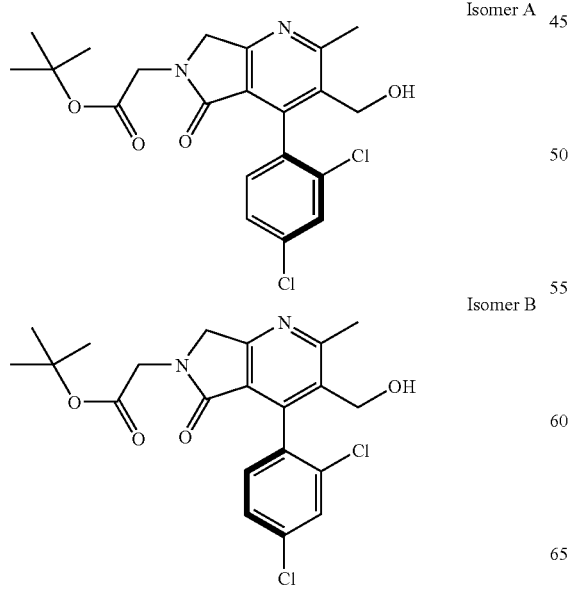

Isomer A

Isomer B

The Example 50C (5.7 g) was separated by super-critical fluid chromatography (Chiralpak® AD 250×4.6 mm ID; 10 μm; 35° C.; Flow Rate: 2.0 mL/min; Mobile Phase: $CO_2$/IPA: 82/18; Injection Volume: 5 μL; Detector Wavelength: 220 nm) to give both isomer A (2.43 g, RT=5.1 min, 100% ee) and isomer B (2.55 g, RT=7.1 min, 100% ee) as an off-white solid.

Example 50D (R)-tert-Butyl 2-(3-(chloromethyl)-4-(2,4-dichlorophenyl)-2-methyl-5-oxo-5H-pyrrolo[3,4-b]pyridin-6(7H)-yl)acetate

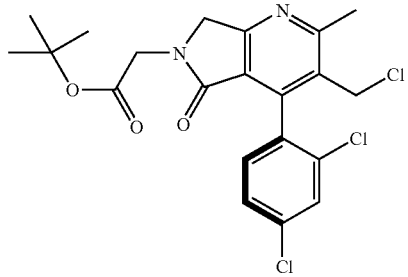

To a mixture of Example 50C (isomer B, 763 mg, 1.74 mmol) and $Et_3N$ (0.97 mL, 6.98 mmol) in $CH_2Cl_2$ (15 mL) at 0° C. was added mesyl chloride (0.41 mL, 5.24 mmol) dropwise. The stirred mixture was kept at ambient temperature overnight and evaporated under reduced pressure. The residue was partitioned between EtOAc and $H_2O$ and the aqueous layer was extracted further with EtOAc (2×). The combined organic extracts were washed with brine, dried ($Na_2SO_4$) and concentrated in vacuo. The crude product was chromatographed (40 g column, 0 to 100% EtOAc/Hexanes) to give Example 50D (785.7 mg, 99%) as a white solid. $^1H$ NMR (500 MHz, $CDCl_3$) δ 1.45 (s, 9H), 2.86 (s, 3H), 4.14 and 4.29 ($AB_q$, J=17.6, 2H), 4.31 (part of $AB_q$, J=7.1, 1H), 4.52-4.60 (m, 3H), 7.27 (d, J=8.3, 1H), 7.39 (dd, J=8.3, 2.2 Hz, 1H), 7.54 (d, J=1.7, 1H). $[M+H]^+$=455.1.

Example 50E (S)-2-(3-((tert-Butoxycarbonylamino)methyl)-4-(2,4-dichlorophenyl)-2-methyl-5-oxo-5H-pyrrolo[3,4-b]pyridin-6(7H)-yl)acetic acid (a novel intermediate)

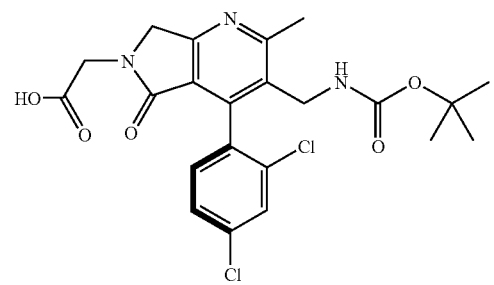

A solution of Example 50D (784 mg, 1.72 mmol) in 7M $NH_3$ in MeOH (140 mL) was heated at 50° C. for 50 min, cooled and concentrated to give crude (S)-tert-butyl 2-(3-(aminomethyl)-4-(2,4-dichlorophenyl)-2-methyl-5-oxo-5H-pyrrolo[3,4-b]pyridin-6(7H)-yl)acetate (1.81 g) as a light orange sticky solid.

To the above material in $CH_2Cl_2$ (8.0 mL) was added TFA (5.0 mL) and the resulting mixture was allowed to stir at ambient temperature for 3 h and evaporated under reduced pressure. The residue was co-evaporated with ethanol several times to give crude (S)-2-(3-(aminomethyl)-4-(2,4-dichlorophenyl)-2-methyl-5-oxo-5H-pyrrolo[3,4-b]pyridin-6(7H)-yl)acetic acid as a yellow solid.

The yellow solid was dissolved in THF (35 mL) and saturated aqueous NaHCO₃ (20 mL) followed by addition of di-tert-butyldicarbonate (1.28 g, 5.85 mmol). The stirred mixture was kept at ambient temperature for 2.5 h and then pH was adjusted to 3 with 1N HCl. The aqueous layer was extracted further with EtOAc (2×). The combined organic extracts were washed with brine, dried (Na₂SO₄) and evaporated under reduced pressure to give crude Example 50E (1.375 g) as a light yellow solid which was used for the next step without further purification. [M+H]⁺=480.2.

Example 50

(S)-2-(3-(Aminomethyl)-4-(2,4-dichlorophenyl)-2-methyl-5-oxo-5H-pyrrolo[3,4-b]pyridin-6(7H)-yl)-N,N-dimethylacetamide, TFA salt

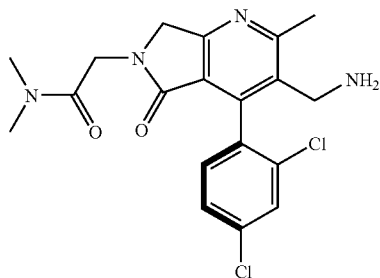

To a solution of Example 50E (100.9 mg, 0.21 mmol) in THF (5.0 mL) was added benzotriazol-1-yloxytripyrrolidinophosphonium hexafluorophosphate (163.9 mg, 0.315 mmol), N,N-diisopropylethylamine (0.15 mL, 0.84 mmol) and 2M NHMe₂/THF (0.157 mL, 0.315 mmol). The reaction mixture was stirred at ambient temperature for 2.5 h and evaporated. The residue was partitioned between EtOAc and H₂O and the aqueous layer was extracted further with EtOAc (2X). The combined organic extracts were washed with H₂O and brine, dried with (Na₂SO₄) and evaporated under reduced pressure to give crude (S)-tert-butyl (4-(2,4-dichlorophenyl)-6(2-dimethylamino)-2-oxoethyl)-2-methyl-5-oxo-6,7-dihydro-5H-pyrrolo[3,4-b]pyridin-3-yl)methylcarbamate (186.1 mg) as a light orange solid.

The above crude product was dissolved in CH₂Cl₂ (1.5 mL) followed by addition of TFA (0.8 mL). The reaction mixture was allowed to stir at ambient temperature for 2.5 h and concentrated in vacuo. The residue was purified by prep HPLC (YMC S5 ODS 30×100 mm, 12 min gradient, 0 to 80% solvent B, 40 mL/min) to give Example 50, TFA salt (78.9 mg, 98.2% ee, 70% yield over 2 steps) as an off-white powder. ¹H NMR (500 MHz, CD₃OD) δ 2.83 (s, 3H), 2.94 (s, 3H), 3.07(s, 3H), 3.95 and 4.19 (AB$_q$, J=14.3 Hz, 2H), 4.39 and 4.51 (AB$_q$, J=17.0 Hz, 2H), 7.33 (d, J=8.3 Hz, 1H), 7.51 (d, J=8.3 Hz, 1H), 7.69 (s, 1H). HRMS: Calculated for C₁₉H₂₁Cl₂N₄O₂: 407.1042. Found: 407.1046 [M+H]⁺.

Procedure B: Example 50 can alternatively be prepared using the procedure described for Example 77.

Procedure C: Example 50 was also obtained by separation of racemate by Berger SFC on a Chirapak® AD-H, 5 g, 30×250 mm column using an isocratic gradient of 25% EtOH/75% CO₂ containing 0.1% diethylamine to afford individual enantiomers.

Example 50

(S)-2-(3-(Aminomethyl)-4-(2,4-dichlorophenyl)-2-methyl-5-oxo-5H-pyrrolo[3,4-b]pyridin-6(7H)-yl)-N,N-dimethylacetamide, TFA salt

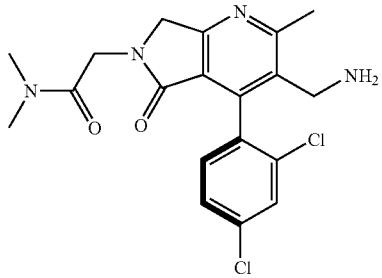

Example 50 (Enantiomer B; slower-moving): Purity by chiral analytical HPLC: Berger SFC analytical HPLC [Chiralpak® AD 4.6×250 mm; 25% EtOH/75% CO₂ containing 0.1% DEA): >99% ee. LCMS: Anal. Calcd. for C₁₉H₂₀Cl₂N₄O₂: 406.08. Found: 407.55 [M+H]⁺.

Using the procedure A described above for Example 50, the following compounds (Examples 51 to 65) were prepared:

Example 51

(S)-3-(Aminomethyl)-4-(2,4-dichlorophenyl)-2-methyl-6-(2-(4-morpholinopiperidin-1-yl)-2-oxoethyl)-6,7-dihydro-5H-pyrrolo[3,4-b]pyridin-5-one, TFA salt

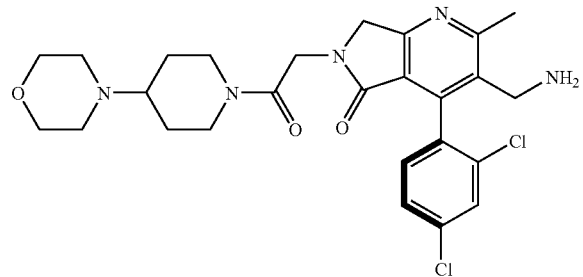

¹H NMR (500 MHz, CD₃OD) δ 1.53-1.69 (m, 1H), 1.71-1.83 (m, 1H), 2.10-2.31 (m, 2H), 2.71 (t, J=12.6 Hz, 1H), 2.85 (s, 3H), 3.10-3.26 (m, 3H), 3.44-3.56 (m, 3H), 3.71-3.88 (m, 2H), 3.96 and 4.21 (AB$_q$, J=14.3 Hz, 2H), 4.02-4.17 (m, 3H), 4.35-4.69 (m, 5H), 7.36 (d, J=8.3 Hz, 1H), 7.51 (d, J=8.3 Hz, 1H), 7.68 (s, 1H). HRMS: Calculated for C₂₆H₃₂Cl₂N₅O₃: 532.1882. Found: 532.1869 [M+H]⁺.

Example 52

(S)-3-(Aminomethyl)-4-(2,4-dichlorophenyl)-2-methyl-6-(2-morpholino-2-oxoethyl)-6,7-dihydro-5H-pyrrolo[3,4-b]pyridin-5-one, TFA salt

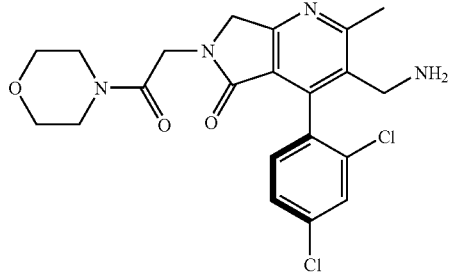

¹H NMR (500 MHz, CD₃OD) δ 2.75 (s, 3H), 3.45 (broad, s, 4H), 3.57 (broad, dd, J=18.2, 4.4 Hz, 4H), 3.86 and 4.11 (AB$_q$, J=14.6 Hz, 2H), 4.33-4.42 (AB$_q$, J=16.8 Hz, 2H), 4.50 (s, 2H), 7.24 (dd, J=8.2, 3.3 Hz, 1H), 7.42 (dd, J=8.2, 2.2 Hz, 1H), 7.59 (s, 1H). HRMS: Calculated for C₂₁H₂₃Cl₂N₄O₃: 449.1147. Found: 449.1135 [M+H]⁺.

Example 53

(S)-3-(Aminomethyl)-4-(2,4-dichlorophenyl)-2-methyl-6-(2-oxo-2-(4-(2-(pyrrolidin-1-yl)ethyl)piperazin-1-yl)ethyl)-6,7-dihydro-5H-pyrrolo[3,4-b]pyridin-5-one, TFA salt

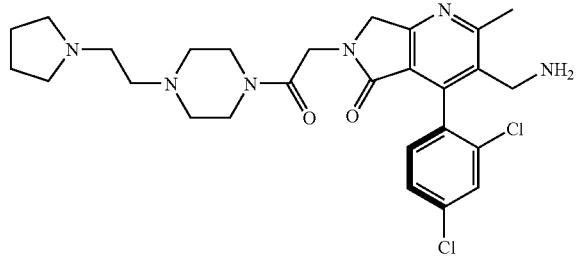

$^1$H NMR (500 MHz, CD$_3$OD) δ 2.02 (broad, s, 4H), 2.75 (s, 3H), 2.78-3.58 (m, 12H), 3.69 (broad, s, 4H), 3.87 and 4.11 (AB$_q$, J=14.3 Hz, 2H), 4.38 and 4.45 (AB$_q$, J=16.9 Hz, 2H), 4.50 (s, 2H), 7.26 (d, J=8.3 Hz, 1H), 7.42 (d, J=8.3 Hz, 1H), 7.59 (s, 1H). HRMS: Calculated for C$_{27}$H$_{35}$Cl$_2$N$_6$O$_2$: 545.2199. Found: 545.2201 [M+H]$^+$.

Example 54

(S)-3-(Aminomethyl)-4-(2,4-dichlorophenyl)-2-methyl-6-(2-(4-(4-methylpiperazin-1-yl)piperidin-1-yl)-2-oxoethyl)-6,7-dihydro-5H-pyrrolo[3,4-b]pyridin-5-one, TFA salt

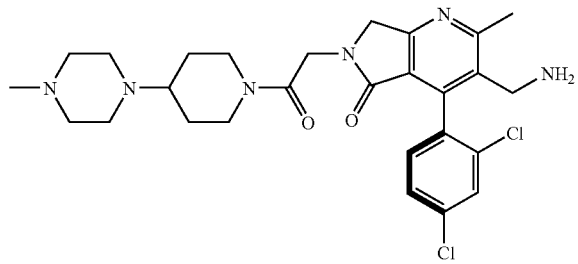

$^1$H NMR (500 MHz, CD$_3$OD) δ 1.42-1.58 (m, 1H), 1.59-1.72 (m, 1H), 1.90-2.11 (m, 2H), 2.62 (t, J=12.9 Hz, 1H), 2.75 (s, 3H), 2.85 (s, 3H), 3.08 (t, J=12.9 Hz, 1H), 3.23-3.57 (m, 9H), 3.87 and 4.11 (AB$_q$, J=14.3 Hz, 2H), 3.98 (d, J=-14.3 Hz, 1H), 4.27-4.58 (m, 5H), 7.26 (d, J=8.3 Hz, 1H), 7.41 (d, J=8.3 Hz, 1H), 7.59 (s, 1H). HRMS: Calculated for C$_{27}$H$_{35}$Cl$_2$N$_6$O$_2$: 545.2199. Found: 545.2199 [M+H]$^+$.

Example 55

(S)-2-(3-(Aminomethyl)-4-(2,4-dichlorophenyl)-2-methyl-5-oxo-5H-pyrrolo[3,4-b]pyridin-6(7H)-yl)-N-ethyl-N-methylacetamide, TFA salt

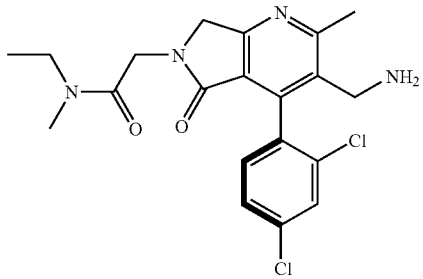

$^1$H NMR (500 MHz, CD$_3$OD) δ 1.10 and 1.23 (t, J=7.15, 3H, rotamers), 2.84 (s, 3H), 2.92 and 3.05 (s, 3H, rotamers), 3.35-3.49 (m, 2H), 3.96 and 4.20 (AB$_q$, J=14.6 Hz, 2H), 4.34-4.64 (m, 4H), 7.34 (d, J=8.3 Hz, 1H), 7.51 (dd, J=8.3, 2.2 Hz, 1H), 7.68 (d, J=1.7 Hz, 1H). HRMS: Calculated for C$_{20}$H$_{23}$Cl$_2$N$_4$O$_2$: 421.1198. Found: 421.1200 [M+H]$^+$.

Example 56

(S)-2-(3-(Aminomethyl)-4-(2,4-dichlorophenyl)-2-methyl-5-oxo-5H-pyrrolo[3,4-b]pyridin-6(7H)-yl)-N-methyl-N-propylacetamide, TFA salt

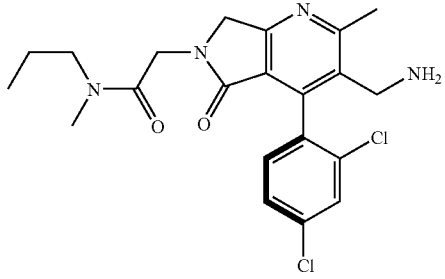

$^1$H NMR (500 MHz, CD$_3$OD) δ 0.88 and 0.96 (t, J=7.3 Hz, 3H, rotamers), 1.56 and 1.68 (q, J=7.2 Hz, 2H, rotamers), 2.84 (s, 3H), 2.92 and 3.06 (s, 3H, rotamers), 3.26-3.41 (m, 2H), 3.96 and 4.20 (AB$_q$, J=14.3 Hz, 2H), 4.33-4.61 (m, 4H), 7.34 (d, J=7.7 Hz, 1H), 7.51 (d, J=8.3 Hz, 1H), 7.68 (s, 1H). HRMS: Calculated for C$_{21}$H$_{25}$Cl$_2$N$_4$O$_2$: 435.1355. Found: 435.1368 [M+H]$^+$.

Example 57

(S)-2-(3-(Aminomethyl)-4-(2,4-dichlorophenyl)-2-methyl-5-oxo-5H-pyrrolo[3,4-b]pyridin-6(7H)-yl)-N,N-diethylacetamide, TFA salt

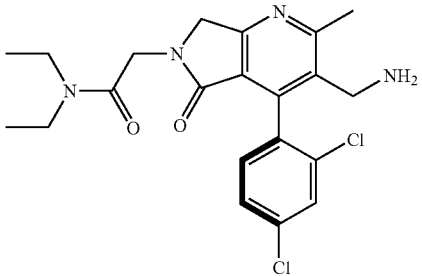

$^1$H NMR (500 MHz, CD$_3$OD) δ 1.12 (t, J=7.2 Hz, 3H), 1.24 (t, J=7.2 Hz, 3H), 2.84 (s, 3H), 3.34-3.48 (m, 4H), 3.96 and 4.20 (AB$_q$, J=14.3 Hz, 2H), 4.40 and 4.52 (AB$_q$, J=16.7 Hz, 2H), 4.61 (s, 2H), 7.34 (d, J=8.3 Hz, 1H), 7.51 (d, J=8.3 Hz, 1H), 7.69 (s, 1H). HRMS: Calculated for C$_{21}$H$_{25}$Cl$_2$N$_4$O$_2$: 435.1355. Found: 435.1366 [M+H]$^+$.

Example 58

(S)-3-(Aminomethyl)-4-(2,4-dichlorophenyl)-2-methyl-6-(2-oxo-2-(pyrrolidin-1-yl)ethyl)-6,7-dihydro-5H-pyrrolo[3,4-b]pyridin-5-one, TFA salt

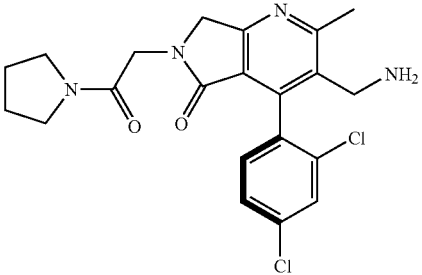

$^1$H NMR (500 MHz, CD$_3$OD) δ 1.83-1.95 (m, 2H), 1.96-2.09 (m, 2H), 2.84 (s, 3H), 3.43 (t, J=6.9 Hz, 2H), 3.52 (t, J=6.9 Hz, 2H), 3.96 and 4.20 (AB$_q$, J=14.3 Hz, 2H), 4.33 and 4.44 (AB$_q$, J=17.1 Hz, 2H), 4.62 (s, 2H), 7.34 (d, J=8.3 Hz, 1H), 7.51 (d, J=8.3 Hz, 1H), 7.69 (s, 1H). HRMS: Calculated for C$_{21}$H$_{23}$Cl$_2$N$_4$O$_2$: 433.1198. Found: 433.1194 [M+H]$^+$.

Example 59

(S)-3-Aminomethyl)-4-(2,4-dichlorophenyl)-2-methyl-6-(2-oxo-2-piperidin-1-yl)ethyl)-6,7-dihydro-5H-pyrrolo[3,4-b]pyridin-5-one, TFA salt

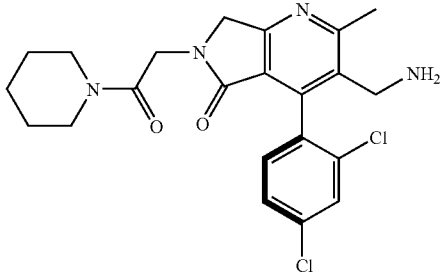

$^1$H NMR (500 MHz, CD$_3$OD) δ 1.55 (m, 2H), 1.65 (m, J=24.2, 3.9 Hz, 4H), 2.84 (s, 3H), 3.47 (t, J=5.3, 2H), 3.52 (t, J=5.0, 2H), 3.96 and 4.20 (AB$_q$, J=14.6 Hz, 2H), 4.41 and 4.50 (AB$_q$, J=16.8 Hz, 2H), 4.59 (s, 2H), 7.34 (dd, J=8.3, 2.2 Hz, 1H), 7.51 (dd, J=8.3, 1.7 Hz, 1H), 7.68 (s, 1H). HRMS: Calculated for C$_{22}$H$_{25}$Cl$_2$N$_4$O$_2$: 447.1355. Found: 447.1362 [M+H]$^+$.

Example 60

(S)-2-(3-(Aminomethyl)-4-(2,4-dichlorophenyl)-2-methyl-5-oxo-5H-pyrrolo[3,4-b]pyridin-6(7H)-yl)-N-isopropyl-N-methylacetamide, TFA salt

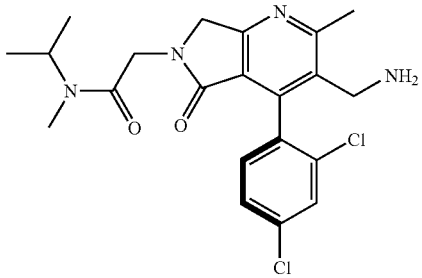

$^1$H NMR (400 MHz, Solvent) δ 1.11, 1.13 and 1.24 (rotamers, d, J=3.5, 3.5, and 6.6 Hz, resp., 6H total), 2.79 and 2.91 (s, 3H, rotamers), 2.84 (s, 3H), 3.96 and 4.20 (AB$_q$, J=14.50 Hz, 2H), 4.13 and 4.73 (m, 1H, rotamers), 4.33 and 4.55 (m, 2H). 4.50 (s, 2H), 7.34 (d, J=7.91 Hz, 1H), 7.52 (dd, J=8.4, 2.2 Hz, 1H), 7.69 (d, J=2.2 Hz, 1H). HRMS: Calculated for C$_{21}$H$_{25}$Cl$_2$N$_4$O$_2$: 435.1355. Found: 435.1365 [M+H]$^+$.

Example 61

(S)-2-(3-(Aminomethyl)-4-(2,4-dichlorophenyl)-2-methyl-5-oxo-5H-pyrrolo[3,4-b]pyridin-6(7H)-yl)-N-(1,3-dimethyl-1H-pyrazol-5-yl)acetamide, TFA salt

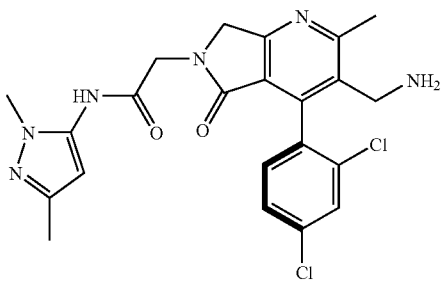

$^1$H NMR (500 MHz, CD$_3$OD) δ 2.19 (s, 3H), 2.85 (s, 3H), 3.67 (s, 3H), 3.97 and 4.21 (AB$_q$, J=14.6 Hz, 2H), 4.41 and 4.52 (AB$_q$, J=17.0 Hz, 2H), 4.67 (s, 2H), 6.14 (s, 1H), 7.35 (d, J=8.3 Hz, 1H), 7.51 (d, J=8.3 Hz, 1H), 7.69 (s, 1H). HRMS: Calculated for C$_{22}$H$_{23}$Cl$_2$N$_6$O$_2$: 473.1260. Found: 473.1269 [M+H]$^+$.

Example 62

(S)-2-(3-(Aminomethyl)-4-(2,4-dichlorophenyl)-2-methyl-5-oxo-5H-pyrrolo[3,4-b]pyridin-6(7H)-yl)-N-(1-ethyl-1H-pyrazol-5-yl)acetamide, TFA salt

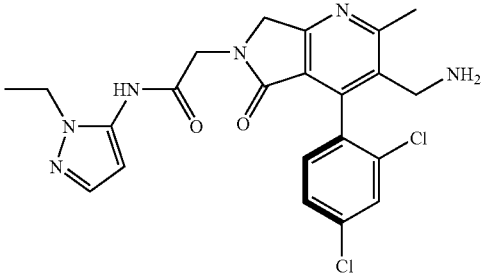

$^1$H NMR (500 MHz, CD$_3$OD) δ 1.34 (t, J=7.2 Hz, 3H), 2.85 (s, 3H), 3.97 and 4.20 (AB$_q$, J=14.8 Hz, 2H), 4.05 (q, J=7.2 Hz, 2H), 4.43 and 4.53 (AB$_q$, J=17.1 Hz, 2H),), 4.68 (s, 2H), 6.24 (s, 1H), 7.34 (d, J=8.3 Hz, 1H), 7.42 (s, 1H), 7.52 (d, J=8.3 Hz, 1H), 7.70 (s, 1H). HRMS: Calculated for C$_{22}$H$_{23}$Cl$_2$N$_6$O$_2$: 473.1260. Found: 473.1276 [M+H]$^+$.

Example 63

(S)-2-(3-Aminomethyl)-4-(2,4-dichlorophenyl)-2-methyl-5-oxo-5H-pyrrolo[3,4-b]pyridin-6(7H)-yl)-N-(1-methyl-1H-pyrazol-5-yl)acetamide, TFA salt

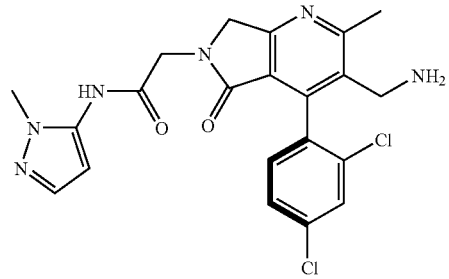

$^1$H NMR (500 MHz, CD$_3$OD) δ 2.85 (s, 3H), 3.72 (s, 3H), 3.96 and 4.20 (AB$_q$, J=14.3 Hz, 2H), 4.44 and 4.53 (AB$_q$, J=17.3 Hz, 2H),), 4.68 (s, 2H), 6.25 (s, 1H), 7.35 (d, J=8.2 Hz, 1H), 7.39 (s, 1H), 7.51 (dd, J=8.2, 2.20 Hz, 1H),), 7.70 (d, J=2.2 Hz, 1H). HRMS: Calculated for C$_{21}$H$_{21}$Cl$_2$N$_6$O$_2$: 459.1103. Found: 459.1105 [M+H]$^+$.

Example 64

(S)-2-(3-(Aminomethyl)-4-(2,4-dichlorophenyl)-2-methyl-5-oxo-5H-pyrrolo[3,4-b]pyridin-6(7H)-yl)-N-(1-methyl-1H-pyrazol-3-yl)acetamide, TFA salt

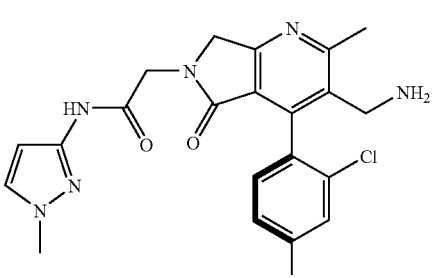

$^1$H NMR (500 MHz, CD$_3$OD) δ 2.85 (s, 3H), 3.77 (s, 3H), 3.96 and 4.20 (AB$_q$, J=14.3 Hz, 2H), 4.35 and 4.47 (AB$_q$, J=17.1 Hz, 2H), 4.66 (s, 2H), 6.44 (broad, s, 1H), 7.35 (d, J=8.3 Hz, 1H), 7.44 (broad, s, 1H), 7.50 (d, J=8.3 Hz, 1H), 7.67 (s, 1H). HRMS: Calculated for $C_{21}H_{21}Cl_2N_6O_2$: 459.1103. Found: 459.1118 [M+H]$^+$.

Example 65

(S)-2-(3-(Aminomethyl)-4-(2,4-dichlorophenyl)-2-methyl-5-oxo-5H-pyrrolo[3,4-b]pyridin-6(7H)-yl)-N-((1-methyl-1H-pyrazol-3-yl)methyl)acetamide, TFA salt

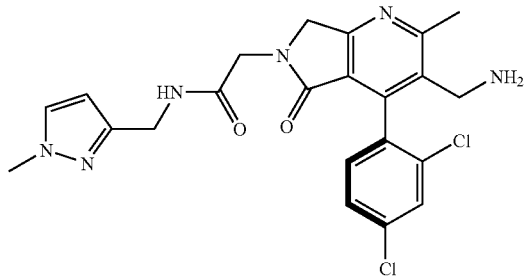

$^1$H NMR (400 MHz, CD$_3$OD) δ 2.74 (s, 3H), 3.73 (s, 3H), 3.86 and 4.10 (AB$_q$, J=14.5 Hz, 2H), 4.11 and 4.23 (AB$_q$, J=16.7 Hz, 2H), 4.26 (s, 2H), 4.52 (s, 2H), 6.10 (d, J=2.20 Hz, 1H), 7.24 (d, J=8.4 Hz, 1H), 7.37-7.46 (m, 2H), 7.59 (d, J=1.8 Hz, 1H). HRMS: Calculated for $C_{22}H_{23}Cl_2N_6O_2$: 473.1260. Found: 473.1248 [M+H]$^+$.

Example 66

2-(3-(Aminomethyl)-4-(2,4-dichlorophenyl)-2-methyl-5-oxo-5H-pyrrolo[3,4-b]pyridin-6(7H)-yl)acetic acid, TFA salt

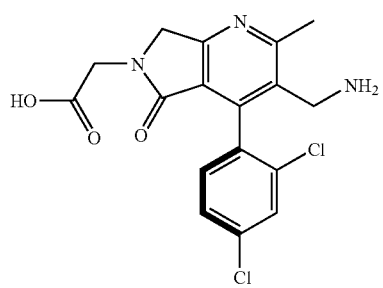

A solution of Example 50D (racemate, 31.3 mg, 0.068 mmol) in 7M NH$_3$ in MeOH (1.25 mL) was heated at 100° C. in Microwave for 15 min, cooled and evaporated under the reduced pressure. The residue was dissolved in CH$_2$Cl$_2$ (0.5 mL) followed by addition of TFA (0.13 mL) and the resulting mixture was allowed to stir at ambient temperature for 2.5 h and concentrated in vacuo. The crude product was purified by prep HPLC (Phenomenex Luna 5μ C18, 21.2×100 mm, 18 min gradient, 0 to 80% solvent B, 40 mL/min) to give Example XX, TFA salt (17.2 mg, 51.2% yield) as a white solid. $^1$H NMR (400 MHz, CD$_3$OD) δ 2.75 (s, 3H), 3.86 and 4.10 (AB$_q$, J=14.5 Hz, 2H), 4.19 and 4.27 (AB$_q$, J=18.0 Hz, 2H), 4.53 (s, 2H), 7.24 (d, J=8.4 Hz, 1H), 7.42 (dd, J=8.4, 2.2 Hz, 1H), 7.60 (d, J=2.2 Hz, 1H). [M+H]$^+$=380.12.

Examples 67 and 68

(R)-2-(3-(Aminomethyl)-4-(2,4-dichlorophenyl)-2-methyl-5-oxo-5H-pyrrolo[3,4-b]pyridin-6(7H)-yl) acetic acid, TFA salt and (S)-2-(3-(Aminomethyl)-4-(2,4-dichlorophenyl)-2-methyl-5-oxo-5H-pyrrolo[3,4-b]pyridin-6(7H)-yl)acetic acid, TFA salt Example 67

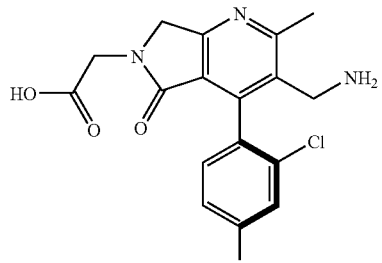

Example 68

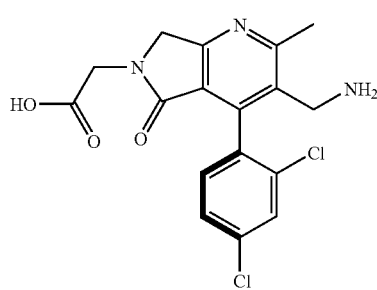

Examples 67A and 68A (R)-tert-Butyl 2-(3-(aminomethyl)-4-(2,4-dichlorophenyl)-2-methyl-5-oxo-5H-pyrrolo[3,4-b]pyridin-6(7H)-yl)acetate and (S)-tert-Butyl 2-(3-(aminomethyl)-4-(2,4-dichlorophenyl)-2-methyl-5-oxo-5H-pyrrolo[3,4-b]pyridin-6(7H)-yl)acetate Example 67A

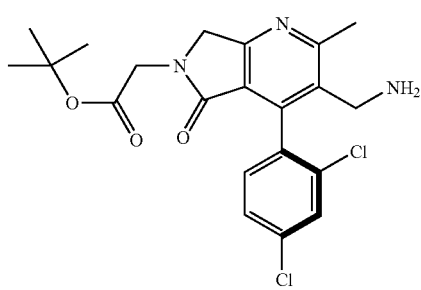

Example 68A

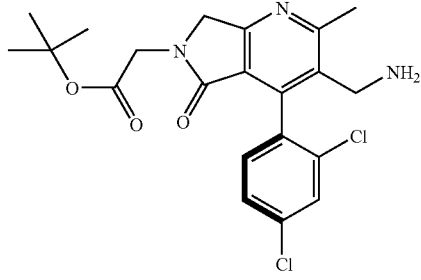

A solution of Example 50D (racemate, 393.4 mg, 0.863 mmol) in 7M NH$_3$ in MeOH (10 mL) was heated at 100° C. in Microwave for 20 min, cooled and concentrated under the reduced pressure. The residue was separated by Chiral Column (Chiralpak, 5 cm×50 cm, 20 μ) eluting with 12 to 25% solvent B (solvent A=heptanes+0.1% DEA, solvent B=IPA+ 0.1% DEA) to give both Example 2A, isomer A (84.7 mg, 98% ee) and isomer B (97.8 mg, 98% ee) as colorless solids.

Examples 67 and 68

(R)-2-(3-(Aminomethyl)-4-(2,4-dichlorophenyl)-2-methyl-5-oxo-5H-pyrrolo[3,4-b]pyridin-6(7H)-yl)acetic acid, TFA salt and (S)-2-(3-(Aminomethyl)-4-(2,4-dichlorophenyl)-2-methyl-5-oxo-5H-pyrrolo[3,4-b]pyridin-6(7H)-yl)acetic acid, TFA salt Example 67

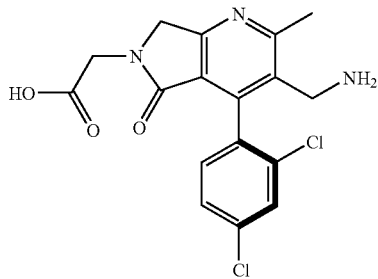

Example 68

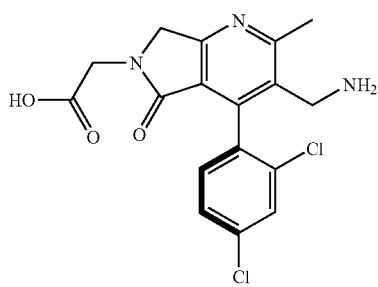

Example 67. A mixture of Example 67A (28 mg, 0.06 mmol) and TFA (0.26 mL) in CH$_2$Cl$_2$ (1 mL) was allowed to stir at ambient temperature for 3 h and evaporated under reduced pressure. The residue was purified by prep HPLC (Phenomenex Luna 5μ C18, 21.2×100 mm, 18 min gradient, 0 to 80% solvent B, 40 mL/min) to give Example 67, isomer A, TFA salt (21.8 mg, 72% yield) as an off-white solid. $^1$H NMR (500 MHz, CD$_3$OD) δ 2.75 (s, 3H), 3.86 and 4.10 (AB$_q$, J=14.6 Hz, 2H), 4.18-4.26 (AB$_q$, J=18.2 Hz, 2H), 4.53 (s, 2H), 7.24 (d, J=8.3 Hz, 1H), 7.42 (d, J=8.3 Hz, 1H), 7.60 (s, 1H). [M+H]$^+$=380.2

Example 68. A mixture of Example 68A (27 mg, 0.06 mmol) and TFA (0.4 mL) in CH$_2$Cl$_2$ (2 mL) was allowed to stir at ambient temperature for 2.5 h and evaporated under reduced pressure. The residue was purified by prep HPLC (Phenomenex Luna 5μ C18, 21.2×100 mm, 18 min gradient, 0 to 80% solvent B, 40 mL/min) to give Example 2, isomer B TFA salt (21.3 mg, 71.8% yield) as an off-white solid. $^1$H NMR (500 MHz, CD$_3$OD) δ 2.75 (s, 3H), 3.86 and 4.10 (AB$_q$, J=14.30 Hz, 2H), 4.19-4.26 (AB$_q$, J=18.0 Hz, 2H), 4.53 (s, 2H), 7.24 (d, J=8.3 Hz, 1H), 7.42 (d, J=8.3 Hz, 1H), 7.60 (s, 1H). HRMS: Calculated for C$_{17}$H$_{16}$Cl$_2$N$_3$O$_3$: 380.0569. Found: 380.0558 [M+H]$^+$.

Example 69

(S)-3-(Aminomethyl)-4-(2,4-dichlorophenyl)-2-methyl-6-(2-(5-(methylsulfonyl)indolin-1-yl)-2-oxoethyl)-6,7-dihydro-5H-pyrrolo[3,4-b]pyridin-5-one, TFA salt

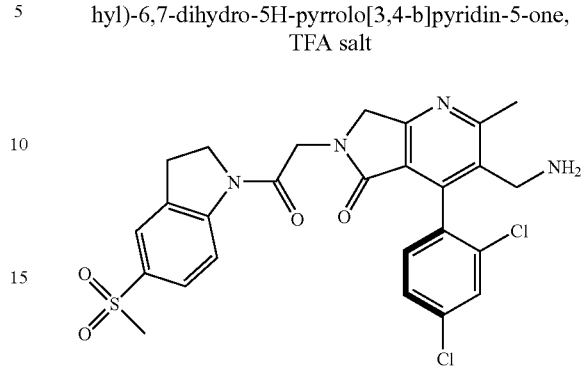

A mixture of Example 50E (31.4 mg, 0.065 mmol), EDCI (49.8 mg, 0.26 mmol), HOAT (13.3 mg, 0.097 mmol) and 5-(methylsulfonyl)indoline (16.7 mg, 0.084 mmol) was stirred at ambient temperature for 1 h and evaporated under reduced pressure. The residue was partitioned between EtOAc and H$_2$O and the aqueous layer was extracted further with EtOAc. The combined organic layers were washed with brine, dried (NaSO$_4$) and concentrated in vacuo. The residue was then dissolved in CH$_2$Cl$_2$ (1.0 mL) followed by addition of TFA (0.5 mL). The reaction mixture was allowed to stir at ambient temperature for 3 h and concentrated in vacuo. The crude product was purified by prep HPLC (Phenomenex Luna 5μ, 21.2×250 mm, 15 min gradient, 30 to 90% solvent B, 40 mL/min) to give Example 3, TFA salt (3.5 mg, 8% yield in 2 steps) as an off-white powder. $^1$H NMR (500 MHz, CD$_3$OD) δ 2.77 (s, 3H), 2.99 (s, 3H), 3.25 (t, J=8.5 Hz, 2H), 3.88 and 4.12 (AB$_q$, J=14.3 Hz, 2H), 4.18 (t, J=8.5 Hz, 2H), 4.44 and 4.55 (AB$_q$, J=16.0 Hz, 2H), 4.58 (s, 2H), 7.26 (d, J=8.3 Hz, 1H), 7.43 (d, J=8.3 Hz, 1H), 7.60 (s, 1H), 7.66 (d, J=8.3 Hz, 1H), 7.71 (s, 1H), 8.13 (d, J=8.8 Hz, 1H). HRMS: Calculated for C$_{26}$H$_{25}$Cl$_2$N$_4$O$_4$S: 559.0974. Found: 559.0985 [M+H]$^+$.

Using the procedures described in Example 69 the following compounds (Examples 70 to 75) were prepared:

Example 70

(S)-3-Aminomethyl)-(2,4-dichlorophenyl)-6-(2-(4-isopropylpiperazin-1-yl)-2-oxoethyl)-2-methyl-6,7-dihydro-5H-pyrrolo[3,4-b]pyridin-5-one, TFA salt

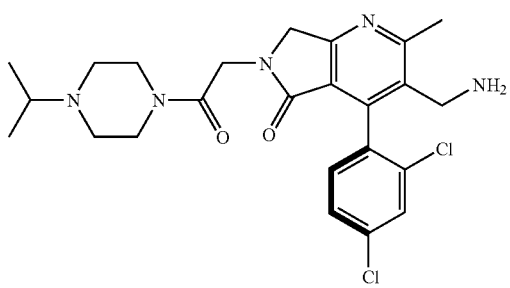

$^1$H NMR (500 MHz, CD$_3$OD) δ 1.37 (d, J=6.6 Hz, 6H), 2.84 (s, 3H), 2.98-3.15 (m, 2H), 3.19-3.35 (m, 1H), 3.39-3.63 (m, 4H), 3.96 and 4.20 (AB$_q$, J=14.6 Hz, 2H), 4.14-4.25 (m, 1H), 4.37-4.73 (m, 5H), 7.35 (d, J=8.3 Hz, 1H), 7.51 (d, J=8.3 Hz, 1H), 7.68 (s, 1H). HRMS: Calculated for C$_{24}$H$_{30}$Cl$_2$N$_5$O$_2$: 490.1777. Found: 490.1759 [M+H]$^+$.

Example 71

(S)-3-(Aminomethyl)-4-(2,4-dichlorophenyl)-2-methyl-6-(2-oxo-2-(4-(pyrimidin-2-yl)piperazin-1-yl)ethyl)-6,7-dihydro-5H-pyrrolo[3,4-b]pyridin-5-one, TFA salt

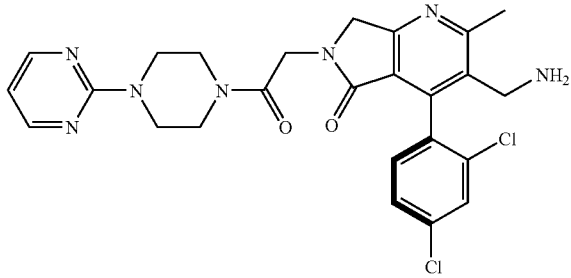

$^1$H NMR (500 MHz, CD$_3$OD) δ 2.75 (s, 3H), 3.48-3.61 (m, 4H), 3.74 (t, J=5.0 Hz, 2H), 3.81 (t, J=4.4 Hz, 2H), 3.87 and 4.11 (AB$_q$, J=14.8 Hz, 2H), 4.39 and 4.49 (AB$_q$, J=17.0 Hz, 2H), 4.52 (s, 2H), 6.57 (t, J=5.0 Hz, 1H), 7.25 (d, J=8.3 Hz, 1H), 7.42 (d, J=8.3 Hz, 1H), 7.60 (s, 1H), 8.27 (d, J=5.0 Hz, 2H). HRMS: Calculated for C$_{25}$H$_{26}$Cl$_2$N$_7$O$_2$: 526.1525. Found: 526.1512 [M+H]$^+$.

Example 72

(S)-2-(3-(Aminomethyl)-4-(2,4-dichlorophenyl)-2-methyl-5-oxo-5H-pyrrolo[3,4-b]pyridin-6(7H)-yl)-N,N-dipropylacetamide, TFA salt

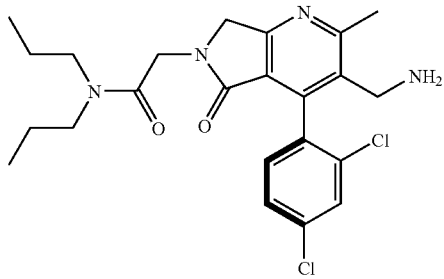

$^1$H NMR (400 MHz, CD$_3$OD) δ 0.78 (t, J=7.5 Hz, 3H), 0.87 (t, J=7.5 Hz, 3H), 1.39-1.52 (m, 2H), 1.53-1.67 (m, 2H), 2.74 (s, 3H), 3.15-13.25 (m, 4H), 3.86 and 4.10 (AB$_q$, J=14.5 Hz, 2H), 4.31 and 4.44 (AB$_q$, J=16.7 Hz, 2H), 4.51 (s, 2H), 7.24 (d, J=7.9 Hz, 1H), 7.42 (dd, J=8.1, 1.10 Hz, 1H), 7.59 (d, J=1.3 Hz, 1H). HRMS: Calculated for C$_{23}$H$_{29}$Cl$_2$N$_4$O$_2$: 463.1668. Found: 463.1672 [M+H]$^+$.

Example 73

(S)-2-(3-(Aminomethyl)-4-(2,4-dichlorophenyl)-2-methyl-5-oxo-5H-pyrrolo[3,4-b]pyridin-6(7H)-yl)-N-(tetrahydro-2H-pyran-4-yl)acetamide, TFA salt

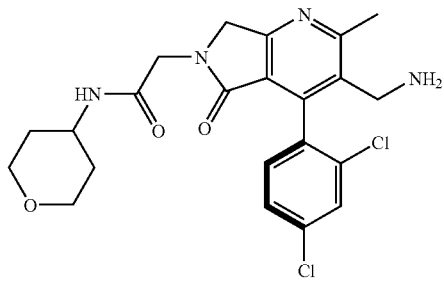

$^1$H NMR (400 MHz, CD$_3$OD) δ 1.32-1.50 (m, 2H), 1.65-1.81 (m, 2H), 2.74 (s, 3H), 3.36 (t, J=11.4 Hz, 2H), 3.71-3.93 (m, 4H), 4.00-4.30 (m, 3H), 4.52 (s, 2H), 7.24 (d, J=7.9 Hz, 1H), 7.42 (dd, J=8.1, 2.0 Hz, 1H), 7.60 (d, J=2.2, 1H). HRMS: Calculated for C$_{22}$H$_{25}$Cl$_2$N$_4$O$_3$: 463.1304. Found: 463.1306 [M+H]$^+$.

Example 74

(S)-3-Aminomethyl)-4-(2,4-dichlorophenyl)-6-(2-(4,4-dimethyloxazoldin-3-yl)-2-oxoethyl)-2-methyl-6,7-dihydro-5H-pyrrolo[3,4-b]pyridin-5-one, TFA salt

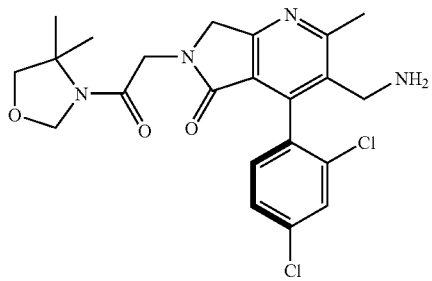

$^1$H NMR (500 MHz, CD$_3$OD) δ 1.35 (d, J=5.5 Hz, 6H), 2.75 (s, 3H), 3.67 (s, 2H), 3.87 and 4.11 (AB$_q$, J=14.5 Hz, 2H), 4.08 and 4.20 (AB$_q$, J=16.8 Hz, 2H), 4.51 (s, 2H), 4.97 (s, 2H), 7.25 (d, J=8.3 Hz, 1H), 7.42 (dd, J=8.3, 1.6 Hz, 1H), 7.59 (d, J=1.6 Hz, 1H). HRMS: Calculated for C$_{22}$H$_{25}$Cl$_2$N$_4$O$_3$: 463.1304. Found: 463.1390 [M+H]$^+$.

Example 75

(S)-2-(3-(Aminomethyl)-4-(2,4-dichlorophenyl)-2-methyl-5-oxo-5H-pyrrolo[3,4-b]pyridin-6(7H)-yl)-N-methylacetamide, TFA salt

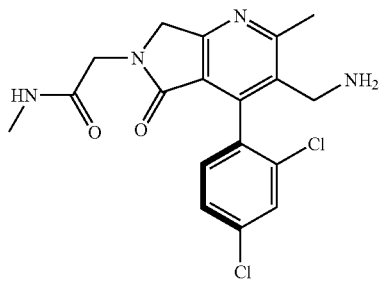

$^1$H NMR (400 MHz, CD$_3$OD) δ 2.63 (s, 3H), 2.74 (s, 3H), 3.86 and 4.11 (AB$_q$, J=14.5 Hz, 2H), 4.08 and 4.20 (AB$_q$, J=16.8 Hz, 2H), 4.50 (s, 2H), 7.25 (d, J=8.3 Hz, 1H), 7.42 (dd, J=8.3, 1.6 Hz, 1H), 7.59 (d, J=1.6 Hz, 1H). HRMS: Calculated for C$_{18}$H$_{19}$Cl$_2$N$_4$O$_2$: 393.0885. Found: 393.0894 [M+H]$^+$.

Example 76

(S)-2-(3-(Aminomethyl)-4-(2,4-dichlorophenyl)-2-methyl-5-oxo-5H-pyrrolo[3,4-b]pyridin-6(7H)-yl)-N,N-diisopropylacetamide, TFA salt

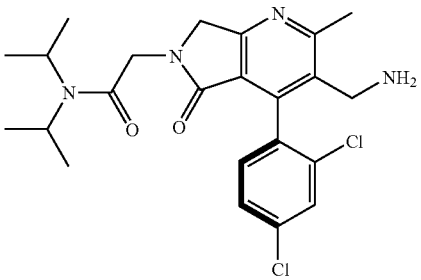

To a stirred mixture of Example 50E (173.4 mg, 0.152 mmol) and triphenylphosphine resin (0.31 g, 0.458 mmol) in CH$_2$Cl$_2$ (4 mL) at ambient temperature was added trichloroacetonitrile (45.9 μL, 0.458 mmol) dropwise. The stirred mixture was kept at ambient temperature for 2.5 h and then cooled to 0° C. followed by addition of diisopropyl amine (64.2 μL, 0.458 mmol) and Et₃N (63.8 μL, 0.458 mmol). The stirred mixture was kept at 0° C. for 35 min and at ambient temperature for another 30 min and filtrated. The filtrate was concentrated in vacuo and the residue was dissolved in CH₂Cl₂ (2.0 mL) followed by addition of TFA (0.7 mL). The reaction mixture was allowed to stir at ambient temperature for 2.5 h and concentrated in vacuo. The crude product was purified by prep HPLC (Phenomenex, Luna 5μ, 21.2×250 mm, 14 min gradient, 10 to 90% solvent B, 40 mL/min) to give Example 4, TFA salt (12.4 mg, 14% yield) as an off-white powder. ¹H NMR (500 MHz, CD₃OD) δ 1.11-1.21 (m, 6H), 1.27 (q, J=6.6 Hz, 6H), 2.75 (s, 3H), 3.42-3.52 (m, 1H), 3.86 and 4.10 (AB$_q$, J=14.6 Hz, 2H), 3.89-3.98 (m, 1H), 426 abd 4.38 (AB$_q$, J=16.8 Hz, 2H), 4.49 (s, 2H), 7.25 (d, J=8.3 Hz, 1H), 7.42 (d, J=8.3 Hz, 1H), 7.59 (s, 1H). HRMS: Calculated for C₂₃H₂₉Cl₂N₄O₂: 463.1668. Found: 463.1656 [M+H]⁺.

Example 77

(S)-tert-Butyl 2-(((S)-3-(aminomethyl)-4-(2,4-dichlorophenyl)-2-methyl-5-oxo-5H-pyrrolo[3,4-b]pyridin-6(7H)-yl)methyl)pyrrolidine-1-carboxylate, TFA salt

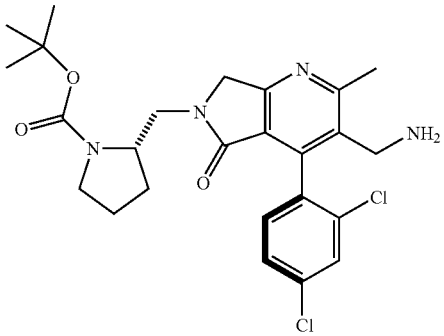

Example 77A (R)-Benzyl 6-(((S)-1-(tert-butoxycarbonyl)pyrrolidin-2-yl)methyl)-4-(2,4-dichlorophenyl)-2-methyl-5-oxo-6,7-dihydro-5H-pyrrolo[3,4-b]pyridine-3-carboxylate

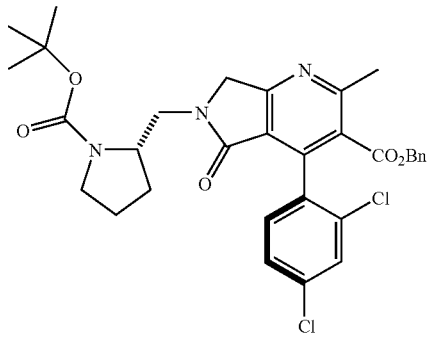

A mixture of (S)-3-benzyl 5-ethyl 6-(chloromethyl)-4-(2,4-dichlorophenyl)-2-methylpyridine-3,5-dicarboxylate (248 mg, 0.503 mmol), (S)-tert-butyl 2-(aminomethyl)pyrrolidine-1-carboxylate (231.7 mg, 1.157 mmol) and triethylamine (161 μL, 1.157 mmol) in N,N-dimethylacetamide (10 mL) was heated to 100° C. for 3 h and then cooled to ambient temperature. The resulting mixture was partitioned between EtOAc and H₂O and the aqueous layer was extracted further with EtOAc (2×). The combined organic extracts were washed with H₂O and brine, dried (Na₂SO₄) and evaporated under reduced pressure. The residue was purified by flash chromatography (40 g column, 0 to 100% EtOAc/Hexanes) to give Example 77A (240.4 mg, 78% yield) as a light yellow solid. [M+H-Boc]⁺=510.2.

Example 77B (R)-6-(((S)-1-(tert-Butoxycarbonyl)pyrrolidin-2-yl)methyl)-4-(2,4-dichlorophenyl)-2-methyl-5-oxo-6,7-dihydro-5H-pyrrolo[3,4-b]pyridine-3-carboxylic acid

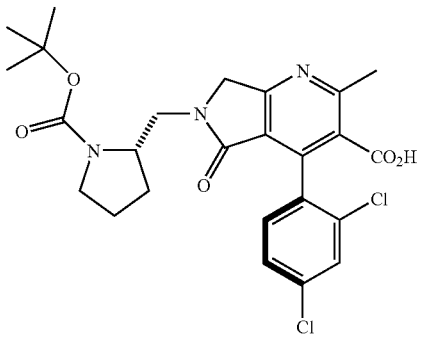

A stirred mixture of Example 77A (235.9 mg, 0.386 mmol) and 10% palladium on carbon (47 mg) in EtOAc (8 mL) was under hydrogen (balloon) at ambient temperature for 3 h. The reaction mixture was filtered through a pad of Celite, which was washed with MeOH and CH₂Cl₂. The filtrate was evaporated under reduced pressure to give crude Example 77B (200.7 mg, 100% yield) as a light yellow solid. [M+H-Boc]⁺= 420.1.

Example 77C (S)-tert-Butyl 2-(((S)-4-(2,4-dichlorophenyl)-3-(hydroxymethyl)-2-methyl-5-oxo-5H-pyrrolo[3,4-b]pyridin-6(7H)-yl)methyl)pyrrolidine-1-carboxylate

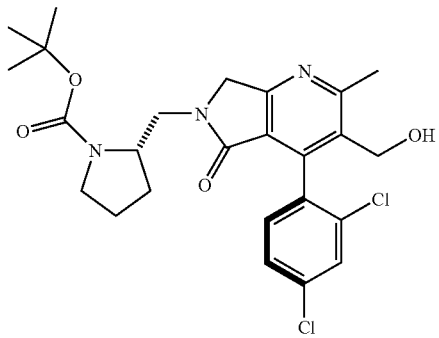

To a stirred mixture of Example 77B (200 mg, 0.384 mmol) and triphenylphosphine resin (1.04 g, 1.536 mmol) in CH₂Cl₂ (10 mL) at ambient temperature was added trichloroacetonitrile (0.15 mL, 1.536 mmol) dropwise. The stirred mixture was kept at ambient temperature for 1.5 h and filtrated. The filtrate was concentrated in vacuo to give crude (S)-tert-butyl 2-(((R)-3-(chlorocarbonyl)-4-(2,4-dichlorophenyl)-2-methyl-5-oxo-5H-pyrrolo[3,4-b]pyridin-6(7H)-yl)methyl)pyrrolidine-1-carboxylate, which was used directly in subsequent reaction.

To a solution of the above acid chloride in THF (7 mL) at 0° C. was added lithium tri-tert-butoxyaluminohydride (1.15 mL, 1.15 mmol) dropwise. The mixture was stirred at 0° C.

for 45 min, quenched with H$_2$O (0.2 mL) and concentrated in vacuo. Purification of the residue by flash chromatography (12 g column, 0 to 100% EtOAc/Hexanes) afforded Example 77C (137.2 mg, 70% in 2 steps) as a light orange solid. [M+H-Boc]$^+$=406.2.

Example 77D (S)-tert-Butyl 2-(((R)-3-(chloromethyl)-4-(2,4-dichlorophenyl)-2-methyl-5-oxo-5H-pyrrolo[3,4-b]pyridin-6(7H)-yl)methyl)pyrrolidine-1-carboxylate

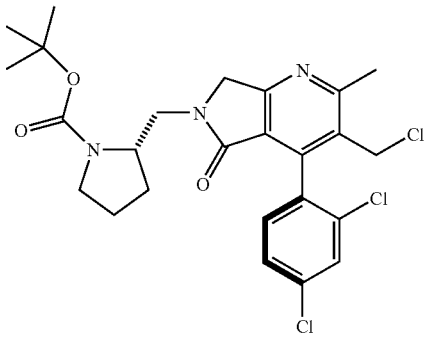

To a mixture of Example 77C (40 mg, 0.079 mmol) and Et$_3$N (44 μL, 0.316 mmol) in CH$_2$Cl$_2$ (1.5 mL) at 0° C. was added mesyl chloride (18.3 μl, 0.237 mmol) dropwise. The stirred mixture was kept at ambient temperature overnight and evaporated under reduced pressure. The residue was partitioned between EtOAc and H$_2$O and the aqueous layer was extracted further with EtOAc (2×). The combined organic extracts were washed with brine, dried (Na$_2$SO$_4$) and concentrated in vacuo. The crude product was chromatographed (4 g column, 0 to 100% EtOAc/Hexanes) to give Example 77D (41.2 mg, 99.4%) as a colorless solid. [M+H-Boc]$^+$=424.1.

Example 77

(S)-tert-Butyl 2-(((S)-3-(aminomethyl)-4-(2,4-dichlorophenyl)-2-methyl-5-oxo-5H-pyrrolo[3,4-b]pyridin-6(7H)-yl)methyl)pyrrolidine-1-carboxylate, TFA salt

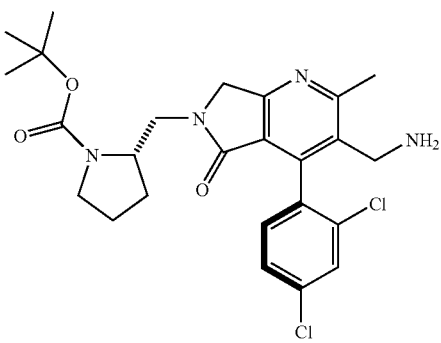

A solution of Example 77D (40 mg, 0.076 mmol) in 7M NH$_3$ in MeOH (4 mL) was heated at 100° C. in Microwave for 15 min, cooled and concentrated in vacuo. The residue was purified by prep HPLC (Luna 5μ C 18, 30×100 mm, 10 min gradient, 0 to 100% solvent B, 40 mL/min) to give Example 77, TFA salt (36.5 mg, 77.5% yield) as an off-white powder. $^1$H NMR (400 MHz, CD$_3$OD) δ 1.38 (s, 9H), 1.69-1.98 (m, 4H), 2.84 (s, 3H), 3.25-3.39 (m, 2H), 3.52-3.68 (m, 2H), 3.95 (part of AB$_q$, J=14.5 Hz, 1H), 4.10-4.26 (m, 2H), 4.46-4.77 (m, 2H), 7.26-7.42 (m, 1H), 7.52 (dd, J=8.1, 2.0 Hz, 1H), 7.69 (d, J=1.8 Hz, 1H). HRMS: Calculated for C$_{25}$H$_{31}$Cl$_2$N$_4$O$_3$: 505.1773. Found: 505.1783 [M+H]$^+$.

Using the procedures described in Example 77, Examples 50 and 78 were prepared:

Example 50

(S)-2-(3-(Aminomethyl)-4-(2,4-dichlorophenyl)-2-methyl-5-oxo-5H-pyrrolo[3,4-b]pyridin-6(7H)-yl)-N,N-dimethylacetamide, TFA salt

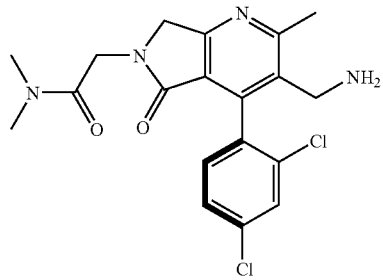

Example 78

(S)-3-(Aminomethyl)-4-(2,4-dichlorophenyl)-2-methyl-6-(oxazol-2-ylmethyl)-6,7-dihydro-5H-pyrrolo[3,4-b]pyridin-5-one, TFA salt

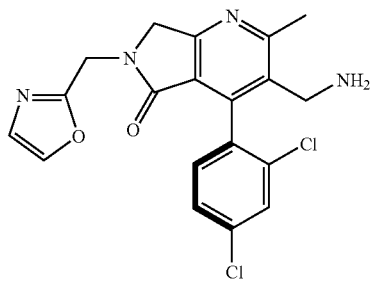

$^1$H NMR (500 MHz, CD$_3$OD) δ 2.74 (s, 3H), 3.86 and 4.10 (AB$_q$, J=14.3 Hz, 2H), 4.53 and 4.57 (AB$_q$, J=19.0 Hz, 2H), 4.75 and 4.83 (AB$_q$, J=16.5 Hz, 2H), 7.03 (s, 1H), 7.25 (d, J=8.3 Hz, 1H), 7.41 (dd, J=8.3, 2.20 Hz, 1H), 7.59 (d, J=1.7 Hz, 1H), 7.79 (s, 1H). HRMS: Calculated for C$_{19}$H$_{17}$Cl$_2$N$_4$O$_2$: 403.0729. Found: 403.0715 [M+H]$^+$.

Example 79

(S)-3-(Aminomethyl)-4-(2,4-dichlorophenyl)-2-methyl-6-((S)-pyrrolidin-2-ylmethyl)-6,7-dihydro-5H-pyrrolo[3,4-b]pyridin-5-one, TFA salt

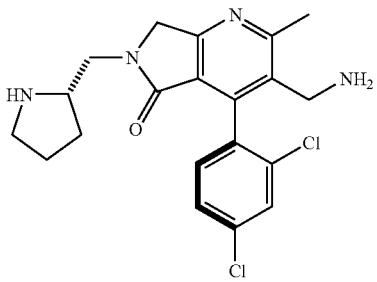

A mixture of Example 77 (28 mg, 0.055 mmol) and TFA (0.7 mL) in CH$_2$Cl$_2$ (1.0 was allowed to stir at ambient temperature for 1 h and evaporated under reduced pressure. The residue was purified by prep HPLC (Luna 5μ C18 (2), 30×100 mm, 10 min gradient, 0 to 60% solvent B, 40 mL/min) to give Example 6, TFA salt (15.9 mg, 45.7% yield) as an off-white solid. $^1$H NMR (400 MHz, CD$_3$OD) δ 1.59-1.75 (m, 1H), 1.83-2.05 (m, 2H), 2.07-2.18 (m, 1H), 2.75 (s, 3H), 3.10-3.30 (m, 2H), 3.64-3.98 (m, 4H), 4.12 (part of AB$_q$, J=14.1 Hz, 1H), 4.50 and 4.61 (AB$_q$, J=18.0 Hz, 2H), 7.26 (d, J=8.4 Hz, 1H), 7.42 (dd, J=8.1, 2.0 Hz, 1H), 7.60 (d, J=2.20 Hz, 1H). HRMS: Calculated for C$_{20}$H$_{23}$Cl$_2$N$_4$O: 405.1249. Found: 405.1256 [M+H]$^+$.

Example 80

(S)-3-(Aminomethyl)-6-(((S)-1-(cyclopropylsulfonyl)pyrrolidin-2-yl)methyl)-4-(2,4-dichlorophenyl)-2-methyl-6,7-dihydro-5H-pyrrolo[3,4-b]pyridin-5-one, TFA salt

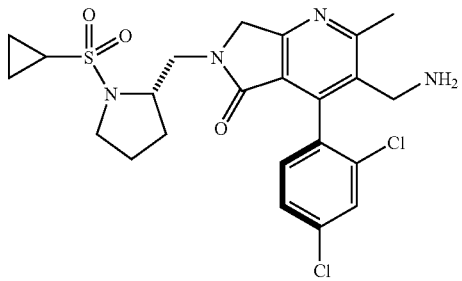

Example 80A (S)-4-(2,4-Dichlorophenyl)-3-(hydroxymethyl)-2-methyl-6-((S)-pyrrolidin-2-ylmethyl)-6,7-dihydro-5H-pyrrolo[3,4-b]pyridin-5-one

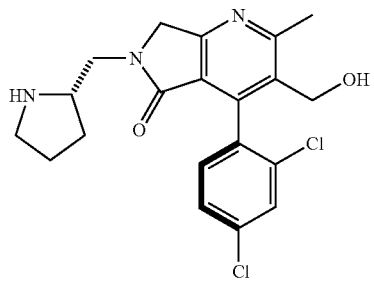

A mixture of Example 77C (84 mg, 0.166 mmol) and TFA (0.7 mL) in CH$_2$Cl$_2$ (1.5 was allowed to stir at ambient temperature for 3 h and evaporated under reduced pressure. The residue was co-evaporated with ethanol (3×) to give Example 80A (123.7 mg) as an orange oil which was used for the next step without further purification. [M+H]$^+$=406.2.

Example 80B (R)-3-Chloromethyl)-6-((S)-1-(cyclopropylsulfonyl)pyrrolidin-2-yl)methyl)-4-(2,4-dichlorophenyl)-2-methyl-6,7-dihydro-5H-pyrrolo[3,4-b]pyridin-5-one

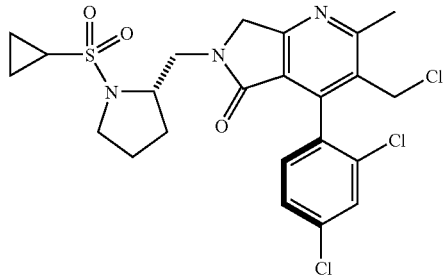

To a solution of Example 80A (123 mg, 0.166 mmol) and Et$_3$N (230.9 µL, 1.66 mmol) in CH$_2$Cl$_2$ (2.5 mL) at 0° C. was added cyclopropanesulfonyl chloride (23.3 mg, 0.166 mmol) in CH$_2$Cl$_2$ (0.5 mL). The stirred mixture was kept at ambient temperature for 2.5 h followed by addition of mesyl chloride (32 µL, 0.415 mmol). The resulting mixture was kept at ambient temperature overnight and evaporated under reduced pressure. The residue was dissolved in EtOAc, washed with brine, dried (Na$_2$SO$_4$) and concentrated in vacuo. The crude product was chromatographed (12 g column, 0 to 100% EtOAc/Hexanes) to give Example 80B (55.2 mg, 62.9%) as a colorless solid. [M+H]$^+$=528.1.

Example 80

(S)-3-(Aminomethyl)-6-(((S)-1-(cyclopropylsulfonyl)pyrrolidin-2-yl)methyl)-4-(2,4-dichlorophenyl)-2-methyl-6,7-dihydro-5H-pyrrolo[3,4-b]pyridin-5-one, TFA salt

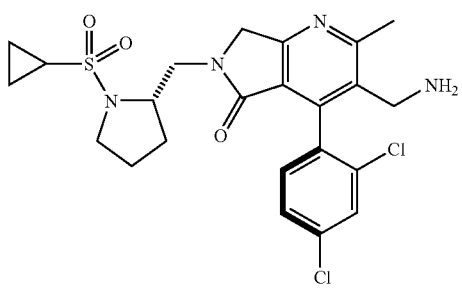

A solution of Example 80B (55 mg, 0.104 mmol) in 7M NH$_3$ in MeOH (5 mL) was heated at 100° C. in Microwave for 15 min, cooled and concentrated in vacuo. The residue was purified by prep HPLC (Luna 5µ C18 (2), 30×100 mm, 12 min gradient, 0 to 80% solvent B, 40 mL/min) to give Example 80, TFA salt (44.9 mg, 69.2% yield) as a white powder. $^1$H NMR (500 MHz, CD$_3$OD) δ 0.81-0.97 (m, 4H), 1.65-1.74 (m, 1H), 1.81-1.93 (m, 2H), 1.91-2.03 (m, 1H), 2.33-2.50 (m, 1H), 2.73 (s, 3H), 3.24-3.31 (m, 1H), 3.34-3.61 (m, 3H), 3.85 (part of AB$_q$, J=14.3 Hz, 1H), 4.06-4.18 (m, 2H), 4.50-4.66 (m, 2H), 7.24 (d, J=8.3 Hz, 1H), 7.42 (d, J=8.3 Hz, 1H), 7.59 (s, 1H). HRMS: Calculated for C$_{23}$H$_{27}$Cl$_2$N$_4$O$_3$S: 509.1181. Found: 509.1190 [M+H]$^+$.

Example 81

(S)-Methyl 2-(3-(aminomethyl)-4-(2,4-dichlorophenyl)-2-methyl-7-oxo-5H-pyrrolo[3,4-b]pyridin-6(7H)-yl)acetate, TFA salt

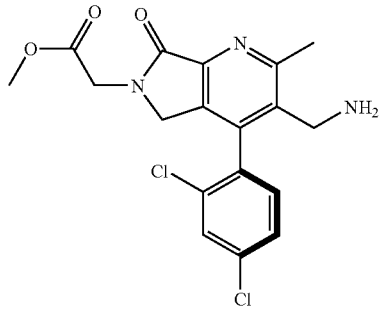

Racemic Example 23 was separated on a Chiralcel® OJ, 20 µ, 5×50 cm column using an isocratic gradient of 15% EtOH-MeOH (50%) containing 0.1% diethylamine in heptane containing 0.1% diethyl amine to afford individual enantiomers.

Example 81 (Enantiomer A; slower-moving): Purity by chiral analytical HPLC [Chiralcel® OJ 4.6×250 mm; 20%

EtOH-MeOH (1:1; containing 0.1% DEA) in heptane (containing 0.1% DEA)]: RT=18.22 min; >97% ee.

Example 82

(R)-Methyl 2-(3-(aminomethyl)-4-(2,4-dichlorophenyl)-2-methyl-7-oxo-5H-pyrrolo[3,4-b]pyridin-6(7H)-yl)acetate, TFA salt

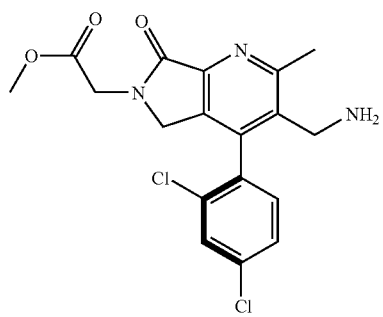

Example 82 (Enantiomer B; faster-moving): Purity by chiral analytical HPLC [Chiralcel® OJ 4.6×250 mm; 15% EtOH-MeOH (1:1; containing 0.1% DEA) in heptane (containing 0.1% DEA)]: RT=15.8 min; >97% ee.

Example 83

(S)-2-(3-(Aminomethyl)-4-(2,4-dichlorophenyl)-2-methyl-7-oxo-5H-pyrrolo[3,4-b]pyridin-6(7H)-yl) acetic acid, TFA salt

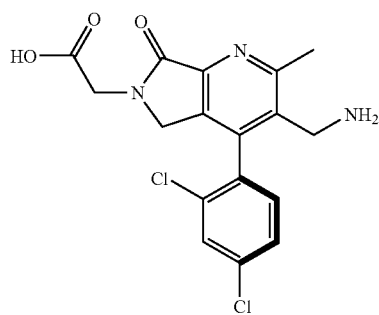

To a solution of Example 81 (20 mg, 0.05 mmol) in THF (0.7 mL) was added aqueous LiOH solution (4.5 mg in 0.5 mL H$_2$O, 0.107 mmol) and the resulting mixture stirred for 2 h. The mixture was acidified to pH=4 with 1N aqueous HCl. Organic volatiles were removed in vacuo and the aqueous phase was extracted with EtOAc (5 mL). The organic extracts was concentrated in vacuo to give the a crude product which was purified by prep HPLC (Phenomenex, 10 min gradient, 15 to 100% B) to give Example 83. TFA salt (7.1 mg, 28%) as a white powder. Phenomenex LUNA C-18 4.6×50 mm, 0-100% over 10 min, A=90% water, 10% acetonitrile, 0.1% TFA, B=10% water, 90% acetonitrile, 0.1% TFA). $^1$H NMR (400 MHz, CD$_3$OD) δ 2.75 (s, 3H), 3.91 and 4.12 (AB$_q$, J=14.5 Hz, 2H), 4.16 and 4.23 (AB$_q$, J=16.3 Hz, 2H), 4.26 and 4.32 (AB$_q$, J=16.0 Hz, 2H), 7.34 (d, J=8.3 Hz, 1H), 7.51 (dd, J=8.3, 2.2 Hz, 1H), 7.71 (d, J=2.2 Hz, 1H). [α]$_D^{25}$+5.84° (c=0.1, MeOH); LCMS: Anal. Calcd. for C$_{17}$H$_{15}$Cl$_2$N$_4$O$_2$: 379.05. Found: 380.18[M+H]$^+$.

Example 84

(S)-2-(3-(Aminomethyl)-4-(2,4-dichlorophenyl)-2-methyl-7-oxo-5H-pyrrolo[3,4-b]pyridin-6(7H)-yl) acetamide, TFA salt

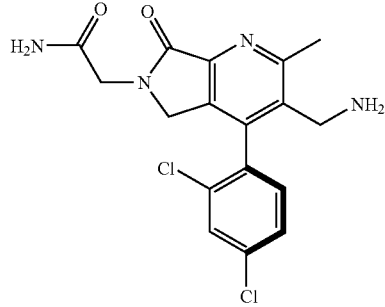

Example 84A (S)-Methyl 2-(3-((tert-butoxycarbonylamino)methyl)-4-(2,4-dichlorophenyl)-2-methyl-7-oxo-5H-pyrrolo[3,4-b]pyridin-6(7H)-yl)acetate

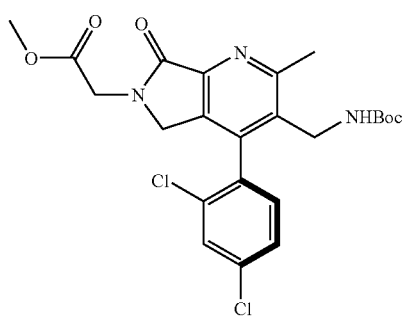

To a mixture of Example 81 (37 mg, 0.094 mmol) in THF (3 mL) was added sat. aq. NaHCO$_3$ (2 mL), and (Boc)$_2$O (50 mg, 0.23 mmol). The resulting mixture was stirred at RT for 2 h diluted with EtOAc (8 mL) and H$_2$O (2 mL). The mixture was stirred for a further 5 min. The organic layer was separated and evaporated in vacuo to yield Example 84A.

Example 84B (S)-tert-Butyl (6-(2-amino-2-oxoethyl)-4-(2,4-dichlorophenyl)-2-methyl-7-oxo-6,7-dihydro-5H-pyrrolo[3,4-b]pyridin-3-yl)methylcarbamate

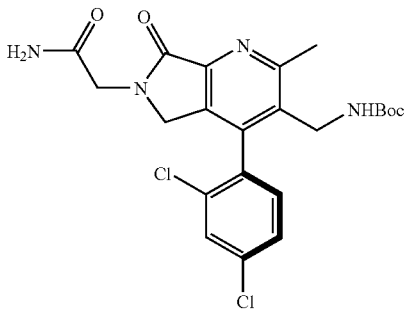

A solution of Example 84A (30 mg, 0.06 mmol) and 7N ammonia in MeOH (1 mL) in sealed tube was irradiated in a microwave reactor at 100° C. for 10 min. After cooling down to ambient temperature, the volatiles were removed in vacuo to give crude amide product. This product was mixed with 7N ammonia in MeOH (2 mL) in sealed tube then irradiated in a microwave reactor at 100° C. for another 10 min. After cooling down to ambient temperature, the volatiles were removed in vacuo to give Example 84B.

Example 84

(S)-2-(3-(Aminomethyl)-4-(2,4-dichlorophenyl)-2-methyl-7-oxo-5H-pyrrolo[3,4-b]pyridin-6(7H)-yl)acetamide, TFA salt

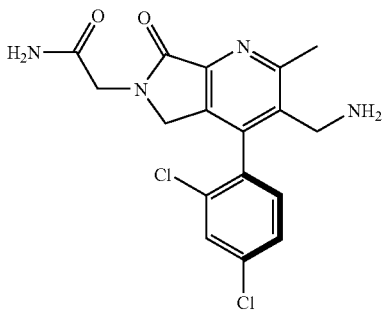

To a solution of Example 84B product in CH$_2$Cl$_2$ (1 mL) was added TFA (0.5 mL) and the resulting mixture stirred for 1 h. Solvent were removed and the residue purified by prep HPLC (Phenomenex, 10 min gradient, 15 to 100% B) to give Example 84. TFA salt (12 mg, 39%) as white powder. Phenomenex LUNA C-18 4.6×50 mm, 0-100% over 10 min, A=90% water, 10% methanol, 0.1% TFA. B=10% water, 90% methanol, 0.1% TFA). $[\alpha]_D^{25}$+6.30 (c=0.1, MeOH); Purity by chiral analytical HPLC [Chiralcel® OJ 4.6×250 mm; 15% EtOH-MeOH (1:1; containing 0.1% DEA) in heptane (containing 0.1% DEA)]: >98% ee. $^1$H NMR (400 MHz, CD$_3$OD) δ 2.84 (s, 3H), 4.02 and 4.24 (AB$_q$, J=14.1 Hz, 2H), 4.24 and 4.33 (AB$_q$, J=18.5 Hz, 2H), 4.28 and 4.35 (AB$_q$, J=17.0 Hz, 2H), 7.45 (d, J=8.3 Hz, 1H), 7.59 (dd, J=8.3, 2.2 Hz, 1H), 7.78 (d, J=2.2 Hz, 1H). LCMS: Anal. Calcd. for C$_{17}$H$_{16}$Cl$_2$N$_4$O$_2$: 378.07. Found: 379.12 [M+H]$^+$. HRMS: Anal. Calcd. for C$_{17}$H$_{18}$Cl$_2$N$_4$O$_2$: 379.0729. Found: 379.0732 [M+H]$^+$.

Example 85

(S)-2-(3-(Aminomethyl)-4-(2,4-dichlorophenyl)-2-methyl-7-oxo-5H-pyrrolo[3,4-b]pyridin-6(7H)-yl)-N-methylacetamide, TFA salt

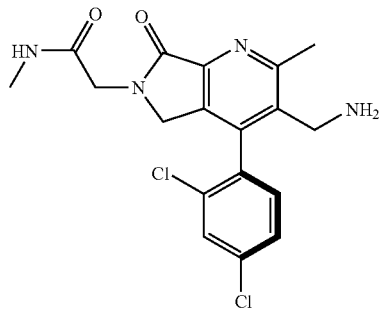

Example 85A (S)-tert-Butyl (4-(2,4-dichlorophenyl)-2-methyl-6-(2-(methylamino)-2-oxoethyl)-7-oxo-6,7-dihydro-5H-pyrrolo[3,4-b]pyridin-3-yl)methylcarbamate

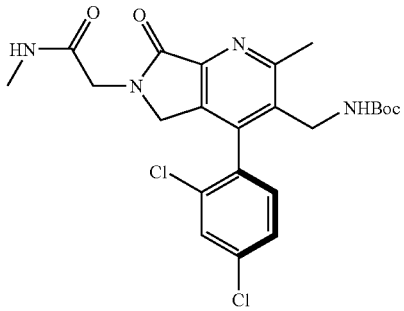

A mixture of Example 84A (16 mg, 0.032 mmol), methyl amine (0.4 mL, 40% wt. in H$_2$O) and MeOH (0.6 mL) in sealed tube was irradiated in a microwave reactor at 100° C. for 20 min. After cooling down to ambient temperature, the volatiles were removed in vacuo to give crude amide product.

Example 85

(S)-2-(3-(Aminomethyl)-4-(2,4-dichlorophenyl)-2-methyl-7-oxo-5H-pyrrolo[3,4-b]pyridin-6(7H)-yl)-N-methylacetamide, TFA salt

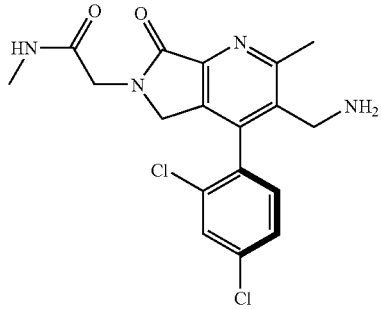

To a solution of Example 85A in CH$_2$Cl$_2$ (1 mL) was added TFA (0.5 mL) and the resulting mixture stirred for 1 h. Solvent were removed and the residue purified by prep HPLC (Phenomenex, 10 min gradient, 15 to 100% B) to give Example 85. TFA salt (11 mg, 66%) as white powder. Phenomenex LUNA C-18 4.6×50 mm, 0-100% over 10 min, A=90% water, 10% methanol, 0.1% TFA. B=10% water, 90% methanol, 0.1% TFA). $^1$H NMR (400 MHz, CD$_3$OD) δ 2.72 (s, 3H), 2.84 (s, 3H), 4.01 and 4.27 (AB$_q$, J=14.5 Hz, 2H), 4.23 and 4.33 (AB$_q$, J=18.1 Hz, 2H), 4.27 and 4.31 (AB$_q$, J=16.0 Hz, 2H), 7.45 (d, J=8.3 Hz, 1H), 7.58 (dd, J=8.3, 2.2 Hz, 1H), 7.78 (d, J=2.2 Hz, 1H). $[\alpha]_D^{25}$+23.80 (c=0.1, MeOH). LCMS: Anal. Calcd. for C$_{18}$H$_{18}$Cl$_2$N$_4$O$_2$: 392.08. Found: 393.16 [M+H]$^+$. HRMS: Anal. Calcd. for C$_{18}$H$_{20}$Cl$_2$N$_4$O$_2$: 393.0885. Found: 393.0882 [M+H]$^+$. Purity by chiral analytical HPLC [Chiralcel® OJ 4.6×250 mm; 20% EtOH-MeOH (1:1; containing 0.1% DEA) in heptane (containing 0.1% DEA)]: RT=12.16 min; >97% ee.

Example 86

(S)-2-(3-(Aminomethyl)-4-(2,4-dichlorophenyl)-2-methyl-7-oxo-5H-pyrrolo[3,4-b]pyridin-6(7H)-yl)-N,N-dimethylacetamide, TFA salt

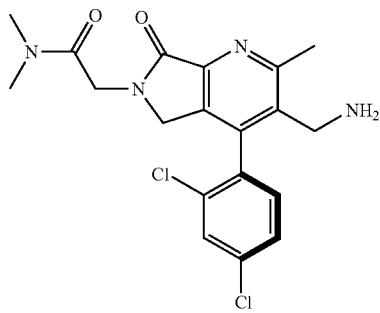

Example 86A (S)-2-(3-((tert-Butoxycarbonylamino)methyl)-4-(2,4-dichlorophenyl)-2-methyl-7-oxo-5H-pyrrolo[3,4-b]pyridin-6(7H)-yl)acetic acid

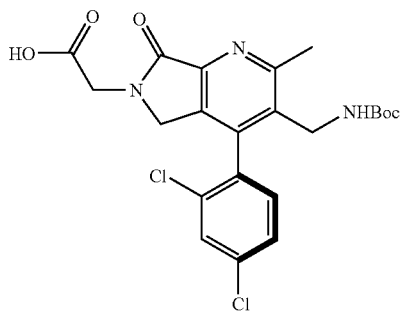

To a solution of Example 84A (130 mg, 0.26 mmol) in THF (3 mL) was added aqueous LiOH solution (19 mg in 2 mL $H_2O$, 0.45 mmol) and the resulting mixture stirred for 2 h. The mixture was acidified to pH=4 with 1N aqueous HCl. Organic volatiles were removed in vacuo and the aqueous phase was extracted with EtOAc (20 ml). The organic extracts was concentrated in vacuo to give Example 86A (125 mg, 99%).

Example 86B (S)-tert-Butyl (4-(2,4-dichlorophenyl)-6-(2-(dimethylamino)-2-oxoethyl)-2-methyl-7-oxo-6,7-dihydro-5H-pyrrolo[3,4-b]pyridin-3-yl)methylcarbamate

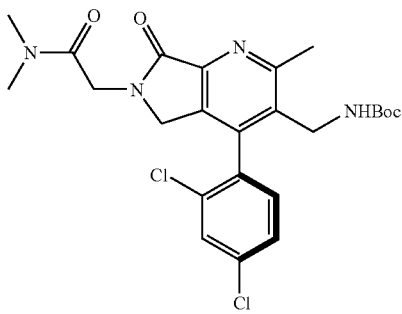

To a mixture of Example 86A (21 mg, 0.044 mmol), PyBOP (34 mg, 0.065 mmol), dimethyl amine (0.1 mL, 2M in THF) in THF was added diisopropyl ethyl amine (0.03 mL, 0.17 mmol). The mixture was stirred at ambient temperature overnight. Solvents were removed and the residue was purified by prep HPLC (Phenomenex, 10 min gradient, 15 to 100% B) to give Example 86B (17.4 mg, 78%) as a white solid. Phenomenex LUNA C-18 4.6×50 mm, 0-100% over 10 min, A=90% water, 10% methanol, 0.1% TFA. B=10% water, 90% methanol, 0.1% TFA). Found: 507.29 $[M+H]^+$.

Example 86

(S)-2-(3-(Aminomethyl)-4-(2,4-dichlorophenyl)-2-methyl-7-oxo-5H-pyrrolo[3,4-b]pyridin-6(7H)-yl)-N,N-dimethylacetamide, TFA salt

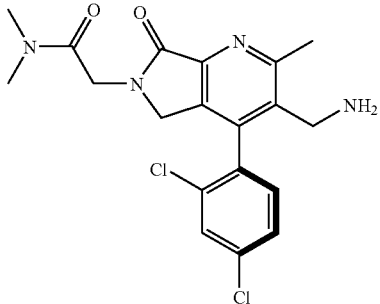

To a solution of Example 86B in $CH_2Cl_2$ (1 mL) was added TFA (0.3 mL) and the resulting mixture stirred for 2 h. Solvent were removed and the residue purified by prep HPLC (Phenomenex, 10 min gradient, 15 to 100% B) to give Example 86. TFA salt (10.4 mg, 58%) as a white powder. Phenomenex LUNA C-18 4.6×50 mm, 0-100% over 10 min, A=90% water, 10% methanol, 0.1% TFA, B=10% water, 90% methanol, 0.1% TFA). $^1$H NMR (400 MHz, $CD_3OD$) δ 2.84 (s, 3H), 2.93 (s, 3H), 3.09 (s, 3H), 4.02 and 4.27 ($AB_q$, J=14.0 Hz, 2H), 4.23 and 4.30 ($AB_q$, J=18.0 Hz, 2H), 4.48 and 4.56 ($AB_q$, J=17.0 Hz, 2H), 7.45 (d, J=8.3 Hz, 1H), 7.58 (dd, J=8.3, 2.2 Hz, 1H), 7.78 (d, J=2.2 Hz, 1H). $[α]_D^{25}$+12.00 (c=0.1, MeOH). LCMS: Anal. Calcd. for $C_{19}H_{20}Cl_2N_4O_2$: 406.10. Found: 407.19 $[M+H]^+$. HRMS: Anal. Calcd. for $C_{19}H_{21}Cl_2N_4O_2$: 407.1042. Found: 407.1031 $[M+H]^+$.

Example 87

(S)-6-(2-(4-Acetylpiperazin-1-yl)-2-oxoethyl)-3-(aminomethyl)-4-(2,4-dichlorophenyl)-2-methyl-5,6-dihydropyrrolo[3,4-b]pyridin-7-one, TFA salt

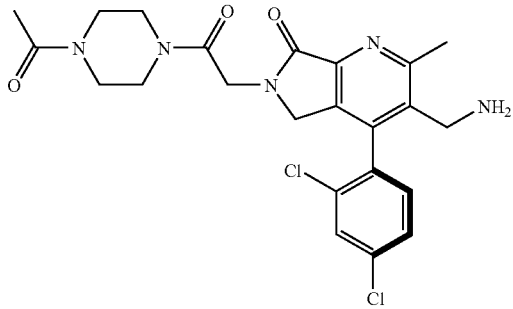

Example 87 was prepared by using the same method described above for Example 86, with the exception that in step 86B, dimethyl amine was replaced by 1-acetylpiperazine. $^1$H NMR (400 MHz, $CD_3OD$) δ 2.12 (s, 1.5H), 2.13 (s, 1.5H), 2.84 (m, 3H), 3.50-3.72 (m, 8H), 4.02 and 4.27 ($AB_q$, J=14.0 Hz, 2H), 4.23 and 4.33 ($AB_q$, J=18.0 Hz, 2H), 4.52 and 4.63 ($AB_q$, J=17.0 Hz, 2H), 7.45 (d, J=8.3 Hz, 1H), 7.58 (dd, J=8.3, 2.2 Hz, 1H), 7.78 (d, J=2.2 Hz, 1H). $[α]_D^{25}$+16.5° (c=0.1, MeOH). LCMS: Anal. Calcd. for $C_{23}H_{25}Cl_2N_5O_3$:

489.13. Found: 490.31 [M+H]⁺. HRMS: Anal. Calcd. for $C_{23}H_{26}Cl_2N_5O_3$: 490.1413. Found: 490.1416 [M+H]⁺.

Example 88

(S)-1-(2-(3-(Aminomethyl)-4-(2,4-dichlorophenyl)-2-methyl-7-oxo-5H-pyrrolo[3,4-b]pyridin-6(7H)-yl)acetyl)piperidine-4-carboxamide, TFA salt

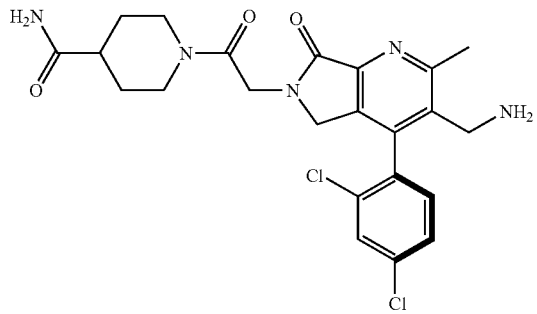

Example 88 was prepared by using the same method described above for Example 86, with the exception that in step 86B, dimethyl amine was replaced by piperidine-4-carboxamide. ¹H NMR (400 MHz, CD₃OD) δ 1.45-1.95 (m, 4H), 2.40-2.55 (m, 2H), 2.86 (s, 3H), 3.10-3.22 (m, 1H), 3.90-4.65 (m, 8H), 7.45 (d, J=8.3 Hz, 1H), 7.59 (dd, J=8.3, 2.2 Hz, 1H), 7.78 (d, J=2.2 Hz, 1H). [α]$_D^{25}$+15.10 (c=0.1, MeOH). LCMS: Anal. Calcd. for $C_{23}H_{25}Cl_2N_5O_3$: 489.13. Found: 490.30 [M+H]⁺. HRMS: Anal. Calcd. for $C_{23}H_{26}Cl_2N_5O_3$: 490.1413. Found: 490.1405 [M+H]⁺.

Example 89

(S)-3-(Aminomethyl)-4-(2,4-dichlorophenyl)-2-methyl-6-(2-(4-(methylsulfonyl)piperazin-1-yl)-2-oxoethyl)-5,6-dihydropyrrolo[3,4-b]pyridin-7-one, TFA salt

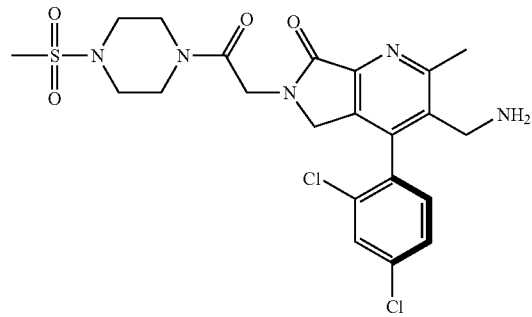

Example 89 was prepared by using the same method described above for Example 86, with the exception that in step 86B dimethyl amine was replaced by 1-(methylsulfonyl)piperazine. ¹H NMR (400 MHz, acetone-d₆) δ 2.72 (s, 3H), 2.81 (s, 3H), 3.10-3.18 (m, 2H), 3.22-3.30 (m, 2H), 3.55-3.62 (m, 2H), 3.65-3.73 (m, 2H), 4.16 (S, 2H), 4.44 and 4.55 (AB$_q$, J=16.7 Hz, 2H), 4.68 and 5.13 (AB$_q$, J=15.8 Hz, 2H), 7.55 (dd, J=8.3, 2.0 Hz, 1H), 7.74 (d, J=2.0 Hz, 1H), 7.77 (d, J=8.3 Hz, 1H). [α]$_D^{25}$+16.30 (c=0.1, MeOH). LCMS: Anal. Calcd. for $C_{22}H_{25}Cl_2N_5O_3S$: 525.10. Found: 526.22 [M+H]⁺. HRMS: Anal. Calcd. for $C_{22}H_{26}Cl_2N_5O_3S$: 526.1069. Found: 526.1093 [M+H]⁺.

Example 90

(S)-2-(3-(Aminomethyl)-4-(2,4-dichlorophenyl)-2-methyl-7-oxo-5H-pyrrolo[3,4-b]pyridin-6(7H)-yl)-N,N-diethylacetamide, TFA salt

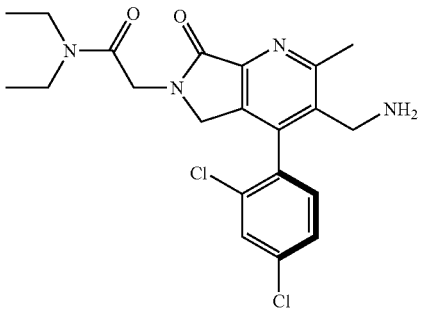

Example 90 was prepared by using the same method described above for Example 86, with the exception that in step 86B, dimethyl amine was replaced by diethylamine. ¹H NMR (400 MHz, CD₃OD) δ 1.10 (t, J=7.0 Hz, 3H), 1.26 (t, J=7.0 Hz, 3H), 2.84 (s, 3H), 3.38 (q, J=7.0 Hz, 2H), 3.43 (q, J=7.0 Hz, 2H), 4.06 and 4.26 (AB$_q$, J=14.5 Hz, 2H), 4.24 and 4.31 (AB$_q$, J=18.0 Hz, 2H), 4.47 and 4.58 (AB$_q$, J=17.0 Hz, 2H), 7.45 (dd, J=8.3, 2.0 Hz, 1H), 7.59 (d, J=2.0 Hz, 1H), 7.79 (d, J=8.3 Hz, 1H). [α]$_D^{25}$+19.40 (c=0.1, MeOH). LCMS: Anal. Calcd. for $C_{21}H_{25}Cl_2N_4O_2$: 434.13. Found: 435.25 [M+H]⁺. HRMS: Anal. Calcd. for $C_{21}H_{25}Cl_2N_4O_2$: 435.1355. Found: 435.1341 [M+H]⁺.

Example 91

(S)-2-(3-(Aminomethyl)-4-(2,4-dichlorophenyl)-2-methyl-7-oxo-5H-pyrrolo[3,4-b]pyridin-6(7H)-yl)-N-(1-methyl-1H-pyrazol-5-yl)acetamide, TFA salt

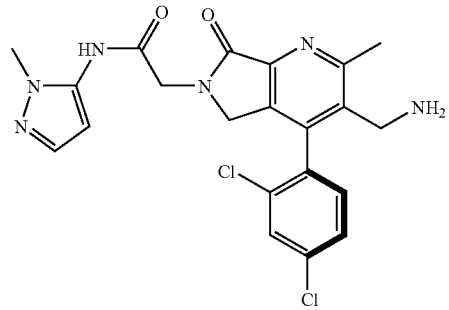

Example 91 was prepared by using the same method described above for Example 86, with the exception that in step 86B dimethyl amine was replaced by 3-amino-2-methylpyrazole. ¹H NMR (400 MHz, CD₃OD) δ 2.85 (s, 3H), 3.76 (s, 3H), 4.06 and 4.26 (AB$_q$, J=14.5 Hz, 2H), 4.28 and 4.40 (AB$_q$, J=18.0 Hz, 2H), 4.42 and 4.51 (AB$_q$, J=17.1 Hz, 2H), 6.39 (d, J=2.2 Hz, 1H), 7.41 (d, J=2.2 Hz, 1H), 7.46 (dd, J=8.3, 2.0 Hz, 1H), 7.56 (d, J=2.0 Hz, 1H), 7.76 (d, J=8.3 Hz, 1H). [ ]$_D^{25}$+31.90 (c=0.1, MeOH). LCMS: Anal. Calcd. for $C_{21}H_{16}Cl_2N_6O_2$: 458.10. Found: 459.25 [M+H]⁺. HRMS: Anal. Calcd. for $C_{21}H_{17}Cl_2N_6O_2$: 459.1103. Found: 459.1113 [M+H]⁺.

Example 92

(S)-3-(Aminomethyl)-4-(2,4-dichlorophenyl)-2-methyl-6-(2-oxo-2-(pyrrolidin-1-yl)ethyl)-5H-pyrrolo[3,4-b]pyridin-7(6H)-one, TFA salt

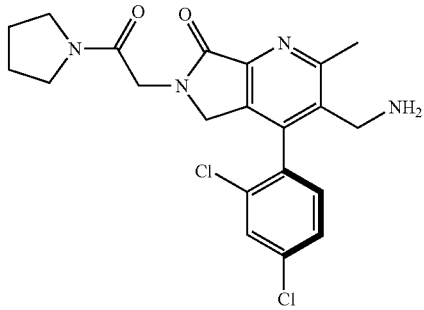

Example 92 was prepared by using the same method described above for Example 86, with the exception that in step 86B dimethyl amine was replaced by pyrrolidine. $^1$H NMR (400 MHz, CD$_3$OD) δ 1.80-2.05 (m, 4H), 2.84 (s, 3H), 3.35-3.58 (m, 4H), 4.01 and 4.24 (AB$_q$, J=14.5 Hz, 2H), 4.28 and 4.34 (AB$_q$, J=17.5 Hz, 2H), 4.40 and 4.49 (AB$_q$, J=17.0 Hz, 2H), 7.45 (d, J=2.2 Hz, 1H), 7.58 (dd, J=8.3, 2.0 Hz, 1H), 7.78 (d, J=8.3 Hz, 1H). [α]$_D^{25}$+24.1° (c=0.1, MeOH). LCMS: Anal. Calcd. for C$_{21}$H$_{23}$Cl$_2$N$_4$O$_2$: 432.11. Found: 433.22 [M+H]$^+$. HRMS: Anal. Calcd. for C$_{21}$H$_{24}$Cl$_2$N$_4$O$_2$: 433.1198. Found: 433.1204 [M+H]$^+$.

Example 93

(S)-3-(Aminomethyl)-4-(2,4-dichlorophenyl)-2-methyl-6-(2-morpholino-2-oxoethyl)-5H-pyrrolo[3,4-b]pyridin-7(6H)-one, TFA salt

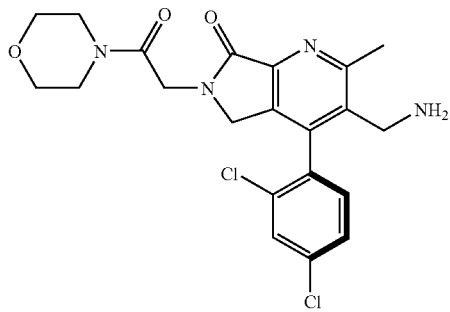

Example 93 was prepared by using the same method described above for Example 86, with the exception that in step 86B dimethyl amine was replaced by morpholine. $^1$H NMR (400 MHz, CD$_3$OD) δ 2.84 (s, 3H), 3.50-3.73 (m, 8H), 4.01 and 4.24 (AB$_q$, J=14.5 Hz, 2H), 4.22 and 4.30 (AB$_q$, J=17.6 Hz, 2H), 4.50 and 4.58 (AB$_q$, J=17.2 Hz, 2H), 7.44 (d, J=2.2 Hz, 1H), 7.60 (dd, J=8.3, 2.0 Hz, 1H), 7.79 (d, J=8.3 Hz, 1H). [α]$_D^{25}$+24.30 (c=0.1, MeOH). LCMS: Anal. Calcd. for C$_{21}$H$_{23}$Cl$_2$N$_4$O$_2$: 448.11. Found: 449.23 [M+H]$^+$. HRMS: Anal. Calcd. for C$_{21}$H$_{23}$Cl$_2$N$_4$O$_2$: 449.1147. Found: 449.1144 [M+H]$^+$.

Example 94

(S)-2-(3-(Aminomethyl)-4-(2,4-dichlorophenyl)-2-methyl-7-oxo-5H-pyrrolo[3,4-b]pyridin-6(7H)-yl)-N-(pyridin-3-ylmethyl)acetamide, TFA salt

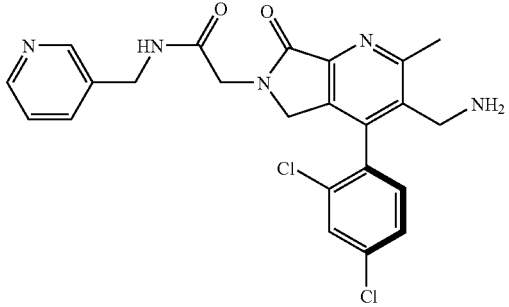

Example 94 was prepared by using the same method described above for Example 86, with the exception that in step 86B, dimethyl amine was replaced by 3-(aminomethyl)pyridine. $^1$H NMR (400 MHz, CD$_3$OD) δ 2.84 (s, 3H), 4.01 and 4.23 (AB$_q$, J=14.5 Hz, 2H), 4.27 and 4.37 (AB$_q$, J=18.0 Hz, 2H), 4.36 and 4.40 (AB$_q$, J=17.0 Hz, 2H), 4.55 (m, 2H), 7.44 (d, J=2.2 Hz, 1H), 7.61 (dd, J=8.3, 2.0 Hz, 1H), 7.79 (d, J=8.3 Hz, 1H), 7.86 (dd, J=7.9, 5.8 Hz, 1H), 8.30-8.37 (m, 1H), 8.64-8.68 (m, 1H), 8.70-8.73 (m, 1H). [α]$_D^{25}$+16.30 (c=0.1, MeOH). LCMS: Anal. Calcd. for C$_{23}$H$_{21}$Cl$_2$N$_5$O$_2$: 469.11. Found: 470.26 [M+H]$^+$.

Example 95

(S)-3-(Aminomethyl)-4-(2,4-dichlorophenyl)-2-methyl-6-(2-(4-methylpiperazin-1-yl)-2-oxoethyl)-5H-pyrrolo[3,4-b]pyridin-7(6H)-one, TFA salt

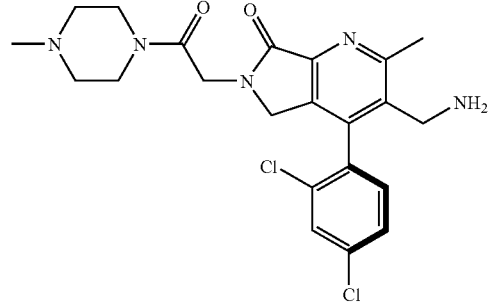

Example 95 was prepared by using the same method described above for Example 86, with the exception that in step 86B, dimethyl amine was replaced by 1-methylpiperazine. $^1$H NMR (400 MHz, acetone-d$_6$) δ 2.78 (s, 3H), 2.96 (s, 3H), 3.02-3.90 (m, 8H), 4.10-4.80 (m, 4H) 4.82 and 5.24 (AB$_q$, J=15.8 Hz, 2H), 7.59 (dd, J=8.3, 2.2 Hz, 1H), 7.70 (d, J=8.3 Hz, 1H), 7.76 (d, J=2.2 Hz, 1H). LCMS: Anal. Calcd. for C$_{22}$H$_{25}$Cl$_2$N$_5$O$_2$: 461.14. Found: 462.24 [M+H]$^+$.

Example 96

(S)-3-(Aminomethyl)-4-(2,4-dichlorophenyl)-6-(2-(4-ethylpiperazin-1-yl)-2-oxoethyl)-2-methyl-5H-pyrrolo[3,4-b]pyridin-7(6H)-one, TFA salt

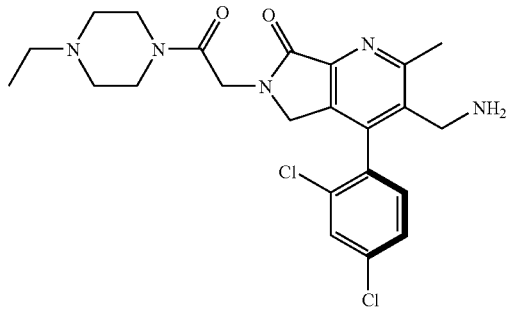

Example 96 was prepared by using the same method described above for Example 86, with the exception that in step 86B, dimethyl amine was replaced by 1-ethylpiperazine. $^1$H NMR (400 MHz, CD$_3$OD) δ 1.36 (t, J=7.1 Hz, 3H), 2.85 (s, 3H), 3.24 (q, J=7.1 Hz, 2H), 3.00-3.55 (m, 8H), 4.02 and 4.23 (AB$_q$, J=14.5 Hz, 2H), 4.21 and 4.30 (AB$_q$, J=18.0 Hz, 2H), 4.40-4.75 (m, 2H), 7.45 (d, J=8.3 Hz, 1H), 7.59 (dd, J=8.3, 2.0 Hz, 1H), 7.79 (d, J=2.0 Hz, 1H). LCMS: Anal. Calcd. for C$_{23}$H$_{27}$Cl$_2$N$_5$O$_2$: 475.15. Found: 476.27 [M+H]$^+$.

Example 97

(S)-2-(3-(Aminomethyl)-4-(2,4-dichlorophenyl)-2-methyl-7-oxo-5H-pyrrolo[3,4-b]pyridin-6(7H)-yl)-N-methyl-N-(1-methylpiperidin-4-yl)acetamide, TFA salt

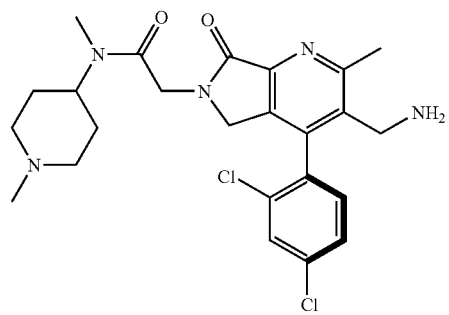

Example 97 was prepared by using the same method described above for Example 86, with the exception that in step 97B, dimethyl amine was replaced by 1-methyl-4-(methylamino)piperidine. $^1$H NMR (400 MHz, CD$_3$OD) δ 1.70-2.20 (m, 3H), 2.75-3.00 (m, 9H), 3.05-3.20 (m, 2H), 3.50-3.70 (m, 2H), 3.90-4.70 (m, 8H), 7.45 (d, J=8.3 Hz, 1H), 7.59 (dd, J=8.3, 2.0 Hz, 1H), 7.79 (d, J=2.0 Hz, 1H), [α]$_D^{25}$+16.30 (c=0.1, MeOH). LCMS: Anal. Calcd. for C$_{24}$H$_{29}$Cl$_2$N$_5$O$_2$: 489.17. Found: 490.29 [M+H]$^+$.

Example 98

(S)-3-(Aminomethyl)-4-(2,4-dichlorophenyl)-6-(4-methoxybenzyl)-2-methyl-5H-pyrrolo[3,4-b]pyridin-7(6H)-one, TFA salt

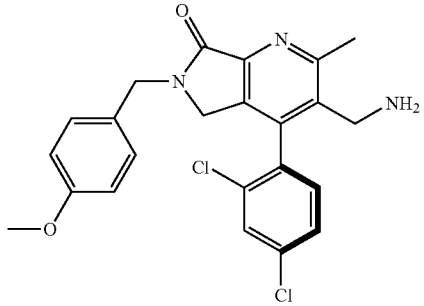

Example 98A (R)-Ethyl 4-(2,4-dichlorophenyl)-6-(4-methoxybenzyl)-2-methyl-7-oxo-6,7-dihydro-5H-pyrrolo[3,4-b]pyridine-3-carboxylate

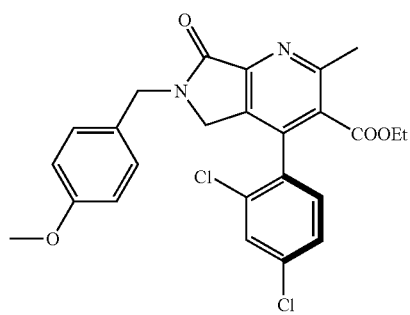

obtained by chiral SFC separation. (HPLC: Chiralpack® AD 4.6×250 mm; 20% IPA/80% CO$_2$). Example 98A was the faster-eluting enantiomer.

Example 98

(S)-3-(Aminomethyl)-4-(2,4-dichlorophenyl)-6-(4-methoxybenzyl)-2-methyl-5H-pyrrolo[3,4-b]pyridin-7(6H)-one, TFA salt

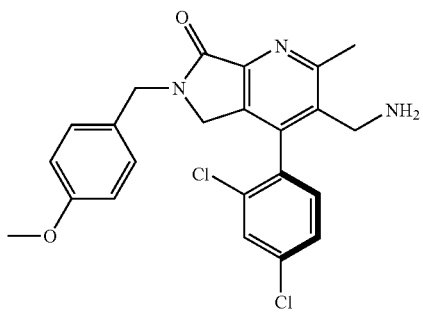

Example 98 was prepared from Example 98A using a procedure similar to that used for Example 5. [α]$_D^{25}$+6.640 (c=0.1, MeOH); purity by chiral analytical HPLC [Chiralcel® OJ 4.6×250 mm; 20% EtOH-MeOH(1:1) in heptain: 91% ee. LCMS: Anal. Calcd. for C$_{23}$H$_{21}$Cl$_2$N$_3$O$_2$: 441.10. Found: 442.34 [M+H]$^+$.

Example 99

(R)-3-(Aminomethyl)-4-(2,4-dichlorophenyl)-2-methyl-6-(((S)-tetrahydrofuran-2-yl)methyl)-5H-pyrrolo[3,4-b]pyridin-7(6H)-one, TFA salt

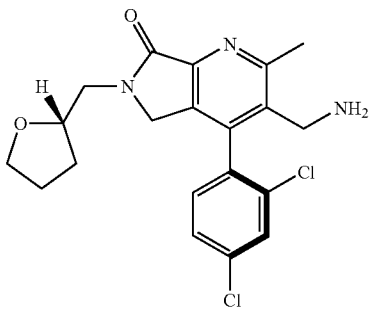

Example 99 was prepared by using the same method described for Example 5, with the exception that in step 5A, (S)-(+)-tetrahydrofurfurylamine was used instead of benzylamine. The obtained mixture of diastereomer was separated on a Chiralcel® OJ, 20 g, 5×50 cm column using an isocratic gradient of 5% to 15% EtOH-MeOH (50%) in heptane containing 0.1% diethyl amine to afford individual diastereomers.

Example 99 (Diastereomer A; faster-moving): $[\alpha]_D^{25}$+ 17.8° (c=0.085, MeOH); Purity by chiral analytical HPLC [Chiralcel® OJ 4.6×250 mm; 15% EtOH-MeOH (1:1; containing 0.1% DEA) in heptane (containing 0.1% DEA)]: 90% ee. $^1$H NMR (400 MHz, CD$_3$OD) δ 1.55-170 (m, 1H), 1.80-1.93 (m, 2H), 1.98-2.10 (m, 1H), 2.83 (s, 3H), 3.50-3.85 (m, 4H), 3.95-4.50 (m, 5H), 7.41-7.49 (m, 1H), 7.56-7.63 (m, 1H), 7.77-7.80 (m, 1H). LCMS: Anal. Calcd. for C$_{20}$H$_{21}$Cl$_2$N$_3$O$_2$: 405.10. Found: 406.13 [M+H]$^+$. HRMS: Anal. Calcd. for C$_{21}$H$_{21}$Cl$_2$N$_3$O$_2$: 405.1010. Found: 406.1094 [M+H]$^+$.

Example 100

(S)-3-(Aminomethyl)-4-(2,4-dichlorophenyl)-2-methyl-6-(((S)-tetrahydrofuran-2-yl)methyl)-5H-pyrrolo[3,4-b]pyridin-7(6H)-one, TFA salt

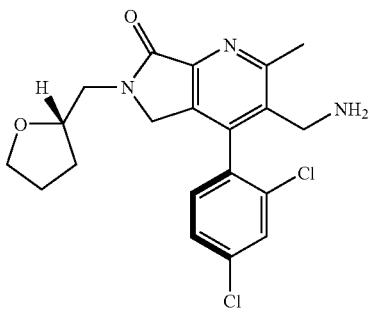

Example 100 (Enantiomer B; slower-moving): $[\alpha]_D^{25}$+ 24.750 (c=0.0985, MeOH); Purity by chiral analytical HPLC [Chiralcel® OJ 4.6×250 mm; 15% EtOH-MeOH (1:1; containing 0.1% DEA) in heptane (containing 0.1% DEA)]: 94% ee. $^1$H NMR (400 MHz, CD$_3$OD) δ 1.55-1.68 (m, 1H), 1.85-1.95 (m, 2H), 2.00-2.10 (m, 1H), 2.84 (s, 3H), 3.50-3.85 (m, 4H), 4.02 and 4.24 (AB$_q$, J=14.5 Hz, 2H), 4.08-4.18 (m, 1H), 4.32 (s, 2H), 7.45 (d, J=8.3 Hz, 1H). 7.59 (dd, J=8.3, 2.0 Hz, 1H), 7.79 (d, J=2.0 Hz, 1H). LCMS: Anal. Calcd. for C$_{20}$H$_{21}$Cl$_2$N$_3$O$_2$: 405.10. Found: 406.11 [M+H]$^+$. HRMS: Anal. Calcd. for C$_{21}$H$_{21}$Cl$_2$N$_3$O$_2$: 405.1010. Found: 406.1081 [M+H]$^+$.

Example 101

(S)-3-(Aminomethyl)-4-(2,4-dichlorophenyl)-2-methyl-6-((5-methylisoxazol-3-yl)methyl)-6,7-dihydro-5H-pyrrolo[3,4-b]pyridin-5-one, TFA salt

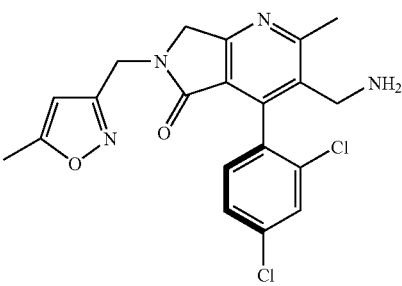

Example 101 was prepared by using the same method described above for Example 37, with the exception that (5-methyl-3-isoxazolyl)methyl amine was used instead of t-butyl 3-aminopropanoate. $^1$H NMR (400 MHz, CD$_3$OD) δ 2.38 (s, 3H), 2.82 (s, 3H), 3.94 and 4.18 (AB$_q$, J=14.5 Hz, 2H), 4.57 (s, 2H), 4.72 and 4.78 (AB$_q$, J=15.8 Hz, 2H), 6.08 (s, 1H), 7.32 (d, J=8.3 Hz, 1H), 7.53 (dd, J=8.3, 2.0 Hz, 1H), 7.71 (d, J=2.0 Hz, 1H). LCMS: Anal. Calcd. for C$_{20}$H$_{18}$Cl$_2$N$_4$O$_2$: 416.08. Found: 417.15 [M+H]$^+$. HRMS: Anal. Calcd. for C$_{20}$H$_{18}$Cl$_2$N$_4$O$_2$: 416.0807. Found: 417.0869 [M+H]$^+$.

Example 102

(S)-3-(Aminomethyl)-4-(2,4-dichlorophenyl)-6-((1,5-dimethyl-1H-pyrazol-3-yl)methyl)-2-methyl-6,7-dihydro-5H-pyrrolo[3,4-b]pyridin-5-one, TFA salt

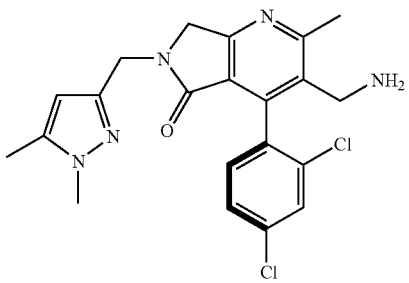

Example 102 was prepared by using the same method described above for Example 37, with the exception that 1,5-dimethyl-1H-pyrazole-3-yl methyl amine was used instead of t-butyl 3-aminopropanoate. $^1$H NMR (400 MHz, CD$_3$OD) δ 2.23 (s, 3H), 2.81 (s, 3H), 3.72 (s, 3H), 3.93 and 4.17 (AB$_q$, J=14.5 Hz, 2H), 4.45 (s, 2H), 4.58 and 4.64(AB$_q$, J=15.0 Hz, 2H), 5.97 (s, 1H), 7.33 (d, J=8.3 Hz, 1H), 7.51 (dd, J=8.3, 2.0 Hz, 1H), 7.68 (d, J=2.0 Hz, 1H). LCMS: Anal. Calcd. for C$_{21}$H$_{21}$Cl$_2$N$_5$O: 429.11. Found: 430.21 [M+H]$^+$. HRMS: Anal. Calcd. for C$_{21}$H$_{21}$Cl$_2$N$_5$O: 429.1123. Found: 430.1220 [M+H]$^+$.

Example 103

(S)-3-(Aminomethyl)-4-(2,4-dichlorophenyl)-6-((1-ethyl-1H-pyrazol-5-yl)methyl)-2-methyl-6,7-dihydro-5H-pyrrolo[3,4-b]pyridin-5-one, TFA salt

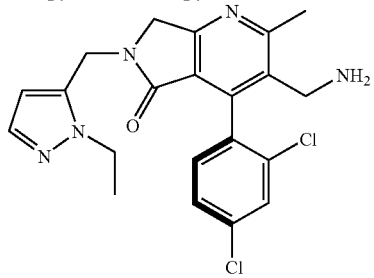

Example 103 was prepared by using the same method described above for Example 37, with the exception that (1-ethyl-1H-pyrazole-5-yl)methyl amine was used instead of t-butyl 3-aminopropanoate. $^1$H NMR (400 MHz, CD$_3$OD) δ 1.22 (t, J=8.3 Hz, 3H), 2.81 (s, 3H), 3.95 and 4.18 (AB$_q$, J=14.5 Hz, 2H), 4.16 (q, J=8.3 Hz, 2H), 4.42 and 4.48(AB$_q$, J=15.0 Hz, 2H), 4.78 and 4.88(AB$_q$, J=15.8 Hz, 2H), 6.33 (d, J=1.7 Hz, 1H), 7.32 (d, J=8.3 Hz, 1H), 7.45 (d, J=1.7 Hz, 1H), 7.53 (dd, J=8.3, 2.0 Hz, 1H), 7.71 (d, J=2.0 Hz, 1H). LCMS: Anal. Calcd. for C$_{21}$H$_{21}$Cl$_2$N$_5$O: 429.11. Found: 430.12 [M+H]$^+$. HRMS: Anal. Calcd. for C$_{21}$H$_{21}$Cl$_2$N$_5$O: 429.1123. Found: 430.1212 [M+H]$^+$.

Example 104

(S)-tert-Butyl (6-(2-amino-2-oxoethyl)-4-(2,4-dichlorophenyl)-2-methyl-5-oxo-6,7-dihydro-5H-pyrrolo[3,4-b]pyridin-3-yl)methylcarbamate

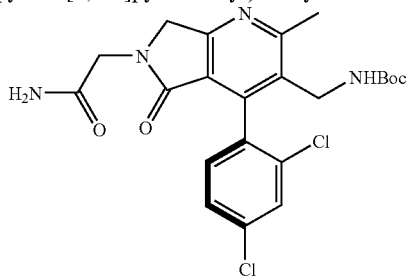

A mixture of Example 50E (70 mg, 0.146 mmol), HOBT.H$_2$O (29.6 mg, 0.218 mmol), ammonium chloride (15.6 mg, 0.292 mmol) in DMF (0.5 mL) was added EDCI (42 mg, 0.218 mmol), diisopropylethyl amine (0.101 mL, 0.58 mmol). The mixture was stirred at ambient temperature overnight then diluted with EtOAc (10 mL) and H$_2$O (2.5 mL). The organic layer was separated and evaporated in vacuo to yield a crude Example 104 product.

Example 105

(S)-2-(3-(Aminomethyl)-4-(2,4-dichlorophenyl)-2-methyl-5-oxo-5H-pyrrolo[3,4-b]pyridin-6(7H)-yl)acetamide, TFA salt

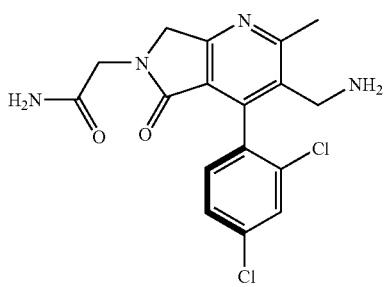

To a solution of Example 104 product in CH$_2$Cl$_2$ (1 mL) was added TFA (0.5 mL) and the resulting mixture stirred for 3 h. Solvent were removed and the residue purified by prep HPLC (Phenomenex Axia, 8 min gradient, 0 to 100% B) to give Example 105. TFA salt (8.6 mg, 12%) as white powder. $^1$H NMR (400 MHz, CD$_3$OD) δ 2.76 (s, 3H), 3.88 and 4.12 (AB$_q$, J=15.0 Hz, 2H), 4.13 and 4.24 (AB$_q$, J=17.2 Hz, 2H), 4.54 (s, 2H), 7.26 (d, J=8.3 Hz, 1H), 7.45 (dd, J=8.3, 2.2 Hz, 1H), 7.62 (d, J=2.2 Hz, 1H). LCMS: Anal. Calcd. for C$_{17}$H$_{16}$Cl$_2$N$_4$O$_2$: 378.06. Found: 379.00 [M+H]$^+$. HRMS: Anal. Calcd. for C$_{17}$H$_{16}$Cl$_2$N$_4$O$_2$: 378.0650. Found: 379.0739 [M+H]$^+$.

Example 106

3-(Aminomethyl)-4-(2,4-dichlorophenyl)-2-methyl-6-(tetrahydro-2H-pyran-4-yl)-6,7-dihydro-5H-pyrrolo[3,4-b]pyridin-5-one hydrochloride

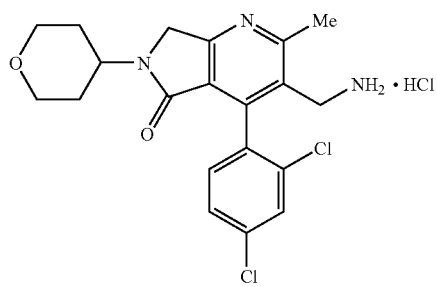

Example 106A

Benzyl 4-(2,4-dichlorophenyl)-2-methyl-5-oxo-tetrahydro-2H-pyran-4-yl)-6,7-dihydro-5H-pyrrolo[3,4-b]pyridine-3-carboxylate

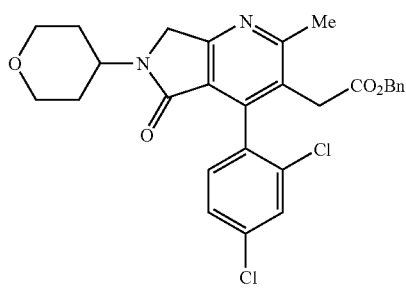

To a solution of Example 2D (0.38 g, 0.76 mmol) in 10 mL of absolute ethanol was added 4-aminotetrahydropyran (0.18 g, 1.8 mmol). The reaction was heated in a sealed vial in the microwave at 150° C. for 30 min. The reaction was diluted with ethyl acetate, washed with 1N HCl, sat'd aq. NaHCO$_3$ and brine, dried (MgSO$_4$) and concentrated to a foam. The residue was purified by flash chromatography (elution with 2:1 EtOAc/hexane) to afford 230 mg (60%) of Example 106A as an off-white solid. LRMS (ESI): 511.2/513.2 [M+H]$^+$.

Example 106B 4-(2,4-Dichlorophenyl)-3-(hydroxymethyl)-2-methyl-6-(tetrahydro-2H-pyran-4-yl)-6,7-dihydro-5H-pyrrolo[3,4-b]pyridin-5-one

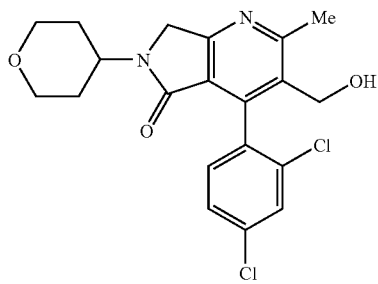

A mixture of Example 106A (230 mg, 0.45 mmol) and 10% Pd/C (100 mg) in 20 mL of ethyl acetate was stirred under $H_2$ (1 atm, maintained by balloon) for 8 h at ambient temperature. The mixture was filtered through a pad of Celite and concentrated to afford a carboxylic acid which was used directly. To a solution of this acid (130 mg, 0.31 mmol) in 6 mL of THF was added ethyl chloroformate (45 µL, 0.47 mmol) and triethylamine (110 µL, 0.77 mmol) and the mixture was stirred at ambient temperature for 1 h. The mixture was filtered to remove the insolubles and then there was added sodium borohydride (18 mg, 0.47 mmol) in a minimal amount of water. The mixture was allowed to stir at ambient temperature for 18 h. The reaction was quenched with 1N HCl, extracted with ethyl acetate, and the organics were washed with brine, dried ($MgSO_4$) and concentrated. The residue was purified by flash chromatography (elution with 10% MeOH/EtOAc) to afford 40 mg (32%) of Example 106B as an oil. LRMS (ESI): 407.2/409.2 $[M+H]^+$.

Example 106

3-(Aminomethyl)-4-(2,4-dichlorophenyl)-2-methyl-6-(tetrahydro-2H-pyran-4-yl)-6,7-dihydro-5H-pyrrolo[3,4-b]pyridin-5-one hydrochloride

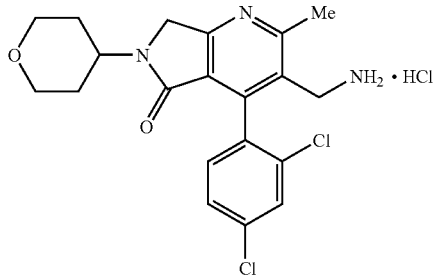

To a solution of Example 106B (33 mg, 0.08 mmol) in 2 mL of $CH_2Cl_2$ was added triethylamine (33 µL, 0.24 mmol) and methanesulfonyl chloride (19 µL, 0.24 mmol). The mixture was allowed to stir at ambient temperature for 18 h. The mixture was heated for 2 h in a sealed vial to drive the reaction completely to the chloride stage. The mixture was diluted with ethyl acetate, washed with 1N HCl and brine, dried ($MgSO_4$) and concentrated to afford the chloride which was used directly. To this chloride (25 mg, 0.06 mmol) in 2 mL of methanol was added ammonia (6 mL of 2M $NH_3$ in ethanol, 12 mmol) and the mixture was heated in the microwave at 100¡C for 15 min. The mixture was diluted with sat'd aq $NaHCO_3$ and extracted twice with $CH_2Cl_2$. The organics were dried ($Na_2SO_4$) and concentrated. The residue was taken up in ethanol/ether and then there was added HCl (33 µL of 4N HCl in dioxane, 0.14 mmol). The resulting slurry was concentrated to dryness and the solid was triturated twice with ether and dried in vacuo. The solid was taken up in distilled water, filtered and lyophilized to dryness overnight to afford 10 mg (50%) of Example 106 as a white powder. $^1H$ NMR (DMSO-$D_6$): δ 8.31 (broad s, 3H), 7.79 (d, 1H, J=1.7 Hz), 7.56 (dd, 1H, J=8.2, 2.2 Hz), 7.47 (d, 1H, J=8.2 Hz), 4.54 ($AB_q$, 2H), 4.15-4.05 (m, 2H), 3.95-3.88 (m, 2H), 3.62-3.55 (m, 1H), 3.40-3.30 (m, 2H), 2.79 (s, 3H), 1.82-1.72 (m, 2H), 1.65-1.57 (m, 2H). LRMS (ESI): 406.2/408.2 $[M+H]^+$.

Example 107

3-(Aminomethyl)-4-(2,4-dichlorophenyl)-2-methyl-6-(tetrahydro-2H-pyran-4-yl)-6,7-dihydro-5H-pyrrolo[3,4-b]pyridin-5-one hydrochloride

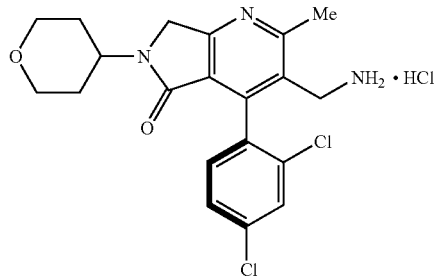

Example 107A

Ethyl 2-(chloromethyl)-5-cyano-4-(2,4-dichlorophenyl)-6-methylnicotinate (a novel intermediate)

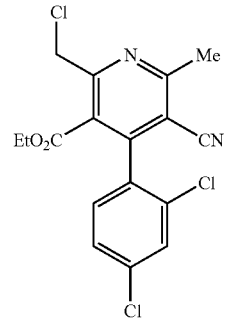

To a solution of 2,4-dichlorobenzaldehyde (3.1 g, 17.8 mmol) in 30 mL of isopropanol was added ethyl 4-chloroacetoacetate (3.22 g, 19.6 mmol), benzylamine (100 µL, 0.89 mmol) and acetic acid (76 µL, 1.36 mmol). The mixture was allowed to stir at ambient temperature for 2 days. Then there was added 3-aminocrotonitrile (1.61 g, 19.6 mmol) and the mixture was allowed to stir at ambient temperature for 24 h. The mixture had become a thick slurry. The mixture was diluted with an additional 15 mL of isopropanol and then there was added 10 mL of 12N HCl. The reaction was stirred at ambient temperature for 3 h, at which time the mixture was homogeneous. The reaction was diluted with $H_2O$ and extracted with ethyl acetate. The organics were washed with sat'd aq. $NaHCO_3$ and brine, dried ($MgSO_4$), filtered through a pad of silica gel and concentrated to afford a dihydropyridine which was used directly. The residue (6.5 g, 17.8 mmol) was taken up in 60 mL of glacial acetic acid and then there was added 25 mL of 70% $HNO_3$. The mixture was allowed to stir at ambient temperature for 4 h. The mixture was carefully poured into $H_2O$ and was extracted twice with ethyl acetate. The organics were washed with sat'd aq. $NaHCO_3$ and brine, dried ($MgSO_4$) and concentrated. The residue was purified by flash chromatography (elution with 6:1 hexane/EtOAc) to afford Example 107A (2.2 g, 32%) as an oil which slowly solidified upon standing. LRMS (ESI): 383.1/385.1 [M+H]+.

Example 107B 4-(2,4-Dichlorophenyl)-2-methyl-5-oxo-6-(tetrahydro-2H-pyran-4-yl)-6,7-dihydro-5H-pyrrolo[3,4-b]pyridine-3-carbonitrile

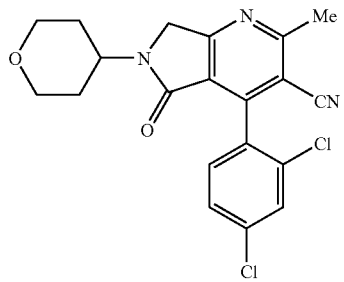

To a solution of Example 107A (290 mg, 0.76 mmol) in 8 mL of absolute ethanol was added 4-aminotetrahydropyran (168 mg, 1.66 mmol). The reaction was heated in a sealed vial in the microwave at 150° C. for 30 min. The reaction was diluted with ethyl acetate, washed with 1N HCl, sat'd aq. NaHCO$_3$ and brine, dried (MgSO$_4$), filtered through a pad of silica gel and concentrated to afford 270 mg (88%) of Example 107B as an off-white solid, which was sufficiently pure to be used without purification. LRMS (ESI): 402.2/404.2 [M+H]+.

Example 107C

Chiral separation of 4-(2,4-dichlorophenyl)-2-methyl-5-oxo-6-(tetrahydro-2H-pyran-4-yl)-6,7-dihydro-5H-pyrrolo[3,4-b]pyridine-3-carbonitrile into individual atropisomers

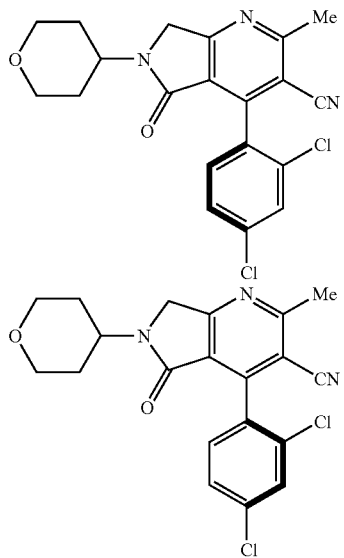

A 0.40 g sample of racemic Example 107B was separated by chiral HPLC (Chiralcel AD column, 20µ, 5×50 cm column, elution with 30% i-PrOH/heptane) to afford the two individual atropisomers.

Example 107C-1 (Atropisomer 1; faster-moving): 165 mg, purity by chiral analytical HPLC [Chiralcel AD 4.6×250 mm; 30% i-PrOH/heptane, retention time 6.8 min]: >99% ee.

Example 107C-2 (Atropisomer 2; slower-moving): 160 mg, purity by chiral analytical HPLC [Chiralcel AD 4.6×250 mm; 30% i-PrOH/heptane, retention time 14.8 min]: >99% ee.

Example 107

3-(Aminomethyl)-4-(2,4-dichlorophenyl)-2-methyl-6-(tetrahydro-2H-pyran-4-yl)-6,7-dihydro-5H-pyrrolo[3,4-b]pyridin-5-one hydrochloride

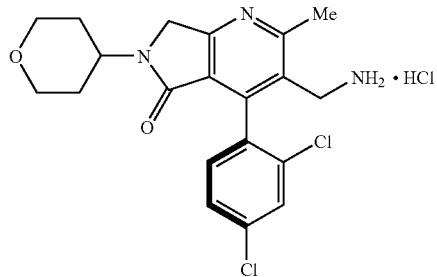

To a solution of Example 107C-1 (100 mg, 0.25 mmol) in 10 mL of THF in a thick-walled test tube with screw cap was added wet RaNi (~300 mg, 2400 grade in water, added wet), followed by hydrazine (117 µL, 3.7 mmol). The tube was tightly capped. Gas evolution was observed. The mixture was allowed to stir at ambient temperature for 4 h. The mixture was filtered through a pad of Celite and concentrated in vacuo. The residue was purified by reverse-phase prep HPLC (elution with solvent gradient 0% MeOH/H$_2$O+0.1% TFA to 100% MeOH+0.1% TFA). Clean fractions were combined, free-based with sat'd NaHCO$_3$ and extracted twice with CH$_2$Cl$_2$. The combined organics were dried (Na$_2$SO$_4$) and concentrated. The residue was taken up in 8:1 Et$_2$O/EtOH and then added 4N HCl in dioxane (50 µL). The resulting white precipitate was filtered, washed with ether and dried in vacuo. The solid was dissolved in 1 mL water, filtered and lyophilized to afford the title compound of Example 107 (25 mg, 23%) as a white solid. $^1$H NMR (DMSO-D$_6$): δ 8.35 (broad s, 3H), 7.78 (d, 1H, J=1.7 Hz), 7.56 (dd, 1H, J=8.2, 2.2 Hz), 7.49 (d, 1H, J=8.2 Hz), 4.54 (ABq, 2H), 4.15-4.05 (m, 2H), 3.95-3.88 (m, 2H), 3.60-3.54 (m, 1H), 3.40-3.30 (m, 2H), 2.79 (s, 3H), 1.82-1.72 (m, 2H), 1.65-1.57 (m, 2H). LRMS (ESI): 406.2/408.2 [M+H]+.

Example 108

3-Aminomethyl-4-(2,4-dichlorophenyl)-2-methyl-6-tetrahydro-2H-pyran-4-yl)-6,7-dihydro-5H-pyrrolo[3,4-b]pyridin-5-one hydrochloride

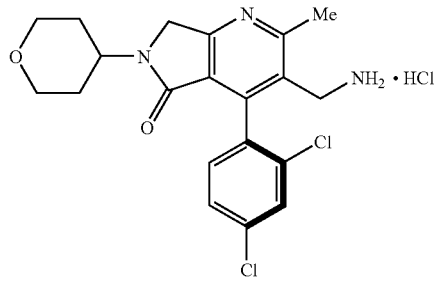

Following the procedures described in Example 107, Example 107C-2 (Atropisomer 2, 68 mg, 0.17 mmol) was converted into the title compound of Example 108 (30 mg, 40%) as a white solid. $^1$H NMR (DMSO-D$_6$): δ 8.31 (broad s, 3H), 7.79 (d, 1H, J=1.7 Hz), 7.56 (dd, 1H, J=8.2, 2.2 Hz), 7.49 (d, 1H, J=8.2 Hz), 4.54 (AB$_q$, 2H), 4.15-4.05 (m, 2H), 3.95-3.88 (m, 2H), 3.60-3.54 (m, 1H), 3.40-3.30 (m, 2H), 2.79 (s, 3H), 1.82-1.72 (m, 2H), 1.65-1.57 (m, 2H). LRMS (ESI): 406.2/408.2 [M+H]+.

Example 109

3-(Aminomethyl)-4-(2,4-dichlorophenyl)-2-methyl-6-(tetrahydro-1,1-dioxo-2H-thiopyran-4-yl)-6,7-dihydro-5H-pyrrolo[3,4-b]pyridin-5-one hydrochloride

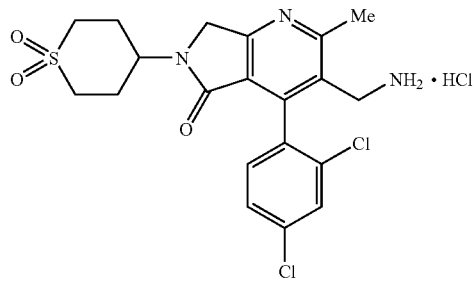

Example 109A

Benzyl 4-(2,4-dichlorophenyl)-2-methyl-5-oxo-6-tetrahydro-2H-thiopyran-4-yl)-6,7-dihydro-5H-pyrrolo[3,4-b]pyridine-3-carboxylate

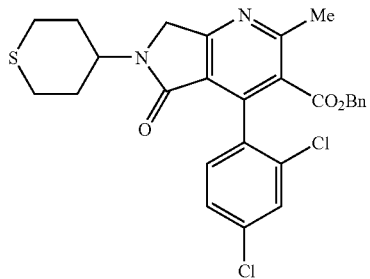

To a solution of Example 2D (0.63 g, 1.28 mmol) in 10 mL of absolute ethanol was added 4-aminotetrahydrothiopyran (0.5 g, 4.3 mmol). The reaction was heated in a sealed vial in the microwave at 150° C. for 30 min. The reaction was diluted with ethyl acetate, washed with 1N HCl, sat'd aq. NaHCO$_3$ and brine, dried (MgSO$_4$) and concentrated to a foam. The residue was purified by flash chromatography (elution with 2:1 EtOAc/hexane) to afford 375 mg (56%) of Example 109A as an off-white solid. LRMS (ESI): 527.2/529.2 [M+H]$^+$.

Example 109B

Benzyl 4-(2,4-dichlorophenyl)-2-methyl-5-oxo-6-(tetrahydro-1,1-dioxo-2H-thiopyran-4-yl)-6,7-dihydro-5H-pyrrolo[3,4-b]pyridine-3-carboxylate

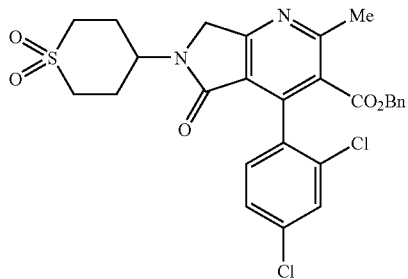

To a solution of Example 109A (0.20 g, 0.38 mmol) in 10 mL of methylene chloride was added m-chloroperbenzoic acid (206 mg of ~70% pure m-CPBA, ~0.83 mmol). The reaction was allowed to stir at ambient temperature for 2 h. The reaction was diluted with EtOAc, washed with sat'd aq Na$_2$CO$_3$ and brine, dried (MgSO$_4$), filtered through a pad of silica gel and concentrated in vacuo to afford 210 mg (98%) of Example 109B, which was sufficiently pure to be used without purification. LRMS (ESI): 559.2/561.2 [M+H]$^+$.

Example 109

3-Aminomethyl)-4-(2,4-dichlorophenyl)-2-methyl-6-(tetrahydro-1,1-dioxo-2H-thiopyran-4-yl)-6,7-dihydro-5H-pyrrolo[3,4-b]pyridin-5-one hydrochloride

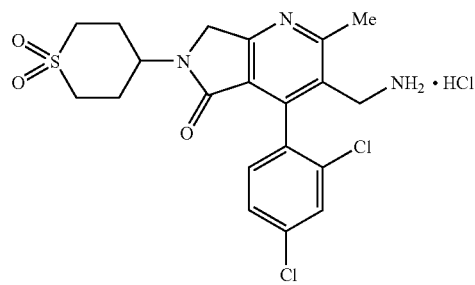

Following the procedures described in Example 106, Example 109B (210 mg, 0.38 mmol) was converted into the title compound of Example 109 as an off-white solid. $^1$H NMR (DMSO-D$_6$): δ 8.28 (broad s, 3H), 7.79 (d, 1H, J=2.2 Hz), 7.56 (dd, 1H, J=8.2, 1.7 Hz), 7.46 (d, 1H, J=8.3 Hz), 4.58 (AB$_q$, 2H), 4.31-4.23 (m, 1H), 4.12-4.05 (m, 1H), 3.60-3.54 (m, 1H), 3.40-3.30 (m, 2H), 3.12-3.07 (m, 2H), 2.78 (s, 3H), 2.30-2.20 (m, 2H), 2.05-1.96 (m, 2H). LRMS (ESI): 454.2/456.2 [M+H]$^+$.

Example 110

6-(2-Aminoethyl)-3-(aminomethyl)-4-(2,4-dichlorophenyl)-2-methyl-6,7-dihydro-5H-pyrrolo[3,4-b]pyridin-5-one hydrochloride

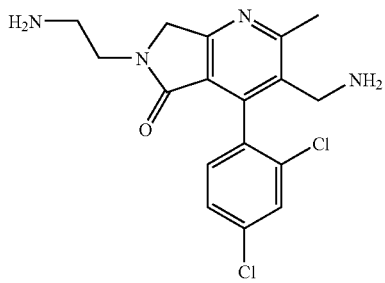

Example 110A

Benzyl 6-(2-(tert-butoxycarbonylamino)ethyl)-4-(2,4-dichlorophenyl)-2-methyl-5-oxo-6,7-dihydro-5H-pyrrolo[3,4-b]pyridine-3-carboxylate

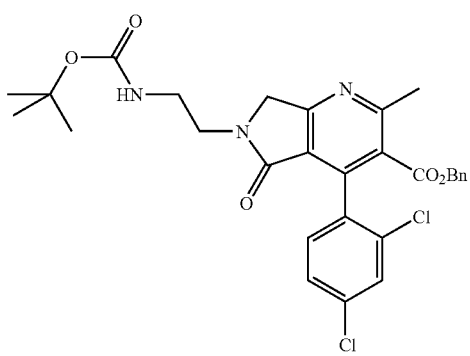

A mixture of Example 2D (2.56 g, 5.21 mmol), t-butyl-N-(2-aminoethyl) carbamate (0.92 g, 5.73 mmol) and triethylamine (1.08 mL, 7.82 mmol) in acetonitrile (150 mL) was heated in a sealed vial at 110° C. for 3 h. The solvent was evaporated, and the residue was purified by flash chromatography (elution with 0-100% EtOAc/Hexanes) to afford 2.45 g (83%) of Example 110A as an off-white solid. $^1$H NMR (400 MHz, CDCl$_3$): δ 1.34 (s, 9H), 2.73 (s, 3H), 3.36 (m 2H), 3.65 (m 2H), 4.51 (AB$_q$, 2H), 5.09 (AB$_q$, 2H), 6.98 (d, 1H), 7.11 (m, 3H), 7.28 (m, 4H). LRMS (ESI): 470.2 (M+H-BOC)$^+$.

Example 110B 6-(2-(tert-Butoxycarbonylamino)ethyl)-4-(2,4-dichlorophenyl)-2-methyl-5-oxo-6,7-dihydro-5H-pyrrolo[3,4-b]pyridine-3-carboxylic acid

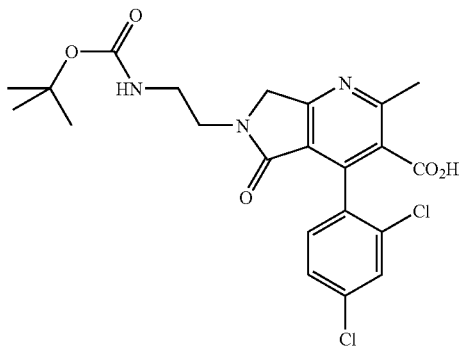

A mixture of Example 110A (2.45 g, 4.30 mmol) and 10% Pd/C (122 mg) in 120 mL of methanol was stirred under H$_2$ (1 atm, maintained by balloon) for 2 h at ambient temperature. The mixture was filtered through a pad of Celite and concentrated to afford 2.08 g (100%) of Example 110B as an solid which was carried on to the next reaction without further purification. $^1$H NMR (400 MHz, CDCl$_3$): δ 1.34 (s, 9H), 2.74 (s, 3H), 3.36 (m 2H), 3.65 (m 2H), 4.50 (AB$_q$, 2H), 7.14 (d, 1H, J=8.0 Hz), 7.28 (m, 1H), 7.48 (s, 1H). LRMS (ESI): 480.2 [M+H]$^+$.

Example 110C tert-Butyl 2-(4-(2,4-dichlorophenyl)-3-(hydroxymethyl)-2-methyl-5-oxo-5H-pyrrolo[3,4-b]pyridin-6(7H)-yl)ethylcarbamate

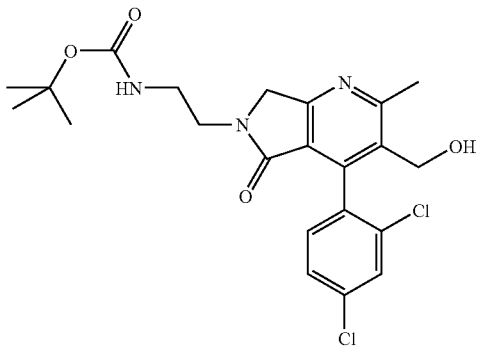

To a solution of Example 110B (2.04 g, 4.13 mmol) in 60 mL of CH$_2$Cl$_2$ was added DMF (5 drops) and oxalyl chloride (2M in CH$_2$Cl$_2$, 4.13 mL, 8.26 mmol). The mixture was allowed to stir at ambient temperature for 1 h. The solvent was evaporated, and the residue was dissolved in THF (60 mL), the resulting solution was cooled down to −78° C., and LAH (1M in THF, 4.1 mL, 4.1 mmol) was added. Stirred for 15 min. The reaction was quenched with 0.1N aq HCl and extracted into EtOAc. The combined organic layers were washed with water and brine, dried (MgSO$_4$) and evaporated, the residue was purified by flash chromatography (elution with 0-100% EtOAc/Hexanes) to afford 2.45 g (83%) of Example 110C as a solid. $^1$H NMR (400 MHz, CDCl$_3$): δ 1.36 (s, 9H), 2.86 (s, 3H), 3.39 (m 2H), 3.67 (m 2H), 4.46-4.58 (m, 4H), 7.19 (d, 1H, J=8.0 Hz), 7.28 (dd, 1H, J=8.0, 1.4 Hz), 7.54 (s, 1H). LRMS (ESI): 466.3 [M+H]$^+$.

Example 110D tert-Butyl 2-(3-(aminomethyl)-4-(2,4-dichlorophenyl)-2-methyl-5-oxo-5H-pyrrolo[3,4-b]pyridin-6(7H)-yl)ethylcarbamate

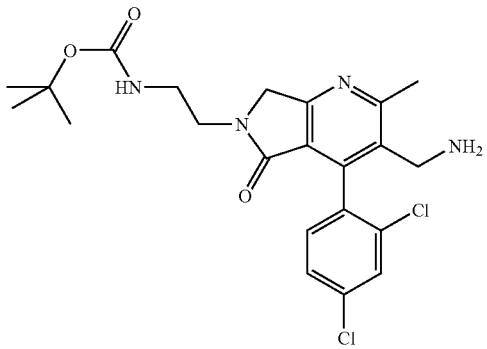

To a solution of Example 110C (30 mg, 0.065 mmol) in 1.5 mL of methylene chloride was added triethylamine (26 μL, 0.19 mmol) and mathanesulfonyl chloride (15 μL, 0.19 mmol). The mixture was refluxed for 1 h. The solvent was evaporated, and the residue was purified by flash chromatography (elution with 0-100% EtOAc/Hexanes) to yield a chloride intermediate. A mixture of the obtained chloride and 7N ammonia in MeOH (1 mL) was irradiated in a sealed tube in a microwave reactor at 120° C. for 20 min. The solvent was evaporated, and the residue was purified by flash chromatography (elution with 0-10% MeOH/CH$_2$Cl$_2$) to afford 12 mg (59% for 2 steps) of Example 110D as an oil. LRMS (ESI): 365.2 (M+H-BOC)$^+$.

Example 110

6-(2-Aminoethyl)-3-(aminomethyl)-4-(2,4-dichlorophenyl)-2-methyl-6,7-dihydro-5H-pyrrolo[3,4-b]pyridin-5-one, TFA salt

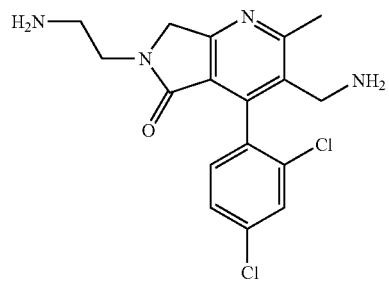

The mixture of Example 110D (10 mg, 0.02 mmol) in 1 ml of 40% TFA in CH$_2$Cl$_2$ was stirred at ambient temperature for 60 min. The solvent was evaporated, and the residue was purified by prep HPLC (Phenomenex, 10 min gradient, 20 to 100% B) and lyophilized to dryness overnight to afford 4.9 mg (38%) of Example 110 as an TFA salt. LRMS (ESI): 365.2 [M+H]$^+$.

Example 111

Ethyl 2-(3-aminomethyl)-4-(2,4-dichlorophenyl)-2-methyl-5-oxo-5H-pyrrolo[3,4-b]pyridin-6(7H)-yl)ethylcarbamate TFA salt

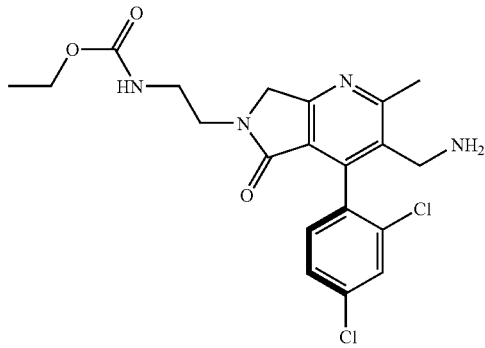

Examples 111A and 111B

Chiral separation of tert-butyl 2-(4-(2,4-dichlorophenyl)-3-(hydroxymethyl)-2-methyl-5-oxo-5H-pyrrolo[3,4-b]pyridin-6(7H)-yl)ethylcarbamate into individual atropisomers Example 111A

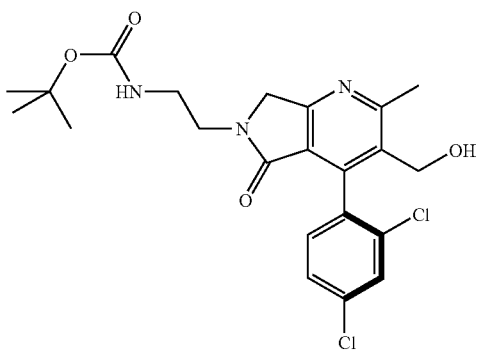

Example 111B

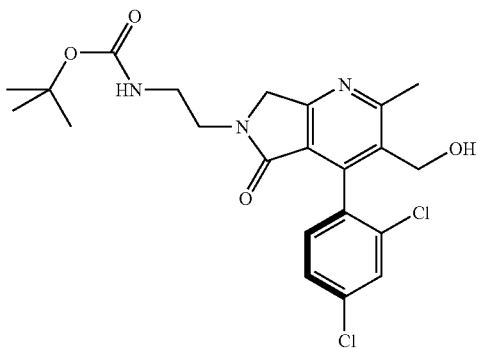

A 1.95 g sample of racemic Example 110C was separated by chiral HPLC (Chiralcel OD column, 20 μ, 5×50 cm column, elution with 0-10% i-PrOH/heptane) to afford the two individual atropisomers.

Example 111A (Atropisomer 1; faster-moving): 740 mg, purity by chiral analytical HPLC [Chiralcel OD 4.6×250 mm; 12% i-PrOH/heptane, retention time 6.5 min]: >99% ee.

Example 111B (Atropisomer 2; slower-moving): 662 mg, purity by chiral analytical HPLC [Chiralcel OD 4.6×250 mm; 12% i-PrOH/heptane, retention time 11.0 min]: >99% ee.

Example 111

Ethyl 2-(3-(aminomethyl)-4-(2,4-dichlorophenyl)-2-methyl-5-oxo-5H-pyrrolo[3,4-b]pyridin-6(7H)-yl)ethylcarbamate TFA salt

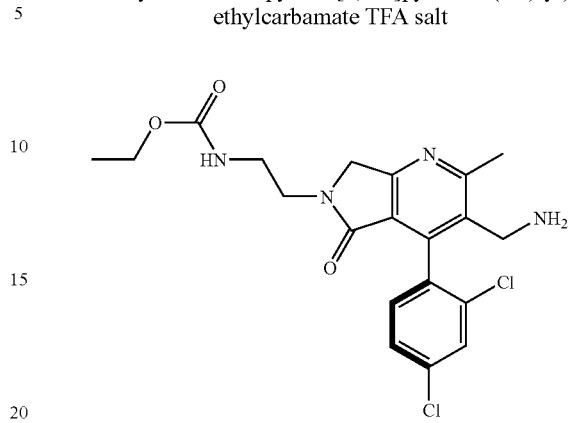

Example 111B (58 mg, 0.12 mmol) in 1 mL of 4M HCl in 1,4-dioxane was stirred at ambient temperature for 15 min. The mixture was concentrated in vacuo. The residue was dissolved in 2 ml of $CH_2Cl_2$, $Et_3N$ (25 μL 0.18 mmol) and ethyl chloroformate (13 μL, 0.13 mmol) were added into the solution. The resulting mixture was stirred at ambient temperature for 15 min. The mixture was filtered through a pad of $SiO_2$ gel. The solvent was evaporated and the residue was treated with MsCl (19 μL, 0.24 mmol) and $Et_3N$ (50 mL, 0.36 mmol) in 3 mL of $CH_2Cl_2$. The reaction was stirred at 50° C. for 1 h and concentrated to give a crude product which was subjected to flash chromatography (silica gel, 0-15% MeOH/$CH_2Cl_2$) to yield a chloride intermediate. A mixture of the obtained chloride and 2N ammonia in MeOH (2 mL) was irradiated in a sealed tube in a microwave reactor at 100° C. for 16 min. The volatiles were removed in vacuo. the residue was purified by prep HPLC (Phenomenex, 10 min gradient, 20 to 100% B) and lyophilized to dryness overnight to afford 12 mg (18% for 3 steps) of Example 111 as an TFA salt. $^1$H NMR (400 MHz, DMSO-$D_6$): δ 1.08 (m, 3H), 2.76 (s, 3H), 3.19 (m 2H), 3.48 (m 2H), 3.88 (m, 4H), 4.55 (Ab$_q$, 2H), 7.18 (s, 1H). 7.39 (d, 1H, J=4.0 Hz), 7.57 (d, 1H, J=4.0 Hz), 7.80 (s, 1H), 8.12 (s, 2H). LRMS (ESI): 437.2 [M+H]$^+$.

Example 112

N-(2-(3-(aminomethyl)-4-(2,4-dichlorophenyl)-2-methyl-5-oxo-5H-pyrrolo[3,4-b]pyridin-6(7H)-yl)ethyl)acetamide TFA salt

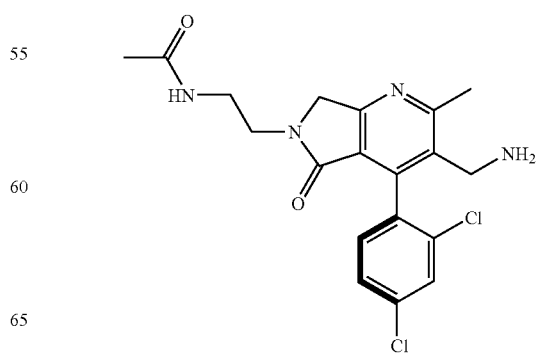

Example 112 was prepared using the same method described above for Example 111, with the exception that ethyl chloroformate was replaced with acetyl chloride. LRMS (ESI): 407.2 [M+H]+.

Example 112-1

N-(2-(3-(aminomethyl)-4-(2,4-dichlorophenyl)-2-methyl-5-oxo-5H-pyrrolo[3,4-b]pyridin-6(7H)-yl)ethyl)acetamide TFA salt

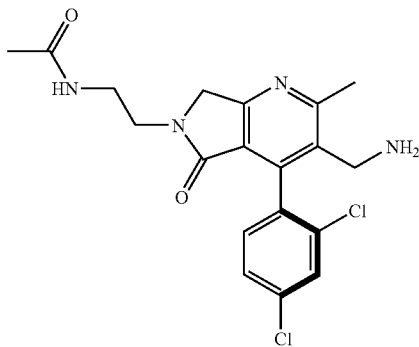

Example 112-1 was prepared using the same method described above for Example 112, with the exceptions that ethyl chloroformate was replaced with acetyl chloride and Example 111B was replaced with Example 111A. LRMS (ESI): 407.2 [M+H]+.

Example 113

3-(2-(3-(Aminomethyl)-4-(2,4-dichlorophenyl)-2-methyl-5-oxo-5H-pyrrolo[3,4-b]pyridin-6(7H)-yl)ethyl)oxazolidin-2-one hydrochloride

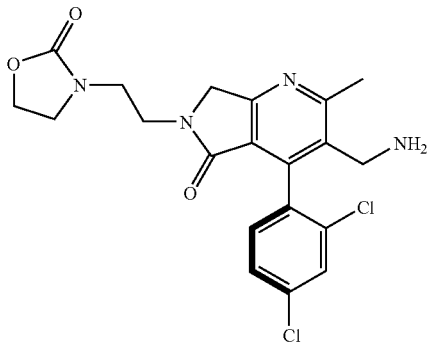

Example 111B (78 mg, 0.17 mmol) in 1 mL of 4M HCl in 1,4-dioxane was stirred at ambient temperature for 15 min. The mixture was concentrated in vacuo. The residue was dissolved in 2 ml of methanol, $K_2CO_3$ (230 mg, 1.7 mmol) and 2-bromomethyl chloroformate (46 mg, 0.25 mmol) were added into the solution. The resulting mixture was stirred at ambient temperature for 15 min. The mixture was filtered through a pad of $SiO_2$ gel. The solvent was evaporated and the residue was treated with MsCl (0.13 mL, 1.70 mmol) and $Et_3N$ (0.23 mL, 1.70 mmol) in 3 mL of $CH_2Cl_2$. The reaction was kept at ambient temperature for 12 h and concentrated to give a crude product which was subjected to flash chromatography (silica gel, 100% EtOAc) to yield a chloride intermediate. A mixture of the obtained chloride and 2N ammonia in MeOH (3 mL) was irradiated in a sealed tube in a microwave reactor at 100° C. for 20 min. The volatiles were removed in vacuo. The crude product was purified by flash chromatography (elution with 0-1.0% MeOH/$CH_2Cl_2$), treated with 2N HCl in MeOH, and evaporated to afford 10.1 mg (13% for 4 steps) of Example 113 as a solid. $^1$H NMR (400 MHz, $CDCl_3$): δ 2.82 (s, 3H), 3.51-3.76 (m 8H), 4.22 (m 2H), 4.50 (m, 2H), 7.14 (d, 1H, J=8.3 Hz), 7.35 (dd, 1H, J=8.3, 1.7 Hz), 7.54 (d, 2H, J=1.3 Hz). LRMS (ESI): 435.1 [M+H]+.

Example 114

3-(Aminomethyl)-4-(2,4-dichlorophenyl)-2-methyl-6-(2-(2-oxopyrrolidin-1-yl)ethyl)-6,7-dihydro-5H-pyrrolo[3,4-b]pyridin-5-one TFA salt

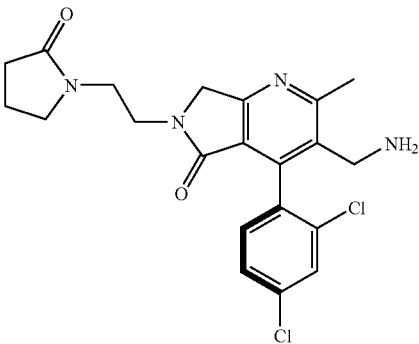

Example 114 was prepared using the same method described above for Example 113, with the exceptions that 2-bromomethyl chloroformate was replaced with 4-bromobutyryl chloride. LRMS (ESI): 433.2 [M+H]+.

Example 115

N-(2-(3-(aminomethyl)-4-(2,4-dichlorophenyl)-2-methyl-5-oxo-5H-pyrrolo[3,4-b]pyridin-6(7H)-yl)ethyl)cyclopropanesulfonamide hydrochloride

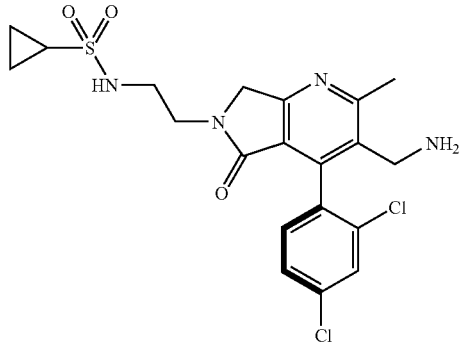

Example 111B (70 mg, 0.15 mmol) in 1 mL of 4M HCl in 1,4-dioxane was stirred at ambient temperature for 15 min. The mixture was concentrated in vacuo. The residue was dissolved in 2 ml of $CH_2Cl_2$, $Et_3N$ (0.2 mL, 1.5 mmol) and cyclopropanesulfonyl chloride (25 mg, 0.18 mmol) were added into the solution. The resulting mixture was stirred at ambient temperature for 6 h. MsCl (92 μL, 1.2 mmol) was added. The reaction was kept at ambient temperature for 1 h and concentrated to give a crude product which was subjected to flash chromatography (silica gel, 100% EtOAc) to yield a chloride intermediate. A mixture of the obtained chloride and 2N ammonia in MeOH (2 mL) was irradiated in a sealed tube in a microwave reactor at 140° C. for 30 min. The volatiles were removed in vacuo. The crude product was purified by flash chromatography (elution with 0-10% MeOH/$CH_2Cl_2$), treated with 2N HCl in MeOH, and evaporated to afford 18 mg (24% for 4 steps) of Example 115 as a solid. $^1$H NMR (400 MHz, $CDCl_3$): δ 0.92 (m, 2H), 1.11 (d, 2H, J=2.7 Hz), 2.35 (m 1H), 2.84 (s, 3H), 3.44 (broad s, 2H), 3.66-3.78 (m, 4H), 4.51 (s, 2H) 7.16 (d, 1H, J=8.2 Hz), 7.35 (dd, 1H, J=8.3, 1.6 Hz), 7.54 (d, 2H, J J=1.6 Hz). LRMS (ESI): 469.1 [M+H]+.

Example 116

N-(2-(3-(aminomethyl)-4-(2,4-dichlorophenyl)-2-methyl-5-oxo-5H-pyrrolo[3,4-b]pyridin-6(7H)-yl)ethyl)benzenesulfonamide hydrochloride

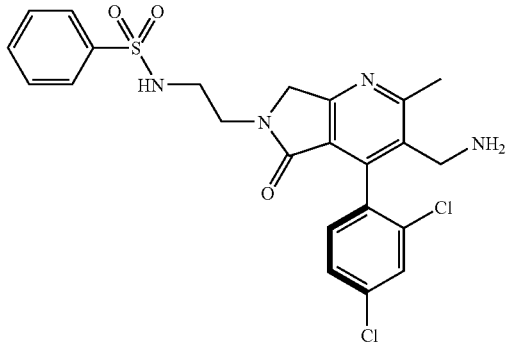

Example 116 was prepared using the same method described above for Example 115, with the exception that cyclopropanesulfonyl chloride was replaced with benzenesulfonyl chloride. $^1$H NMR (400 MHz, CDCl$_3$): δ 2.84 (s, 3H), 3.24 (m, 2H), 3.66 (m, 3H), 3.76 (d, 1H, J=13.8 Hz), 4.34 (AB$_q$, 2H), 7.15 (d, 1H, J=8.3 Hz), 7.40 (m, 3H), 7.54 (m, 2H), 7.79 (d, 2H, J=7.1 Hz). LRMS (ESI): 505.1 [M+H]+.

Example 117

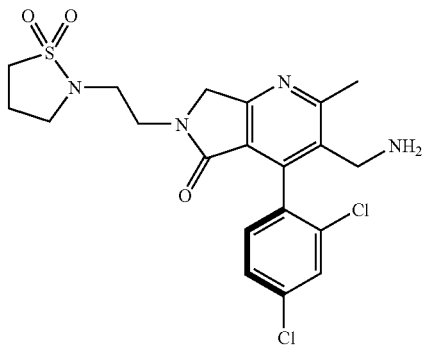

Example 111B (85 mg, 0.18 mmol) in 1 mL of 4M HCl in 1,4-dioxane was stirred at ambient temperature for 15 min. The mixture was concentrated in vacuo. The residue was dissolved in 2 ml of THF, t-BuONa (86 mg, 0.9 mmol) and 3-chloropropanesulfonyl chloride (39 mg, 0.22 mmol) were added into the solution. The resulting mixture was stirred at ambient temperature for 1 h. The mixture was filtered through a pad of SiO$_2$ gel. The solvent was evaporated and the residue was treated with MsCl (0.08 mL, 1.0 mmol) and Et$_3$N (0.14 mL, 1.0 mmol) in 5 mL of CH$_2$Cl$_2$. The reaction was kept at ambient temperature for 3 h and concentrated to give a crude product which was subjected to flash chromatography (silica gel, 100% EtOAc) to yield a chloride intermediate (43 mg, 48%). A mixture of the obtained chloride and 2N ammonia in MeOH (3 mL) was irradiated in a sealed tube in a microwave reactor at 120° C. for 20 min. The volatiles were removed in vacuo. The crude product was purified by flash chromatography (elution with 0-10% MeOH/CH$_2$Cl$_2$), treated with 2N HCl in MeOH, and evaporated to afford 12 mg (30%) of Example 117 as a solid. $^1$H NMR (400 MHz, CDCl$_3$): δ 2.27 (m, 2H), 2.83 (s, 3H), 3.02 (m, 2H), 3.27 (m, 2H), 3.35 (m, 2H), 3.61-3.78 (m, 4H), 4.53 (AB$_q$, 2H), 7.14 (d, 1H, J=8.3 Hz), 7.36 (dd, 1H, J=7.7, 1.6 Hz), 7.53 (d, 1H, J=1.7 Hz). LRMS (ESI): 469.1 [M+H]+.

Example 118 tert-Butyl 2-(3-(aminomethyl)-4-(2,4-dichlorophenyl)-2-methyl-5-oxo-5H-pyrrolo[3,4-b]pyridin-6(7H)-yl)ethyl(methyl)carbamate

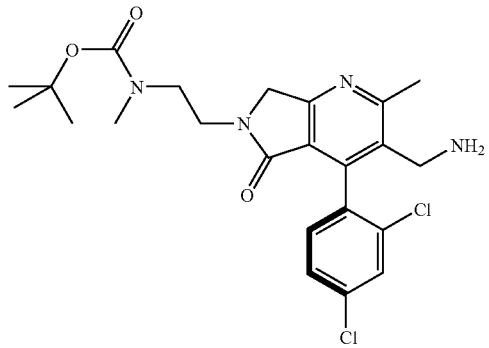

Example 118A

Benzyl 6-(2-tert-butoxycarbonyl(methyl)amino)ethyl)-4-(2,4-dichlorophenyl)-2-methyl-5-oxo-6,7-dihydro-5H-pyrrolo[3,4-b]pyridine-3-carboxylate

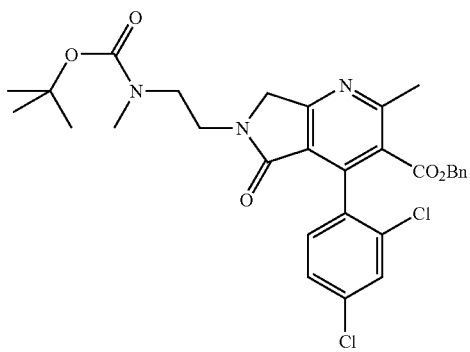

Example 118A was prepared using the same method described above for Example 110A with the exception that tert-butyl 2-aminoethyl carbamate was replaced with tert-butyl 2-aminoethyl(methyl) carbamate. LRMS (ESI): 584.3 [M+H]+.

Example 118B 6-(2-(tert-Butoxycarbonyl(methyl)amino)ethyl)-4-(2,4-dichlorophenyl)-2-methyl-5-oxo-6,7-dihydro-5H-pyrrolo[3,4-b]pyridine-3-carboxylic acid

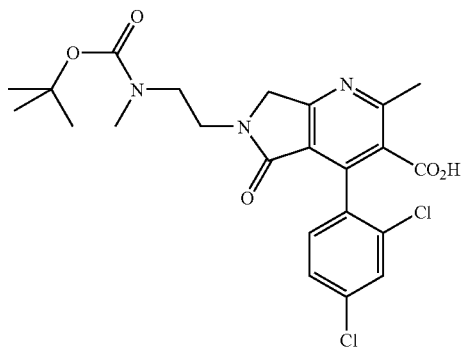

Example 118B was prepared using the same method described above for Example 110B with the exception that Example 110A was replaced with Example 118A. LRMS (ESI): 394.2 (M+H-BOC)⁺.

Example 118C tert-Butyl 2-(4-(2,4-dichlorophenyl)-3-(hydroxymethyl)-2-methyl-5-oxo-5H-pyrrolo[3,4-b]pyridin-6(7H)-yl)ethyl(methyl)carbamate

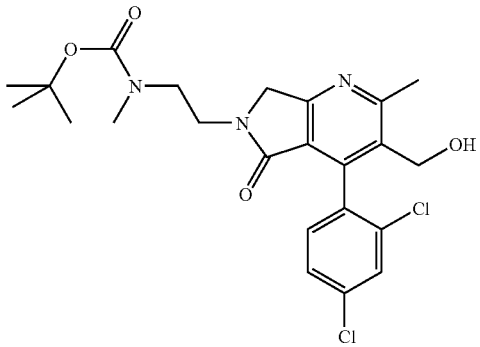

Example 118C was prepared using the same method described above for Example 110C with the exception that Example 110B was replaced with Example 118B. LRMS (ESI): 380.2/480.2 (M+H-BOC/M+H)⁺.

Examples 118D and 118E

Chiral separation tert-butyl 2-(4-(2,4-dichlorophenyl)-3-(hydroxymethyl)-2-methyl-5-oxo-5H-pyrrolo[3,4-b]pyridin-6(7H)-yl)ethyl(methyl)carbamate into individual atropisomers Example 118D

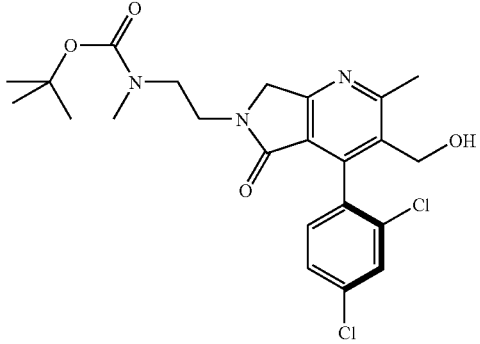

Example 118E

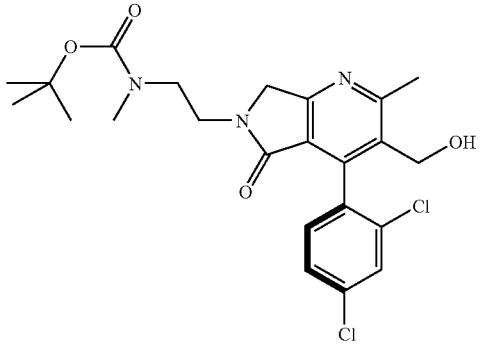

A 875 mg sample of racemic Example 118C was separated by chiral HPLC (Chiralcel OD column, 20 g, 5×50 cm column, elution with 0-10% i-PrOH/heptane) to afford the two individual atropisomers.

Example 118D (Atropisomer 1; faster-moving): 248 mg, purity by chiral analytical HPLC [Chiralcel OD 4.6×250 mm; 12% i-PrOH/heptane, retention time 11.5 min]: >99% ee.

Example 118E (Atropisomer 2; slower-moving): 240 mg, purity by chiral analytical HPLC [Chiralcel OD 4.6×250 mm; 12% i-PrOH/heptane, retention time 17.5 min]: >99% ee. ¹H NMR (400 MHz, CDCl₃): δ 1.35 (s, 9H), 2.85 (m, 6H), 3.54 (m, 2H), 3.69 (broad s, 2H), 4.45-4.50 (m, 4H), 7.17 (d, 1H, J=8.3 Hz), 7.36 (dd, 1H, J=8.3, 1.7 Hz), 7.53 (d, 1H, J=1.7 Hz). LRMS (ESI): 380.2/480.2 [M+H]⁺.

Example 118 tert-Butyl 2-(3-(aminomethyl)-4-(2,4-dichlorophenyl)-2-methyl-5-oxo-5H-pyrrolo[3,4-b]pyridin-6(7H)-yl)ethyl(methyl)carbamate

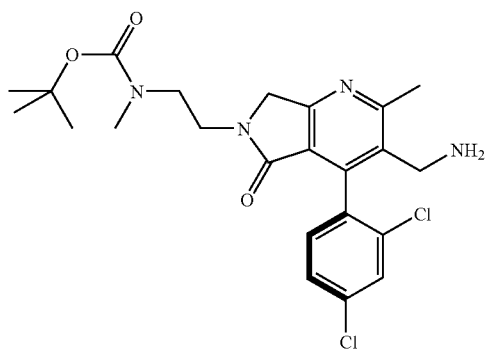

Example 118 was prepared using the same method described above for Example 110D with the exception that Example 110C was replaced with Example 118E. ¹H NMR (400 MHz, CDCl₃): δ 1.35 (s, 9H), 2.83 (s, 3H), 2.86 (s, 3H), 3.45 (m, 1H), 3.691-3.77(m, 3H), 4.48 (m, 2H), 7.12 (d, 1H, J=8.3 Hz), 7.36 (dd, 1H, J—8.3, 2.2 Hz), 7.53 (d, 1H, J=2.2 Hz). LRMS (ESI): 379.2/479.2 [M+H]⁺.

Example 119

3-(Aminomethyl)-4-(2,4-dichlorophenyl)-2-methyl-6-(2-(methylamino)ethyl)-6,7-dihydro-5H-pyrrolo[3,4-b]pyridin-5-one hydrochloride

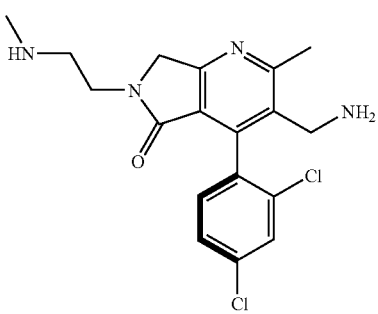

Example 118 (15.8 mg, 0.03 mmol) in 1 mL of 4M HCl in 1,4-dioxane was stirred at ambient temperature for 15 min. The mixture was concentrated in vacuo evaporated to afford 13.2 mg (98%) of Example 119 as a yellow solid. NMR (400 MHz, DMSO-D₆): δ 2.81 (s, 3H), 3.15 (d, 2H, J=5.5 Hz), 3.56 (m, 1H), 3.70(m, 1H), 3.79 (m, 1H), 4.07 (m, 1H), 4.61 (m, 5H), 7.56 (s, 2H), 7.77 (s, 1H), 8.58 (s, 2H), 9.05(m, 1H). LRMS (ESI): 379.2 [M+H]⁺.

Example 120

N-(2-(3-(Aminomethyl)-4-(2,4-dichlorophenyl)-2-methyl-5-oxo-5H-pyrrolo[3,4-b]pyridin-6(7H)-yl)ethyl)-N-methylethanesulfonamide hydrochloride

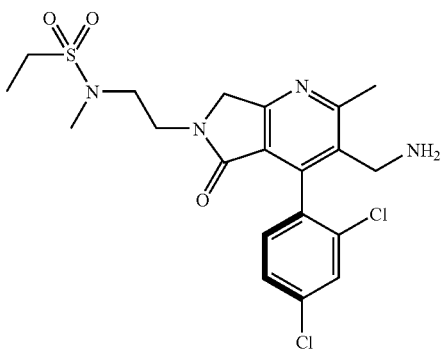

Example 120A 3-(Chloromethyl)-4-(2,4-dichlorophenyl)-2-methyl-6-(2-(methylamino)ethyl)-6,7-dihydro-5H-pyrrolo[3,4-b]pyridin-5-one hydrochloride

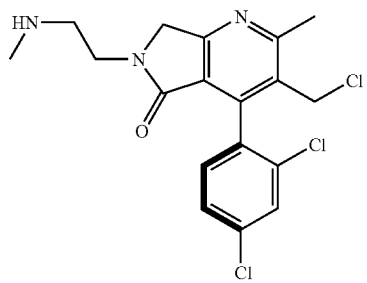

To a solution of Example 118E (240 mg, 0.50 mmol) in 5 ml of CH$_2$Cl$_2$, Et$_3$N (0.7 mL, 5 mmol) and methanesulfonyl chloride (0.39 mL, 5 mmol) were added. The resulting mixture was stirred at ambient temperature overnight. The mixture was concentrated in vacuo. The residue was subjected to flash chromatography (silica gel, 100% EtOAc) to afford a solid, which was stirred in 10 ml of 4N—HCl in 1,4-dioxane at ambient temperature for 30 min, the reaction mixture was concentrated to afford 186 mg (86%) of Example 120A as a solid, which was sufficiently pure to be used without purification. LRMS (ESI): 398.1/400.1 [M+H]$^+$.

To a solution of Example 120A (40 mg, 0.09 mmol) in 2 ml of CH$_2$Cl$_2$, Et$_3$N (0.13 mL, 0.93 mmol) and ethanesulfonyl chloride (100 mg, 0.93 mmol) were added. The resulting mixture was stirred at ambient temperature overnight The reaction was concentrated to give a crude product which was subjected to flash chromatography (silica gel, 100% EtOAc) to yield a chloride intermediate. A mixture of the obtained chloride and 2N ammonia in MeOH (2 mL) was irradiated in a sealed tube in a microwave reactor at 120° C. for 15 min. The volatiles were removed in vacuo. The crude product was purified by flash chromatography (elution with 0-10% MeOH/CH$_2$Cl$_2$), treated with 2N HCl in MeOH, and evaporated to afford 11 mg (24% for 2 steps) of Example 120 as a solid. $^1$H NMR (400 MHz, CDCl$_3$): δ 1.25 (m, 3H), 2.83 (s, 3H), 2.90 (s, 3H), 2.94 (m, 2H), 3.61-3.80 (m, 4H), 4.52(s, 3H), 7.14 (d, 1H, J=8.3 Hz), 7.36 (dd, 1H, J=2.2, 8.2 Hz), 7.53 (d, 1H, J=1.6 Hz), LRMS (ESI): 471.1 [M+H]$^+$.

Example 121

N-(2-(3-(aminomethyl)-4-(2,4-dichlorophenyl)-2-methyl-5-oxo-5H-pyrrolo[3,4-b]pyridin-6(7H)-yl)ethyl)-N-methylmethanesulfonamide TFA salt

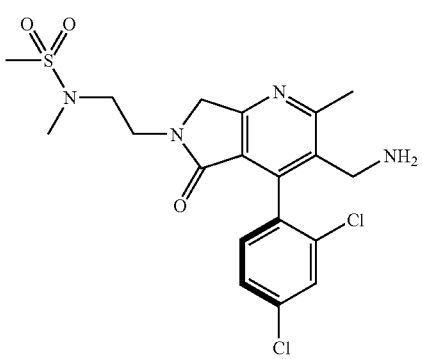

Example 121 was prepared using the same method described above for Example 120, with the exceptions that ethanesulfonyl chloride was replaced with methanesulfonyl chloride and TFA salt was obtained instead of HCl salt. $^1$H NMR (400 MHz, DMSO-D$_6$): δ 2.73 (s, 3H), 2.76 (s, 3H), 2.82 (s, 3H), 3.28 (m, 2H), 3.63 (m, 3H), 4.08(m, 1H), 4.55 (s, 2H), 7.40 (d, 1H, J=2.2 Hz), 7.55 (dd, 1H, J=1.7, 8.3 Hz), 7.79 (d, 1H, J=2.0 Hz), 8.2 (s, 2H). LRMS (ESI): 457.2 [M+H]$^+$.

Example 122

N-(2-(3-(aminomethyl)-4-(2,4-dichlorophenyl)-2-methyl-5-oxo-5H-pyrrolo[3,4-b]pyridin-6(7H-)-yl)ethyl)-N-methylcyclopropanesulfonamide hydrochloride

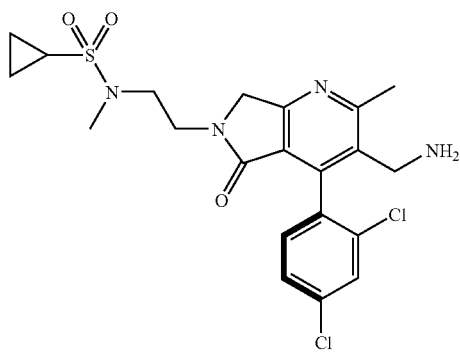

Example 122 was prepared using the same method described above for Example 120 with the exception that ethanesulfonyl chloride was replaced with cyclopropanesulfonyl chloride. $^1$H NMR (400 MHz, CDCl$_3$): δ 0.93-1.26 (m, 4H), 2.22 (m, 1H), 2.83(s, 3H), 2.90 (s, 3H), 3.48 (m, 2H), 3.61-3.78 (4H), 4.52 (s, 2H), 7.15 (d, 1H, J=8.3 Hz), 7.35 (dd, 1H, J=8.3, 1.6 Hz), 7.53 (d, 1H, J=1.7 Hz), LRMS (ESI): 483.1 [M+H]$^+$.

Example 123

N-(2-(3-(aminomethyl)-4-(2,4-dichlorophenyl)-2-methyl-5-oxo-5H-pyrrolo[3,4-b]pyridin-6(7H)-yl)ethyl)-1,1,1-trifluoro-N-methylmethanesulfonamide hydrochloride

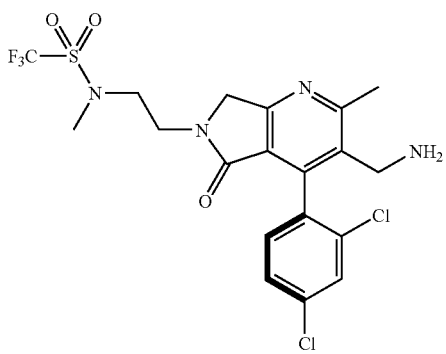

Example 123 was prepared using the same method described above for Example 120 with the exception that ethanesulfonyl chloride was replaced with trifluoroacetic anhydride. LRMS (ESI): 511.1 [M+H]$^+$.

Example 124

3-(Aminomethyl)-4-(2,4-dichlorophenyl)-2-methyl-6-(piperidin-4-yl)-6,7-dihydro-5H-pyrrolo[3,4-b]pyridin-5-one TFA salt

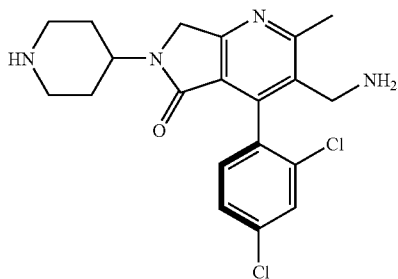

Example 124A

Benzyl 6-(1-(tert-butoxycarbonyl)piperidin-4-yl)-4-(2,4-dichlorophenyl)-2-methyl-5-oxo-6,7-dihydro-5H-pyrrolo[3,4-b]pyridine-3-carboxylate

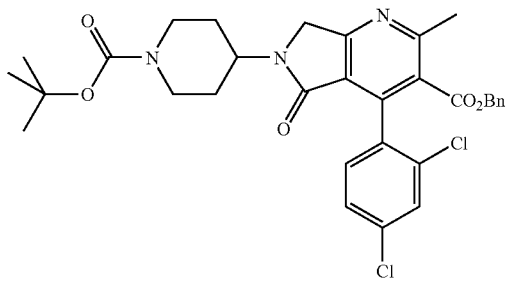

A mixture of Example 2D (1.60 g, 3.26 mmol), 4-amino-1-N-BOC-piperidine (716 m g, 3.58 mmol) and triethylamine (0.68 mL, 4.89 mmol) in acetonitrile (100 mL) was heated in a sealed vial at 110° C. for 3 h. The solvent was evaporated, and the residue was purified by flash chromatography (elution with 0-100% EtOAc/Hexanes) to afford 1.32 g (66%) of Example 124A as a solid. $^1$H NMR 15' (400 MHz, CDCl$_3$): δ 1.46 (s, 9H), 1.60-1.88 (m, 5H), 2.73 (s, 3H), 2.75 (m, 2H), 4.20-4.42 (m, 4H), 5.10(m, 2H), 7.00-7.11 (m, 4H), 7.30 (m, 4H), LRMS (ESI): 554.2 (M+H-t-Bu)$^+$.

Example 124B 6-(1-(tert-Butoxycarbonyl)piperidin-4-yl)-4-(2,4-dichlorophenyl)-2-methyl-5-oxo-6,7-dihydro-5H-pyrrolo[3,4-b]pyridine-3-carboxylic acid

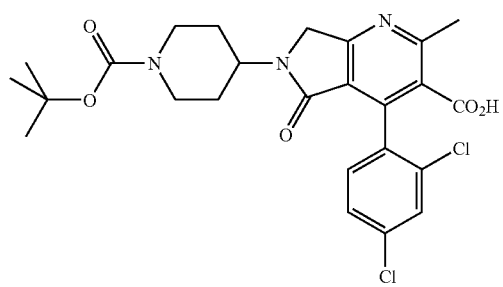

A mixture of Example 124A (1.32 g, 2.17 mmol) and 10% Pd/C (66 mg) in 90 mL of methanol was stirred under H$_2$ (1 atm, maintained by balloon) for 2 h at ambient temperature. The mixture was filtered through a pad of Celite and concentrated to afford 1.10 g (98%) of Example 124B as a solid which was sufficiently pure to be used without purification. $^1$H NMR (400 MHz, CDCl$_3$): δ 1.46 (s, 9H), 1.63-1.81 (m, 4H), 2.75 (m, 4H), 3.46 (s, 2H), 4.20-4.43 (m, 4H), 7.16 (d, 1H), 7.27 (d, 1H), 7.46 (s, 1H). LRMS (ESI): 464.1 (M+H-t-Bu)$^+$.

Example 124C tert-Butyl 4-(4-(2,4-dichlorophenyl)-3-(hydroxymethyl)-2-methyl-5-oxo-5H-pyrrolo[3,4-b]pyridin-6(7H)-yl)piperidine-1-carboxylate

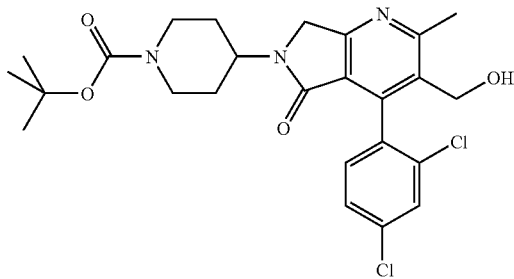

To a solution of Example 124B (1.38 g, 2.66 mmol) in 80 mL of CH$_2$Cl$_2$ was added DMF (3 drops) and oxalyl chloride (2M in CH$_2$Cl$_2$L, 1.4 mL, 2.80 mmol). The mixture was allowed to stir at ambient temperature for 1 h. Triethylamine (0.74 mL, 5.32 mmol) was added. The solvent was evaporated, and the residue was, purified by flash chromatography (elution with 0-100% EtOAc/Hexanes) to afford a solid which was dissolved in THF (100 mL), the resulting solution was cooled down to −78° C., and LAH (1M in THF, 2.7 mL, 2.7 mmol) was added. Stirred for 30 min. The reaction solution was filtered through a pad of SiO$_2$ gel. The volatiles were removed in vacuo to afford 1.38 g of crude Example 124C as an oil. LRMS (ESI): 450.2 (M+H-t-Bu)$^+$.

Examples 124D and 124E

Chiral separation of tert-butyl 4-(4-(2,4-dichlorophenyl)-3-(hydroxymethyl)-2-methyl-5-oxo-5H-pyrrolo[3,4-b]pyridin-6(7H)-yl)piperidine-1-carboxylate into individual atropisomers Example 124D

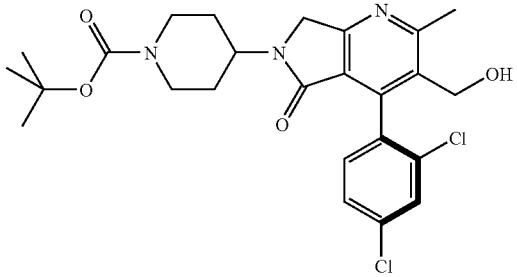

Example 124E

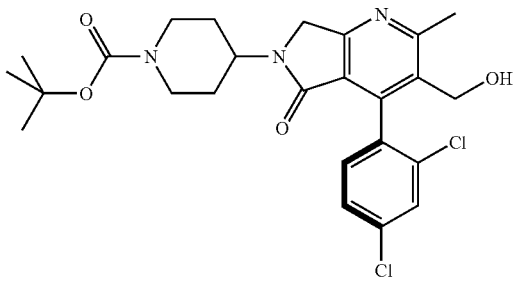

A 1.38 g sample of crude racemic Example 124C was separated by chiral HPLC (Chiralcel OD column, 20 µ, 5×50 cm column, elution with 0-20% i-PrOH/heptane) to afford the two individual atropisomers.

Example 124D (Atropisomer 1; faster-moving): 313 mg, purity by chiral analytical HPLC [Chiralcel OD 4.6×250 mm; 20% i-PrOH/heptane, retention time 7.7 min]: >99% ee.

Example 124E (Atropisomer 2; slower-moving): 292 mg, purity by chiral analytical HPLC [Chiralcel OD 4.6×250 mm; 20% i-PrOH/heptane, retention time 11.6 min]: >99% ee.

Example 124

3-(Aminomethyl)-4-(2,4-dichlorophenyl)-2-methyl-6-(piperidin-4-yl)-6,7-dihydro-5H-pyrrolo[3,4-b]pyridin-5-one TFA salt

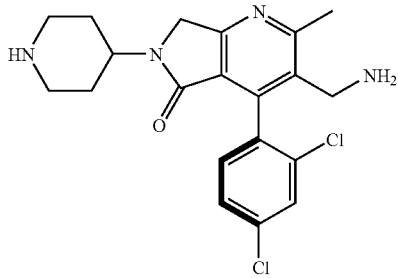

To a solution of Example 124E (50 mg, 0.10 mmol) in 2 ml of CH$_2$Cl$_2$, Et$_3$N (43 µL, 0.3 mmol) and methanesulfonyl chloride (23 µL, 0.3 mmol) were added. The resulting mixture was refluxed for 1 h. The reaction was concentrated to give a crude product which was subjected to flash chromatography (silica gel, 100% EtOAc) to yield a chloride intermediate. A mixture of the obtained chloride and 2N ammonia in MeOH (2 mL) was irradiated in a sealed tube in a microwave reactor at 100° C. for 15 min. The volatiles were removed in vacuo. The residue was stirred in 2 ml of TFA/CH$_2$Cl$_2$ (1:1) for 15 min. The mixture was concentrated, the residue was purified by prep HPLC (Phenomenex, 10 min gradient, 20 to 100% B) and lyophilized to dryness overnight to afford 22 mg (40%) of Example 124 as an TFA salt. $^1$H NMR (400 MHz, DMSO-D$_6$): δ 1.79 (m, 2H), 1.91 (m, 2H), 2.7 (3, 3H), 2.95 (broad s, 2H), 3.32 (d, 2H), 3.59 (d, 1H), 4.12 (m, 2H), 4.45 (m, 2H), 7.38 (d, 1H), 7.49 (d, 1H), 7.72 (s, 1H). LRMS (ESI): 405.2 [M+H]$^+$.

Example 125

3-(Aminomethyl)-4-(2,4-dichlorophenyl)-2-methyl-6-(1-(methylsulfonyl)piperidin-4-yl)-6,7-dihydro-5H-pyrrolo[3,4-b]pyridin-5-one TFA salt

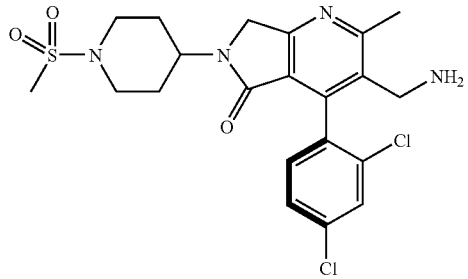

Example 124E (50 mg, 0.10 mmol) in 2 ml of TFA/CH$_2$Cl$_2$ (1:1) was stirred at ambient temperature for 30 min. The mixture was concentrated in vacuo. The residue was dissolved in 2 ml of CH$_2$Cl$_2$, Et$_3$N (43 µL, 0.3 mmol) and methanesulfonyl chloride (23 µL, 0.3 mmol). The resulting mixture was refluxed for 1 h. The reaction was concentrated to give a crude product which was subjected to flash chromatography (silica gel, 100% EtOAc) to yield a chloride intermediate. A mixture of the obtained chloride and 2N ammonia in MeOH (2 mL) was irradiated in a sealed tube in a microwave reactor at 100° C. for 15 min. The volatiles were removed in vacuo. The residue was purified by prep HPLC (Phenomenex, 10 min gradient, 20 to 100% B) and lyophilized to dryness overnight to afford 8 mg (13% for 3 steps) of Example 125 as an TFA salt. LRMS (ESI): 483.2 [M+H]$^+$.

Example 126

6-(1-Acetylpiperidin-4-yl)-3-(aminomethyl)-4-(2,4-dichlorophenyl)-2-methyl-6,7-dihydro-5H-pyrrolo[3,4-b]pyridin-5-one, TFA

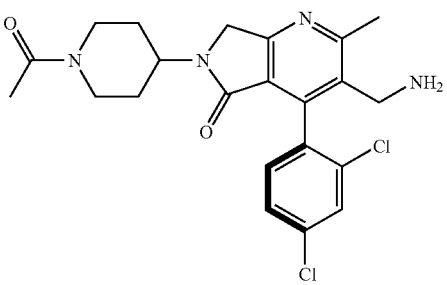

Example 124E (50 mg, 0.10 mmol) in 2 ml of TFA/CH$_2$Cl$_2$ (1:1) was stirred at ambient temperature for 30 min. The mixture was concentrated in vacuo. The residue was dissolved in 2 ml of CH$_2$Cl$_2$, Et$_3$N (27 µ, 0.2 mmol) and acetyl chloride (8 µL, 0.1 mmol). The resulting mixture was refluxed for 30 min. The reaction was concentrated to give a crude product which was subjected to flash chromatography (silica gel, 100% EtOAc) to yield a intermediate, which was dissolved in 2 ml of CH$_2$Cl$_2$, Et$_3$N (43 µL, 0.3 mmol) and methanesulfonyl chloride (23 µL, 0.3 mmol) were added. The resulting mixture was refluxed for 1 h. The reaction was concentrated to give a crude product which was subjected to flash chromatography (silica gel, 100% EtOAc) to yield a chloride intermediate. A mixture of the obtained chloride and 2N ammonia in MeOH (2 mL) was irradiated in a sealed tube in a microwave reactor at 100° C. for 15 min. The volatiles were removed in vacuo. The residue was purified by prep HPLC (Phenomenex, 10 min gradient, 20 to 100% B) and lyophilized to dryness overnight to afford 4 mg (7% for 4 steps) of Example 126 as an TFA salt. LRMS (EST): 447.2 [M+H]+.

Example 127

Ethyl 4-(3-(aminomethyl)-4-(2,4-dichlorophenyl)-2-methyl-5-oxo-5H-pyrrolo[3,4-b]pyridin-6(7H)-yl)piperidine-1-carboxylate TFA salt

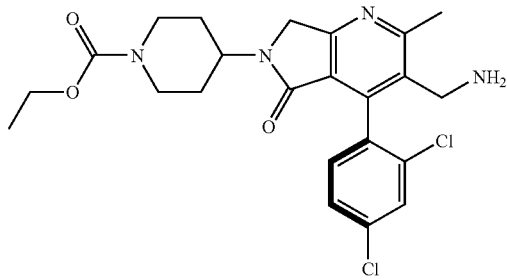

Example 127 was prepared using the same method described above for Example 126 with the exception that acetyl chloride was replaced with ethyl chloroformate. LRMS (ESI): 477.2 [M+H]+.

Example 128

3-(Aminomethyl)-6-((S)-1-(cyclopropylsulfonyl)pyrrolidin-3-yl)-4-(2,4-dichlorophenyl)-2-methyl-6,7-dihydro-5H-pyrrolo[3,4-b]pyridin-5-one hydrochloride

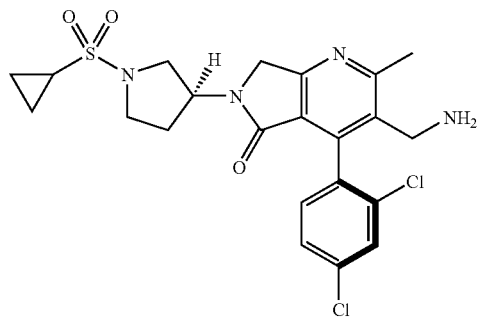

Example 128A

Benzyl 6-((S)-1-(tert-butoxycarbonyl)pyrrolidin-3-yl)-4-(2,4-dichlorophenyl)-2-methyl-5-oxo-6,7-dihydro-5H-pyrrolo[3,4-b]pyridine-3-carboxylate

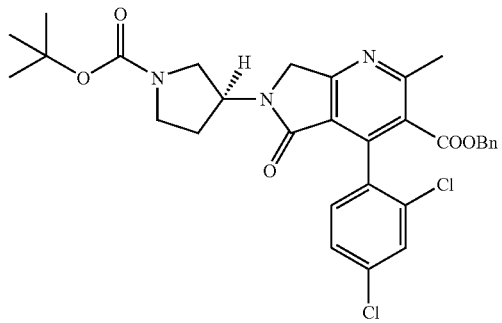

Example 128A was prepared using the same method described above for Example 124 with the exception that 4-amino-1-N-BOC-piperidine was replaced with (S)-(−)-1-BOC-3-aminopyrrolidine. LRMS (ESI): 540.2 (M+H-t-Bu)+.

Example 128B 6-((S)-1-(tert-Butoxycarbonyl)pyrrolidin-3-yl)-4-(2,4-dichlorophenyl)-2-methyl-5-oxo-6,7-dihydro-5H-pyrrolo[3,4-b]pyridine-3-carboxylic acid

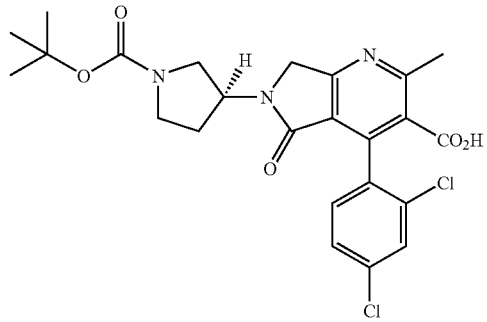

Example 128B was prepared using the same method described above for Example 124B with the exception that Example 124A was replaced with Example 128A. LRMS (ESI): 406.1/450.1 (M+H-BOC/M+H-t-Bu)+.

Example 128C tert-Butyl 3-(4-(2,4-dichlorophenyl)-3-(hydroxymethyl)-2-methyl-5-oxo-5H-pyrrolo[3,4-b]pyridin-6(7H)-yl)pyrrolidine-1-carboxylate

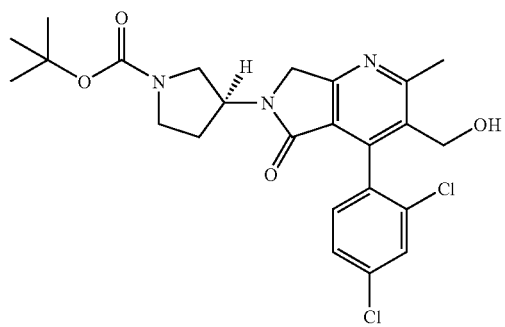

Example 128C was prepared using a procedure similar to Example 124C except that Example 124B was replaced by Example 128B.

Examples 128D and 128E. tert-Butyl 3-(S)-4-(2,4-dichlorophenyl)-3-(hydroxymethyl)-2-methyl-5-oxo-5H-pyrrolo[3,4-b]pyridin-6(7H)-yl)pyrrolidine-1-carboxylate

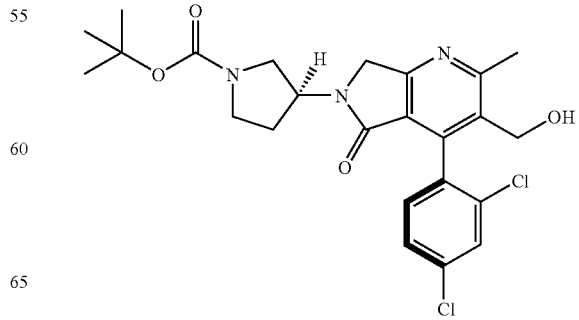

-continued

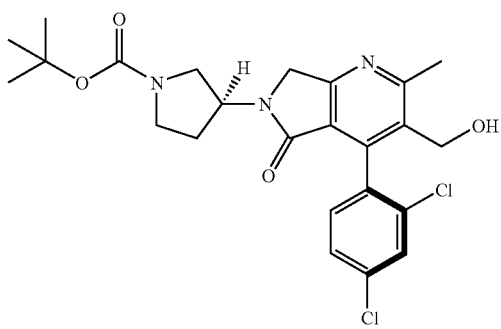

Examples 128D and 128E were prepared using the same method described above for Example 124C with the exception that Example 124C was replaced with Example 128C. Flash chromatography (silica gel, 0-100% EtOAc) yielded two individual atropisomers.

Example 128D (Atropisomer 1; faster-moving): 158 mg, purity by chiral analytical HPLC [Chiralcel OD 4.6×250 mm; 15% i-PrOH/heptane, retention time 11.5 min]: >99% ee. $^1$H NMR (400 MHz, CDCl$_3$): δ 1.45 (s, 9H), 1.47 (m, 2H), 2.10 (broad s, 1H), 2.23 (broad s, 1H), 2.86 (s, 3H), 3.42 (m, 2H), 3.61 (m, 2H), 4.47 (m, 3H), 4.58 (d, 1H), 4.86 (m, 1H), 7.17 (d, 1H, J=8.0), 7.36 (m, 1H), 7.54 (s, 1H). LRMS (ESI): 436.1 [M+H]$^+$.

Example 128E (Atropisomer 2; slower-moving): 170 mg, purity by chiral analytical HPLC [Chiralcel OD 4.6×250 mm; 15% i-PrOH/heptane, retention time 16.3 min]:

Example 128

3-(Aminomethyl)-6-((S)-1-(cyclopropylsulfonyl)pyrrolidin-3-yl)-4-(2,4-dichlorophenyl)-2-methyl-6,7-dihydro-5H-pyrrolo[3,4-b]pyridin-5-one hydrochloride

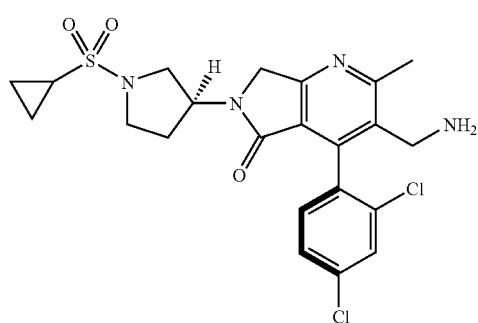

Example 128 was prepared using the same method described above for Example 115 with the exception that Example 111B was replaced with Example 128D. $^1$H NMR (400 MHz, CDCl$_3$): δ 1.00 (m, 2H), 1.20 (m, 2H), 2.17 (s, 1H), 2.35 (m, 2H), 2.83 (s, 3H), 3.47 (m, 2H), 3.63-3.78 (m, 4H), 4.51 (AB$_q$, 2H), 4.96 (m, 1H), 7.15 (d, 1H, J=8.3), 7.36 (dd, H, J=8.2, 2.2 Hz), 7.54 (d, 1H, J=1.7 Hz). LRMS (ESI): 495.0 [M+H]$^+$.

Example 129

3-((S)-3-(Aminomethyl)-4-(2,4-dichlorophenyl)-2-methyl-5-oxo-5H-pyrrolo[3,4-b]pyridin-6(7H)-yl)pyrrolidin-1-ylsulfonyl)benzonitrile hydrochloride

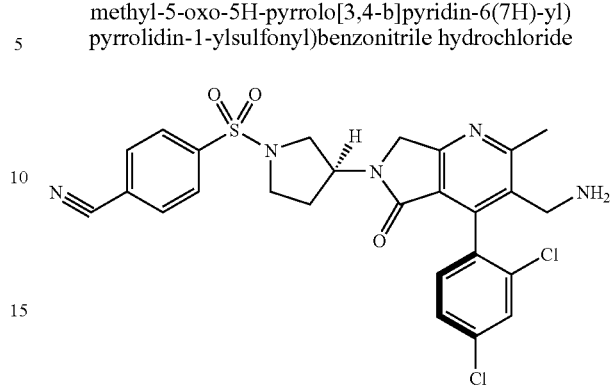

Example 129 was prepared using the same method described above for Example 115 with the exceptions that Example 111B was replaced with Example 128D and cyclopropanesulfonyl chloride was replaced with 4-cyanobenzenesulfonyl chloride. $^1$H NMR (400 MHz, CDCl$_3$): δ 2.02-2.20 (m, 2H), 2.84 (s, 3H), 3.20 (m, 1H), 3.45 (m, 2H), 3.63 (m, 2H), 3.74 (m, 1H) 4.31 (d, 2H, J=4.9 Hz), 4.75 (m, 1H), 7.10 (d, 1H, J=7.7 Hz), 7.35 (dd, H, J=7.7, 1.7 Hz), 7.55 (d, 1H, J=1.4 Hz), 7.82 (d, 2H, J=8.2 Hz), 7.93 (d, 2H, J=8.2 Hz), LRMS (ESI): 556.0/558.0 [M+H]$^+$.

Example 130

Ethyl 3-(S)-3-aminomethyl)-4-(2,4-dichlorophenyl)-2-methyl-5-oxo-5H-pyrrolo[3,4-b]pyridin-6(7H)-yl)pyrrolidine-1-carboxylate hydrochloride

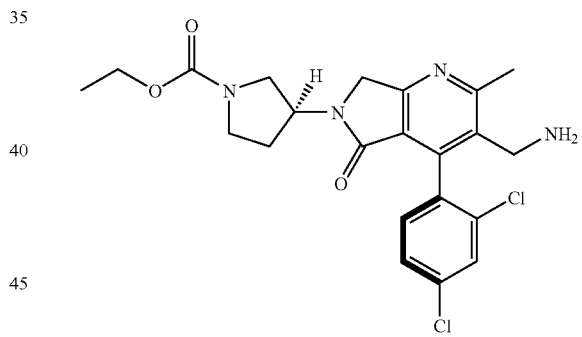

Example 130 was prepared using the same method described above for Example 115 with the exceptions that Example 111B was replaced with Example 128D and cyclopropanesulfonyl chloride was replaced with ethyl chloroformate. LRMS (ESI): 463.0 [M+H]$^+$.

What is claimed is:

1. A compound of formula (I)

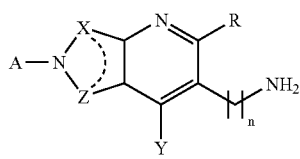

wherein

⁀ represents one or two double bonds in the 5-membered ring of I, and the six-membered ring of I is an aromatic ring;

n is 1 or 2;

R is;

X and Z are the same or different and are independently selected from the group consisting of $CH_2$, CH, C=O, C=$CR_3R_4$, C=S, C=$NR_3$, and $CR_3R_4$, wherein $R_3$ and $R_4$ are alkyl or aryl;

A is selected from the group consisting of hydrogen (H), alkyl, cycloalkyl which is cyclopentyl phenyl, phenylalkyl, heteroarylalkyl, where heteroaryl is pyrazolyl, oxazolyl or isooxazolyl, cycloheteroalkyl which is pyrrolidinyl, piperidinyl, tetrahydropyranyl or tetrahydrothiopyranyl, cycloheteroalkylalkyl where the cycloheteroalkyl group is tetrahydrofuranyl, pyrrolidinyl, oxazolidinyl, or thiazolidinyl, —C(O)—$NR_1R_2$, or —C(O)—$OR_1$, wherein any such group may optionally be substituted with 1 to 3 substituents (where possible) independently selected from the group consisting of hydrogen, halo, alkyl, polyhaloalkyl, alkoxy, haloalkoxy, polyhaloalkoxy, carboxy, alkoxycarbonyl, cycloalkyl, heteroarylamino, cycloheteroalkyl, cycloheteroalkylalkyl, cyclopropylsulfonyl, cycloheteroalkylaminocarbonyl, cycloheteroalkylcarbonyl, heteroarylaminocarbonyl, cycloheteroalkyl(alkyl)aminocarbonyl, cycloalkylsulfonyl(alkyl)amino, hydroxy, hydroxyalkyl, cyano, amino, substituted amino, alkylamino, dialkylamino, alkylthio, alkylcarbonyl, alkoxycarbonyl, aminocarbonyl, alkylaminocarbonyl, dialkylaminocarbonyl, (where the alkyls are the same or different), alkylcarbonylamino, alkylsulfonylamino, alkylaminocarbonylamino, alkoxycarbonylamino, alkylsulfonyl, phenylsulfonyl, alkylsulfinyl, and sulfonyl;

wherein heteroaryl in the above substituents is pyrazolyl, isooxazolyl, pyridinyl, or pyrimidinyl; and wherein cycloheteroalkyl in the above substituents is tetrahydrofuranyl, pyrrolidinyl, oxazolidinyl, thiazolidinyl, tetrahydropyranyl, piperidinyl, morpholinyl, piperazinyl, or indolinyl;

$R_1$ and $R_2$ are the same or different and are each independently selected from the group consisting of hydrogen (H), alkyl, phenyl, phenylalkyl, heteroaryl which is pyrazolyl, heteroarylalkyl which is pyrazolylalkyl or pyridinylalkyl, cycloheteroalkyl which is tetrahydropyranyl or piperidinyl, wherein such group may optionally be substituted with 1 to 3 substitutents (where possible) independently selected from the group consisting of hydrogen, and alkyl; and Y is phenyl, wherein said phenyl group may optionally be substituted with 1-5 substituents independently selected from the group consisting of hydrogen, and halo; or a pharmaceutically acceptable salt thereof, all stereoisomers thereof.

2. The compound as defined in claim 1 having the structure

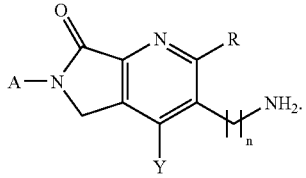

3. A compound having the structure

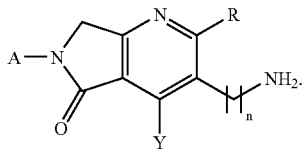

wherein n is 1 or 2;
R is alkyl;

A is selected from the group consisting of hydrogen (H), alkyl, cycloalkyl which is cyclopentyl, phenyl, phenylalkyl, heteroarylalkyl where heteroaryl is pyrazolyl, oxazolyl or isooxazolyl, cycloheteroalkyl which is pyrrolidinyl, piperidinyl, tetrahydropyranyl or tetrahydrothiopyranyl, cycloheteroalkylalkyl where the cycloheteroalkyl group is tetrahydrofuranyl, pyrrolidinyl, oxazolidinyl, or thiazolidinyl, -C(O)-$NR_1R_2$, or -C(O)-$OR_1$, wherein any such group may optionally be substituted with 1 to 3 substituents (where possible) independently selected from the group consisting of hydrogen, halo, alkyl, polyhaloalkyl, alkoxy, haloalkoxy, polyhaloalkoxy, carboxy, alkoxycarbonyl, cycloalkyl, heteroarylamino, cycloheteroalkyl, cycloheteroalkylalkyl, cyclopropylsulfonyl, cycloheteroalkylaminocarbonyl, cycloheteroalkylcarbonyl, heteroarylaminocarbonyl, cycloheteroalkyl(alkyl)aminocarbonyl, cycloalkylsulfonyl(alkyl)amino, hydroxy, hydroxyalkyl, cyano, amino, substituted amino, alkylamino, dialkylamino, alkylthio, alkylcarbonyl. alkoxycarbonyl, aminocarbonyl, alkylaminocarbonyl, dialkylaminocarbonyl, (where the alkyls are the same or different), alkylcarbonylamino, alkylsulfonylamino, alkylaminocarbonylamino, alkoxycarbonylamino, alkylsulfonyl, phenylsulfonyl, alkylsulfinyl, and sulfonyl;

wherein heteroaryl in the above substituents is pyrazolyl, isooxazolyl, pyridinyl, or pyrimidinyl; and wherein cycloheteroalkyl in the above substituents is tetrahydrofuranyl, pyrrolidinyl, oxazolidinyl, thiazolidinyl, tetrahydropyranyl, piperidinyl, morpholinyl, piperazinyl, or indolinyl;

$R_1$ and $R_2$ are the same or different and are each independently selected from the group consisting of hydrogen (H), alkyl, phenyl, phenylalkyl, heteroaryl which is pyrazolyl, heteroarylalkyl which is pyrazolylalkyl or pyridinylalkyl, cycloheteroalkyl which is tetrahydropyranyl or piperidinyl, wherein such group may optionally be substituted with 1 to 3 substituents (where possible) independently selected from the aroup consisting of hydrogen, and alkyl; and Y is phenyl, wherein said phenyl group may optionally be substituted with 1-5 substituents independently selected from the group consisting of hydrogen and halo;

or a pharmaceutically acceptable salt thereof, and all stereoisomers thereof.

4. The compound as defined in claim 1 having the structure

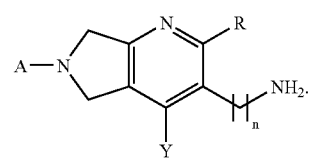

5. The compound as defined in claim 1 having the structure

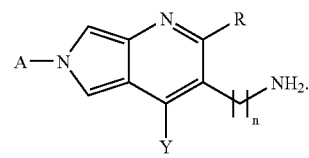

6. The compound as defined in claim 1 selected from
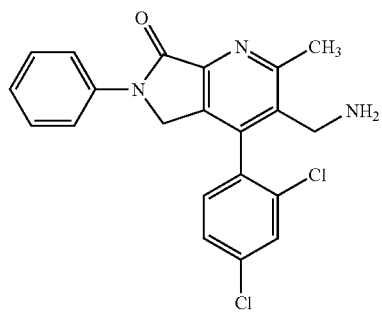
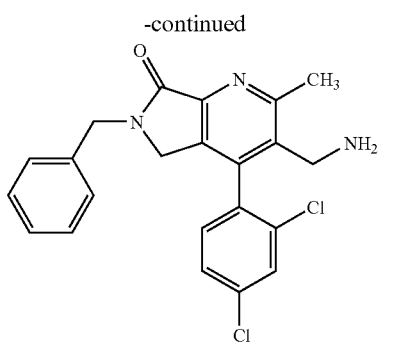
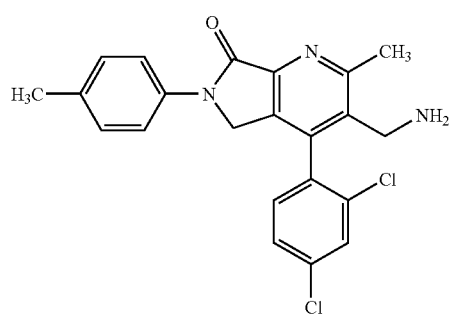
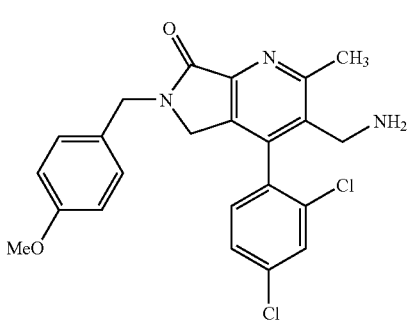
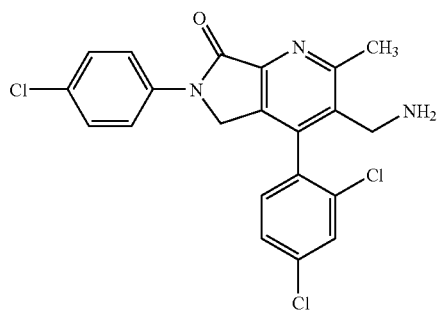
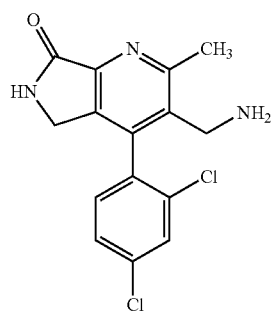
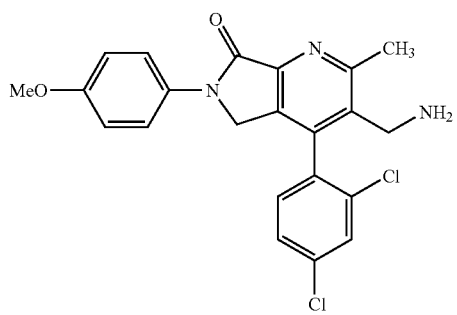
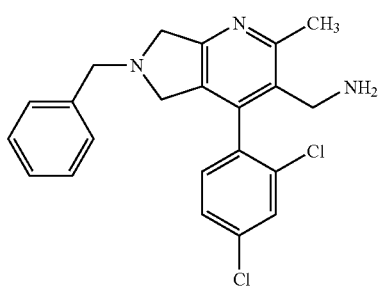
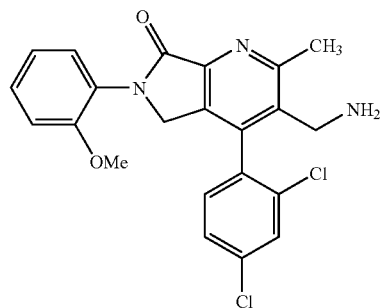
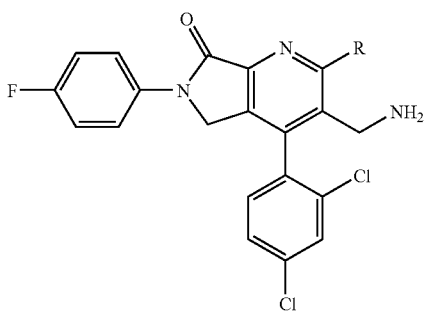

-continued
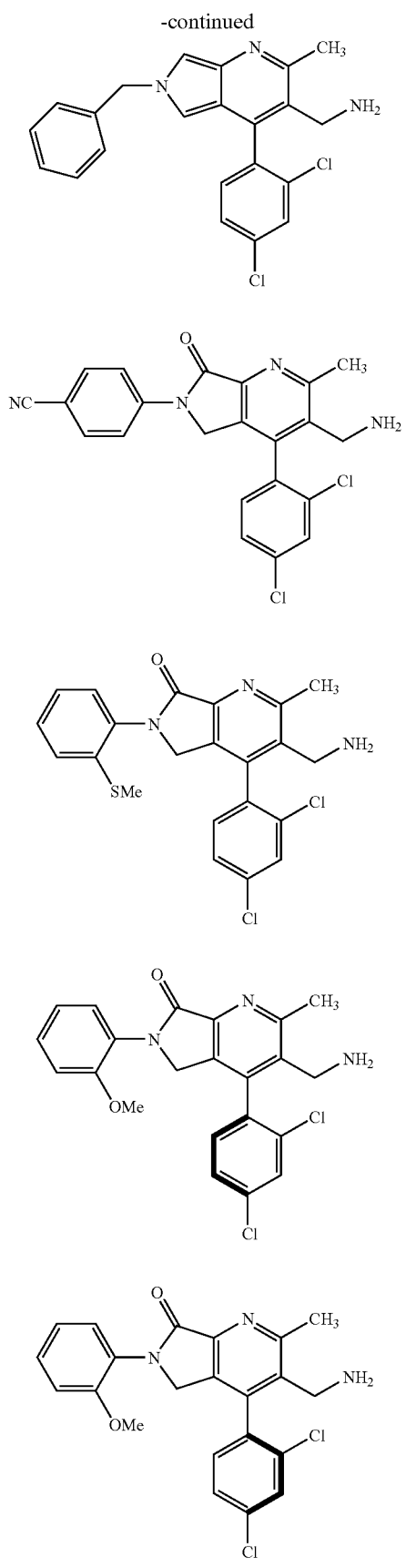
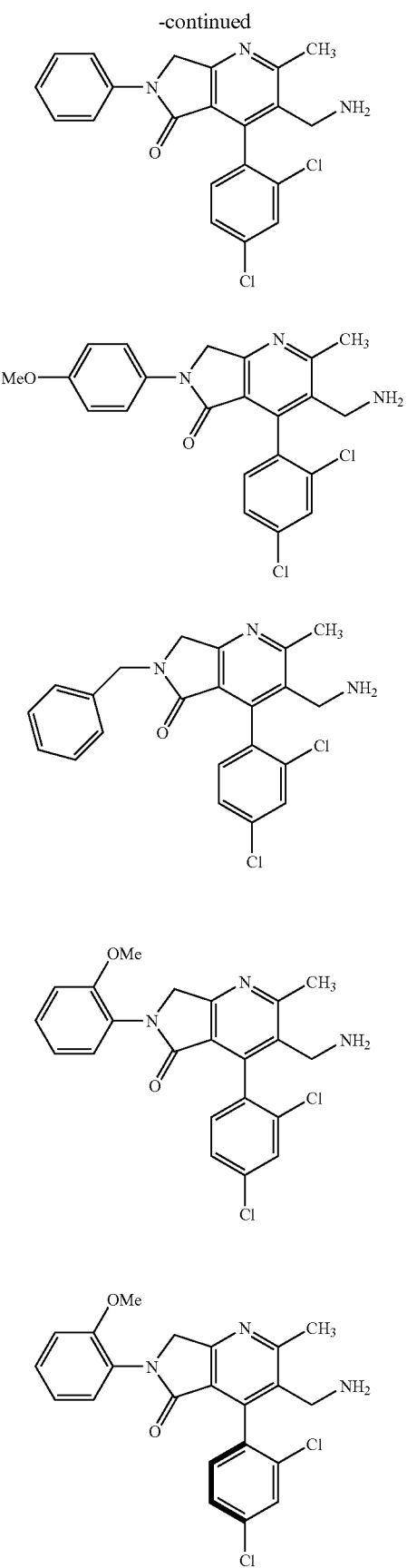

177
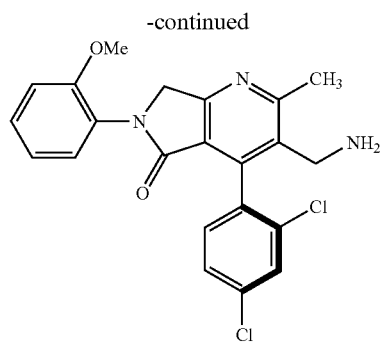
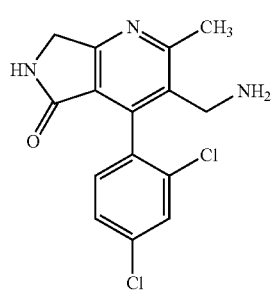
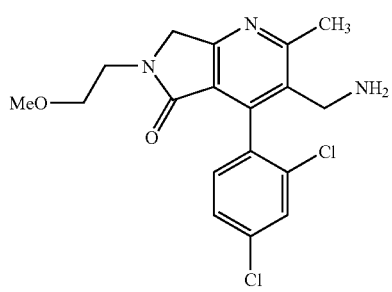
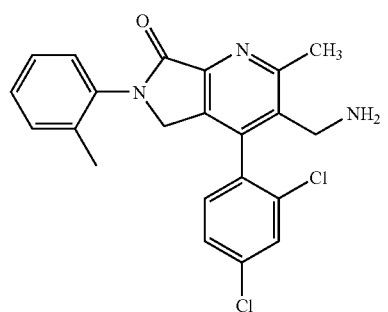
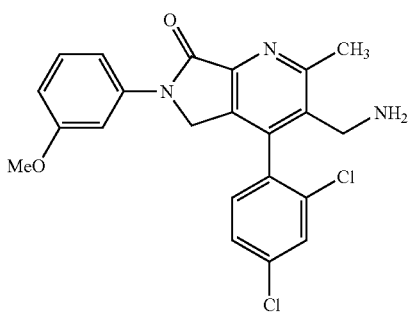
178
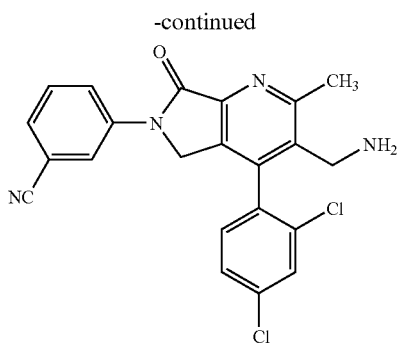
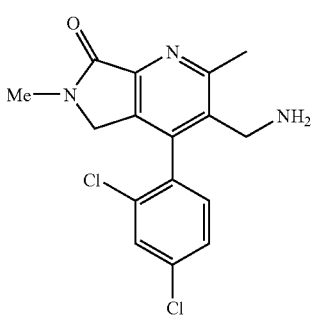
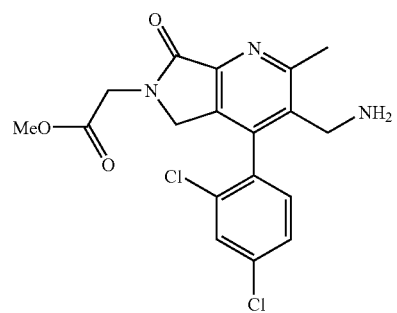
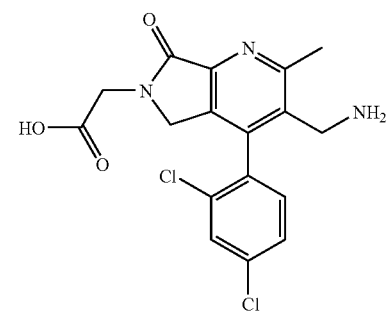
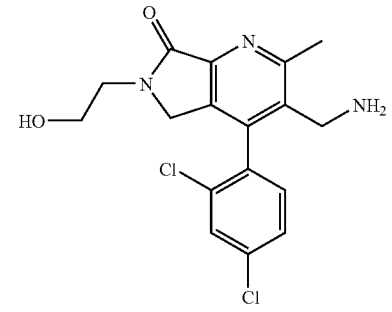

179 -continued
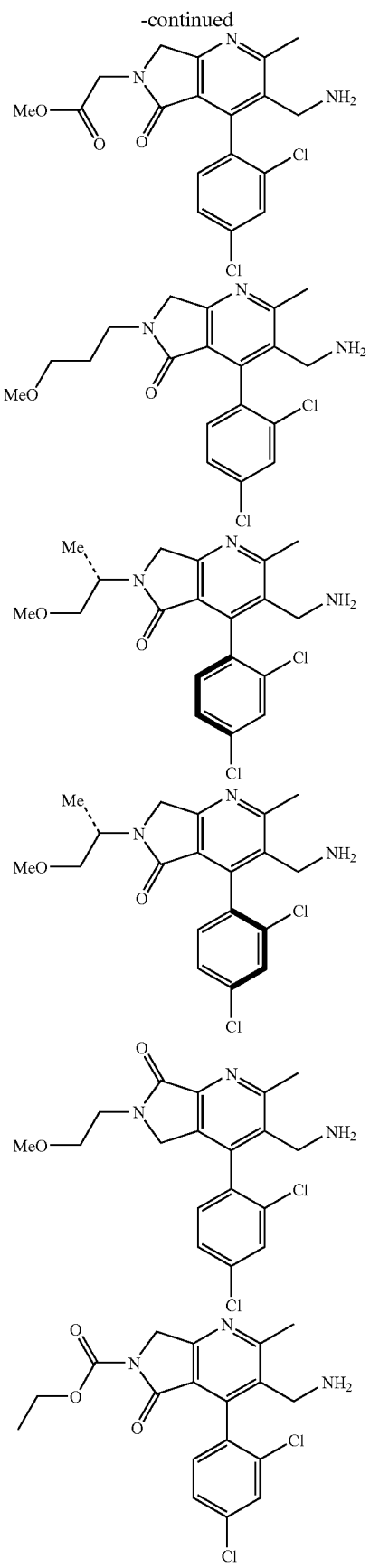
180 -continued
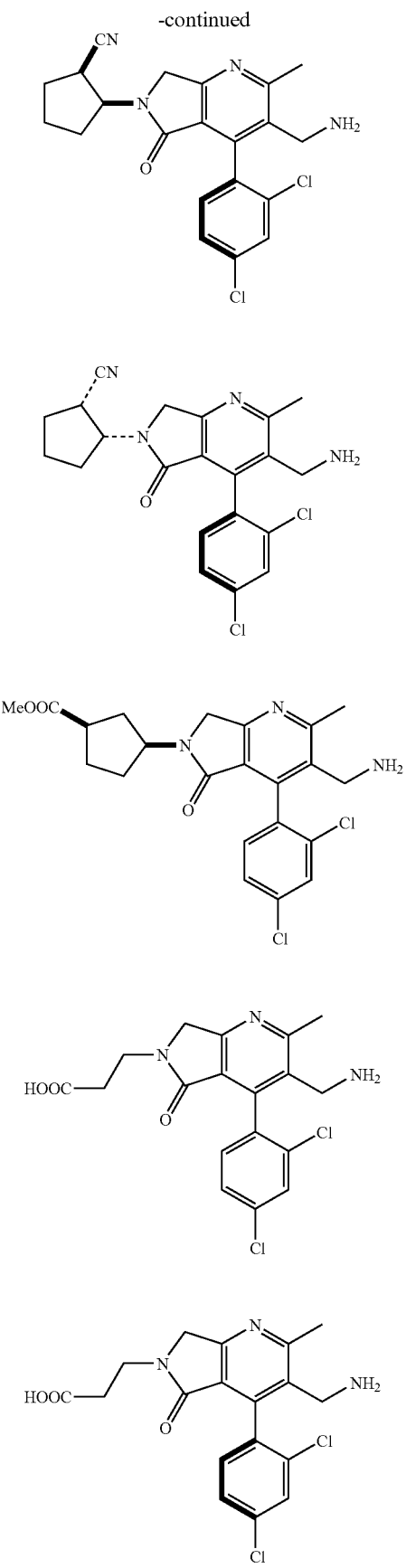

181
-continued
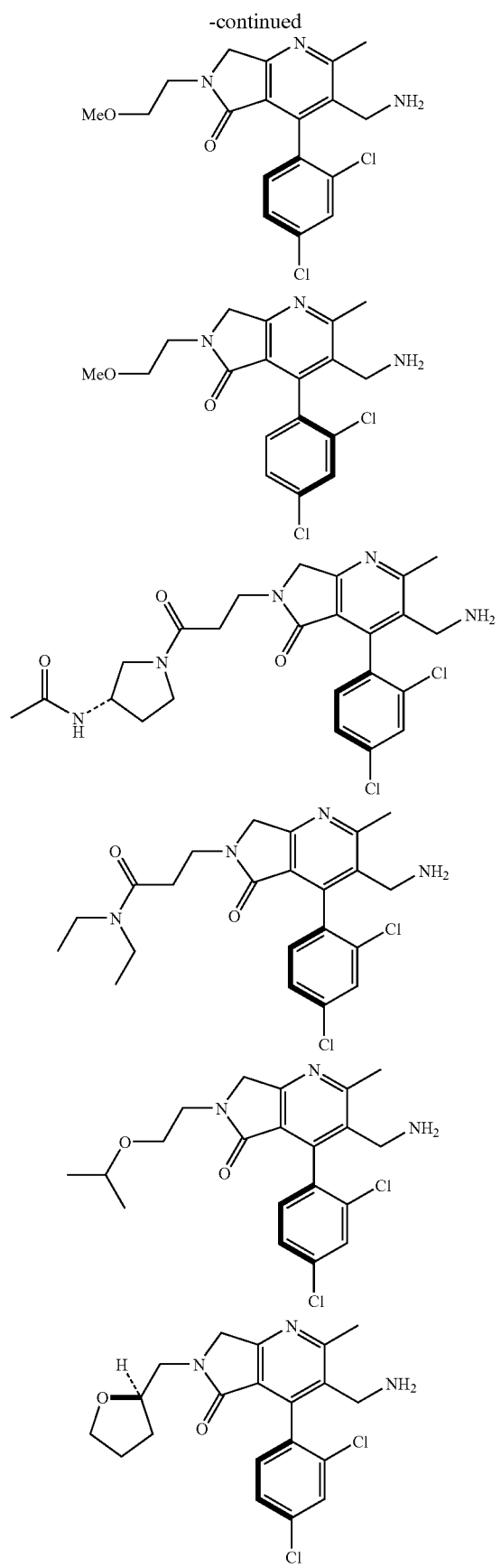
182
-continued
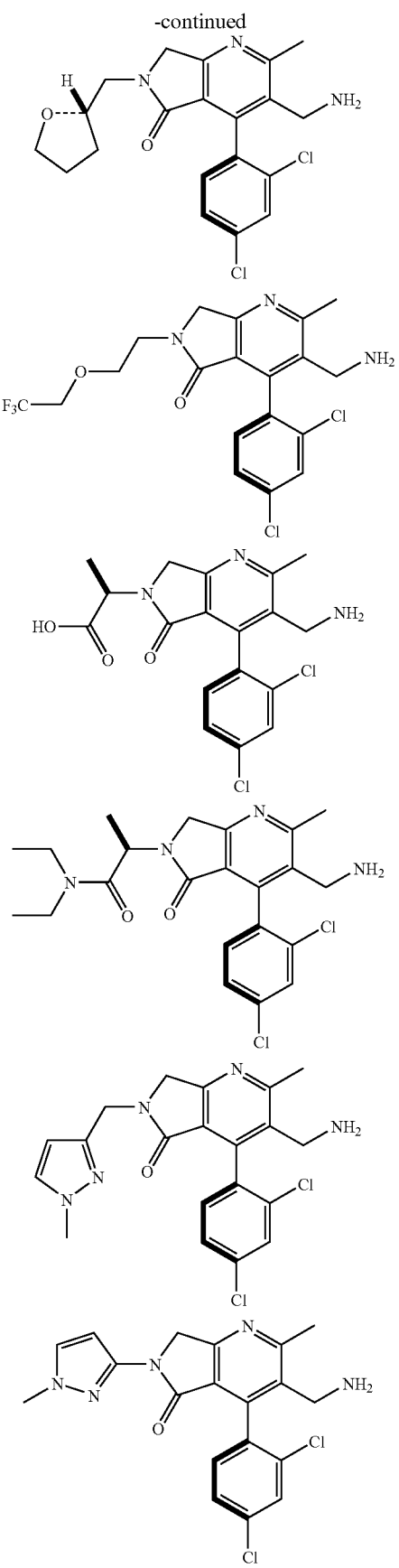

183
-continued
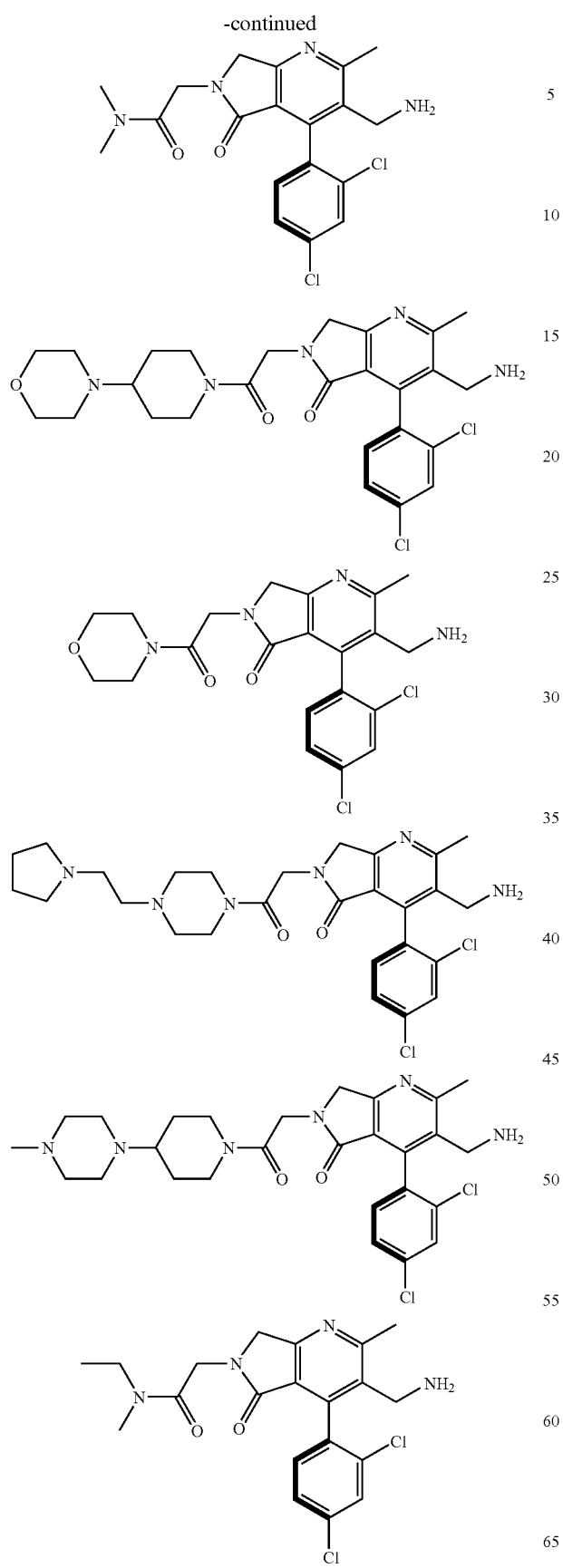
184
-continued
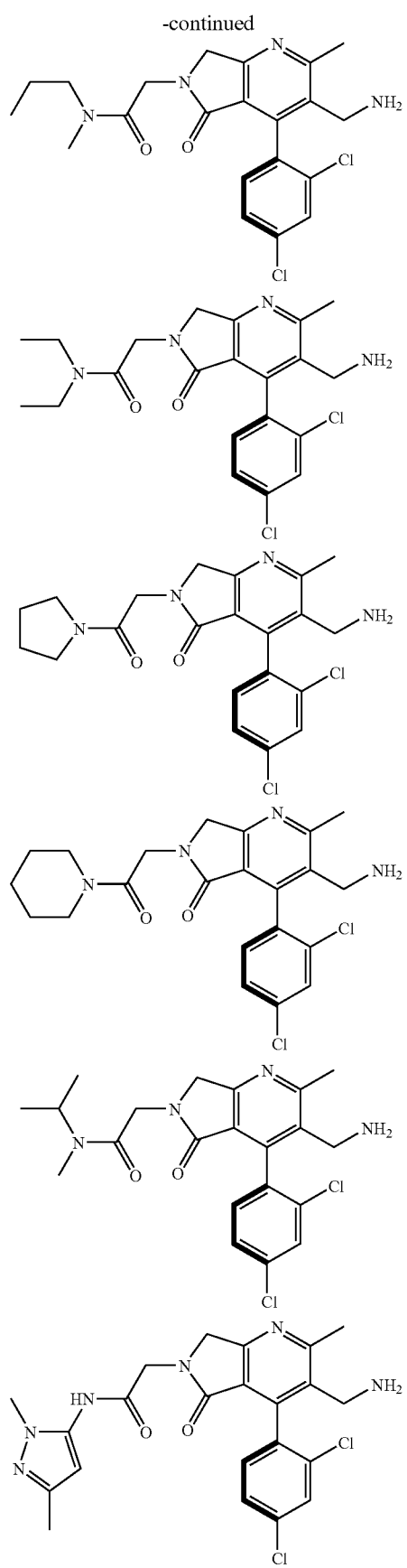

185
-continued
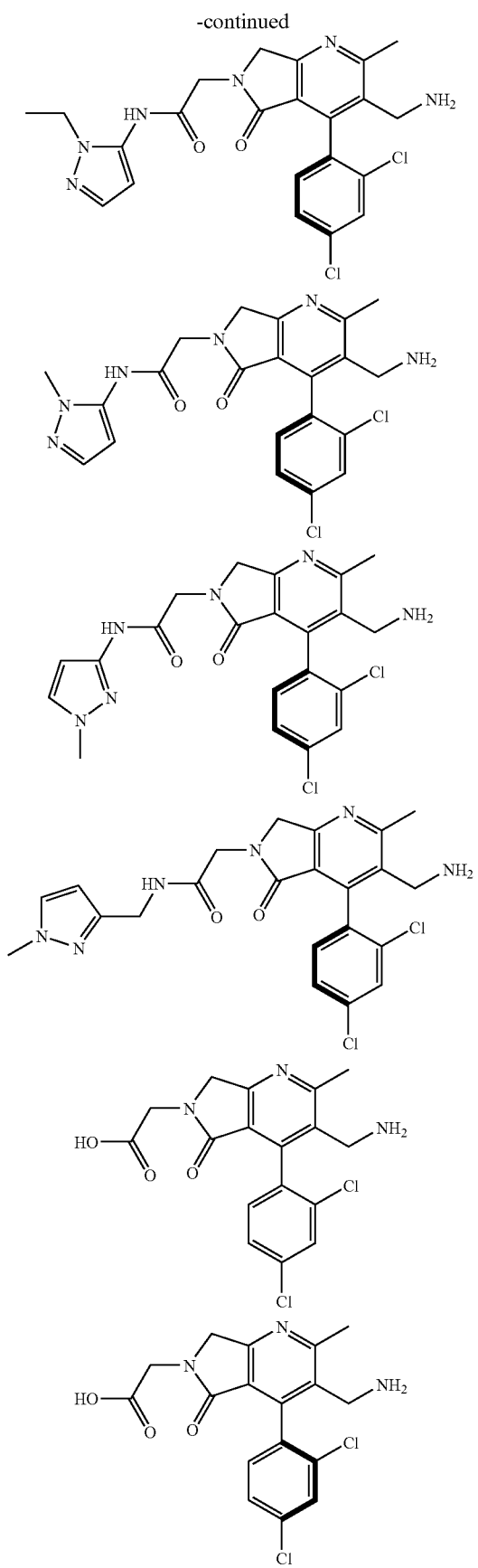
186
-continued
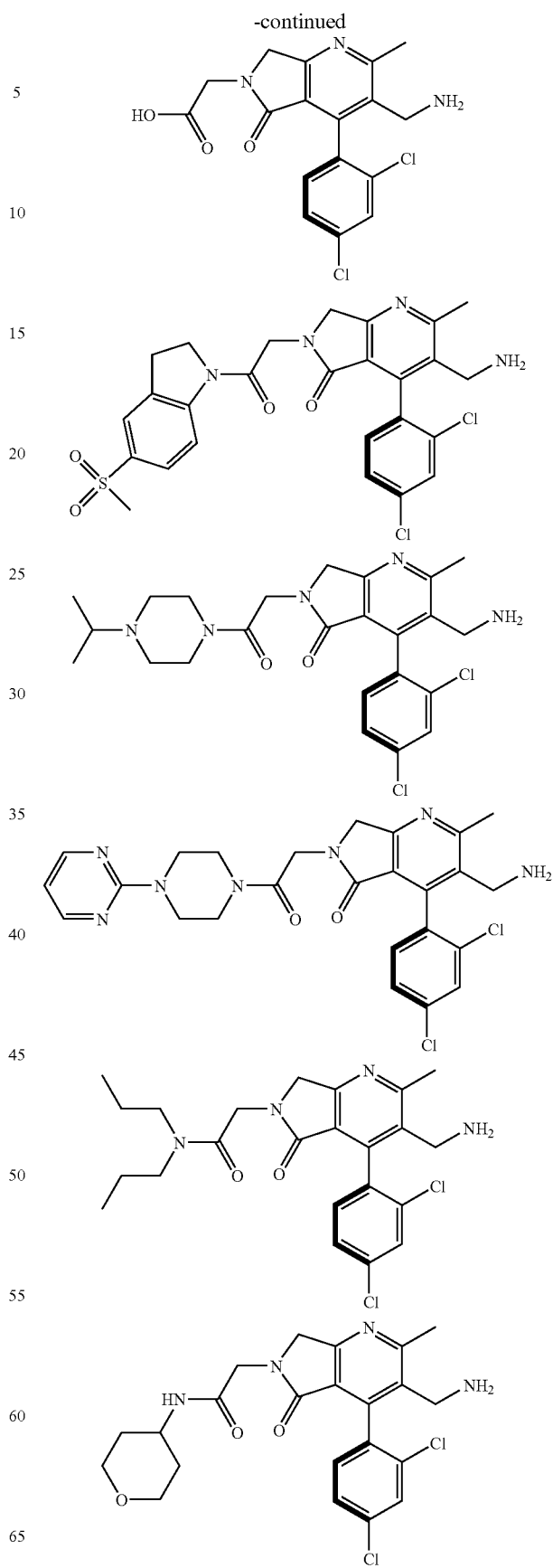

187                                          188
-continued                                  -continued
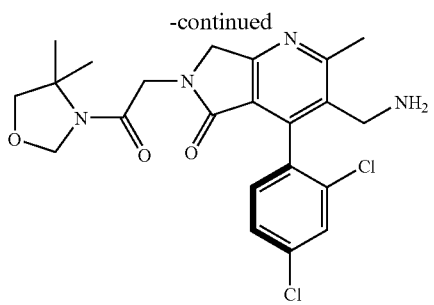
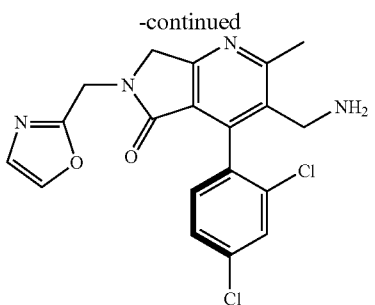
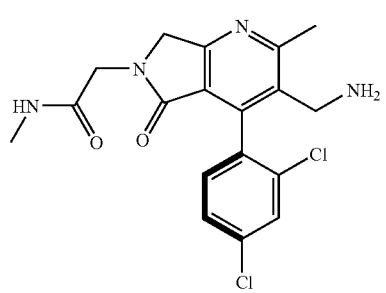
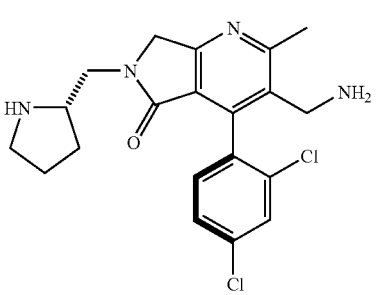
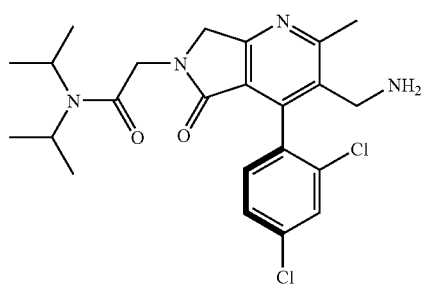
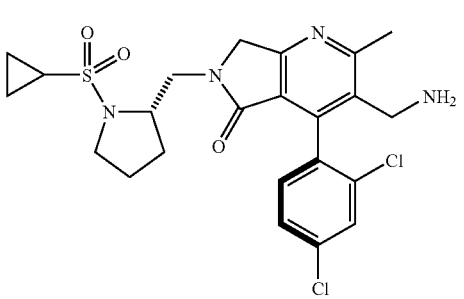
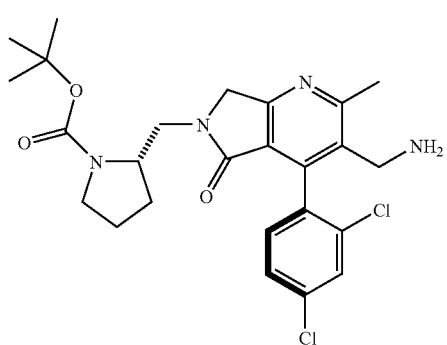
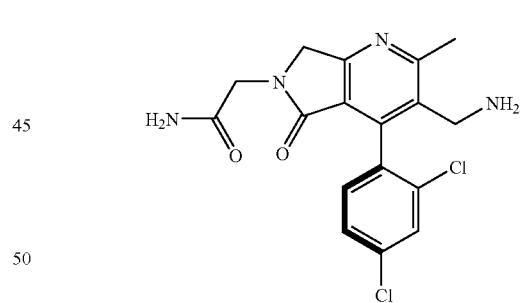
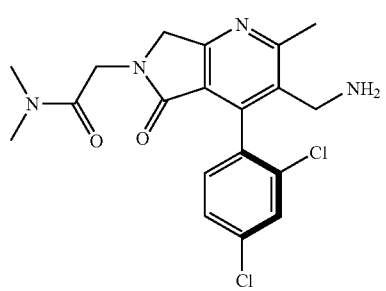
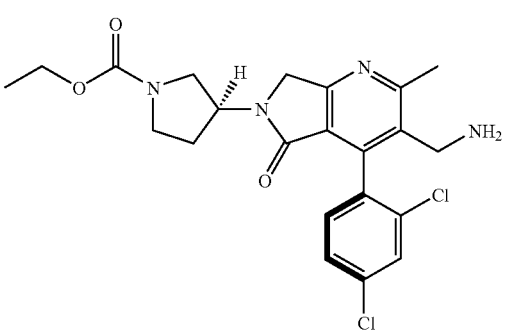

189
-continued
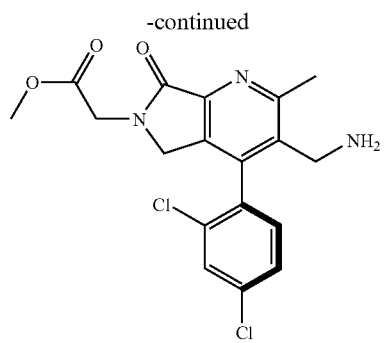
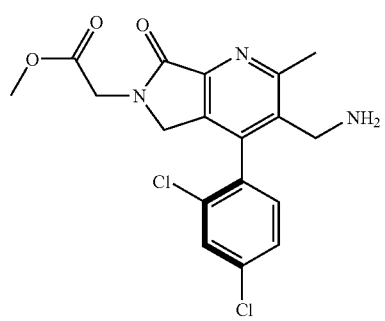
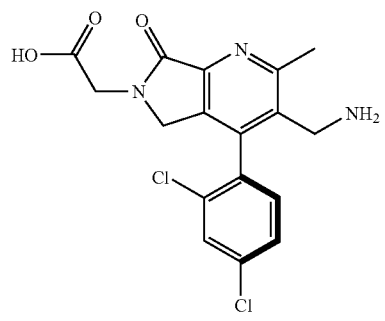
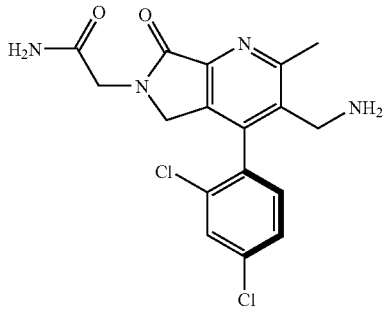
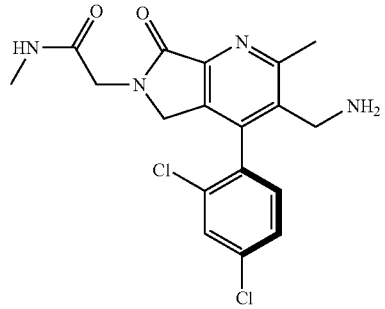
190
-continued
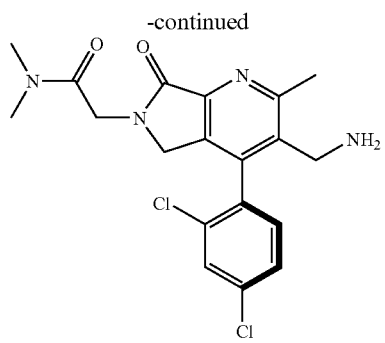
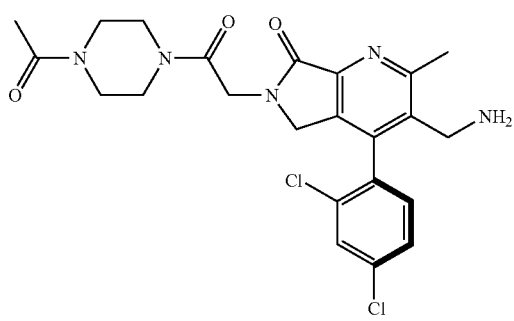
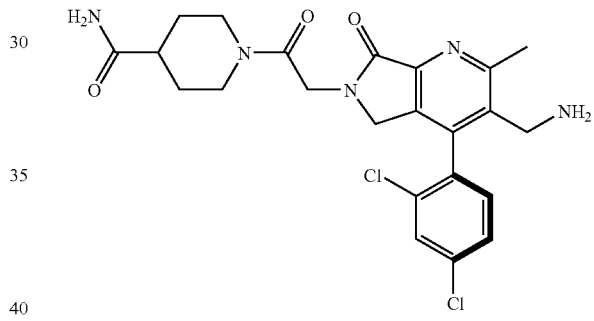
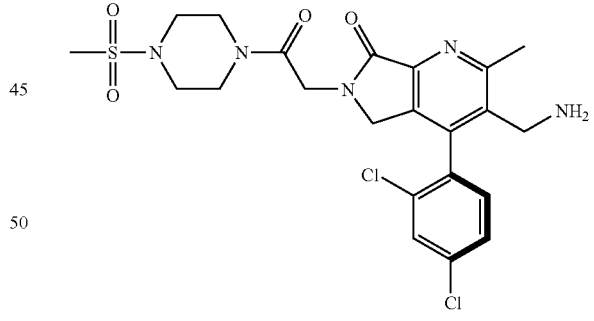
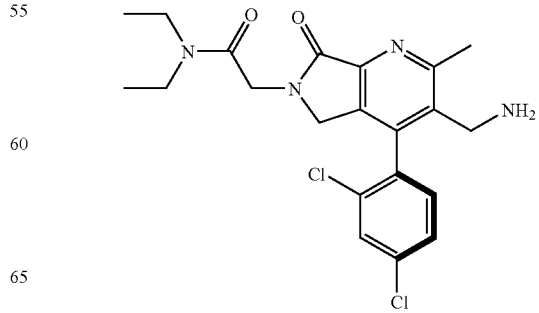

191
-continued
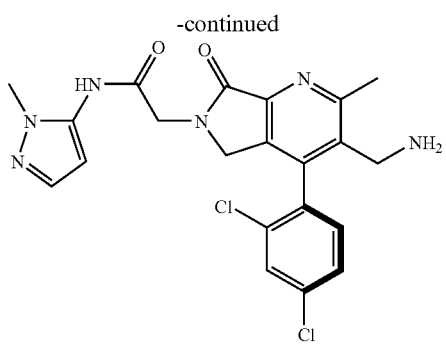
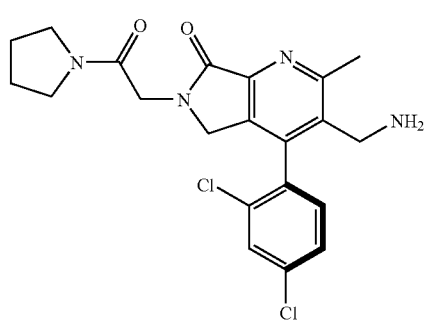
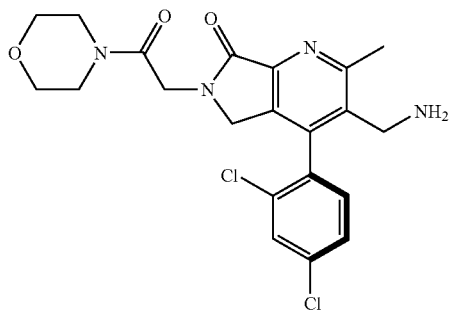
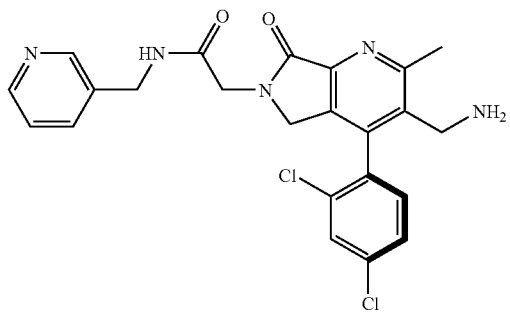
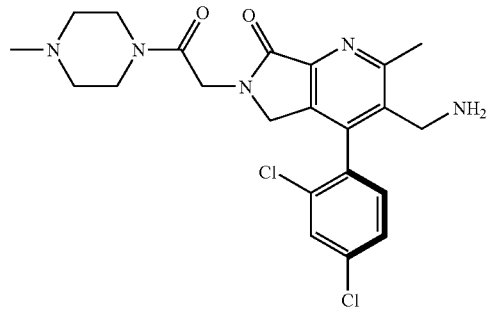
192
-continued
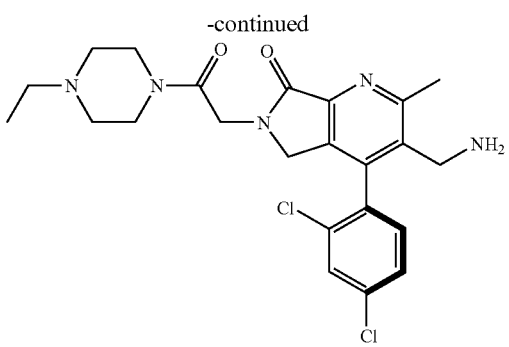
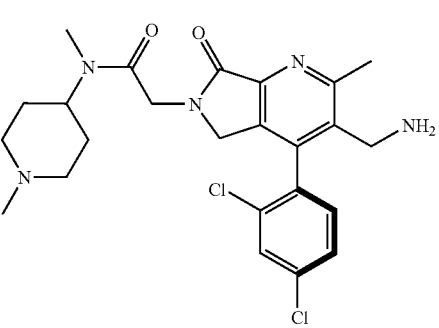
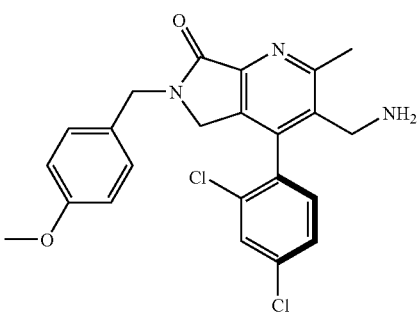
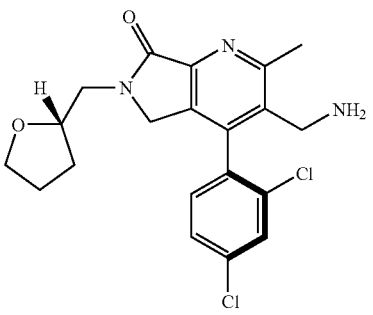
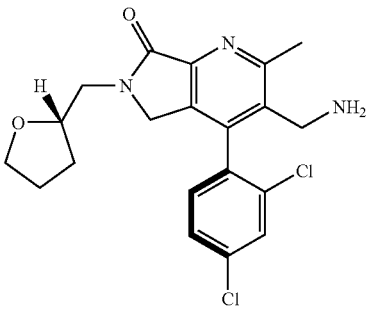

193
-continued
194
-continued
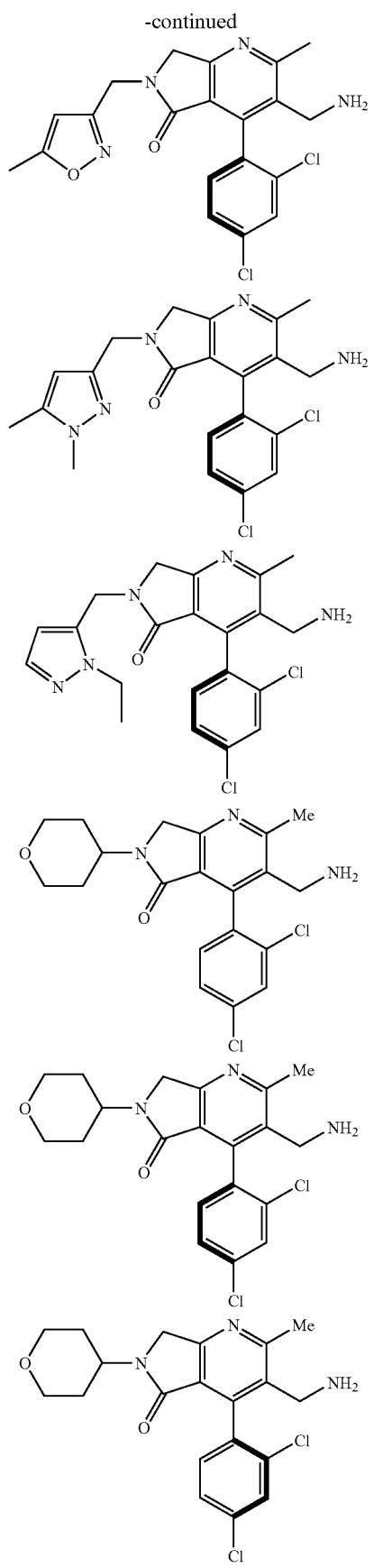
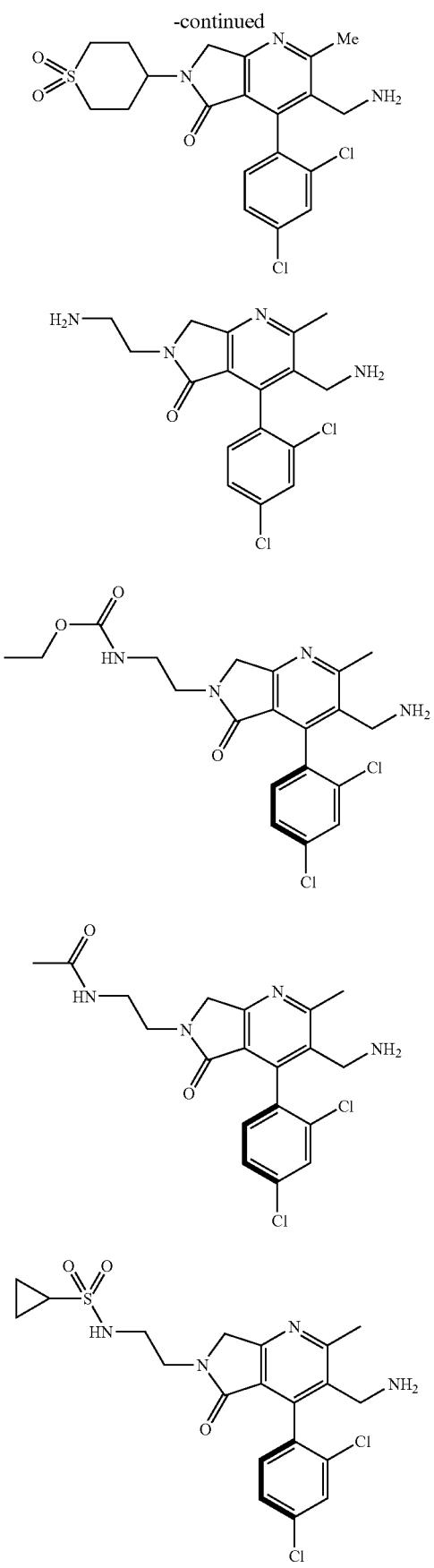

195
-continued
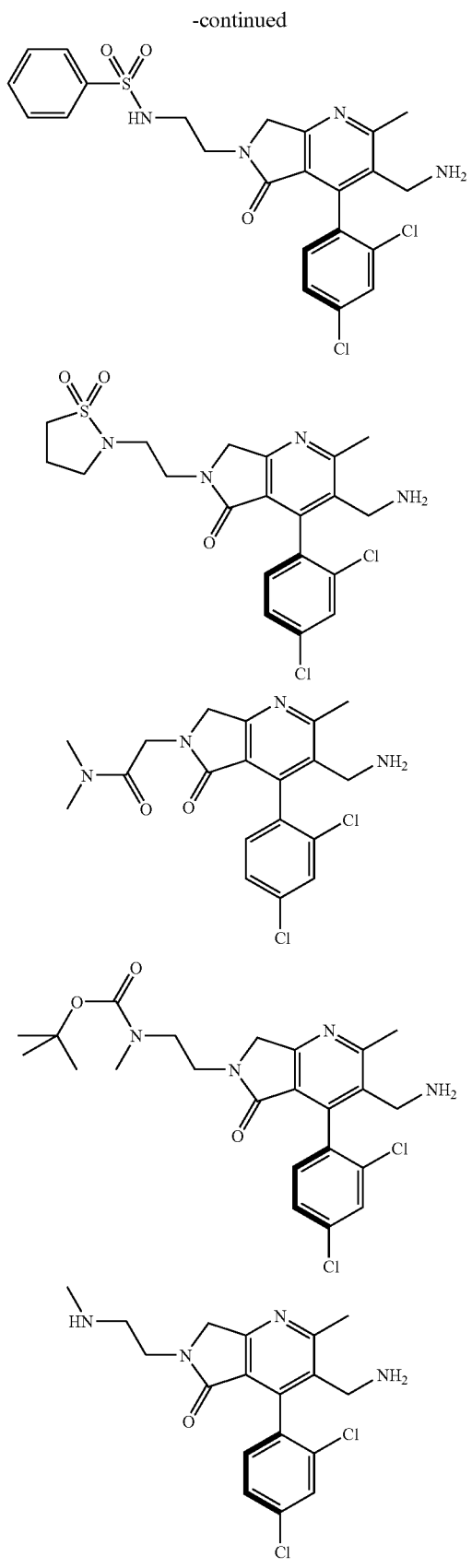
196
-continued
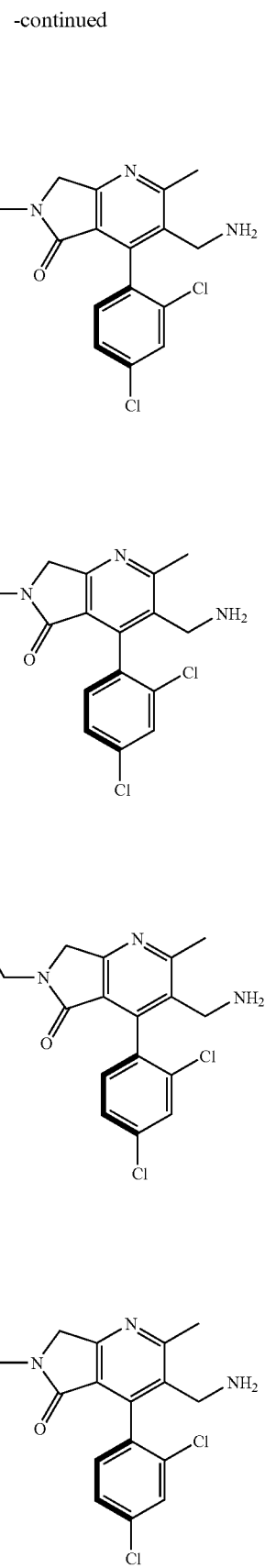

-continued

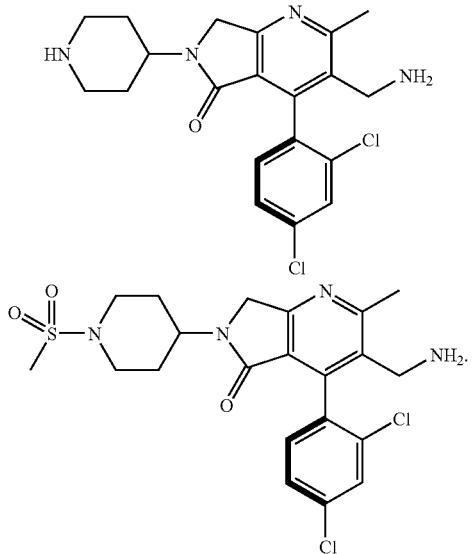

7. A composition comprising a compound as defined in claim 1 and a pharmaceutically acceptable carrier thereof.

8. A composition comprising a compound as defined in claim 1 and a pharmaceutically acceptable salt thereof.

9. A composition comprising a compound as defined in claim 1 in racemic or homochiral form as a free base or a pharmaceutically acceptable salt thereof.

10. A compound having the structure

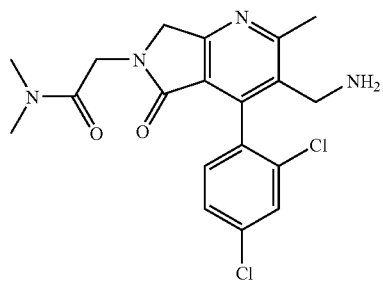

or a pharmaceutically acceptable salt thereof.

11. A compound having the structure

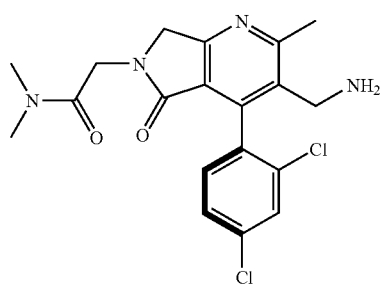

or a pharmaceutically acceptable salt thereof.

12. A compound having the structure

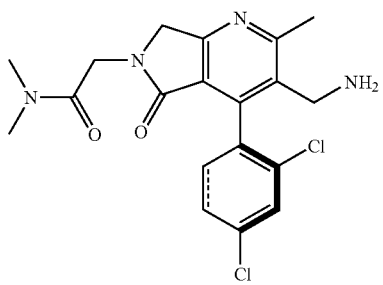

or a pharmaceutically acceptable salt thereof.

13. A composition comprising a compound as defined in claim 10 or a pharmaceutically acceptable salt thereof, and a pharmaceutically acceptable carrier therefor.

14. A composition comprising a compound as defined in claim 11 or a pharmaceutically acceptable salt thereof, and a pharmaceutically acceptable carrier therefor.

15. A composition comprising a compound as defined in claim 12 or a pharmaceutically acceptable salt thereof, and a pharmaceutically acceptable carrier therefor.

16. The compound as defined in claim 10 in racemic or homochiral form as a free base or a pharmaceutically acceptable salt thereof.

17. The compound as defined in claim 11 in homochiral form as a free base or a pharmaceutically acceptable salt thereof.

18. The compound as defined in claim 12 in homochiral form as a free base or a pharmaceutically acceptable salt thereof.

19. A compound having the structure

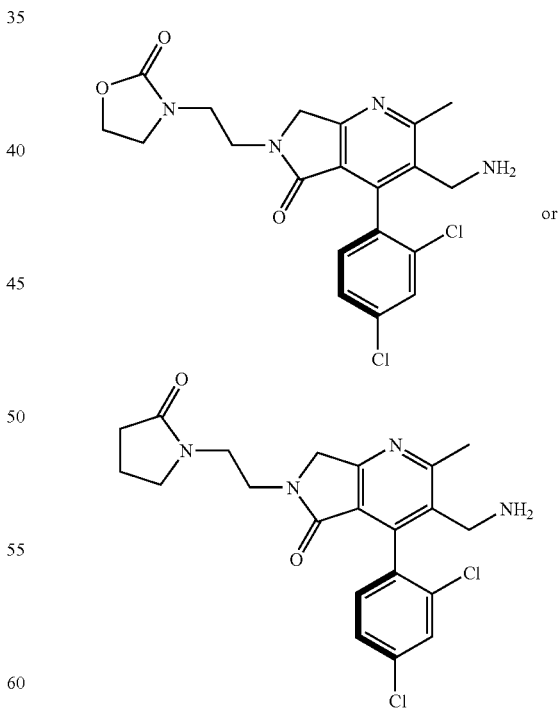

or a pharmaceutically acceptable salt thereof.

* * * * *

UNITED STATES PATENT AND TRADEMARK OFFICE
CERTIFICATE OF CORRECTION

PATENT NO. : 7,521,557 B2  Page 1 of 1
APPLICATION NO. : 11/430657
DATED : April 21, 2009
INVENTOR(S) : Pratik Devasthale et al.

It is certified that error appears in the above-identified patent and that said Letters Patent is hereby corrected as shown below:

Column 1
Line 4, Please insert the following heading under the title of the invention:
-- CROSS-REFERENCE TO RELATED APPLICATION --.

Column 171
Line 1, "is" should read -- is alkyl; --;
Line 7, after "cyclopentyl" insert -- , --;
Line 8, "heteroalkyl," should read -- heteroalkyl --;
Line 36-37, "indepedently" should read -- independently --;
Line 42, "substitutents" should read -- substituents --;
Line 48, before "all" insert -- and --.

Column 172
Line 9, "-C(O)-NR₁R₂, or -C(O)-OR₁," should read -- —C(O) —NR₁R₂, or —C(O) —OR₁, --;
Line 21, "alkylcarbonyl." should read -- alkylcarbonyl, --;
Line 42, "aroup" should read -- group --.

Column 198

Lines 2-14, delete " 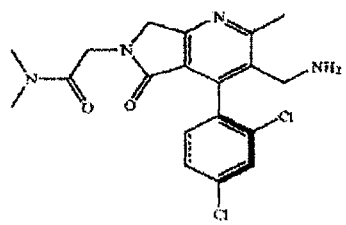 " and insert -- 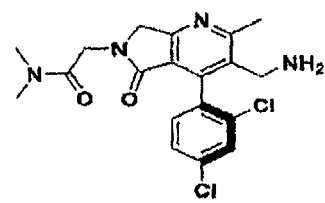 --.

Signed and Sealed this

Ninth Day of November, 2010

David J. Kappos
*Director of the United States Patent and Trademark Office*